US012606639B2

(12) United States Patent

Hu et al.

(10) Patent No.: US 12,606,639 B2
(45) Date of Patent: Apr. 21, 2026

(54) ANTIGEN BINDING PROTEINS

(71) Applicant: GlaxoSmithKline Intellectual Property Development Limited, Stevenage (GB)

(72) Inventors: Erding Hu, Collegeville, PA (US); Matthew Gardener, Stevenage (GB)

(73) Assignee: GlaxoSmith Kline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 19/213,402

(22) Filed: May 20, 2025

(65) Prior Publication Data

US 2025/0361323 A1     Nov. 27, 2025

Related U.S. Application Data

(60) Provisional application No. 63/651,067, filed on May 23, 2024.

(51) Int. Cl.
| | |
|---|---|
| *C07K 16/40* | (2006.01) |
| *A61P 13/12* | (2006.01) |
| *A61K 39/00* | (2006.01) |

(52) U.S. Cl.
CPC .............. *C07K 16/40* (2013.01); *A61P 13/12* (2018.01); *C12Y 304/24079* (2013.01); *A61K 2039/505* (2013.01); *C07K 2317/33* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,703,039 A | 10/1987 | Hawiger et al. | |
| 5,747,035 A | 5/1998 | Presta et al. | |
| 5,869,046 A | 2/1999 | Presta et al. | |
| 6,180,370 B1 * | 1/2001 | Queen ..................... | A61P 19/02 |
| | | | 435/69.6 |
| 12,157,776 B2 | 12/2024 | Freund et al. | |
| 2005/0053973 A1 | 3/2005 | Kolkman et al. | |
| 2005/0089932 A1 | 4/2005 | Kolkman et al. | |
| 2005/0164301 A1 | 7/2005 | Kolkman et al. | |
| 2024/0158534 A1 * | 5/2024 | Freund ................... | C07K 16/40 |

FOREIGN PATENT DOCUMENTS

| | | |
|---|---|---|
| WO | WO 1986/001533 | 3/1986 |
| WO | WO 1991/014438 | 10/1991 |
| WO | WO 1996/032478 | 10/1996 |
| WO | WO 1997/043316 | 11/1997 |
| WO | WO 1999/043713 | 9/1999 |
| WO | WO 2000/009560 | 2/2000 |
| WO | WO 2000/029004 | 5/2000 |
| WO | WO 2006/130834 | 12/2006 |
| WO | WO 2020/198166 | 10/2020 |

OTHER PUBLICATIONS

Conover, Cheryl A. "Key questions and answers about pregnancy-associated plasma protein-A." Trends in endocrinology and metabolism: TEM vol. 23,5 (2012): 242-9. doi:10.1016/j.tem.2012.02.008 (Year: 2012).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Aung et al., Autosomal Dominant Polycystic Kidney Disease Prevalence among a Racially Diverse United States Population, 2002 through 2018. Kidney360. Sep. 22, 2021;2(12):2010-2015.
Suwabe et al., Epidemiology of Autosomal Dominant Polycystic Kidney Disease in Olmsted County. Clin J Am Soc Nephrol. Jan. 7, 2020;15(1):69-79. Epub Dec. 2, 2019.
Willey et al., Analysis of Nationwide Data to Determine the Incidence and Diagnosed Prevalence of Autosomal Dominant Polycystic Kidney Disease in the USA: 2013-2015. Kidney Dis (Basel). Mar. 2019;5(2):107-117. Epub Jan. 9, 2019.
Willey et al., Regional variations in prevalence and severity of autosomal dominant polycystic kidney disease in the United States. Curr Med Res Opin. Jul. 2021;37(7):1155-1162. Epub May 25, 2021.
Avery et al., Establishing in vitro in vivo correlations to screen monoclonal antibodies for physicochemical properties related to favorable human pharmacokinetics. MAbs. Feb./Mar. 2018;10(2):244-255. Epub Jan. 29, 2018.
Ratanji et al., Immunogenicity of therapeutic proteins: influence of aggregation. J Immunotoxicol. Apr.-Jun. 2014;11(2):99-109. Epub Aug. 6, 2013.
Judge et al., Structure of the PAPP-ABP5 complex reveals mechanism of substrate recognition. Nat Commun. Sep. 20, 2022;13(1):5500. Erratum in: Nat Commun. Sep. 28, 2022;13(1):5694.
Oxvig, C., The role of PAPP-A in the IGF system: location, location, location. J Cell Commun Signal. Jun. 2015;9(2):177-87. Epub Jan. 25, 2015.
Mohrin et al., Inhibition of longevity regulator PAPP-A modulates tissue homeostasis via restraint of mesenchymal stromal cells. Aging Cell. Mar. 2021;20(3):e13313. Epub Feb. 9, 2021.
Barrios et al., Pregnancy-Associated Plasma Protein (PAPP)-A2 in Physiology and Disease. Cells. Dec. 18, 2021;10(12):3576.
Kashyap et al., Metalloproteinase PAPP-A regulation of IGF-1 contributes to polycystic kidney disease pathogenesis. JCI Insight. Feb. 27, 2020;5(4):e135700.

(Continued)

*Primary Examiner* — Michael Szperka
*Assistant Examiner* — Lia E Taylor
(74) *Attorney, Agent, or Firm* — Cynthia Lan Martin; Nicole Ginanni

(57) ABSTRACT

The present disclosure relates to antigen binding proteins. More particularly the present disclosure relates to pregnancy associated plasma protein-A (PAPPA) binding proteins, even more particularly PAPPA binding proteins that inhibit cleavage of insulin like growth factor binding protein-2 (IGFBP-2), insulin like growth factor binding protein-4 (IGFBP-4) and insulin like growth factor binding protein-5 (IGFBP-5). The present disclosure further relates to the use of said binding proteins in medicine.

22 Claims, 38 Drawing Sheets

Figure 1A:
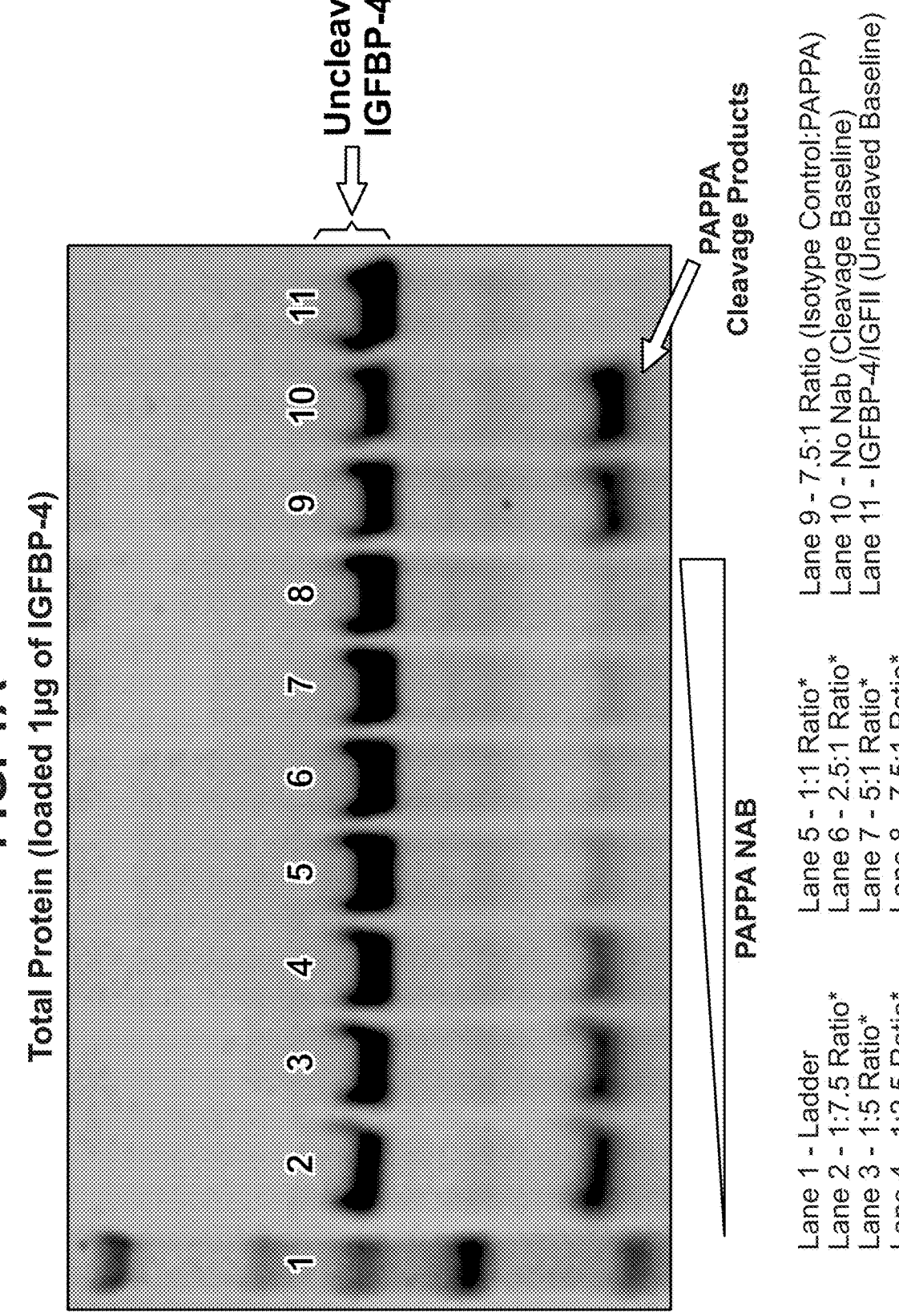

Specification includes a Sequence Listing.

(56)          References Cited

OTHER PUBLICATIONS

Sharma et al., Kidney volume measurement methods for clinical studies on autosomal dominant polycystic kidney disease. PLoS One. May 30, 2017;12(5):e0178488.

Chothia et al., Conformations of immunoglobulin hypervariable regions. Nature. Dec. 21-28, 1989;342(6252):877-83.

Tam et al., Functional, Biophysical, and Structural Characterization of Human IgG1 and IgG4 Fc Variants with Ablated Immune Functionality. Antibodies (Basel). Sep. 1, 2017;6(3):12.

Overgaard et al., Complex of pregnancy-associated plasma protein-A and the proform of eosinophil major basic protein. Disulfide structure and carbohydrate attachment. J Biol Chem. Jan. 24, 2003;278(4):2106-17. Epub Nov. 5, 2002.

Biomarkers Definitions Working Group, Biomarkers and surrogate endpoints: preferred definitions and conceptual framework. Clin Pharmacol Ther. Mar. 2001;69(3):89-95.

Mikkelsen et al., Indirect targeting of IGF receptor signaling in vivo by substrate-selective inhibition of PAPP-A proteolytic activity. Oncotarget. Feb. 28, 2014;5(4):1014-25.

Crook et al., Empirical Bayes functional models for hydrogen deuterium exchange mass spectrometry. Commun Biol. Jun. 15, 2022;5(1):588.

Laursen et al., Pregnancy-associated plasma protein-A (PAPP-A) cleaves insulin-like growth factor binding protein (IGFBP)-5 independent of IGF: implications for the mechanism of IGFBP-4 proteolysis by PAPP-A. FEBS Letters. Jul. 2001;504:36-40.

Atala et al., Juvenile cystic kidneys (jck): a new mouse mutation which causes polycystic kidneys. Kidney Int. May 1993;43(5):1081-5.

Natoli et al., Inhibition of glucosylceramide accumulation results in effective blockade of polycystic kidney disease in mouse models. Nat Med. Jul. 2010; 16(7):788-92. Epub Jun. 20, 2010.

Østergaard et al., Therapeutic effects of lisinopril and empagliflozin in a mouse model of hypertension-accelerated diabetic kidney disease. Am J Physiol Renal Physiol. Aug. 1, 2021;321(2):F149-F161. Epub Jun. 28, 2021.

Dalbøge et al., Nephroprotective Effects of Semaglutide as Mono- and Combination Treatment with Lisinopril in a Mouse Model of Hypertension—Accelerated Diabetic Kidney Disease. Biomedicines. Jul. 11, 2022;10(7):1661.

Loghman-Adham et al., Immortalized epithelial cells from human autosomal dominant polycystic kidney cysts. Am J Physiol Renal Physiol. Sep. 2003;285(3):F397-412. Epub May 6, 2003.

Monget et al., Pregnancy-associated plasma protein-A is involved in insulin-like growth factor binding protein-2 (IGFBP-2) proteolytic degradation in bovine and porcine preovulatory follicles: identification of cleavage site and characterization of IGFBP-2 degradation. Biol Reprod. Jan. 2003;68(1):77-86.

Dyson et al., Beyond affinity: selection of antibody variants with optimal biophysical properties and reduced immunogenicity from mammalian display libraries. MAbs. Jan.-Dec. 2020;12(1):1829335.

Liu et al., High-throughput screening for developability during early-stage antibody discovery using self-interaction nanoparticle spectroscopy. MAbs. Mar.-Apr. 2014;6(2):483-92. Epub Dec. 6, 2013.

Mohrin et al., Pharmacological Inhibition of Longevity Regulator PAPP-A Restrains Mesenchymal Stromal Cell Activity. BioRxiv. Feb. 6, 2020. pp. 1-43.

Invitation to Pay Additional Fees for International Application No. PCT/EP2025/063798, mailed Aug. 25, 2025, 16 Pages.

International Search Report and Written Opinion for International Application No. PCT/EP2025/063798, mailed Oct. 16, 2025, 24 Pages.

* cited by examiner

Total Protein (loaded 1µg of IGFBP-5)

Uncleaved IGFBP-5

PAPPA Cleavage Products

PAPPA NAB

Lane 1 - Ladder
Lane 2 - 1:7.5 Ratio*
Lane 3 - 1:5 Ratio*
Lane 4 - 1:2.5 Ratio*
Lane 5 - 1:1 Ratio*
Lane 6 - 2.5:1 Ratio*
Lane 7 - 5:1 Ratio*
Lane 8 - 7.5:1 Ratio*
Lane 9 - 7.5:1 Ratio (Isotype Control PAPPA)
Lane 10 - No Nab (Cleavage Baseline)
Lane 11 - IGFBP-5 (Uncleaved Baseline)

Figure 2:
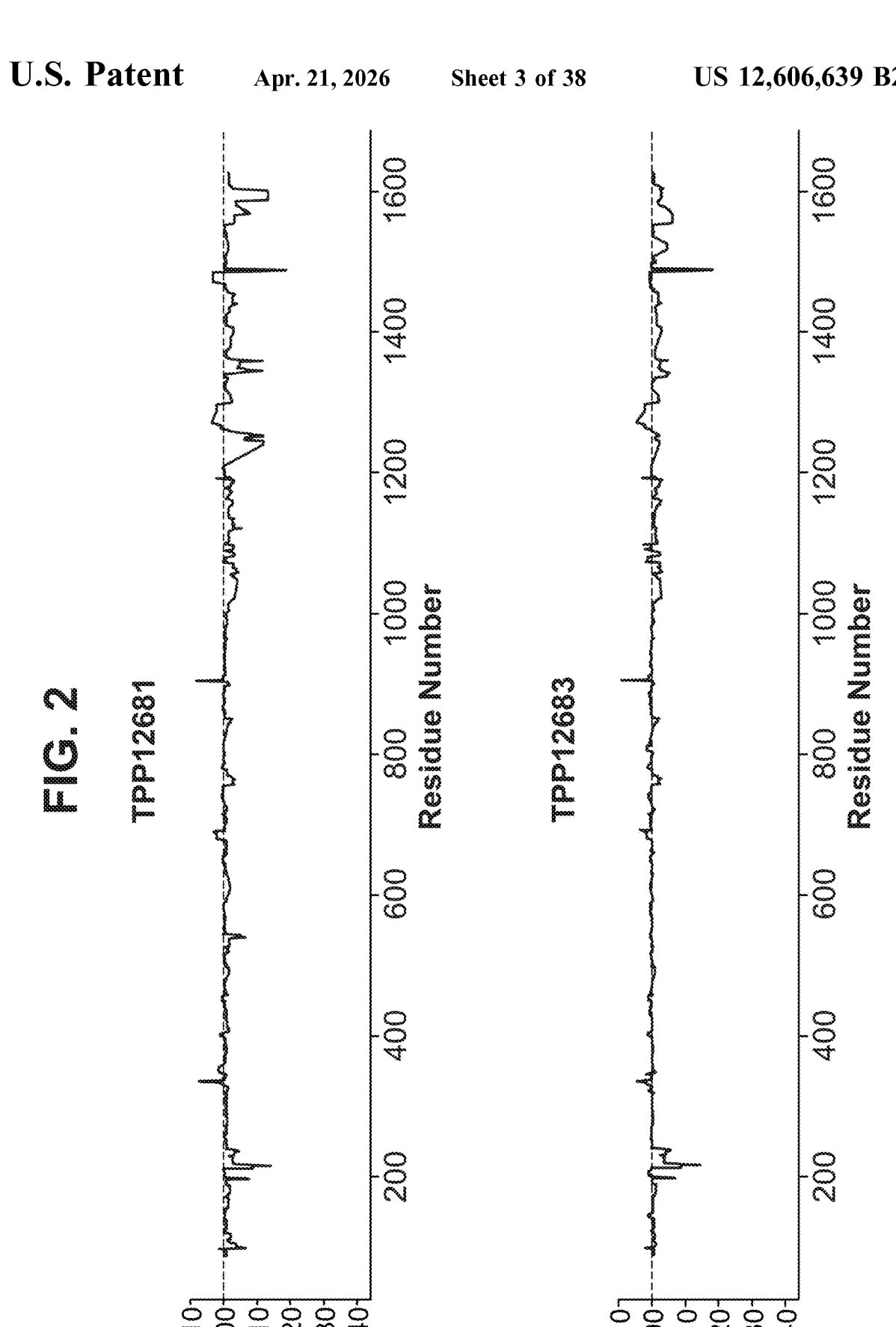

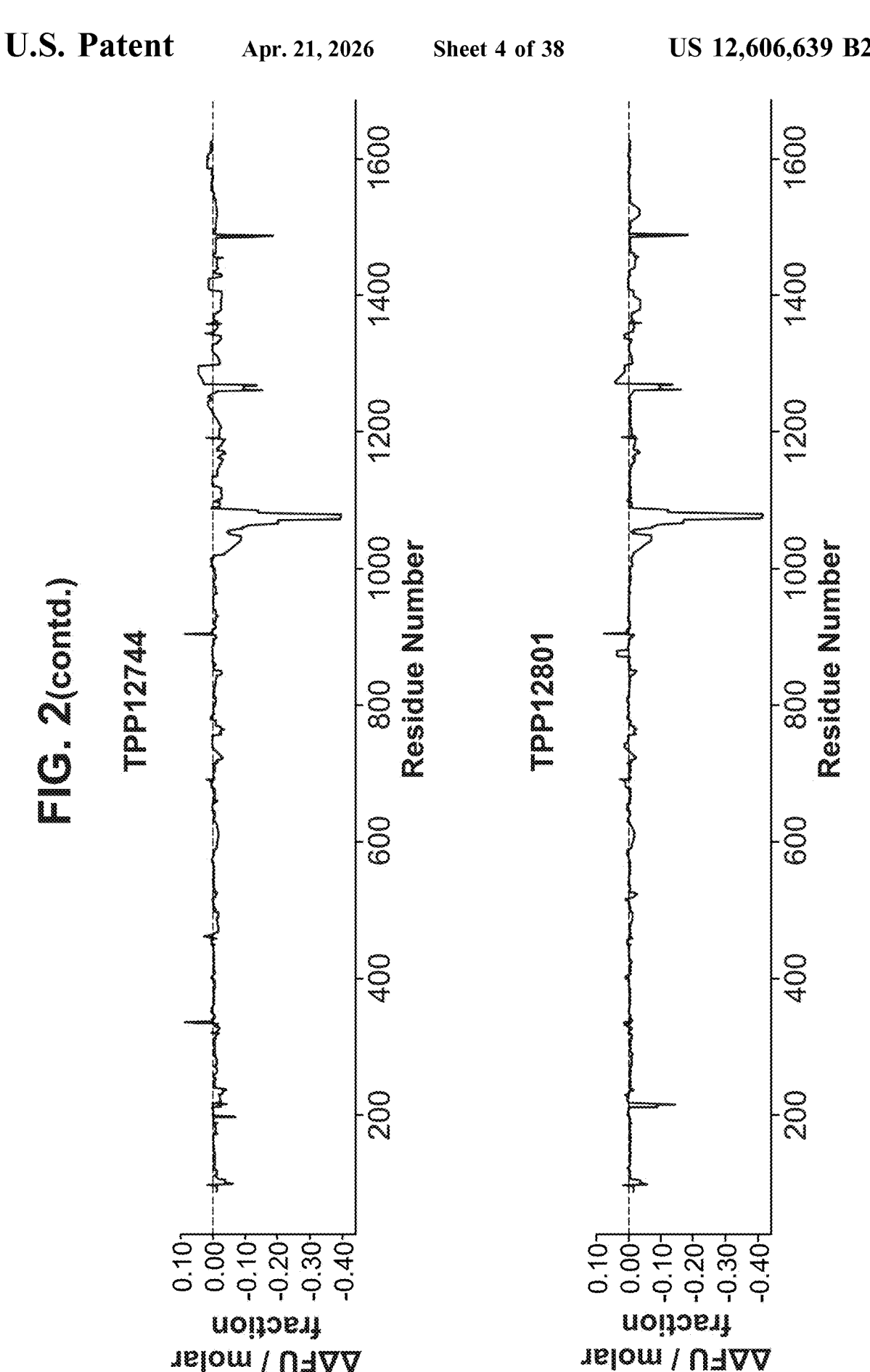
FIG. 2(contd.)

Figure 4:
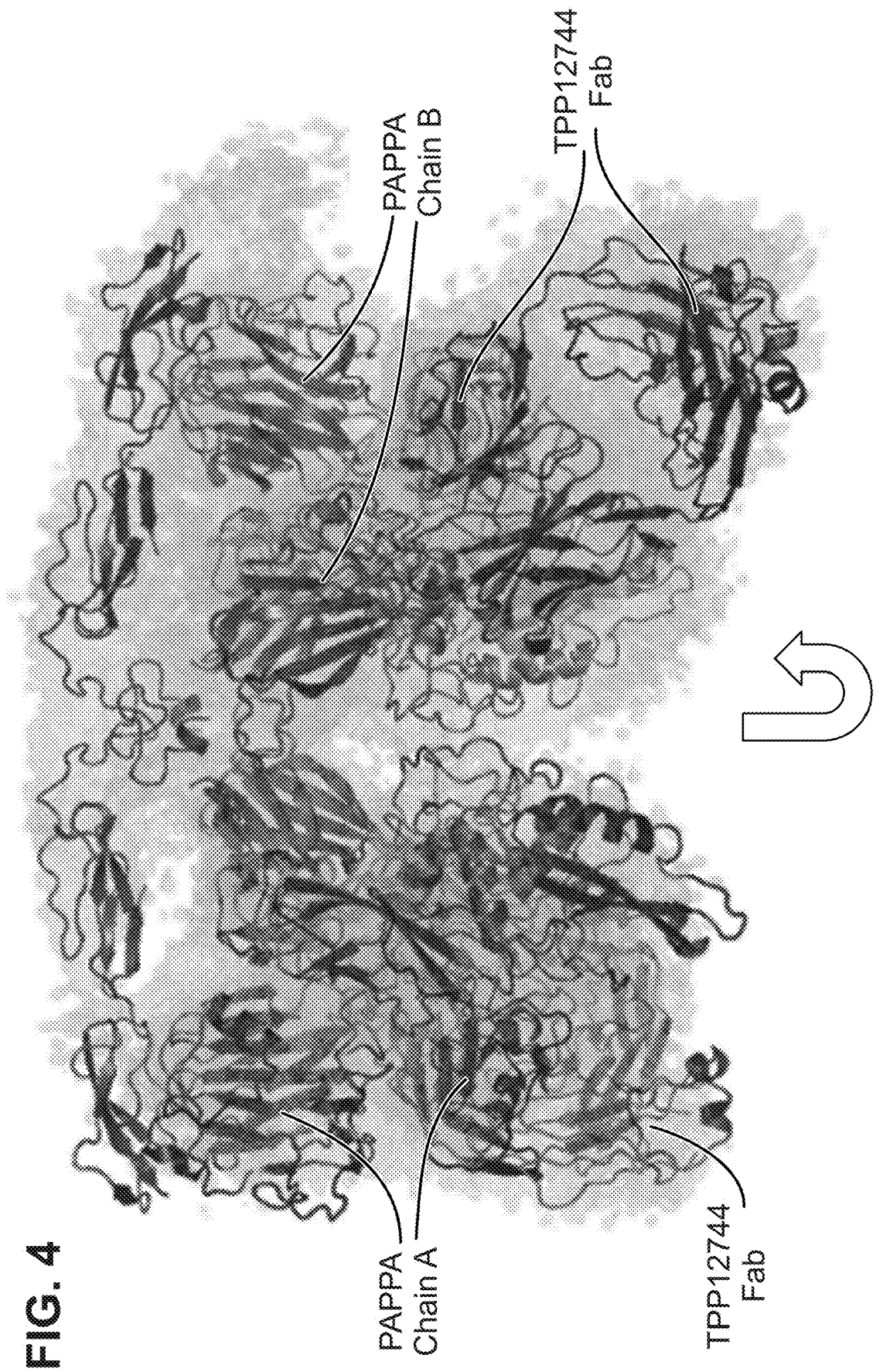

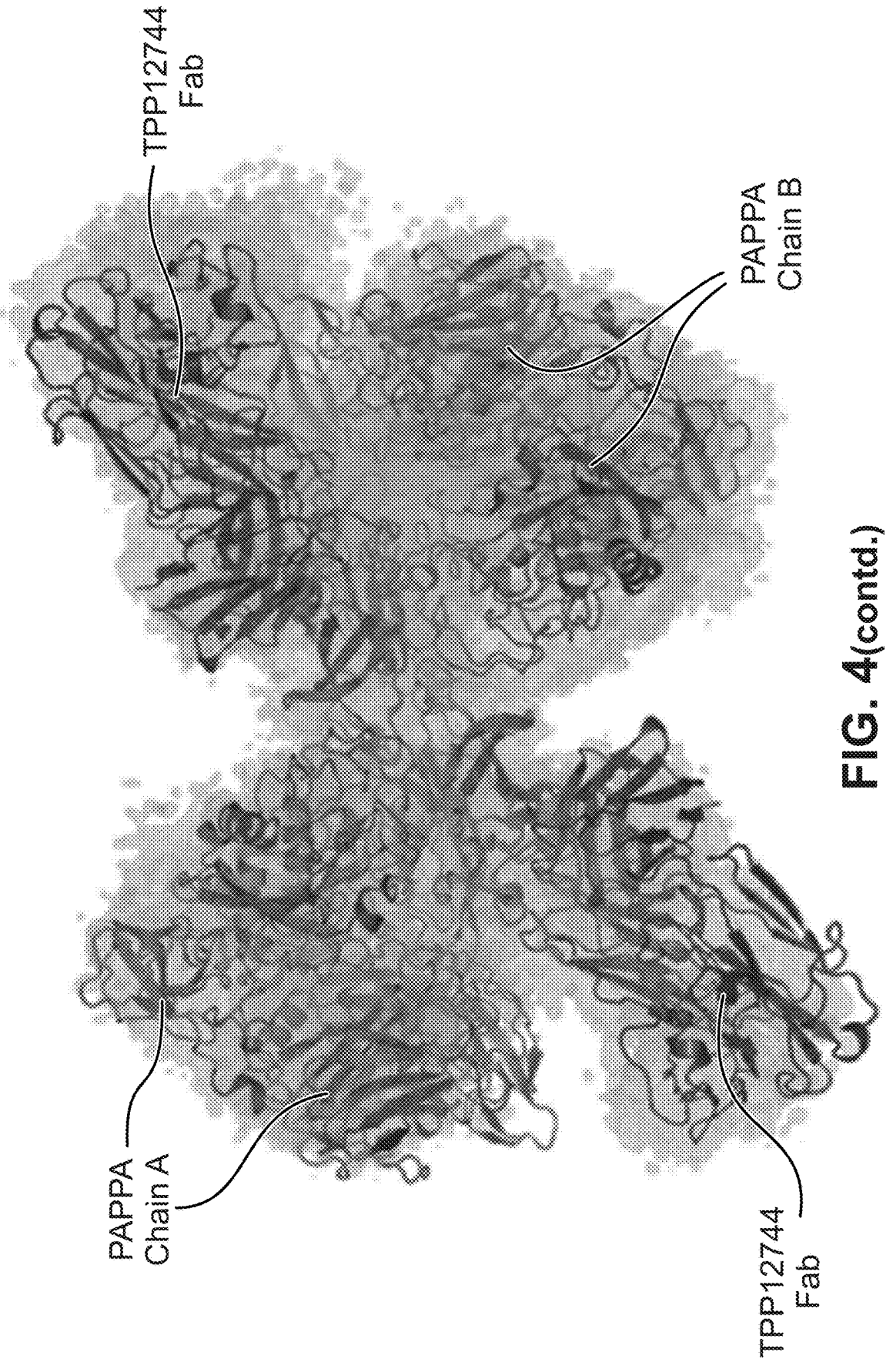
TPP12744
Fab
PAPPA
Chain B
PAPPA
Chain A
TPP12744
Fab
FIG. 4(contd.)

FIG. 6A

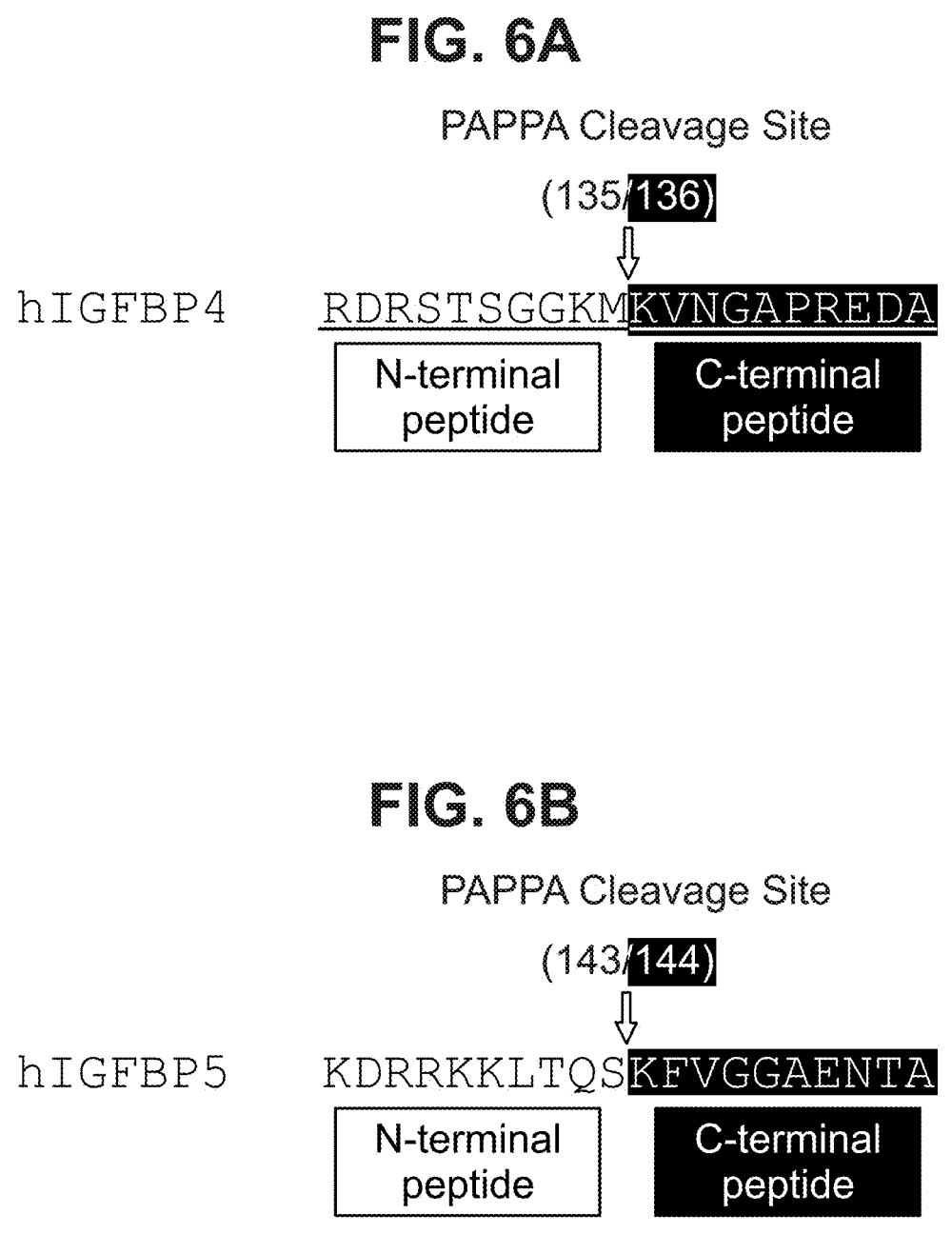

PAPPA Cleavage Site (135/136)

⇓ hIGFBP4     RDRSTSGGKM KVNGAPREDA

N-terminal peptide     C-terminal peptide

FIG. 6B

PAPPA Cleavage Site (143/144)

⇓ hIGFBP5     KDRRKKLTQS KFVGGAENTA

N-terminal peptide     C-terminal peptide

IGFBP4-Ct in ADPKD Plasma

IGFBP4-Fl in ADPKD Plasma

ADPKD Samples: eGFR vs IGFBP4-Ct tKV vs BP4-Ct

Increased BP4-c in DKD Patients

IGFBP4-Ct in DKD

Intact IGFBP4 in A549 Culture Media
(n=3)

—○— hIgG          − −◻− −TPP12744

IGFBP4-Ct in A549 Culture Media
(n=3)

Free-IGF1 in A549 Culture Media
(n=3)

A549 Cellular Assay

Intact IGFBP4 in 9-7 Culture Media
(n=3)

IGFBP4-Ct in 9-7 Culture Media
(n=3)

Urine Albumin - Week 12

Urine Creatinine - Week 12

LOG Urine ACR - Week 12

Urine ACR - Week 12

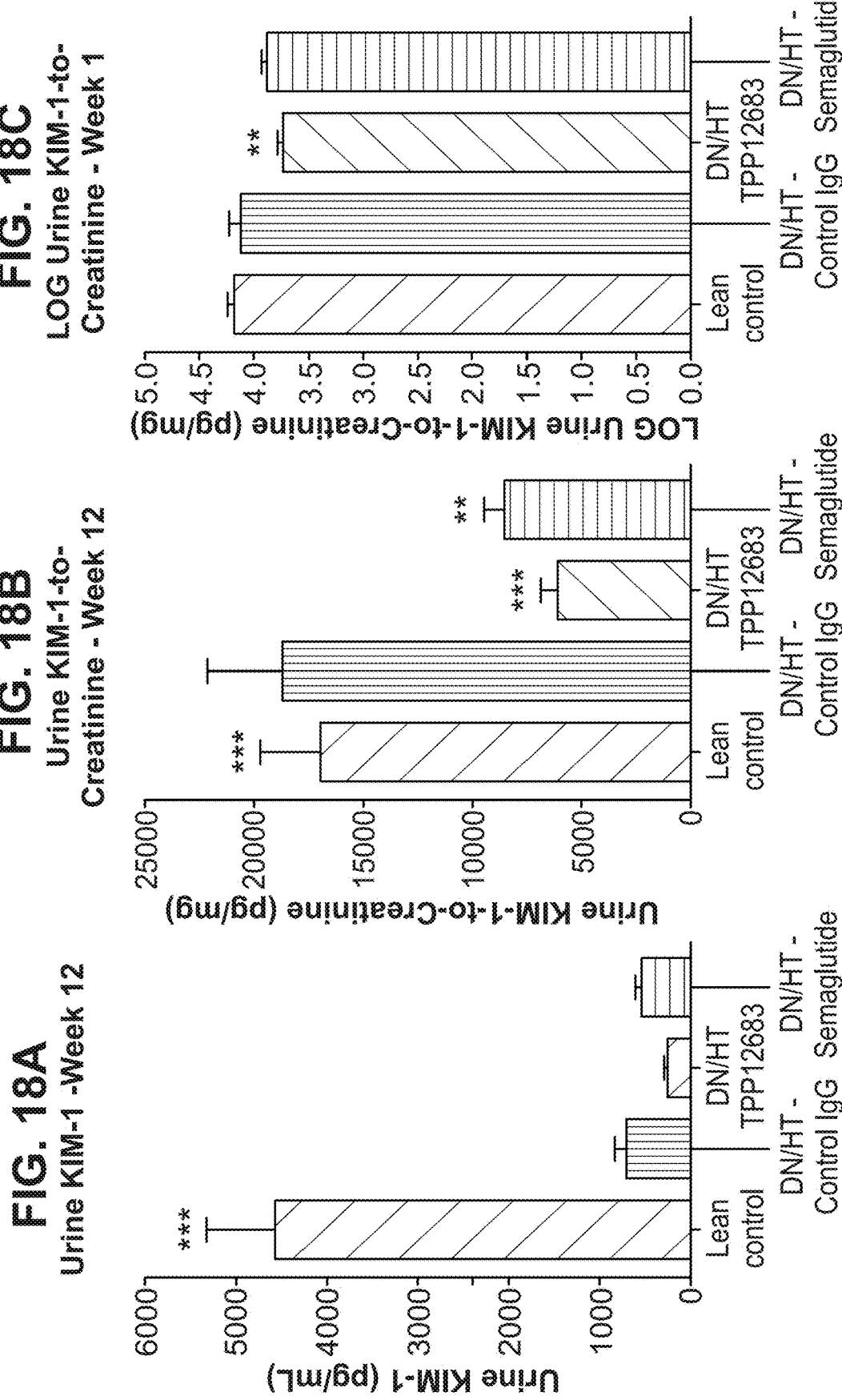

GS3+GS4 fraction

Glomerulosclerosis Index

Kidney Kim-1 - Termination
(Total)

Kidney Kim-1 - Termination
(Relative)

Kidney F4-80 - Termination
(Total)

Kidney F4-80 - Termination
(Relative)

IGFBP4-FI in Cyno Plasma

TPP12744 Decreased IGFBP5-Nt in Cyno Plasma

A18414
A160194
A18894
142995
A19039(Ctrl)
160117(Ctrl)

IGFBP5-Nt (ng/ml)

Time (Days)

SEQUENCE LISTING

```
Sequence total quantity: 127
SEQ ID NO: 1              moltype = AA  length = 1627
FEATURE                  Location/Qualifiers
source                   1..1627
                         mol_type = protein
                         organism = Homo sapiens
SEQUENCE: 1
MRLWSWVLHL GLLSAALGCG LAERPRRARR DPRAGRPPRP AAGPATCATR AARGRRASPP   60
PPPPPGGAWE AVRVPRRRQQ REARGATEEP SPPSRALYFS GRGEQLRLRA DLELPRDAFT  120
LQVWLRAEGG QRSPAVITGL YDKCSYISRD RGWVVGIHTI SDQDNKDPRY FFSLKTDRAR  180
QVTTINAHRS YLPGQWVYLA ATYDGQFMKL YVNGAQVATS GEQVGGIFSP LTQKCKVLML  240
GGSALNHNYR GYIEHFSLWK VARTQREILS DMETHGAHTA LPQLLLQENW DNVKHAWSPM  300
KDGSSPKVEF SNAHGFLLDT SLEPPLCGQT LCDNTEVIAS YNQLSSFRQP KVVRYRVVNL  360
YEDDHKNPTV TREQVDFQHH QLAEAFKQYN ISWELDVLEV SNSSLRRRLI LANCDISKIG  420
DENCDPECNH TLTGHDGGDC RHLRHPAFVK KQHNGVCDMD CNYERFNFDG GECCDPEITN  480
VTQTCFDPDS PHRAYLDVNE LKNILKLDGS THLNIFFAKS SEEELAGVAT WPWDKEALMH  540
LGGIVLNPSF YGMPGHTHTM IHEIGHSLGL YHVFRGISEI QSCSDPCMET EPSFETGDLC  600
NDTNPAPKHK SCGDPGPGND TCGFHSFFNT PYNNFMSYAD DDCTDSFTPN QVARMHCYLD  660
LVYQGWQPSR KPAPVALAPQ VLGHTTDSVT LEWFPPIDGH FFERELGSAC HLCLEGRILV  720
QYASNASSPM PCSPSGHWSP REAEGHPDVE QPCKSSVRTW SPNSAVNPHT VPPACPEPQG  780
CYLELEFLYP LVPESLTIWV TFVSTDWDSS GAVNDIKLLA VSGKNISLGP QNVFCDVPLT  840
IRLWDVGEEV YGIQIYTLDE HLEIDAAMLT STADTPLCLQ CKPLKYKVVR DPPLQMDVAS  900
ILHLNRKFVD MDLNLGSVYQ YWVITISGTE ESEPSPAVTY IHGSGYCGDG IIQKDQGEQC  960
DDMNKINGDG CSLFCRQEVS FNCIDEPSRC YFHDGDGVCE EFEQKTSIKD CGVYTPQGFL 1020
DQWASNASVS HQDQQCPGWV IIGQPAASQV CRTKVIDLSE GISQHAWYPC TISYPYSQLA 1080
```

```
QTTFWLRAYF SQPMVAAAVI VHLVTDGTYY GDQKQETISV QLLDTKDQSH DLGLHVLSCR   1140
NNPLIIPVVH DLSQPFYHSQ AVRVSFSSPL VAISGVALRS FDNFDPVTLS SCQRGETYSP   1200
AEQSCVHFAC EKTDCPELAV ENASLNCSSS DRYHGAQCTV SCRTGYVLQI RRDDELIKSQ   1260
TGPSVTVTCT EGKWNKQVAC EPVDCSIPDH HQVYAASFSC PEGTTFGSQC SFQCRHPAQL   1320
KGNNSLLTCM EDGLWSFPEA LCELMCLAPP PVPNADLQTA RCRENKHKVG SFCKYKCKPG   1380
YHVPGSSRKS KKRAFKTQCT QDGSWQEGAC VPVTCDPPPP KFHGLYQCTN GFQFNSECRI   1440
KCEDSDASQG LGSNVIHCRK DGTWNGSFHV CQEMQGQCSV PNELNSNLKL QCPDGYAIGS   1500
ECATSCLDHN SESIILPMNV TVRDIPHWLN PTRVERVVCT AGLKWYPHPA LIHCVKGCEP   1560
FMGDNYCDAI NNRAFCNYDG GDCCTSTVKT KKVTPFPMSC DLQGDCACRD PQAQEHSRKD   1620
LRGYSHG                                                             1627

SEQ ID NO: 2            moltype = AA  length = 1547
FEATURE                 Location/Qualifiers
source                  1..1547
                        mol_type = protein
                        organism = Homo sapiens
SEQUENCE: 2
REARGATEEP SPPSRALYFS GRGEQLRLRA DLELPRDAFT LQVWLRAEGG QRSPAVITGL   60
YDKCSYISRD RGWVVGIHTI SDQDNKDPRY FFSLKTDRAR QVTTINAHRS YLPGQWVYLA   120
ATYDGQFMKL YVNGAQVATS GEQVGGIFSP LTQKCKVLML GGSALNHNYR GYIEHFSLWK   180
VARTQREILS DMETHGAHTA LPQLLLQENW DNVKHAWSPM KDGSSPKVEF SNAHGFLLDT   240
SLEPPLCGQT LCDNTEVIAS YNQLSSFRQP KVVRYRVVNL YEDDHKNPTV TREQVDFQHH   300
QLAEAFKQYN ISWELDVLEV SNSSLRRRLI LANCDISKIG DENCDPECNH TLTGHDGGDC   360
RHLRHPAFVK KQHNGVCDMD CNYERFNFDG GECCDPEITN VTQTCFDPDS PHRAYLDVNE   420
LKNILKLDGS THLNIFFAKS SEEELAGVAT WPWDKEALMH LGGIVLNPSF YGMPGHTHTM   480
IHEIGHSLGL YHVFRGISEI QSCSDPCMET EPSFETGDLN NDTNPAPKHK SCGDPGPGND   540
TCGFHSFFNT PYNNFMSYAD DDCTDSFTPN QVARMHCYLD LVYQGWQPSR KPAPVALAPQ   600
VLGHTTDSVT LEWFPPIDGH FFERELGSAC HLCLEGRILV QYASNASSPM PCSPSGHWSP   660
REAEGHPDVE QPCKSSVRTW SPNSAVNPHT VPPACPEPQG CYLELEFLYP LVPESLTIWV   720
TFVSTDWDSS GAVNDIKLLA VSGKNISLGP QNVFCDVPLT IRLWDVGEEV YGIQIYTLDE   780
HLEIDAAMLT STADTPLCLQ CKPLKYKVVR DPPLQMDVAS ILHLNRKFVD MDLNLGSVYQ   840
YWVITISGTE ESEPSPAVTY IHGSGYCGDG IIQKDQGEQC DDMNKINGDG CSLFCRQEVS   900
FNCIDEPSRC YFHDGDGVCE EFEQKTSIKD CGVYTPQGFL DQWASNASVS HQDQQCPGWV   960
IIGQPAASQV CRTKVIDLSE GISQHAWYPC TISYPYSQLA QTTFWLRAYF SQPMVAAAVI   1020
VHLVTDGTYY GDQKQETISV QLLDTKDQSH DLGLHVLSCR NNPLIIPVVH DLSQPFYHSQ   1080
AVRVSFSSPL VAISGVALRS FDNFDPVTLS SCQRGETYSP AEQSCVHFAC EKTDCPELAV   1140
ENASLNCSSS DRYHGAQCTV SCRTGYVLQI RRDDELIKSQ TGPSVTVTCT EGKWNKQVAC   1200
EPVDCSIPDH HQVYAASFSC PEGTTFGSQC SFQCRHPAQL KGNNSLLTCM EDGLWSFPEA   1260
LCELMCLAPP PVPNADLQTA RCRENKHKVG SFCKYKCKPG YHVPGSSRKS KKRAFKTQCT   1320
QDGSWQEGAC VPVTCDPPPP KFHGLYQCTN GFQFNSECRI KCEDSDASQG LGSNVIHCRK   1380
DGTWNGSFHV CQEMQGQCSV PNELNSNLKL QCPDGYAIGS ECATSCLDHN SESIILPMNV   1440
TVRDIPHWLN PTRVERVVCT AGLKWYPHPA LIHCVKGCEP FMGDNYCDAI NNRAFCNYDG   1500
GDCCTSTVKT KKVTPFPMSC DLQGDCACRD PQAQEHSRKD LRGYSHG                 1547

SEQ ID NO: 3            moltype = AA  length = 541
FEATURE                 Location/Qualifiers
source                  1..541
                        mol_type = protein
                        organism = Homo sapiens
SEQUENCE: 3
APVALAPQVL GHTTDSVTLE WFPPIDGHFF ERELGSACHL CLEGRILVQY ASNASSPMPC   60
SPSGHWSPRE AEGHPDVEQP CKSSVRTWSP NSAVNPHTVP PACPEPQGCY LELEFLYPLV   120
PESLTIWVTF VSTDWDSSGA VNDIKLLAVS GKNISLGPQN VFCDVPLTIR LWDVGEEVYG   180
IQIYTLDEHL EIDAAMLTST ADTPLCLQCK PLKYKVVRDP PLQMDVASIL HLNRKFVDMD   240
LNLGSVYQYW VITISGTEES EPSPAVTYIH GSGYCGDGII QKDQGEQCDD MNKINGDGCS   300
LFCRQEVSFN CIDEPSRCYF HDGDGVCEEF EQKTSIKDCG VYTPQGFLDQ WASNASVSHQ   360
DQQCPGWVII GQPAASQVCR TKVIDLSEGI SQHAWYPCTI SYPYSQLAQT TFWLRAYFSQ   420
PMVAAAVIVH LVTDGTYYGD QKQETISVQL LDTKDQSHDL GLHVLSCRNN PLIIPVVHDL   480
SQPFYHSQAV RVSFSSPLVA ISGVALRSFD NFDPVTLSSC QRGETYSPAE QSCVHFACEK   540
T                                                                   541

SEQ ID NO: 4            moltype = AA  length = 13
FEATURE                 Location/Qualifiers
source                  1..13
                        mol_type = protein
                        organism = Homo sapiens
SEQUENCE: 4
WYPCTISYPY SQL                                                       13

SEQ ID NO: 5            moltype = AA  length = 27
FEATURE                 Location/Qualifiers
source                  1..27
                        mol_type = protein
                        organism = Homo sapiens
SEQUENCE: 5
CEPFMGDNYC DAINNRAFCN YDGGDCC                                        27

SEQ ID NO: 6            moltype = AA  length = 39
FEATURE                 Location/Qualifiers
```

-continued

```
source                   1..39
                         mol_type = protein
                         organism = Homo sapiens
SEQUENCE: 6
GCEPFMGDNY CDAINNRAFC NYDGGDCCTS TVKTKKVTP                               39

SEQ ID NO: 7             moltype = AA  length = 258
FEATURE                  Location/Qualifiers
source                   1..258
                         mol_type = protein
                         organism = Homo sapiens
SEQUENCE: 7
MLPLCLVAAL LLAAGPGPSL GDEAIHCPPC SEEKLARCRP PVGCEELVRE PGCGCCATCA         60
LGLGMPCGVY TPRCGSGLRC YPPRGVEKPL HTLMHGQGVC MELAEIEAIQ ESLQPSDKDE        120
GDHPNNSFSP CSAHDRRCLQ KHFAKIRDRS TSGGKMKVNG APREDARPVP QGSCQSELHR        180
ALERLAASQS RTHEDLYIIP IPNCDRNGNF HPKQCHPALD GQRGKCWCVD RKTGVKLPGG        240
LEPKGELDCH QLADSFRE                                                     258

SEQ ID NO: 8             moltype = AA  length = 135
FEATURE                  Location/Qualifiers
source                   1..135
                         mol_type = protein
                         organism = Homo sapiens
SEQUENCE: 8
DEAIHCPPCS EEKLARCRPP VGCEELVREP GCGCCATCAL GLGMPCGVYT PRCGSGLRCY         60
PPRGVEKPLH TLMHGQGVCM ELAEIEAIQE SLQPSDKDEG DHPNNSFSPC SAHDRRCLQK        120
HFAKIRDRST SGGKM                                                        135

SEQ ID NO: 9             moltype = AA  length = 102
FEATURE                  Location/Qualifiers
source                   1..102
                         mol_type = protein
                         organism = Homo sapiens
SEQUENCE: 9
KVNGAPREDA RPVPQGSCQS ELHRALERLA ASQSRTHEDL YIIPIPNCDR NGNFHPKQCH         60
PALDGQRGKC WCVDRKTGVK LPGGLEPKGE LDCHQLADSF RE                          102

SEQ ID NO: 10            moltype = AA  length = 10
FEATURE                  Location/Qualifiers
source                   1..10
                         mol_type = protein
                         organism = Homo sapiens
SEQUENCE: 10
KVNGAPREDA                                                               10

SEQ ID NO: 11            moltype = AA  length = 20
FEATURE                  Location/Qualifiers
source                   1..20
                         mol_type = protein
                         organism = Homo sapiens
SEQUENCE: 11
RDRSTSGGKM KVNGAPREDA                                                    20

SEQ ID NO: 12            moltype = AA  length = 272
FEATURE                  Location/Qualifiers
source                   1..272
                         mol_type = protein
                         organism = Homo sapiens
SEQUENCE: 12
MVLLTAVLLL LAAYAGPAQS LGSFVHCEPC DEKALSMCPP SPLGCELVKE PGCGCCMTCA         60
LAEGQSCGVY TERCAQGLRC LPRQDEEKPL HALLHGRGVC LNEKSYREQV KIERDSREHE        120
EPTTSEMAEE TYSPKIFRPK HTRISELKAE AVKKDRRKKL TQSKFVGGAE NTAHPRIISA        180
PEMRQESEQG PCRRHMEASL QELKASPRMV PRAVYLPNCD RKGFYKRKQC KPSRGRKRGI        240
CWCVDKYGMK LPGMEYVDGD FQCHTFDSSN VE                                     272

SEQ ID NO: 13            moltype = AA  length = 143
FEATURE                  Location/Qualifiers
source                   1..143
                         mol_type = protein
                         organism = Homo sapiens
SEQUENCE: 13
LGSFVHCEPC DEKALSMCPP SPLGCELVKE PGCGCCMTCA LAEGQSCGVY TERCAQGLRC         60
LPRQDEEKPL HALLHGRGVC LNEKSYREQV KIERDSREHE EPTTSEMAEE TYSPKIFRPK        120
HTRISELKAE AVKKDRRKKL TQS                                               143

SEQ ID NO: 14            moltype = AA  length = 109
FEATURE                  Location/Qualifiers
source                   1..109
                         mol_type = protein
```

```
                       organism = Homo sapiens
SEQUENCE: 14
KFVGGAENTA HPRIISAPEM RQESEQGPCR RHMEASLQEL KASPRMVPRA VYLPNCDRKG   60
FYKRKQCKPS RGRKRGICWC VDKYGMKLPG MEYVDGDFQC HTFDSSNVE              109

SEQ ID NO: 15          moltype = AA  length = 20
FEATURE                Location/Qualifiers
source                 1..20
                       mol_type = protein
                       organism = Homo sapiens
SEQUENCE: 15
KDRRKKLTQS KFVGGAENTA                                              20

SEQ ID NO: 16          moltype = DNA  length = 990
FEATURE                Location/Qualifiers
source                 1..990
                       mol_type = other DNA
                       organism = synthetic construct
SEQUENCE: 16
gccagcacca agggccccag cgtgttcccc ctggccccca gcagcaagag caccagcggc   60
ggcacagccg ccctgggctg cctggtgaag gactacttcc ccgagcccgt gaccgtgtcc  120
tggaacagcg gagccctgac cagcggcgtg cacaccttcc ccgccgtgct gcagagcagc  180
ggcctgtaca gcctgagcag cgtggtgacc gtgcccagca gcagcctggg cacccagacc  240
tacatctgta acgtgaacca caagcccagc aacaccaagg tggacaagaa ggtggagccc  300
aagagctgtg acaagaccca cacctgcccc ccctgccctg cccccgagct ggccggagcc  360
cccagcgtgt tcctgttccc ccccaagcct aaggacaccc tgatgatcag cagaacccc   420
gaggtgacct gtgtggtggt ggatgtgagc cacgaggacc ctgaggtgaa gttcaactgg  480
tacgtggacg gcgtggaggt gcacaatgcc aagaccaagc ccaggagga gcagtacaac   540
agcacctacc gggtggtgtc cgtgctgacc gtgctgcacc aggattggct gaacggcaag  600
gagtacaagt gtaaggtgtc caacaaggcc ctgcctgccc ctatcgagaa aaccatcagc  660
aaggccaagg gccagcccag agagccccag gtgtacaccc tgcccctag cagagatgag   720
ctgaccaaga accaggtgtc cctgacctgc ctggtgaagg gcttctaccc cagcgacatc  780
gccgtggagt gggagagcaa cggccagccc gagaacaact acaagaccac ccccctgtg   840
ctggacagcg atggcagctt cttcctgtac agcaagctga ccgtggacaa gagcagatgg  900
cagcagggca acgtgttcag ctgctccgtg atgcacgagg ccctgcacaa tcactacacc  960
cagaagagtc tgagcctgtc ccctggcaag                                  990

SEQ ID NO: 17          moltype = AA  length = 330
FEATURE                Location/Qualifiers
source                 1..330
                       mol_type = protein
                       organism = synthetic construct
SEQUENCE: 17
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 18          moltype = DNA  length = 321
FEATURE                Location/Qualifiers
source                 1..321
                       mol_type = other DNA
                       organism = synthetic construct
SEQUENCE: 18
cgtacggtgg ccgcccccag cgtgttcatc ttccccccca gcgatgagca gctgaagagt   60
ggcaccgcca gcgtggtgtg tctgctgaac aacttctacc ccgggaggc caaggtgcag  120
tggaaggtgg acaatgccct gcagagcggc aacagccagg agagcgtgac cgagcaggac  180
agcaaggact ccacctacag cctgagcagc accctgaccc tgagcaaggc cgactacgag  240
agcacaagg tgtacgcctg tgaggtgacc caccagggcc tgtccagccc cgtgaccaag  300
agcttcaacc ggggcgagtg c                                           321

SEQ ID NO: 19          moltype = AA  length = 107
FEATURE                Location/Qualifiers
source                 1..107
                       mol_type = protein
                       organism = synthetic construct
SEQUENCE: 19
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 20          moltype = AA  length = 453
FEATURE                Location/Qualifiers
source                 1..453
                       mol_type = protein
                       organism = synthetic construct
SEQUENCE: 20
QVQLVQSGAE VKKPGASVKV SCKASGYTFT SYAMHWVRQA PGQRLEWMGW MNAGTGATKS   60
```

```
SQKFQGRVTI TRDTSASTAY MELSSLRSED TAVYYCARGP SLETPTTFGM DVWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
AGAPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 21            moltype = AA   length = 123
FEATURE                  Location/Qualifiers
source                   1..123
                         mol_type = protein
                         organism = synthetic construct
SEQUENCE: 21
QVQLVQSGAE VKKPGASVKV SCKASGYTFT SYAMHWVRQA PGQRLEWMGW MNAGTGATKS   60
SQKFQGRVTI TRDTSASTAY MELSSLRSED TAVYYCARGP SMETPTTFGM DVWGQGTTVT   120
VSS                                                                123

SEQ ID NO: 22            moltype = DNA   length = 369
FEATURE                  Location/Qualifiers
source                   1..369
                         mol_type = other DNA
                         organism = synthetic construct
SEQUENCE: 22
caggtgcagc tggtgcagtc tggcgcagag gtgaagaaac caggagcttc tgtgaaggtg   60
agctgcaaag ccagcggcta cactttcact tcctatgcca tgcattgggt gagacaggct   120
ccaggacaga gactggaatg gatgggctgg atgaatgctg gaactggcgc taccaaaagt   180
tcccagaagt ttcagggcag ggtgaccatc accagagata cttctgcaag cacagcctac   240
atggagctga gttcactgag gtctgaagac acagccgtgt actattgtgc taggggacct   300
agcctggaaa cacctactac ctttggcatg gatgtgtggg gacagggaac taccgtgact   360
gtgtcaagc                                                          369

SEQ ID NO: 23            moltype = AA   length = 5
FEATURE                  Location/Qualifiers
source                   1..5
                         mol_type = protein
                         organism = synthetic construct
SEQUENCE: 23
SYAMH                                                              5

SEQ ID NO: 24            moltype = AA   length = 17
FEATURE                  Location/Qualifiers
source                   1..17
                         mol_type = protein
                         organism = synthetic construct
SEQUENCE: 24
WMNAGTGATK SSQKFQG                                                 17

SEQ ID NO: 25            moltype = AA   length = 14
FEATURE                  Location/Qualifiers
source                   1..14
                         mol_type = protein
                         organism = synthetic construct
SEQUENCE: 25
GPSLETPTTF GMDV                                                    14

SEQ ID NO: 26            moltype = AA   length = 214
FEATURE                  Location/Qualifiers
source                   1..214
                         mol_type = protein
                         organism = synthetic construct
SEQUENCE: 26
DIQMTQSPSS VSASVGDRVT ITCRASQGIS RWLAWYQQKP GKAPKLLIYA ASSLQSGVPS   60
RFSGSGSGTD FTLTISSLQP EDFATYYCQQ ENAYPFTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 27            moltype = AA   length = 107
FEATURE                  Location/Qualifiers
source                   1..107
                         mol_type = protein
                         organism = synthetic construct
SEQUENCE: 27
DIQMTQSPSS VSASVGDRVT ITCRASQGIS RWLAWYQQKP GKAPKLLIYA ASSLQSGVPS   60
RFSGSGSGTD FTLTISSLQP EDFATYYCQQ ENAYPFTFGG GTKVEIK               107

SEQ ID NO: 28            moltype = DNA   length = 321
FEATURE                  Location/Qualifiers
source                   1..321
```

```
                         mol_type = other DNA
                         organism = synthetic construct
SEQUENCE: 28
gacatccaga tgactcagtc tccatcttct gtgtctgcta gcgtgggcga tagggtgaca   60
attacctgta gagcctctca gggcattagc agatggctgg catggtacca gcagaaacct  120
ggcaaagccc ctaaactgct gatctatgcc gcttctagcc tgcagtctgg agtgccatca  180
aggttttctg gctctggctc tggcacagac tttaccctga ctatcagctc tctgcagccc  240
gaagatttcg ccacctacta ttgccagcag gaaaacgcct atccctttac ctttggcggc  300
ggcaccaaag tggagatcaa a                                             321

SEQ ID NO: 29             moltype = AA   length = 11
FEATURE                   Location/Qualifiers
source                    1..11
                          mol_type = protein
                          organism = synthetic construct
SEQUENCE: 29
RASQGISRWL A                                                          11

SEQ ID NO: 30             moltype = AA   length = 7
FEATURE                   Location/Qualifiers
source                    1..7
                          mol_type = protein
                          organism = synthetic construct
SEQUENCE: 30
AASSLQS                                                                7

SEQ ID NO: 31             moltype = AA   length = 9
FEATURE                   Location/Qualifiers
source                    1..9
                          mol_type = protein
                          organism = synthetic construct
SEQUENCE: 31
QQENAYPFT                                                              9

SEQ ID NO: 32             moltype = AA   length = 453
FEATURE                   Location/Qualifiers
source                    1..453
                          mol_type = protein
                          organism = synthetic construct
SEQUENCE: 32
QVQLVQSGAE VKKPGASVKV SCKASGYTFT SYAMHWVRQA PGQRLEWMGW INAGTGATKY    60
ARKFQGRVTI TRDTSASTAY MELSSLRSED TAVYYCARGP SMETPTTYGM EVWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
AGAPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 33             moltype = AA   length = 123
FEATURE                   Location/Qualifiers
source                    1..123
                          mol_type = protein
                          organism = synthetic construct
SEQUENCE: 33
QVQLVQSGAE VKKPGASVKV SCKASGYTFT SYAMHWVRQA PGQRLEWMGW INAGTGATKY    60
ARKFQGRVTI TRDTSASTAY MELSSLRSED TAVYYCARGP SMETPTTYGM EVWGQGTTVT   120
VSS                                                                 123

SEQ ID NO: 34             moltype = DNA   length = 369
FEATURE                   Location/Qualifiers
source                    1..369
                          mol_type = other DNA
                          organism = synthetic construct
SEQUENCE: 34
caggtgcagc tggtgcagag cggagccgaa gtgaaaaaac ctggcgcttc agtgaaggtg    60
agctgtaaag ccagcggata cacattcact agctacgcca tgcattgggt gagacaggct   120
ccaggacaga gactggagtg gatgggatgg attaatgccg gaacaggcgc tactaagtat   180
gccaggaagt ttcagggcag ggtgaccatc accagagata cctctgcctc tactgcctat   240
atggagctgt ctagcctgag aagcgaagat accgccgtgt attattgcgc cagaggacca   300
agcatggaga ctccaaccac ttatggaatg gaagtgtggg gacagggaac aacagtgacc   360
gtgtcttct                                                           369

SEQ ID NO: 35             moltype = AA   length = 5
FEATURE                   Location/Qualifiers
source                    1..5
                          mol_type = protein
                          organism = synthetic construct
SEQUENCE: 35
```

```
SYAMH                                                      5

SEQ ID NO: 36          moltype = AA  length = 17
FEATURE                Location/Qualifiers
source                 1..17
                       mol_type = protein
                       organism = synthetic construct
SEQUENCE: 36
WINAGTGATK YARKFQG                                         17

SEQ ID NO: 37          moltype = AA  length = 14
FEATURE                Location/Qualifiers
source                 1..14
                       mol_type = protein
                       organism = synthetic construct
SEQUENCE: 37
GPSMETPTTY GMEV                                            14

SEQ ID NO: 38          moltype = AA  length = 214
FEATURE                Location/Qualifiers
source                 1..214
                       mol_type = protein
                       organism = synthetic construct
SEQUENCE: 38
DIQMTQSPSS VSASVGDRVT ITCRASQGIS RWLAWYQQKP GKAPKLLIYS TSSLQLGVPS  60
RFSGSGSGTD FTLTISSLQP EDFATYYCQQ ENDYPFTGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 39          moltype = AA  length = 107
FEATURE                Location/Qualifiers
source                 1..107
                       mol_type = protein
                       organism = synthetic construct
SEQUENCE: 39
DIQMTQSPSS VSASVGDRVT ITCRASQGIS RWLAWYQQKP GKAPKLLIYS TSSLQLGVPS  60
RFSGSGSGTD FTLTISSLQP EDFATYYCQQ ENDYPFTFGG GTKVEIK              107

SEQ ID NO: 40          moltype = DNA  length = 321
FEATURE                Location/Qualifiers
source                 1..321
                       mol_type = other DNA
                       organism = synthetic construct
SEQUENCE: 40
gacatccaga tgacacagag cccaagtagc gtgtctgcat ctgtgggcga tagggtgaca  60
atcacatgta gggcatctca gggcatttca aggtggctgg catggtatca gcagaaacca  120
ggcaaagccc ctaagttgct gatctacagc acctcttctc tgcagctggg agtgccttct  180
aggttttctg gcagtggctc aggcacagac tttaccctga ccatttctag cctgcagccc  240
gaagactttg ccacatacta ttgccagcag gagaatgact accccttcac ctttggcgga  300
ggcaccaaag tggaaatcaa g                                           321

SEQ ID NO: 41          moltype = AA  length = 11
FEATURE                Location/Qualifiers
source                 1..11
                       mol_type = protein
                       organism = synthetic construct
SEQUENCE: 41
RASQGISRWL A                                               11

SEQ ID NO: 42          moltype = AA  length = 7
FEATURE                Location/Qualifiers
source                 1..7
                       mol_type = protein
                       organism = synthetic construct
SEQUENCE: 42
STSSLQL                                                    7

SEQ ID NO: 43          moltype = AA  length = 9
FEATURE                Location/Qualifiers
source                 1..9
                       mol_type = protein
                       organism = synthetic construct
SEQUENCE: 43
QQENDYPFT                                                  9

SEQ ID NO: 44          moltype = AA  length = 449
FEATURE                Location/Qualifiers
source                 1..449
                       mol_type = protein
```

```
                        organism = synthetic construct
SEQUENCE: 44
EVQLVQSGAE VKKPGESLKI SCKGSGYSFT SYWTGWVRQA PGKGLEWMGI IYPGGSVARY   60
SPSFQGQVTI SADKSISTAY LQWSSLKASD TAVYYCARGP LRSDYPDVWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 45          moltype = AA  length = 119
FEATURE                Location/Qualifiers
source                 1..119
                       mol_type = protein
                       organism = synthetic construct
SEQUENCE: 45
EVQLVQSGAE VKKPGESLKI SCKGSGYSFT SYWTGWVRQA PGKGLEWMGI IYPGGSVARY   60
SPSFQGQVTI SADKSISTAY LQWSSLKASD TAVYYCARGP LRSDYPDVWG QGTMVTVSS   119

SEQ ID NO: 46          moltype = DNA  length = 357
FEATURE                Location/Qualifiers
source                 1..357
                       mol_type = other DNA
                       organism = synthetic construct
SEQUENCE: 46
gaggtgcagc tggtgcagag cggagccgag gtgaagaagc ccggcgagtc tctgaagatc   60
agctgtaagg gcagcggcta cagctttacc agctattgga ccggctgggt gaggcaggcc  120
cctggcaaag gcctggaatg gatgggcatc atctaccctg gcggcagcgt ggccaggtat  180
agcccagct  tccagggaca ggtgaccatt agcgccgaca agagcatcag caccgcctac  240
ctgcagtgga gcagcctgaa ggccagcgac accgccgtgt attattgcgc cagaggcccc  300
ctgaggagcg attatcccga cgtgtggggc cagggcacta tggtgacagt gagcagc      357

SEQ ID NO: 47          moltype = AA  length = 5
FEATURE                Location/Qualifiers
source                 1..5
                       mol_type = protein
                       organism = synthetic construct
SEQUENCE: 47
SYWTG                                                               5

SEQ ID NO: 48          moltype = AA  length = 17
FEATURE                Location/Qualifiers
source                 1..17
                       mol_type = protein
                       organism = synthetic construct
SEQUENCE: 48
IIYPGGSVAR YSPSFQG                                                 17

SEQ ID NO: 49          moltype = AA  length = 10
FEATURE                Location/Qualifiers
source                 1..10
                       mol_type = protein
                       organism = synthetic construct
SEQUENCE: 49
GPLRSDYPDV                                                         10

SEQ ID NO: 50          moltype = AA  length = 214
FEATURE                Location/Qualifiers
source                 1..214
                       mol_type = protein
                       organism = synthetic construct
SEQUENCE: 50
EIVMTQSPAT LSVSPGERAT LSCRASQSVG SYLAWYQQKP GQAPRLLIYR GSTRATGIPA   60
RFSGSGSGTE FTLTISSLQS EDFAVYYCQQ PYVWPITFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 51          moltype = AA  length = 107
FEATURE                Location/Qualifiers
source                 1..107
                       mol_type = protein
                       organism = synthetic construct
SEQUENCE: 51
EIVMTQSPAT LSVSPGERAT LSCRASQSVG SYLAWYQQKP GQAPRLLIYR GSTRATGIPA   60
RFSGSGSGTE FTLTISSLQS EDFAVYYCQQ PYVWPITFGG GTKVEIK              107

SEQ ID NO: 52          moltype = DNA  length = 321
FEATURE                Location/Qualifiers
```

```
source                1..321
                      mol_type = other DNA
                      organism = synthetic construct
SEQUENCE: 52
gagatcgtga tgacccagag ccccgccacc ctgagcgtga gccctggcga gagagcaaca   60
ctgagctgca gggcaagcca gagcgtgggc agctatctgg cctggtatca gcagaaaccc  120
ggccaggccc caaggctcct gatctatagg ggcagcacca gggccaccgg cattccagcc  180
aggtttagcg gaagcggcag cggcaccgag tttaccctga ccattagcag cctgcagagc  240
gaggacttcg ccgtgtacta ctgccagcag ccctacgtgt ggcccatcac ctttggcgga  300
ggcaccaagg tggagatcaa g                                           321

SEQ ID NO: 53          moltype = AA  length = 11
FEATURE                Location/Qualifiers
source                1..11
                      mol_type = protein
                      organism = synthetic construct
SEQUENCE: 53
RASQSVGSYL A                                                       11

SEQ ID NO: 54          moltype = AA  length = 7
FEATURE                Location/Qualifiers
source                1..7
                      mol_type = protein
                      organism = synthetic construct
SEQUENCE: 54
RGSTRAT                                                            7

SEQ ID NO: 55          moltype = AA  length = 9
FEATURE                Location/Qualifiers
source                1..9
                      mol_type = protein
                      organism = synthetic construct
SEQUENCE: 55
QQPYVWPIT                                                          9

SEQ ID NO: 56          moltype = AA  length = 449
FEATURE                Location/Qualifiers
source                1..449
                      mol_type = protein
                      organism = synthetic construct
SEQUENCE: 56
EVQLVQSGAE VKKPGESLKI SCKGSGYSFT SDWIGWVRQA PGKGLEWMGI IYPGGSDTRY   60
SPSFRGQVTI SADKSISTAY LQWSSLKASD TAVYYCARGP LRSDYVDVWG QGTMVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 57          moltype = AA  length = 119
FEATURE                Location/Qualifiers
source                1..119
                      mol_type = protein
                      organism = synthetic construct
SEQUENCE: 57
EVQLVQSGAE VKKPGESLKI SCKGSGYSFT SDWIGWVRQA PGKGLEWMGI IYPGGSDTRY   60
SPSFRGQVTI SADKSISTAY LQWSSLKASD TAVYYCARGP LRSDYVDVWG QGTMVTVSS   119

SEQ ID NO: 58          moltype = DNA  length = 357
FEATURE                Location/Qualifiers
source                1..357
                      mol_type = other DNA
                      organism = synthetic construct
SEQUENCE: 58
gaggtgcagc tggtgcagtc tggagccgaa gtgaaaaaac caggcgagag cctgaaaatc   60
tcctgcaaag gcagcggcta ttcattcacc agcgattgga ttggctgggt tagacaggcc  120
ccaggcaaag gactggaatg gatgggcatc atctatcctg gcggaagcga taccaggtat  180
agtcccagct ttagaggcca ggttaccatc agcgccgata gagccattag cacagcctat  240
ctgcagtgga gctcactgaa agcctctgac accgccgtgt attattgtgc cagaggacct  300
ctgaggtctg attacgtgga tgtgtgggga caggccacta tggtcacagt gtctagc      357

SEQ ID NO: 59          moltype = AA  length = 5
FEATURE                Location/Qualifiers
source                1..5
                      mol_type = protein
                      organism = synthetic construct
SEQUENCE: 59
SDWIG                                                              5
```

-continued

```
SEQ ID NO: 60            moltype = AA   length = 17
FEATURE                  Location/Qualifiers
source                   1..17
                         mol_type = protein
                         organism = synthetic construct
SEQUENCE: 60
IIYPGGSDTR YSPSFRG                                                   17

SEQ ID NO: 61            moltype = AA   length = 10
FEATURE                  Location/Qualifiers
source                   1..10
                         mol_type = protein
                         organism = synthetic construct
SEQUENCE: 61
GPLRSDYVDV                                                           10

SEQ ID NO: 62            moltype = AA   length = 214
FEATURE                  Location/Qualifiers
source                   1..214
                         mol_type = protein
                         organism = synthetic construct
SEQUENCE: 62
EIVMTQSPAT LSVSPGERAT LSCRASQSVG SNLAWYQQKP GQAPRLLIYR ASTRATGIPA    60
RFSGSGSGTE FTLTISSLQS EDFAVYYCQQ PYVWPITFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 63            moltype = AA   length = 107
FEATURE                  Location/Qualifiers
source                   1..107
                         mol_type = protein
                         organism = synthetic construct
SEQUENCE: 63
EIVMTQSPAT LSVSPGERAT LSCRASQSVG SNLAWYQQKP GQAPRLLIYR ASTRATGIPA    60
RFSGSGSGTE FTLTISSLQS EDFAVYYCQQ PYVWPITFGG GTKVEIK                  107

SEQ ID NO: 64            moltype = DNA   length = 321
FEATURE                  Location/Qualifiers
source                   1..321
                         mol_type = other DNA
                         organism = synthetic construct
SEQUENCE: 64
gagatcgtga tgacccagtc tcctgctaca ctgagcgtgt ctccaggaga aagggctact    60
ctgtcatgta gagcttctca gagcgtgggc tctaatctgg cttggtatca gcagaaacca    120
ggacaggccc caaggctgct tatctatagg gcaagtacta gagccacagg catccctgct    180
aggttttcag gctctggaag cggcactgag tttactctga ctatcagctc cctgcagagc    240
gaggatttcg ccgtgtatta ctgtcagcag ccctatgtgt ggccaatcac atttggcgga    300
ggcacaaagg tggagatcaa a                                             321

SEQ ID NO: 65            moltype = AA   length = 11
FEATURE                  Location/Qualifiers
source                   1..11
                         mol_type = protein
                         organism = synthetic construct
SEQUENCE: 65
RASQSVGSNL A                                                         11

SEQ ID NO: 66            moltype = AA   length = 7
FEATURE                  Location/Qualifiers
source                   1..7
                         mol_type = protein
                         organism = synthetic construct
SEQUENCE: 66
RASTRAT                                                              7

SEQ ID NO: 67            moltype = AA   length = 9
FEATURE                  Location/Qualifiers
source                   1..9
                         mol_type = protein
                         organism = synthetic construct
SEQUENCE: 67
QQPYVWPIT                                                            9

SEQ ID NO: 68            moltype = AA   length = 449
FEATURE                  Location/Qualifiers
source                   1..449
                         mol_type = protein
                         organism = synthetic construct
```

-continued

```
SEQUENCE: 68
QLQLQESGPG LVKPSETLSL TCTVSGGSIS SSDYYWGWIR QPPGKGLEWI GSIFYSGSTY    60
YNPSLKSRVT ISVDTSKNQF SLKLSSVTAA DTAVYYCARA TTSSSADYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 69              moltype = AA   length = 119
FEATURE                    Location/Qualifiers
source                     1..119
                           mol_type = protein
                           organism = synthetic construct
SEQUENCE: 69
QLQLQESGPG LVKPSETLSL TCTVSGGSIS SSDYYWGWIR QPPGKGLEWI GSIFYSGSTY    60
YNPSLKSRVT ISVDTSKNQF SLKLSSVTAA DTAVYYCARA TTSSSADYWG QGTLVTVSS    119

SEQ ID NO: 70              moltype = DNA   length = 357
FEATURE                    Location/Qualifiers
source                     1..357
                           mol_type = other DNA
                           organism = synthetic construct
SEQUENCE: 70
cagcttcagc tgcaggagtc aggacctgga ctggtgaaac caagcgaaac cctgtcactg    60
acttgtactg tgagcggcgg ctctatctcc agcagcgatt attattgggg atggatcagg   120
cagcctccag gcaagggact ggaatggatt ggaagcatct tctatagcgg cagcacctac   180
tacaatccct ccctgaaaag cagggtgacc attagcgtgg acacaagcaa gaaccagttc   240
agcctgaaac tgagctctgt gacagccgca gataccgccg tgtactattg tgccaggggc   300
acaacatcaa gctctgccga ttactggggc caggggaactc tggtgacagt gtcttca      357

SEQ ID NO: 71              moltype = AA   length = 7
FEATURE                    Location/Qualifiers
source                     1..7
                           mol_type = protein
                           organism = synthetic construct
SEQUENCE: 71
SSDYYWG                                                               7

SEQ ID NO: 72              moltype = AA   length = 16
FEATURE                    Location/Qualifiers
source                     1..16
                           mol_type = protein
                           organism = synthetic construct
SEQUENCE: 72
SIFYSGSTYY NPSLKS                                                    16

SEQ ID NO: 73              moltype = AA   length = 9
FEATURE                    Location/Qualifiers
source                     1..9
                           mol_type = protein
                           organism = synthetic construct
SEQUENCE: 73
ATTSSSADY                                                            9

SEQ ID NO: 74              moltype = AA   length = 214
FEATURE                    Location/Qualifiers
source                     1..214
                           mol_type = protein
                           organism = synthetic construct
SEQUENCE: 74
DIQMTQSPSS VSASVGDRVT ITCRASQGVS RWLAWYQQKP GKAPKLLIYA ASSLQSGVPS    60
RFSGSGSGTD FTLTISSLQP EDFATYYCQQ GNVPPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 75              moltype = AA   length = 107
FEATURE                    Location/Qualifiers
source                     1..107
                           mol_type = protein
                           organism = synthetic construct
SEQUENCE: 75
DIQMTQSPSS VSASVGDRVT ITCRASQGVS RWLAWYQQKP GKAPKLLIYA ASSLQSGVPS    60
RFSGSGSGTD FTLTISSLQP EDFATYYCQQ GNVPPLTFGG GTKVEIK               107

SEQ ID NO: 76              moltype = DNA   length = 321
FEATURE                    Location/Qualifiers
source                     1..321
```

```
                        mol_type = other DNA
                        organism = synthetic construct
SEQUENCE: 76
gacatccaga tgacacagag cccaagcagc gtgtctgcta gtgtgggaga tagagtgaca    60
atcacctgta gagctagcca gggagtgtct aggtggctgg cttggtatca gcagaaacca   120
ggcaaggctc ctaaactcct gatctatgcc gcctcttcat tgcagtctgg cgtgcctagt   180
aggtttctg gaagcggcag cggcacagat ttcacactga ccatctctag cctgcagccc    240
gaagatttcg ctacctatta ctgtcagcag ggcaatgtgc ctcctctgac atttggagga   300
ggaaccaagg tggagatcaa g                                             321

SEQ ID NO: 77        moltype = AA  length = 11
FEATURE              Location/Qualifiers
source               1..11
                     mol_type = protein
                     organism = synthetic construct
SEQUENCE: 77
RASQGVSRWL A                                                          11

SEQ ID NO: 78        moltype = AA  length = 7
FEATURE              Location/Qualifiers
source               1..7
                     mol_type = protein
                     organism = synthetic construct
SEQUENCE: 78
AASSLQS                                                               7

SEQ ID NO: 79        moltype = AA  length = 9
FEATURE              Location/Qualifiers
source               1..9
                     mol_type = protein
                     organism = synthetic construct
SEQUENCE: 79
QQGNVPPLT                                                             9

SEQ ID NO: 80        moltype = AA  length = 449
FEATURE              Location/Qualifiers
source               1..449
                     mol_type = protein
                     organism = synthetic construct
SEQUENCE: 80
QLQLQESGPG LVKPSETLSL TCTVSGGSIS SSDYYWGWIR QPPGKGLEWI GSIFYSGSTY    60
YNPSLKSRVT ISVDTSKNQF SLKLSSVTAA DTAVYYCARA TTSSSADYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 81        moltype = AA  length = 119
FEATURE              Location/Qualifiers
source               1..119
                     mol_type = protein
                     organism = synthetic construct
SEQUENCE: 81
QLQLQESGPG LVKPSETLSL TCTVSGGSIS SSDYYWGWIR QPPGKGLEWI GSIFYSGSTY    60
YNPSLKSRVT ISVDTSKNQF SLKLSSVTAA DTAVYYCARA TTSSSADYWG QGTLVTVSS    119

SEQ ID NO: 82        moltype = DNA  length = 357
FEATURE              Location/Qualifiers
source               1..357
                     mol_type = other DNA
                     organism = synthetic construct
SEQUENCE: 82
cagctgcagt tgcaggaaag cggccccgga ctggtgaaac caagtgaaac actgagcctg    60
acatgtacag tgagcggcgg ctctatctca agcagcgact attattgggg atggatcaga   120
cagcccctg gcaaaggcct ggaatggatc ggaagcatct ctattctgg cagcacctac    180
tacaacccca gcctgaaatc tagggtgacc atcagcgtgg acaccagcaa gaaccagttt   240
tccctgaaac tgtcaagcgt taccgccgcc gatacagccg tgtactattg tgctagggct   300
actacctcat caagcgccga ctactgggga cagggaacat ggtgacagt gtctagc       357

SEQ ID NO: 83        moltype = AA  length = 7
FEATURE              Location/Qualifiers
source               1..7
                     mol_type = protein
                     organism = synthetic construct
SEQUENCE: 83
SSDYYWG                                                               7
```

```
SEQ ID NO: 84            moltype = AA   length = 16
FEATURE                  Location/Qualifiers
source                   1..16
                         mol_type = protein
                         organism = synthetic construct
SEQUENCE: 84
SIFYSGSTYY NPSLKS                                              16

SEQ ID NO: 85            moltype = AA   length = 9
FEATURE                  Location/Qualifiers
source                   1..9
                         mol_type = protein
                         organism = synthetic construct
SEQUENCE: 85
ATTSSSADY                                                      9

SEQ ID NO: 86            moltype = AA   length = 214
FEATURE                  Location/Qualifiers
source                   1..214
                         mol_type = protein
                         organism = synthetic construct
SEQUENCE: 86
DIQMTQSPSS VSASVGDRVT ITCRASQGIS RWLAWYQQKP GKAPKLLIYA ASSVQSGVPS  60
RFSGSGSGTD FTLTISSLQP EDFATYYCQQ GNVPPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 87            moltype = AA   length = 107
FEATURE                  Location/Qualifiers
source                   1..107
                         mol_type = protein
                         organism = synthetic construct
SEQUENCE: 87
DIQMTQSPSS VSASVGDRVT ITCRASQGIS RWLAWYQQKP GKAPKLLIYA ASSVQSGVPS  60
RFSGSGSGTD FTLTISSLQP EDFATYYCQQ GNVPPLTFGG GTKVEIK               107

SEQ ID NO: 88            moltype = DNA   length = 321
FEATURE                  Location/Qualifiers
source                   1..321
                         mol_type = other DNA
                         organism = synthetic construct
SEQUENCE: 88
gatatccaga tgactcagtc tcccagcagc gtgtctgcat ctgtgggcga tagagtgacc  60
atcacatgta gggcctctca gggcatctca agatggctgg cttggtatca gcagaaaccc  120
ggcaaagccc caaaactgtt gatctatgcc gctagctcag tgcagtctgg agtgccttct  180
agattctcag gctctggatc tggcactgac tttaccctga caattagcag cctgcagcca  240
gaggatttcg ccacctatta ctgtcagcag ggcaatgtgc ctccactgac atttggaggc  300
ggcacaaagg tggaaatcaa g                                          321

SEQ ID NO: 89            moltype = AA   length = 11
FEATURE                  Location/Qualifiers
source                   1..11
                         mol_type = protein
                         organism = synthetic construct
SEQUENCE: 89
RASQGISRWL A                                                   11

SEQ ID NO: 90            moltype = AA   length = 7
FEATURE                  Location/Qualifiers
source                   1..7
                         mol_type = protein
                         organism = synthetic construct
SEQUENCE: 90
AASSVQS                                                        7

SEQ ID NO: 91            moltype = AA   length = 9
FEATURE                  Location/Qualifiers
source                   1..9
                         mol_type = protein
                         organism = synthetic construct
SEQUENCE: 91
QQGNVPPLT                                                      9

SEQ ID NO: 92            moltype = AA   length = 452
FEATURE                  Location/Qualifiers
source                   1..452
                         mol_type = protein
                         organism = synthetic construct
SEQUENCE: 92
```

```
QLQLQESGPG LVKPSETLSL TCTVSGGSIS SSSYNWGWIR QPPGKGLEWI GSISSSGSTY   60
FNPSLKSRVT ISVDTSKNQF SLKLSSVTAA DTAVYYCARS GYRPSFYAMD AWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELA  240
GAPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 93           moltype = AA   length = 122
FEATURE                 Location/Qualifiers
source                  1..122
                        mol_type = protein
                        organism = synthetic construct
SEQUENCE: 93
QLQLQESGPG LVKPSETLSL TCTVSGGSIS SSSYNWGWIR QPPGKGLEWI GSISSSGSTY   60
FNPSLKSRVT ISVDTSKNQF SLKLSSVTAA DTAVYYCARS GYRPSFYAMD AWGQGTTVTV  120
SS                                                                 122

SEQ ID NO: 94           moltype = DNA   length = 366
FEATURE                 Location/Qualifiers
source                  1..366
                        mol_type = other DNA
                        organism = synthetic construct
SEQUENCE: 94
cagctccagc tgcaggagag cggccccggc ctggtgaaac ccagcgaaac cctgagcctg   60
acctgcactg tgagcggcgg cagcatcagc agcagcagct acaattgggg ctggattagg  120
cagcccccg gcaagggcct ggaatggatc ggaagcatta gcagctctgg cagcacctac  180
ttcaacccca gcctcaagag cagggtgacc atcagcgtgg acaccagcaa gaaccagttc  240
agcctgaagc tgagcagcgt gaccgccgcc gataccgccg tgtactactg tgccaggagc  300
ggctataggc ccagcttcta tgccatggat gcctggggc agggcacaac cgtgactgtg  360
tctagc                                                             366

SEQ ID NO: 95           moltype = AA   length = 7
FEATURE                 Location/Qualifiers
source                  1..7
                        mol_type = protein
                        organism = synthetic construct
SEQUENCE: 95
SSSYNWG                                                               7

SEQ ID NO: 96           moltype = AA   length = 16
FEATURE                 Location/Qualifiers
source                  1..16
                        mol_type = protein
                        organism = synthetic construct
SEQUENCE: 96
SISSSGSTYF NPSLKS                                                    16

SEQ ID NO: 97           moltype = AA   length = 12
FEATURE                 Location/Qualifiers
source                  1..12
                        mol_type = protein
                        organism = synthetic construct
SEQUENCE: 97
SGYRPSFYAM DA                                                        12

SEQ ID NO: 98           moltype = AA   length = 213
FEATURE                 Location/Qualifiers
source                  1..213
                        mol_type = protein
                        organism = synthetic construct
SEQUENCE: 98
DIQLTQSPSS VSASVGDRVT ITCRASQDIS YWLAWYQQKP GKAPKLLIYA ASSLQSGVPS   60
RFSGSGSGTD FTLTISSLQP EDFATYYCQQ AYLLHTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 99           moltype = AA   length = 106
FEATURE                 Location/Qualifiers
source                  1..106
                        mol_type = protein
                        organism = synthetic construct
SEQUENCE: 99
DIQLTQSPSS VSASVGDRVT ITCRASQDIS YWLAWYQQKP GKAPKLLIYA ASSLQSGVPS   60
RFSGSGSGTD FTLTISSLQP EDFATYYCQQ AYLLHTFGGG TKVEIK                 106

SEQ ID NO: 100          moltype = DNA   length = 318
FEATURE                 Location/Qualifiers
```

-continued

```
source                    1..318
                          mol_type = other DNA
                          organism = synthetic construct
SEQUENCE: 100
gacatccagc tgacccagag ccccagcagc gtgagcgcca gcgtgggaga cagggtgacc    60
atcacatgca gggcctctca ggacatcagc tactggctgg cctggtatca gcagaagccc   120
ggcaaagccc ccaagctgct gatctatgcc gcctctagcc tgcagagcgg agtgccaagc   180
aggtttagcg gcagcggcag cggcaccgac tttaccctga ccattagctc actgcagccc   240
gaggacttcg ccacctacta ctgccagcag gcctacctgc tgcatacctt cggcggcgga   300
accaaggtgg agatcaag                                                 318

SEQ ID NO: 101           moltype = AA   length = 11
FEATURE                  Location/Qualifiers
source                   1..11
                         mol_type = protein
                         organism = synthetic construct
SEQUENCE: 101
RASQDISYWL A                                                          11

SEQ ID NO: 102           moltype = AA   length = 7
FEATURE                  Location/Qualifiers
source                   1..7
                         mol_type = protein
                         organism = synthetic construct
SEQUENCE: 102
AASSLQS                                                                7

SEQ ID NO: 103           moltype = AA   length = 8
FEATURE                  Location/Qualifiers
source                   1..8
                         mol_type = protein
                         organism = synthetic construct
SEQUENCE: 103
QQAYLLHT                                                               8

SEQ ID NO: 104           moltype = AA   length = 453
FEATURE                  Location/Qualifiers
source                   1..453
                         mol_type = protein
                         organism = synthetic construct
SEQUENCE: 104
QVQLVQSGAE VKKPGASVKV SCKASGYTFT SYAMHWVRQA PGQRLEWMGW MNAGTGATKS    60
SQKFQGRVTI TRDTSASTAY MELSSLRSED TAVYYCARGP SMETPTTFGM DVWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
AGAPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 105           moltype = AA   length = 123
FEATURE                  Location/Qualifiers
source                   1..123
                         mol_type = protein
                         organism = synthetic construct
SEQUENCE: 105
QVQLVQSGAE VKKPGASVKV SCKASGYTFT SYAMHWVRQA PGQRLEWMGW MNAGTGATKS    60
SQKFQGRVTI TRDTSASTAY MELSSLRSED TAVYYCARGP SMETPTTFGM DVWGQGTTVT   120
VSS                                                                 123

SEQ ID NO: 106           moltype = DNA   length = 369
FEATURE                  Location/Qualifiers
source                   1..369
                         mol_type = other DNA
                         organism = synthetic construct
SEQUENCE: 106
caggtgcagc tggtgcagtc tggcgcagag gtgaagaaac caggagcttc tgtgaaggtg    60
agctgcaaag ccagcggcta cacctttcact tcctatgcca tgcattgggt gagacaggct   120
ccaggacaga gactggaatg gatgggctgg atgaatgctg gaactggcgc taccaaaagt   180
tcccagaagt ttcagggcag ggtgaccatc accagagata cttctgcaag cacagcctac   240
atggagctga gttcactgag gtctgaagac acagccgtgt actattgtgc tagggggacct   300
agcatggaaa cacctactac ctttggcatg gatgtgtggg acagggaac taccgtgact   360
gtgtcaagc                                                           369

SEQ ID NO: 107           moltype = AA   length = 5
FEATURE                  Location/Qualifiers
source                   1..5
                         mol_type = protein
                         organism = synthetic construct
```

-continued

```
SEQUENCE: 107
SYAMH                                                                       5

SEQ ID NO: 108      moltype = AA   length = 17
FEATURE             Location/Qualifiers
source              1..17
                    mol_type = protein
                    organism = synthetic construct
SEQUENCE: 108
WMNAGTGATK SSQKFQG                                                          17

SEQ ID NO: 109      moltype = AA   length = 14
FEATURE             Location/Qualifiers
source              1..14
                    mol_type = protein
                    organism = synthetic construct
SEQUENCE: 109
GPSMETPTTF GMDV                                                             14

SEQ ID NO: 110      moltype = AA   length = 214
FEATURE             Location/Qualifiers
source              1..214
                    mol_type = protein
                    organism = synthetic construct
SEQUENCE: 110
DIQMTQSPSS VSASVGDRVT ITCRASQGIS RWLAWYQQKP GKAPKLLIYA ASSLQSGVPS          60
RFSGSGSGTD FTLTISSLQP EDFATYYCQQ ENAYPFTFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                     214

SEQ ID NO: 111      moltype = AA   length = 107
FEATURE             Location/Qualifiers
source              1..107
                    mol_type = protein
                    organism = synthetic construct
SEQUENCE: 111
DIQMTQSPSS VSASVGDRVT ITCRASQGIS RWLAWYQQKP GKAPKLLIYA ASSLQSGVPS          60
RFSGSGSGTD FTLTISSLQP EDFATYYCQQ ENAYPFTFGG GTKVEIK                       107

SEQ ID NO: 112      moltype = DNA   length = 321
FEATURE             Location/Qualifiers
source              1..321
                    mol_type = other DNA
                    organism = synthetic construct
SEQUENCE: 112
gacatccaga tgactcagtc tccatcttct gtgtctgcta gcgtgggcga tagggtgaca          60
attacctgta gagcctctca gggcattagc agatggctgg catggtacca gcagaaacct         120
ggcaaagccc ctaaactgct gatctatgcc gcttctagcc tgcagtctgg agtgccatca         180
aggttttctg gctctggctc tggcacagac tttaccctga ctatcagctc tctgcagccc         240
gaagatttcg ccacctacta ttgccagcag gaaaacgcct atccctttac ctttggcggc         300
ggcaccaaag tggagatcaa a                                                   321

SEQ ID NO: 113      moltype = AA   length = 11
FEATURE             Location/Qualifiers
source              1..11
                    mol_type = protein
                    organism = synthetic construct
SEQUENCE: 113
RASQGISRWL A                                                               11

SEQ ID NO: 114      moltype = AA   length = 7
FEATURE             Location/Qualifiers
source              1..7
                    mol_type = protein
                    organism = synthetic construct
SEQUENCE: 114
AASSLQS                                                                     7

SEQ ID NO: 115      moltype = AA   length = 9
FEATURE             Location/Qualifiers
source              1..9
                    mol_type = protein
                    organism = synthetic construct
SEQUENCE: 115
QQENAYPFT                                                                   9

SEQ ID NO: 116      moltype = DNA   length = 1359
FEATURE             Location/Qualifiers
source              1..1359
```

```
                          mol_type = other DNA
                          organism = synthetic construct
SEQUENCE: 116
caggtgcagc tggtgcagtc tggcgcagag gtgaagaaac caggagcttc tgtgaaggtg   60
agctgcaaag ccagcggcta cacttttcact tcctatgcca tgcattgggt gagacaggct   120
ccaggacaga gactggaatg gatgggctgg atgaatgctg gaactggcgc taccaaaagt   180
tcccagaagt ttcagggcag ggtgaccatc accagagata cttctgcaag cacagcctac   240
atggagctga gttcactgag gtctgaagac acagccgtgt actattgtgc taggggacct   300
agcatggaaa cacctactac ctttggcatg gatgtgtggg gacagggac taccgtgact   360
gtgtcaagcg ccagcaccaa gggccccagc gtgttccccc tggcccccag cagcaagagc   420
accagcggcg gcacagccgc cctgggctgc ctggtgaagg actacttccc cgagcccgtg   480
accgtgtcct ggaacagcgg agccctgacc agcggcgtgc acaccttccc cgccgtgctg   540
cagagcagcg gcctgtacag cctgagcagc gtggtgaccg tgcccagcag cagcctgggc   600
acccagacct acatctgtaa cgtgaaccac aagcccagca caccaaggt ggacaagaag   660
gtggagccca gagctgtga caagacccac acctgccccc cctgccctgc ccccgagctg   720
gccggagccc ccagcgtgtt cctgttcccc cccaagccta aggacaccct gatgatcagc   780
agaacccccg aggtgacctg tgtggtggtg gatgtgagcc acgaggaccc tgaggtgaag   840
ttcaactggt acgtggacgg cgtggaggtg cacaatgcca agacaaagcc cagggaggag   900
cagtacaaca gcacctaccg ggtggtgtcc gtgctgaccg tgctgcacca ggattggctg   960
aacggcaagg agtacaagtg taaggtgtcc aacaaggccc tgcctgcccc tatcgagaaa   1020
accatcagca aggccaaggg ccagcccaga gagccccagg tgtacaccct gccccctagc   1080
agagatgagc tgaccaagaa ccaggtgtcc ctgacctgcc tggtgaaggg cttctacccc   1140
agcgacatcg ccgtggagtg ggagagcaac ggccagcccg agaacaacta caagaccacc   1200
cccccctgtgc tggacagcga tggcagcttc ttcctgtaca gcaagctgac cgtggacaag   1260
agcagatggc agcagggcaa cgtgttcagc tgctccgtga tgcacgaggc cctgcacaat   1320
cactacaccc agaagagtct gagcctgtcc cctggcaag                           1359

SEQ ID NO: 117            moltype = DNA  length = 642
FEATURE                   Location/Qualifiers
source                    1..642
                          mol_type = other DNA
                          organism = synthetic construct
SEQUENCE: 117
gacatccaga tgactcagtc tccatcttct gtgtctgcta gcgtgggcga taggtgacca   60
attacctgta gagcctctca gggcattagc agatggctgg catggtacca gcagaaacct   120
ggcaaagccc ctaaactgct gatctatgcc gcttctagcc tgcagtctgg agtgccatca   180
aggttttctg gctctggctc tggcacagac tttaccctga ctatcagctc tctgcagccc   240
gaagatttcg ccacctacta ttgccagcag gaaaacgcct atcctttac ctttggcggc   300
ggcaccaaag tggagatcaa acgtacggtg gccgccccca gcgtgttcat cttccccccc   360
agcgatgagc agctgaagag tggcaccgcc agcgtggtgt gtctgctgaa caacttctac   420
ccccgggagg ccaaggtgca gtggaaggtg gacaatgccc tgcagagcgg caacagccag   480
gagagcgtga ccgagcagga cagcaaggac tccacctaca gcctgagcag caccctgacc   540
ctgagcaagg ccgactacga gaagcacaag gtgtacgcct gtgaggtgac ccaccagggc   600
ctgtccagcc ccgtgaccaa gagcttcaac cggggcgagt gc                       642

SEQ ID NO: 118            moltype = AA  length = 49
FEATURE                   Location/Qualifiers
source                    1..49
                          mol_type = protein
                          organism = Homo sapiens
SEQUENCE: 118
HQDQQCPGWV IIGQPAASQV CRTKVIDLSE GISQHAWYPC TISYPYSQL                 49

SEQ ID NO: 119            moltype = AA  length = 70
FEATURE                   Location/Qualifiers
source                    1..70
                          mol_type = protein
                          organism = Homo sapiens
SEQUENCE: 119
GPETLCGAEL VDALQFVCGD RGFYFNKPTG YGSSSRRAPQ TGIVDECCFR SCDLRRLEMY    60
CAPLKPAKSA                                                            70

SEQ ID NO: 120            moltype = AA  length = 453
FEATURE                   Location/Qualifiers
source                    1..453
                          mol_type = protein
                          organism = synthetic construct
SEQUENCE: 120
EVQLVESGGG VVQPGRSLRL SCAASGFTFS SYAMHWVRQA PGKGLEWVAV ISYDGSIKYY    60
ADAVKGRFTI SRDNSKNTLY LQMNSLRAED TAVYYCARHN RIYSWGWHTF DIWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
REEMTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                  453

SEQ ID NO: 121            moltype = AA  length = 213
FEATURE                   Location/Qualifiers
```

-continued

```
source                    1..213
                          mol_type = protein
                          organism = synthetic construct
SEQUENCE: 121
IQMTQSPSSL SASVGDRVTI TCRASQDISI YLNWYQQKPG KAPKLLIYGA SSLQSGVPSR    60
FSGSGSGTDF TLTISSLQPE DFATYYCQQA DAGPWKFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 122           moltype = AA  length = 453
FEATURE                  Location/Qualifiers
source                   1..453
                         mol_type = protein
                         organism = synthetic construct
SEQUENCE: 122
EVQLVESGGG VVQPGRSLRL SCAASGFTFS SYAMHWVRQA PGKGLEWVAV ISYDGSIKYY    60
ADAVKGRFTI SRDNSKNTLY LQMNSLRAED TAVYYCARHE RIPPWGFHTF DIWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 123           moltype = AA  length = 214
FEATURE                  Location/Qualifiers
source                   1..214
                         mol_type = protein
                         organism = synthetic construct
SEQUENCE: 123
DIQMTQSPSS LSASVGDRVT ITCRASQGIS IYLNWYQQKP GKAPKLLIYG ASSLQSGVPS    60
RFSGSGSGTD FTLTISSLQP EDFATYYCQQ SDGTPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 124           moltype = AA  length = 447
FEATURE                  Location/Qualifiers
source                   1..447
                         mol_type = protein
                         organism = synthetic construct
SEQUENCE: 124
EVQLVESGGG VVQPGRSLRL SCAASGFTFS SYGMHWVRQA PGKGLEWVAV ISYDGRNKYY    60
ADAVKGRFTI SRDNSKNTLY LQMNSLRAED TAVYYCARYK PMPFDVWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APEAAGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 125           moltype = AA  length = 214
FEATURE                  Location/Qualifiers
source                   1..214
                         mol_type = protein
                         organism = synthetic construct
SEQUENCE: 125
DIQMTQSPSS LSASVGDRVT ITCRASQSIS SYLNWYQQKP GKAPKLLIYE ASILQSGVPS    60
RFSGSGSGTD FTLTISSLQP EDFATYYCGQ SYYTPFPFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 126           moltype = AA  length = 10
FEATURE                  Location/Qualifiers
source                   1..10
                         mol_type = protein
                         organism = Homo sapiens
SEQUENCE: 126
NYCDAINNRA                                                          10

SEQ ID NO: 127           moltype = AA  length = 37
FEATURE                  Location/Qualifiers
source                   1..37
                         mol_type = protein
                         organism = Homo sapiens
SEQUENCE: 127
TSTVKTKKVT PFPMSCDLQG DCACRDPQAQ EHSRKDL                            37
```

ANTIGEN BINDING PROTEINS

CROSS REFERENCE TO RELATED APPLICATIONS

This application is a Non-Provisional Patent Application which claims the benefit of U.S. Provisional Patent Application No. 63/651,067, filed May 23, 2024, which is incorporated herein by reference in its entirety.

SEQUENCE LISTING SUBMITTED ELECTRONICALLY

This application contains a sequence listing, which is provided in XML format with a file name "70501FF.xml". The XML file has a size of 133,537 bytes and was created on May 12, 2025. The sequence listing submitted electronically is part of the specification and is incorporated herein by reference in its entirety.

FIELD OF THE INVENTION

The present disclosure relates to antigen binding proteins. In particular, the present disclosure relates to pregnancy associated plasma protein-A (PAPPA) binding proteins and the use of said PAPPA binding proteins in medicine.

BACKGROUND TO THE INVENTION

Autosomal dominant polycystic kidney disease (ADPKD) is a chronic, progressive disease leading to renal failure that is characterized by relentless growth of kidney tubule-derived cysts and eventual disruption of kidney anatomy and consequential loss of kidney function. More than 50% of patients develop end stage kidney disease (ESKD) by the age of 60. In North American settings, the diagnosed prevalence of ADPKD is estimated to range from 33 to 47 per 100,000 population. In the United States, this equates to approximately 150,000 individuals living with this disease (range 110,000 to 156,000), with a similar number of affected individuals in Europe (Aung T T et al Kidney360 2021; 2 (12): 2010-2015, Suwabe T et al Clin J Am Soc Nephrol. 2020; 15 (1): 69-79, Willey C et al Kidney Dis (Basel). 2019; 5 (2): 107-117, Willey C et al Curr Med Res Opin. 2021; 37 (7): 1155-1162).

Tolvaptan (a small molecule vasopressin V2 receptor antagonist) is currently the only available treatment for ADPKD. However, tolvaptan is associated with tolerability issues (polyuria, polydipsia), treatment discontinuation in up to 25% patients, and liver safety concerns. More specifically, cases of serious liver injury attributed to tolvaptan were observed, indicating the potential for the drug to cause liver injury that could progress to liver failure. Indeed, the earliest case of severe liver injury was observed three months after first treatment with tolvaptan. As a result, Tolvaptan was issued with a "black box warning" by the US Food and Drug Administration and is administered under REMS in the US.

New treatments for ADPKD are thus needed.

SUMMARY OF THE INVENTION

The inventors of the present application discovered PAPPA binding proteins which neutralize the PAPPA-mediated cleavage of IGFBP-2, IGFBP-4 and IGFBP-5 proteins. They surprisingly observed that said binding proteins had superior activity in reducing kidney cyst growth compared to an IGFBP-4 selective binding protein in a polycystic kidney mouse model. Despite inhibiting PAPPA's proteolytic cleavage activity against IGFBP-2, -4 and -5 (as opposed to IGFBP-4 only) said PAPPA binding proteins showed no increase in therapy induced toxicity.

In comparison to comparator anti-PAPPA mAbs, the PAPPA binding proteins disclosed herein have improved properties. For example, the PAPPA binding mAbs disclosed herein demonstrated lower levels of non-specific binding to human heparin. Non-specific binding properties of antibodies when dosed in vivo are thought to be one cause of higher-than-expected clearance, as a consequence of atypical association of the antibody to other in vivo proteins and/or cell membranes.

In addition, in comparison to comparator anti-PAPPA mAbs, the PAPPA binding proteins disclosed herein demonstrated a lower propensity to self-associate. It has been reported that mAbs with high propensity for self-association are more likely to suffer manufacturability liabilities such as poor solubility, viscosity and aggregation risks. Self-association makes it more challenging to formulate said mAbs in high concentration formulations (such as those required for subcutaneous administration). Furthermore, the propensity of mAbs to self-associate (for example as measured by AC-SINS) has been linked to poor pharmacokinetics and higher in vivo clearance (Avery L B et al (2018) mabs; 10 (2): 244-255). In addition, there is evidence that aggregation of therapeutic proteins (e.g. antibodies) can augment a protein-specific immune response, and lead to the formation of anti-drug antibodies (ADAs) which can have detrimental effects on drug safety, efficacy, and pharmacokinetics (Ratanji et al. J Immunotoxicol. 2014 (2): 99-109).

Therefore, provided herein are pregnancy associated plasma protein-A (PAPPA) binding proteins wherein said PAPPA binding proteins inhibit cleavage of insulin like growth factor binding protein-2 (IGFBP-2), insulin like growth factor binding protein-4 (IGFBP-4) and insulin like growth factor binding protein-5 (IGFBP-5).

Further provided herein are PAPPA binding proteins that bind to an epitope within the central M region of human PAPPA. The central M region, more particularly the M1/M2 region of PAPPA is a domain that is spatially adjacent to the catalytic active site and the site of substrate (i.e. IGFBP) binding. As a result, and without wishing to be bound by theory, it is considered that the steric bulk of a PAPPA binding protein that binds to this domain better inhibits substrate access to the catalytic site as compared to PAPPA binding proteins that bind within or near to the C-terminal LNR3 domain, thus improving the pharmacokinetic and pharmacodynamic properties of the binding protein. Moreover, it has been shown herein that PAPPA binding proteins that bind to an epitope within the central M region of PAPPA (more particularly the M1/M2 region) are capable of binding to both PAPPA monomers within a single PAPPA dimer. Without wishing to be bound by theory it is considered that this property confers more complete inhibition of PAPPA's proteolytic cleavage activity due to direct inhibition of both catalytic active sites within a PAPPA dimer, again resulting in improved pharmacokinetic and pharmacodynamic properties.

Further provided herein are PAPPA binding proteins comprising: (a) (i) any one or a combination of CDRs selected from CDRH1, CDRH2, CDRH3 from SEQ ID NOs: 21, 33, 45, 57, 69, 81, 93 and 105, and/or CDRL1, CDRL2, CDRL3 from SEQ ID NOs: 27, 39, 51, 63, 75, 87, 99 and 111; or (ii) a CDR variant of (i), wherein the variant has 1, 2, or 3 amino acid modifications; or (b) a VH region comprising a sequence at least 80% identical to the sequence of SEQ ID NOs: 21, 33, 45, 57, 69, 81, 93 or 105; and/or a VL region comprising a sequence at least 80% identical to the sequence of SEQ ID NOs: 27, 39, 51, 63, 75, 87, 99 or 111.

Further provided herein are PAPPA binding proteins comprising the following 6 CDRs: a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 55; or b) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

Further provided herein are nucleic acid sequences that encode the PAPPA binding proteins disclosed herein. Further provided herein are expression vectors comprising the nucleic acid sequences disclosed herein. Further provided herein are recombinant host cell comprising the nucleic acid sequences or the expression vectors disclosed herein.

Further provided herein are methods for the production of a PAPPA binding protein, said methods comprising culturing the host cells disclosed herein under conditions suitable for expression of said nucleic acid or vector(s), whereby a PAPPA binding protein is produced. PAPPA binding proteins produced by the methods disclosed herein are also provided. Further provided herein are cell lines engineered to express the PAPPA binding proteins disclosed herein.

Further provided herein are pharmaceutical compositions comprising the PAPPA binding proteins disclosed herein and a pharmaceutically acceptable excipient.

Further provided herein are methods for the treatment of a disease in a subject in need thereof comprising administering to said subject a therapeutically effective amount of the PAPPA binding proteins or pharmaceutical compositions disclosed herein. Further provided herein are the PAPPA binding proteins or pharmaceutical compositions as disclosed herein for use in the treatment of a disease in a subject. Further provided herein is the use of the PAPPA binding proteins or pharmaceutical compositions disclosed herein in the manufacture of a medicament for use in the treatment of a disease.

Further provided herein are methods of determining whether a subject suspected of suffering with a PKD is a candidate for treatment with a PAPPA binding protein, said method comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level the subject is identified as a candidate for treatment with a PAPPA binding protein.

Further provided herein are methods of identifying a susceptibility to develop PKD in a subject, comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level it is indicative of a susceptibility to develop PKD.

Further provided herein are methods of treating a PKD in a subject said method comprising a) selecting a subject that is identified as having high levels of an IGFBP-C-terminal (Ct) fragment and/or an IGFBP-N-terminal (Nt) fragment relative to a reference level having previously subjected a biological sample obtained from said subject to at least one assay to measure the level of an IGFBP-Ct fragment and/or an IGFBP-Nt fragment and b) administering a PAPPA binding protein to said subject.

Finally, further provided herein are methods of monitoring the effectiveness of a PAPPA binding protein in treating PKD in a subject said method comprising a) subjecting a first biological sample obtained from the subject to at least one assay to measure the level of an IGFBP-C-terminal (Ct) fragment, an IGFBP-N-terminal (Nt) fragment and/or an IGFBP-full length polypeptide, b) subjecting a second biological sample obtained from the subject to at least one assay to measure the level of an IGFBP-C-terminal (Ct) fragment, an IGFBP-N-terminal (Nt) fragment and/or an IGFBP-full length polypeptide wherein said second biological sample is obtained from the subject following treatment with the PAPPA binding protein; and c) comparing the level of said IGFBP-C-terminal (Ct) fragment, IGFBP-N-terminal (Nt) fragment and/or IGFBP-full length polypeptide obtained in steps a) and b), wherein decreased levels of said IGFBP-Ct fragment and/or IGFBP-Nt fragment in the second biological sample relative to the levels of said IGFBP-Ct fragment and/or IGFBP-Nt fragment in the first biological sample and/or increased levels of said IGFBP-full length polypeptide in the second biological sample relative to the levels of said IGFBP-full length polypeptide in the first biological sample is indicative of therapeutic efficacy in the treatment of the subjects PKD.

DESCRIPTION OF DRAWINGS/FIGURES

Figure 1B:
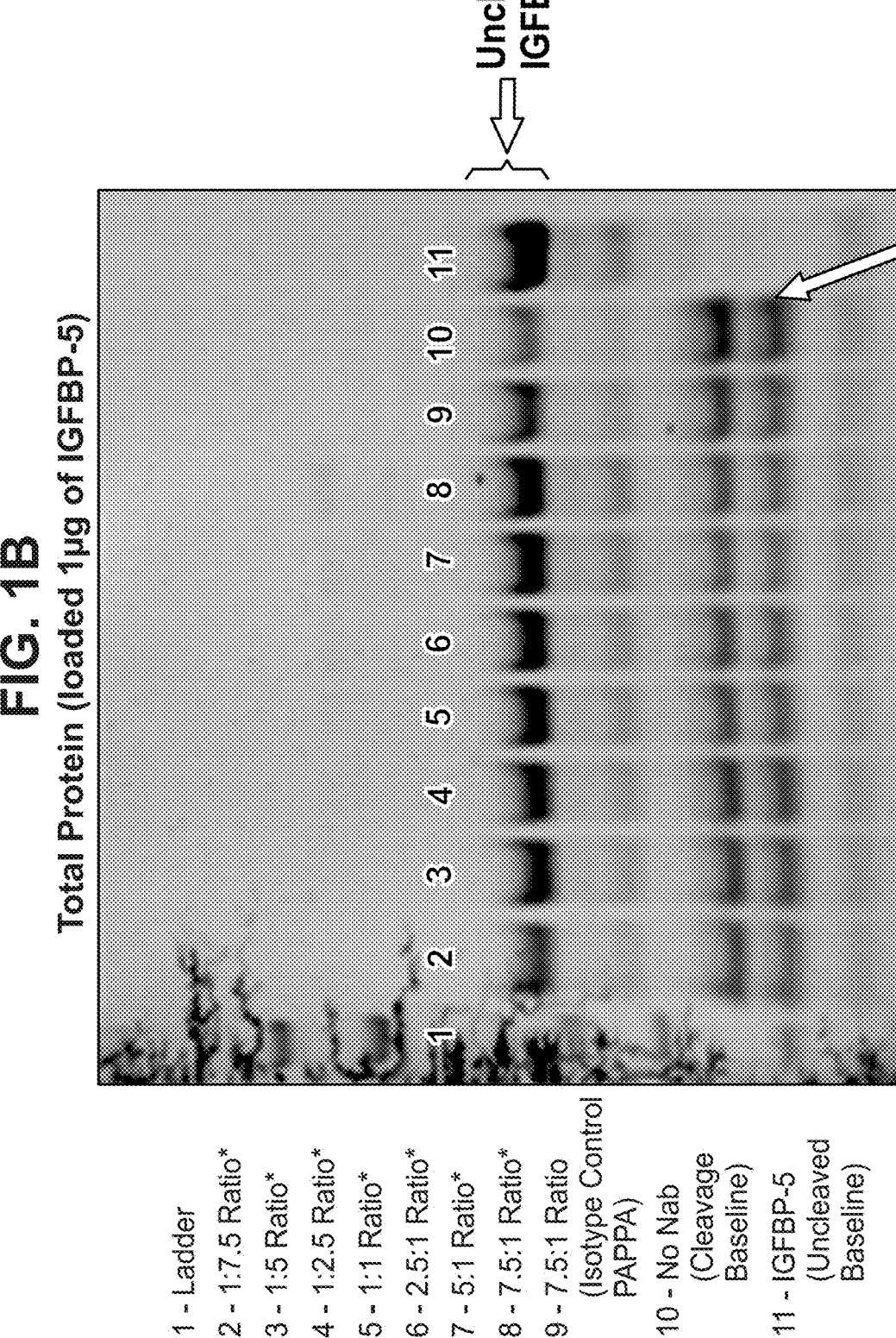

FIG. 1A-1B: Western blot showing that the Ansh labs mAb (NAB in Figure) inhibited cleavage of IGFBP-4 (FIG. 1A) in vitro, whereas it did not inhibit cleavage of IGFBP-5 (FIG. 1B). For both FIG. 1A and FIG. 1B, the lanes were loaded as follows: Lane 1: Ladder, Lane 2:1:7.5 ratio, Lane 3:1:5 ratio, Lane 4:1:2.5 ratio, Lane 5:1:1 ratio, Lane 6:2.5:1 ratio, Lane 7:5:1 ratio, Lane 8:7.5:1 Ratio, Lane 9:7:5.1 ratio (isotype control:PAPPA), Lane 10: No NAB (cleavage baseline) and Lane 11: IGFBP (uncleaved baseline).

FIG. 2: Differential fractional uptake values for each residue of PAPPA in complex with each mAb (TPP12681, TPP12683, TPP12744 and TPP12801) as indicated, as calculated in the HDExaminer software. Values represent the average over all labelling time points.

Figure 3:
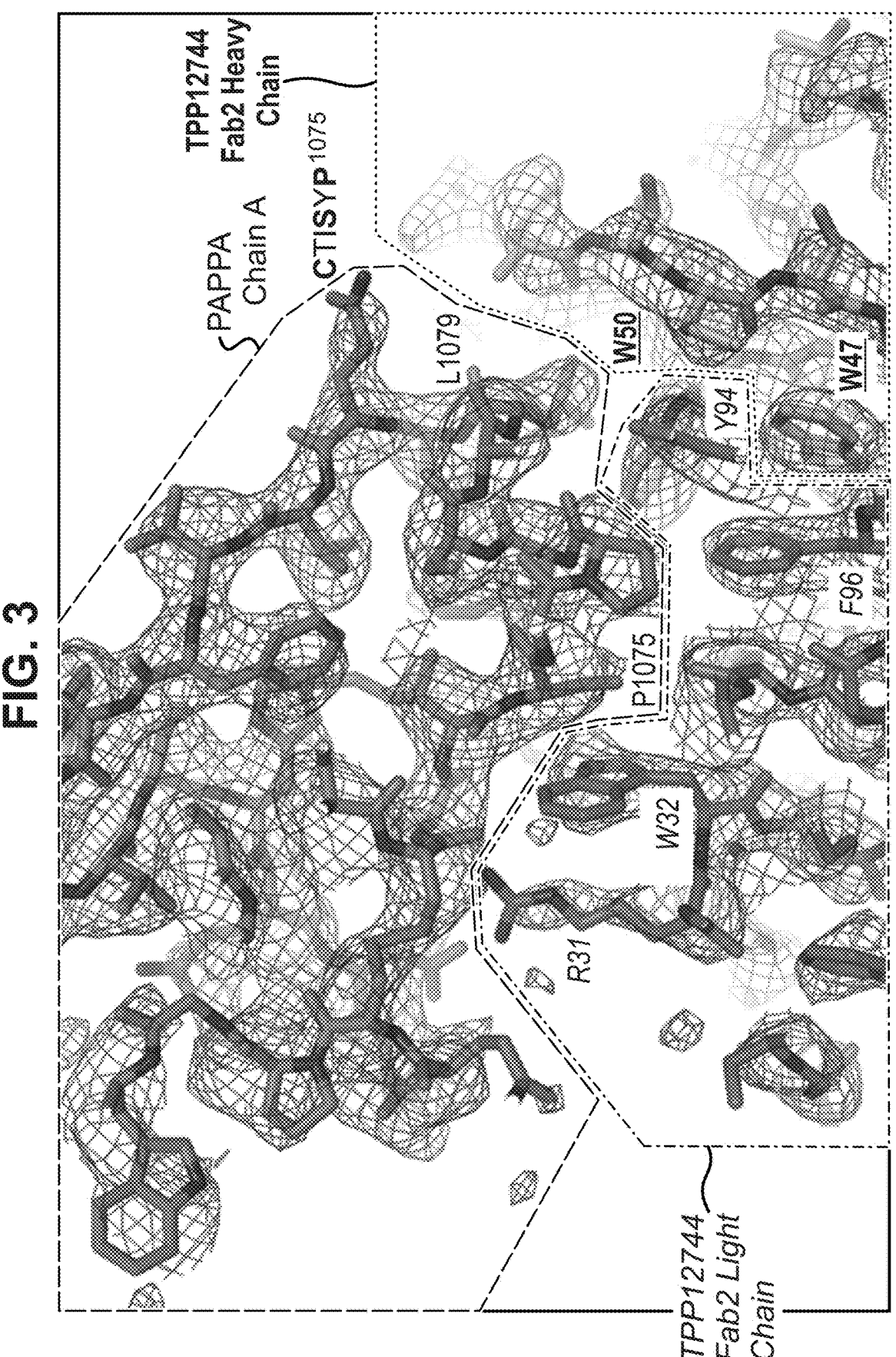

FIG. 3: 3D cryo-electron potential map and model of PAPPA-Fab2 interface. This structure was obtained from modelling into the focused classified map.

FIG. 4: The structure of PAPPA-Fab (protein cartoon format) obtained from modelling into the map (shown as a mesh). Two Fabs can be observed simultaneously engaging with the PAPPA dimer.

Figure 5:
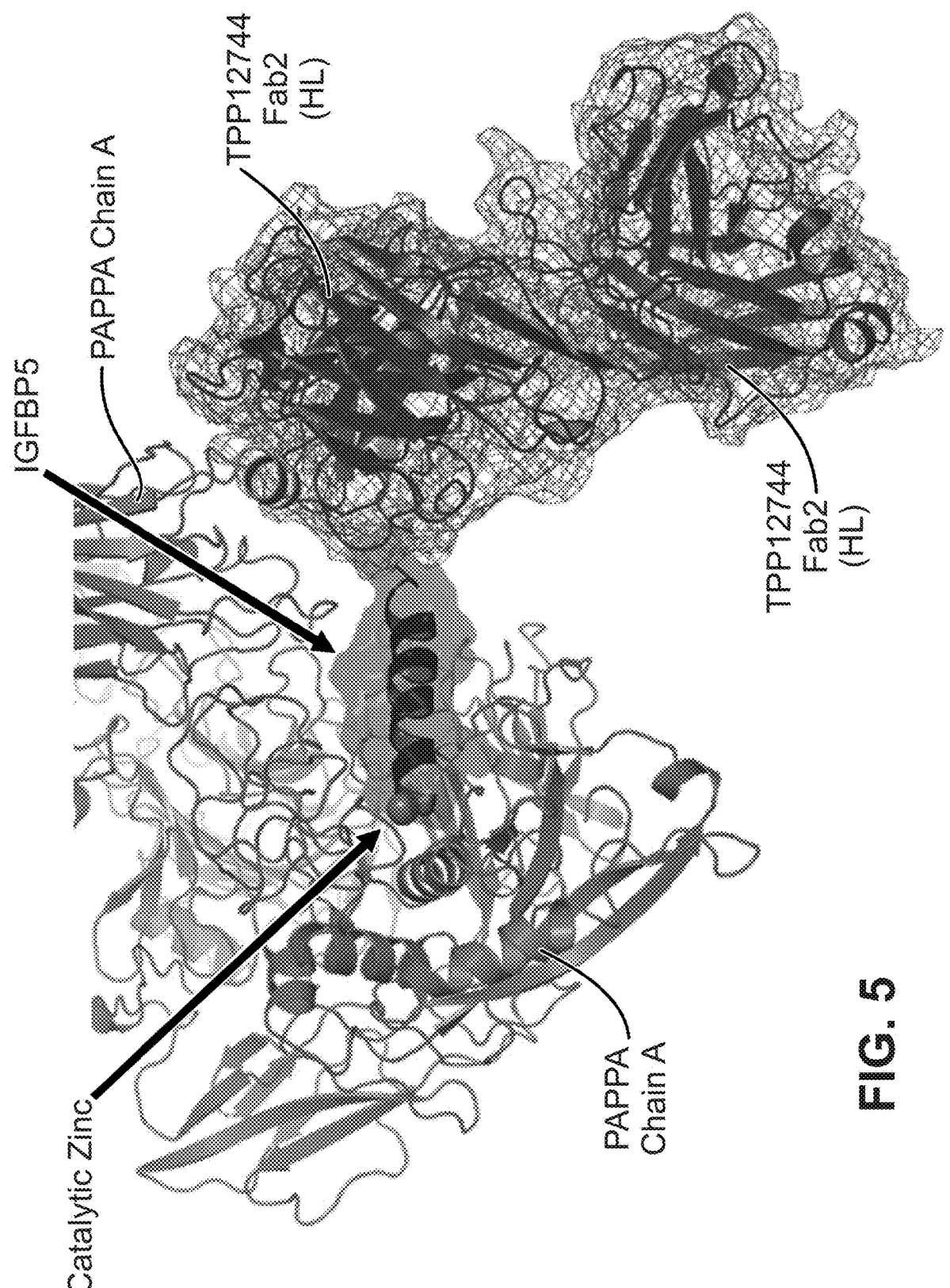

FIG. 5: The PAPPA-TPP12744 Fab2 displayed in protein cartoon format with a mesh over the Fab. IGFBP5 peptide (from the PAPPA complex of RCDB: 7UFG) was superimposed using the Proteins residues from the catalytic domain of the two proteins. The transparent surface of IGFBP5 is shown to project into the mesh of TPP12744, suggesting the full IGFBP5 substrate would clash with the binding of TPP12744.

FIG. 6A-6B: Illustration of the PAPPA cleavage sites on both human IGFBP4 (FIG. 6A) and human IGFBP5 (FIG. 6B).

Figure 7A:
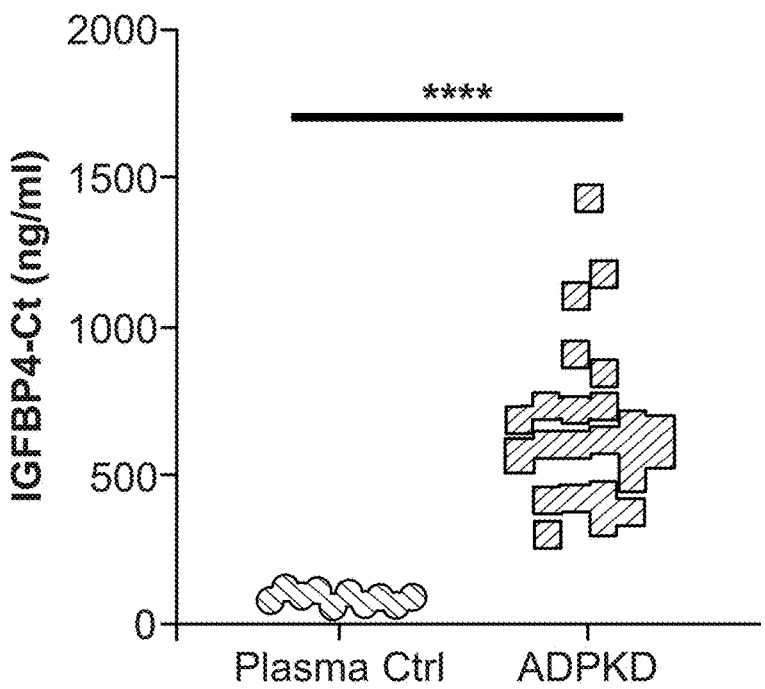
Figure 7B:
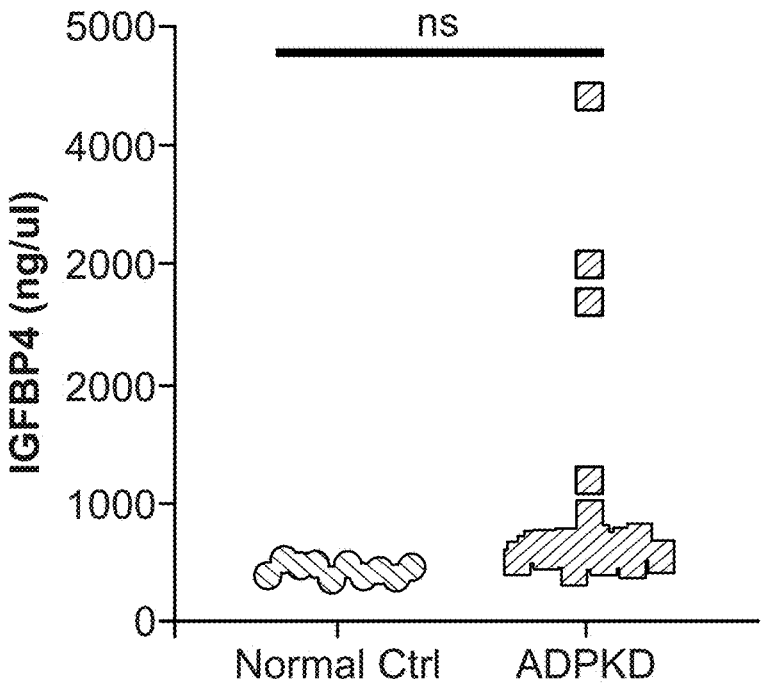
Figure 7C:
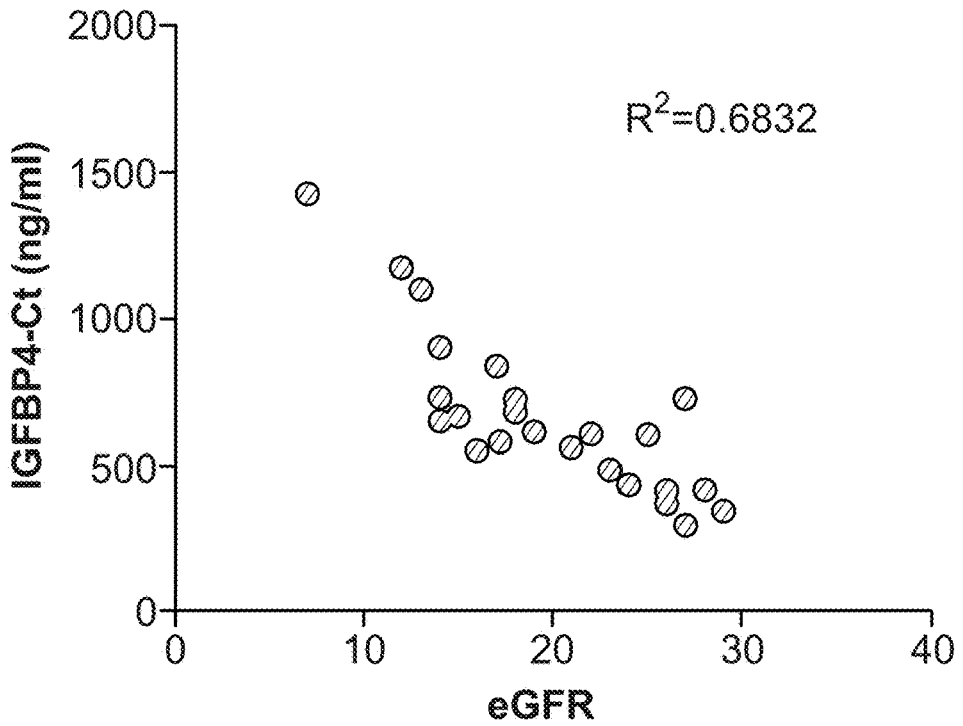
Figure 7D:
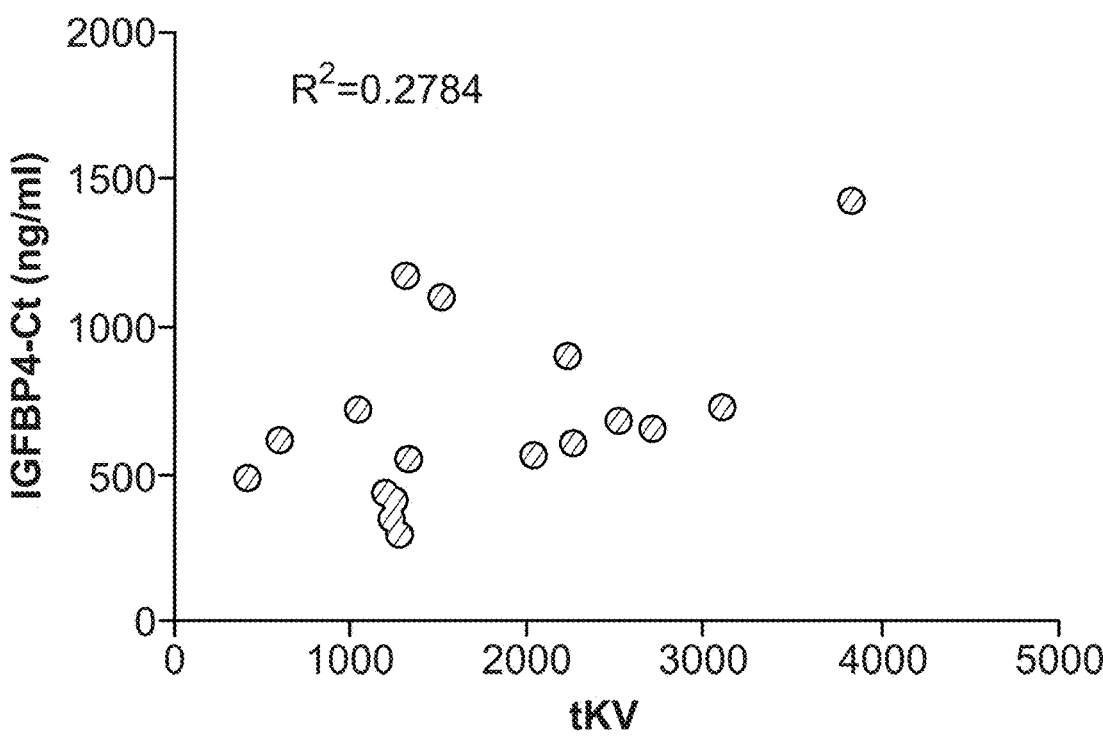

FIG. 7A-7D: IGFBP4-Ct (FIG. 7A) and IGFBP4-FI (FIG. 7B) levels in ADPKD patient plasma samples (n=24). Inverse correlation between IGFBP4-Ct and eGFR was shown in (FIG. 7C), and positive correlation of IGFBP4-Ct (BP4-Ct) with tKV (n=16) (FIG. 7D).

Figure 8:
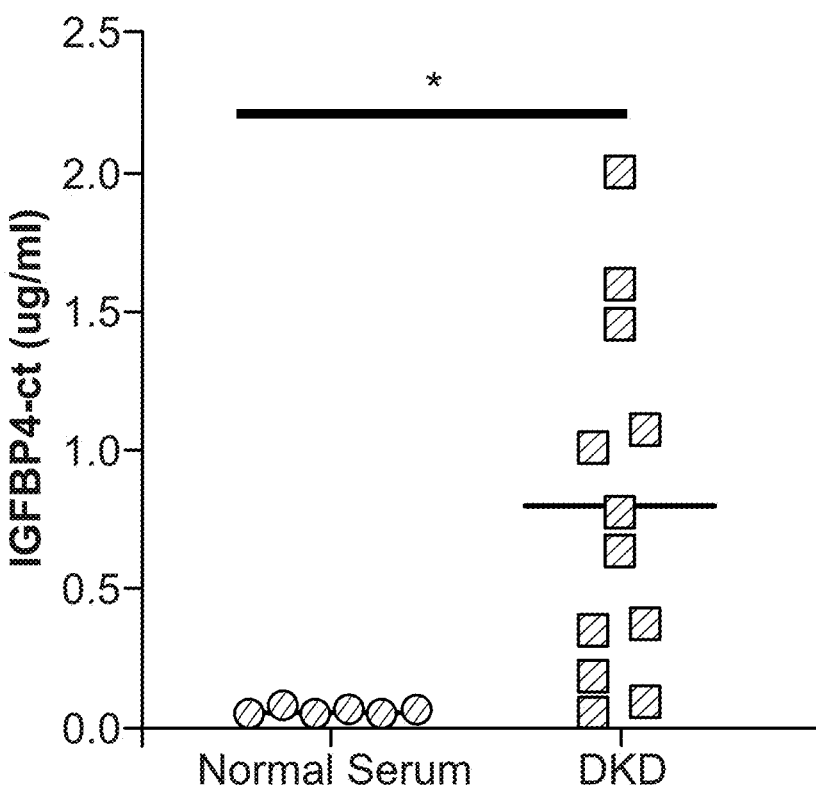

FIG. 8: Distribution of IGFBP4-Ct fragment (ug/ml) in plasma from DKD patients as compared to serum control (*p<0.05)

Figure 9A:
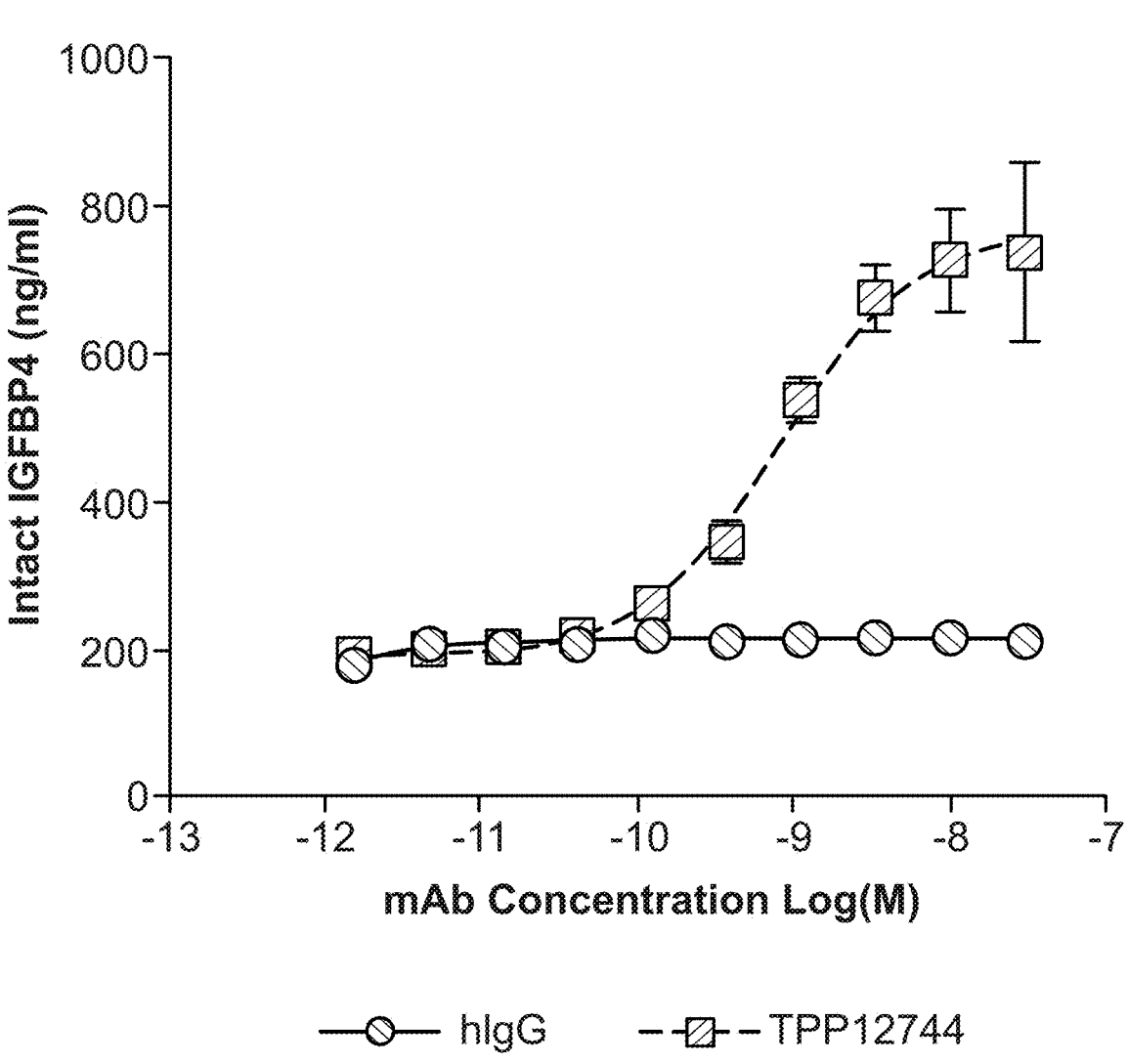
Figure 9B:
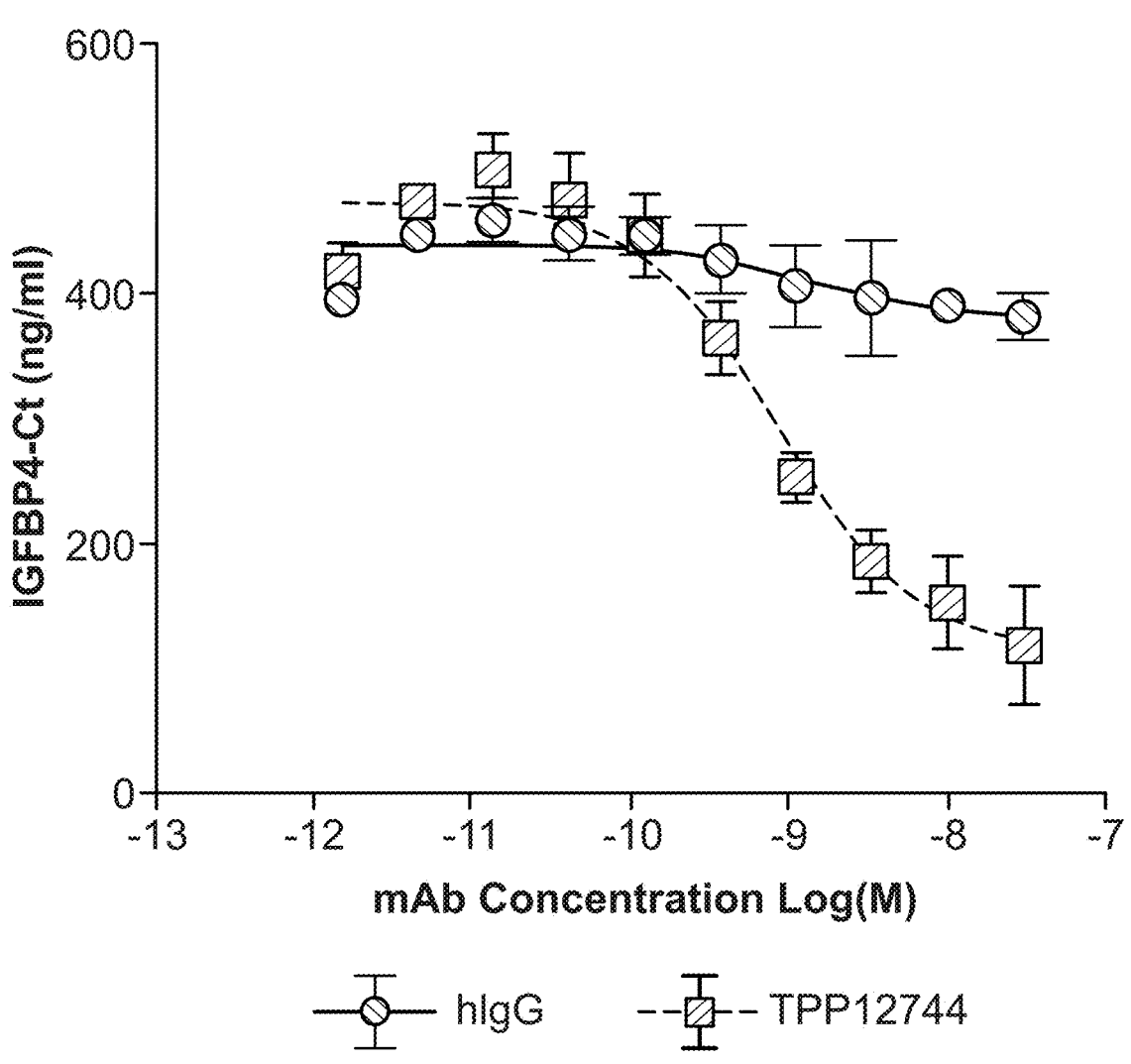
Figure 9C:
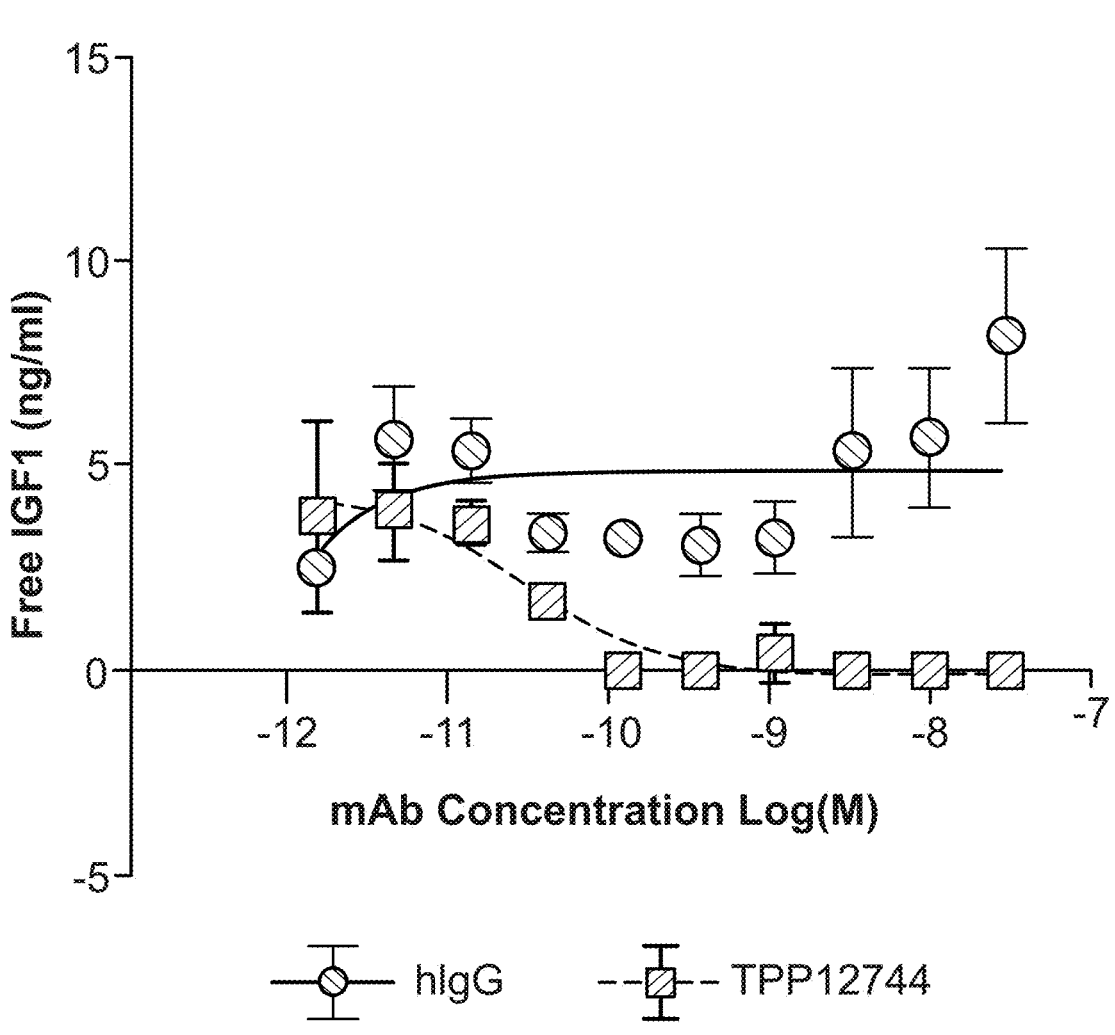

FIG. 9A-9C: TPP12744 dose-dependently increased intact IGFBP4 (EC50=0.8 nM, $pEC_{50}$=9.09, FIG. 9A), decreased IGFBP4-Ct fragments ($IC_{50}$=0.8 nM, $pIC_{50}$=9.07, FIG. 9B) and free-IGF-1 ($IC_{50}$=0.03 nM, $pIC_{50}$=10.53, FIG. 9C) in A549 cells. The human IgG control had no effect on any of these endpoints.

Figure 10:
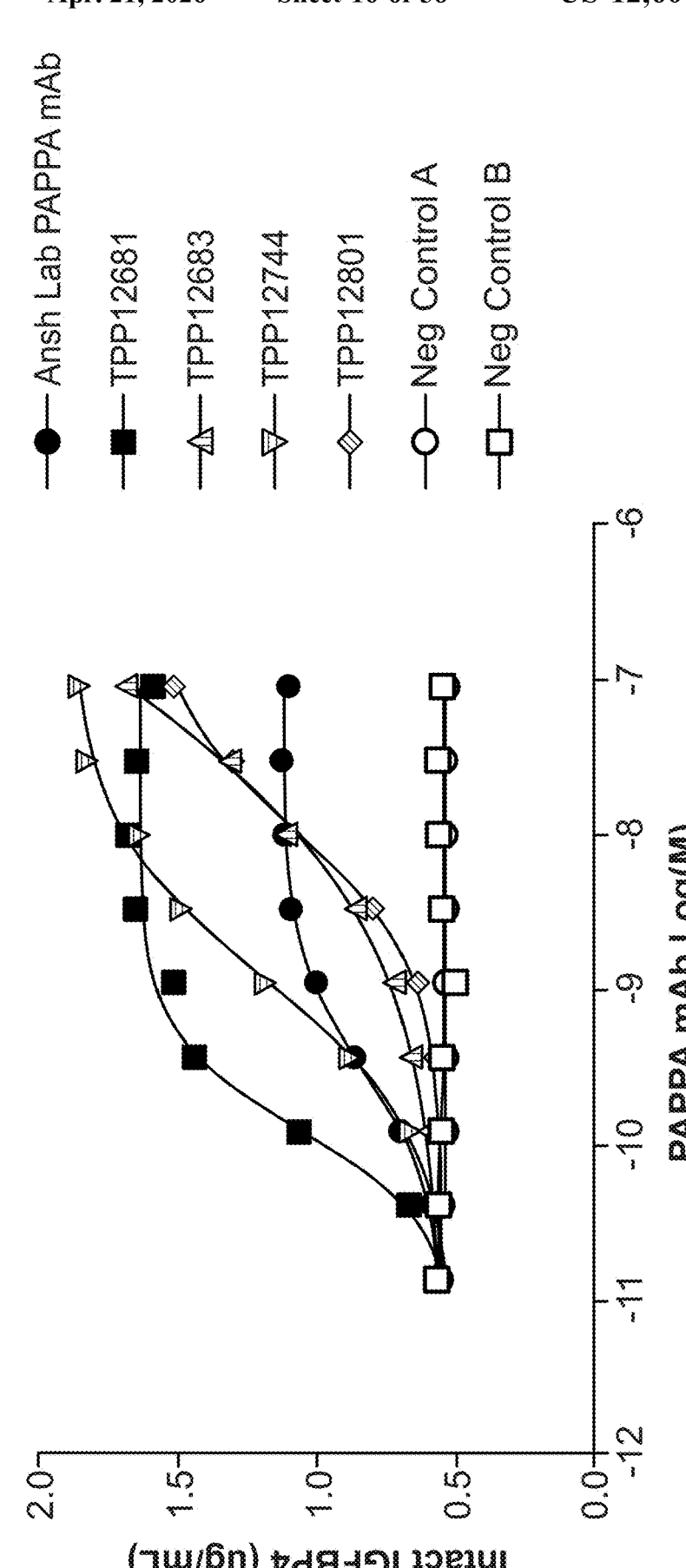

FIG. 10: anti-PAPPA mAbs resulted in dose-dependent induction of IGFBP4-FL levels in A549 cell supernatant. Neg Control A & B were two negative control IgG against unrelated antigens (anti-RSV mAbs). Ansh labs PAPPA mAb was used as positive control.

Figure 11A:
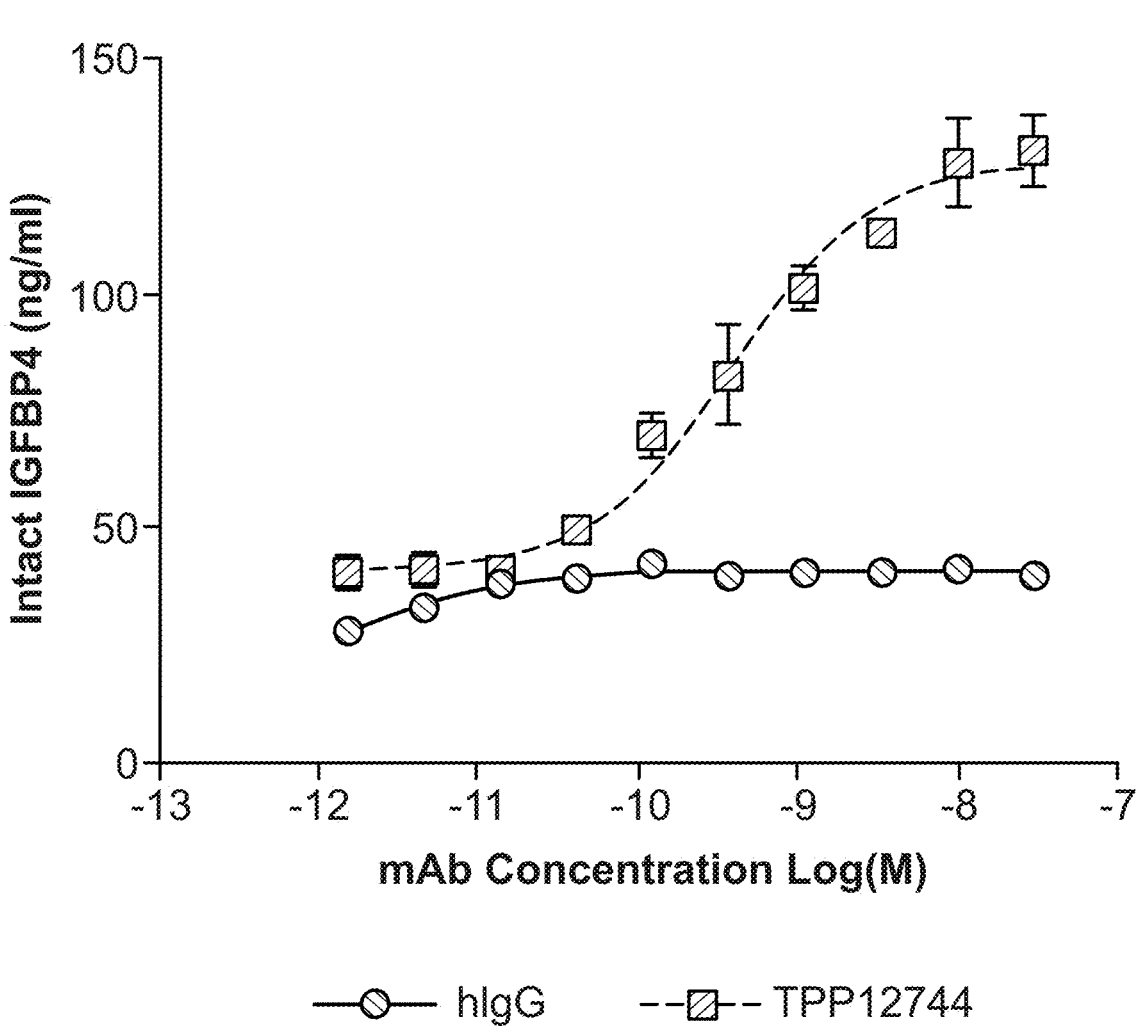
Figure 11B:
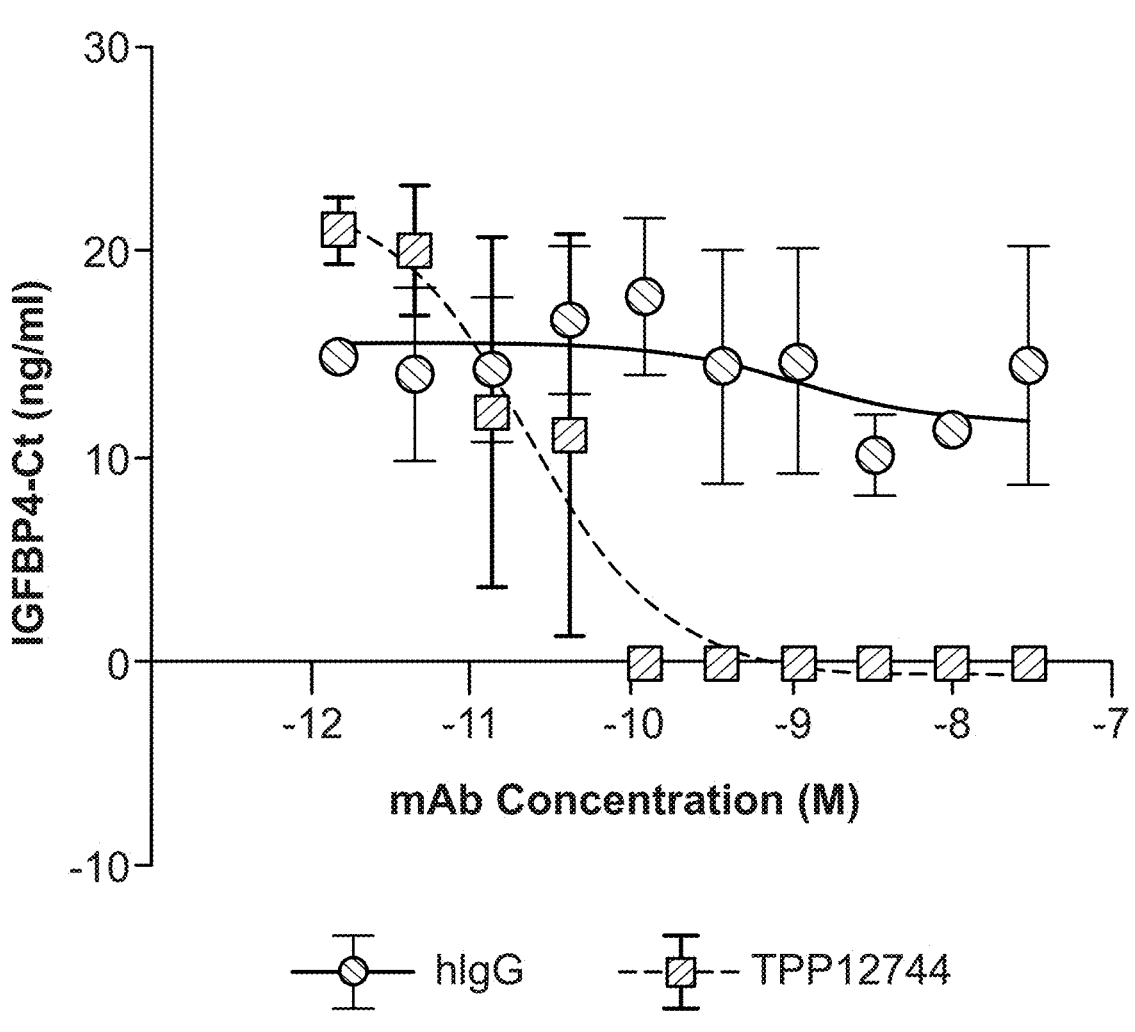

FIG. 11A-11B: TPP12744 dose-dependently increased intact IGFBP4 (EC50=0.4 nM, $pEC_{50}$=9.41, FIG. 11A) and decreased IGFBP4-Ct fragments ($IC_{50}$=0.02 nM, $pIC_{50}$=10.64, FIG. 11B) in ADPKD patient derived cystic 9-7 cells.

Figure 12A:
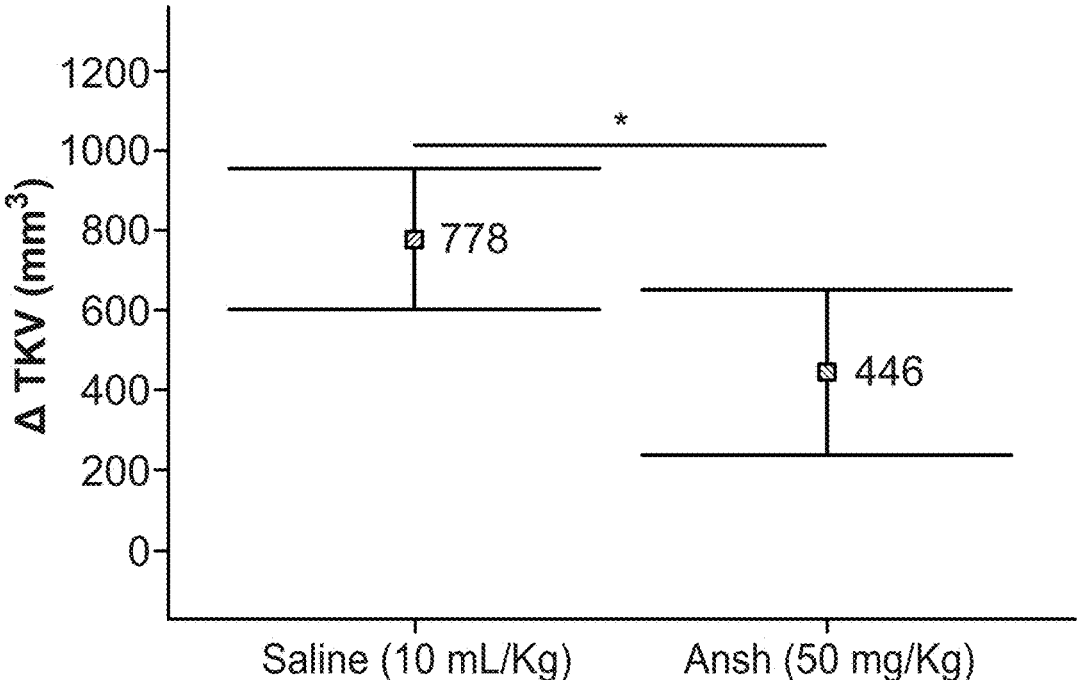
Figure 12B:
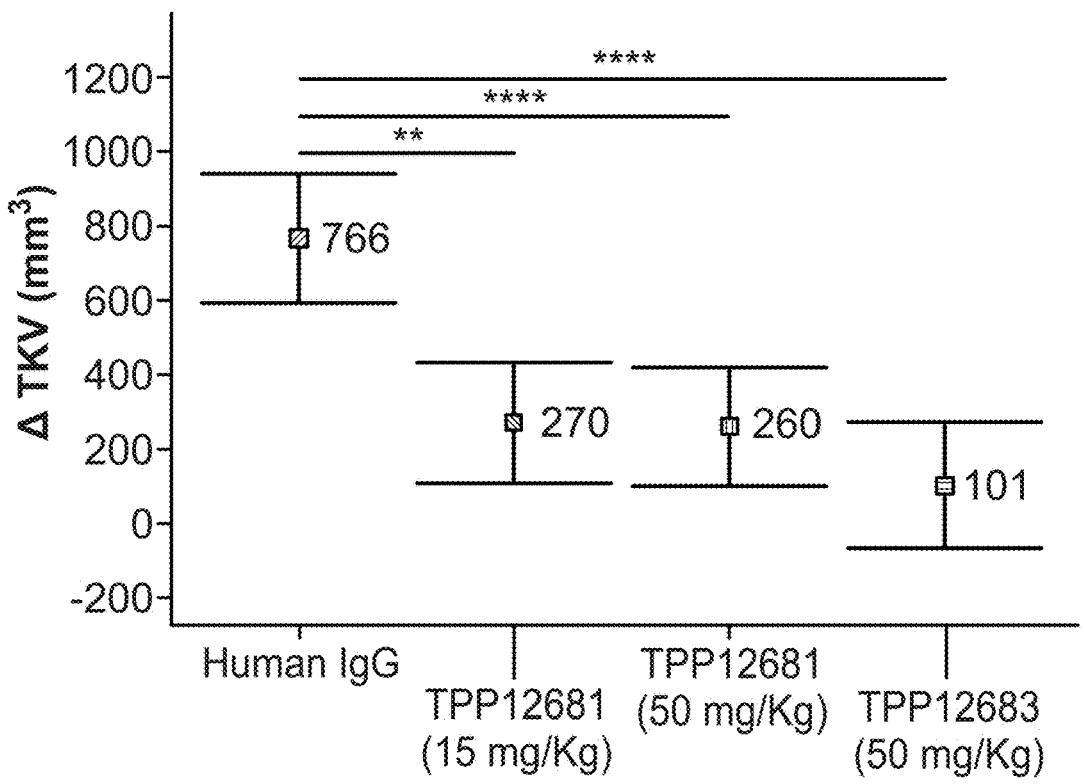

FIG. 12A-12B: Effect of Ansh Labs PAPPA mAb (FIG. 12A) or anti-PAPPA mAbs TPP12681 or TPP12683 (FIG. 12B) on ATKV in JCK mouse model. Changes in total kidney volume were plotted as ATKV in mm3 with a Bonferroni correction applied to the ANCOVA model which included baseline TKV and tibia length as covariates+95% confidence interval (* p<0.05 vs Saline). ATKV was measured as tKV at end of 6 wk study (subtracting tKV at baseline) by MRI.

Figure 13A:
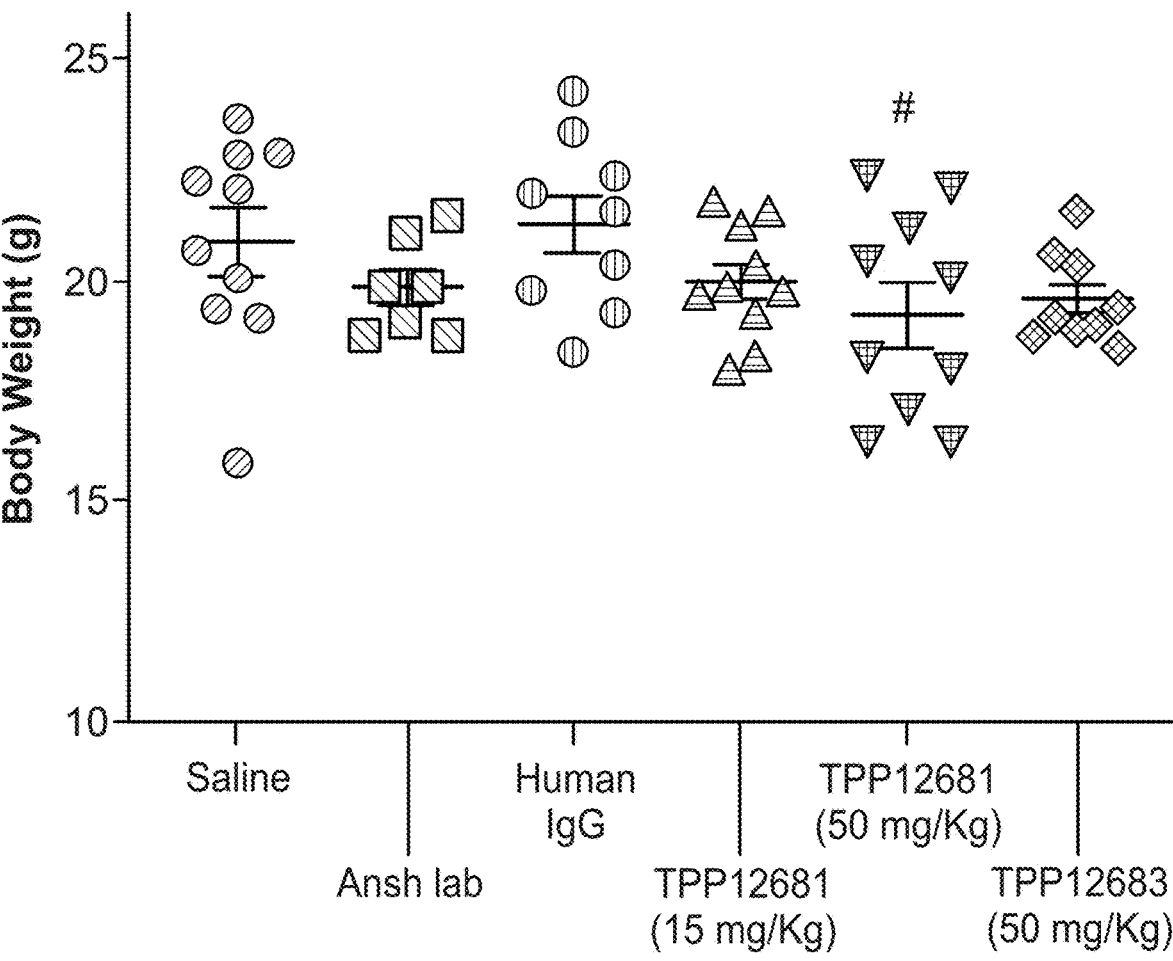
Figure 13B:
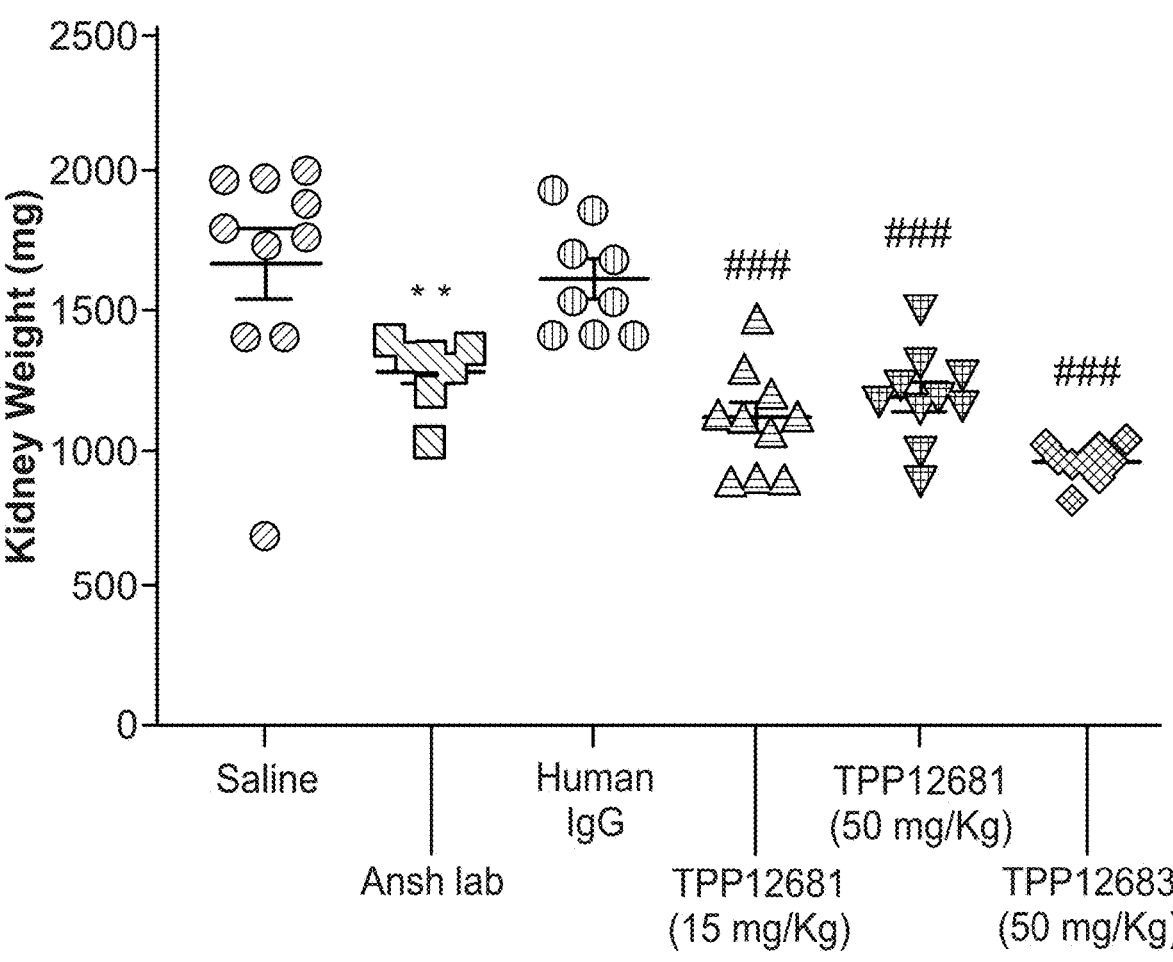

FIG. 13A-13B: Effect of anti-PAPPA mAb treatments on body weight and total kidney weight. FIG. 13A shows end of study body weight plotted as mean±SEM without normalization to tibia length. Comparison between Saline control and Ansh labs groups was done with an unpaired t-test using Welch's correction (not significant, p>0.05), comparisons to Human IgG used ordinary one-way ANOVA with a Dunnett's multiple comparison test IgG (#p<0.05 (not significant p>0.05). FIG. 13B shows end of study total kidney weight (left+right) plotted as mean+SEM without normalization to tibia length. Comparison between Saline control and Ansh labs groups was done with an unpaired t-test using Welch's correction (** p<0.01), comparisons to Human IgG used ordinary one-way ANOVA with a Dunnett's multiple comparison test (###p<0.001).

Figure 14:
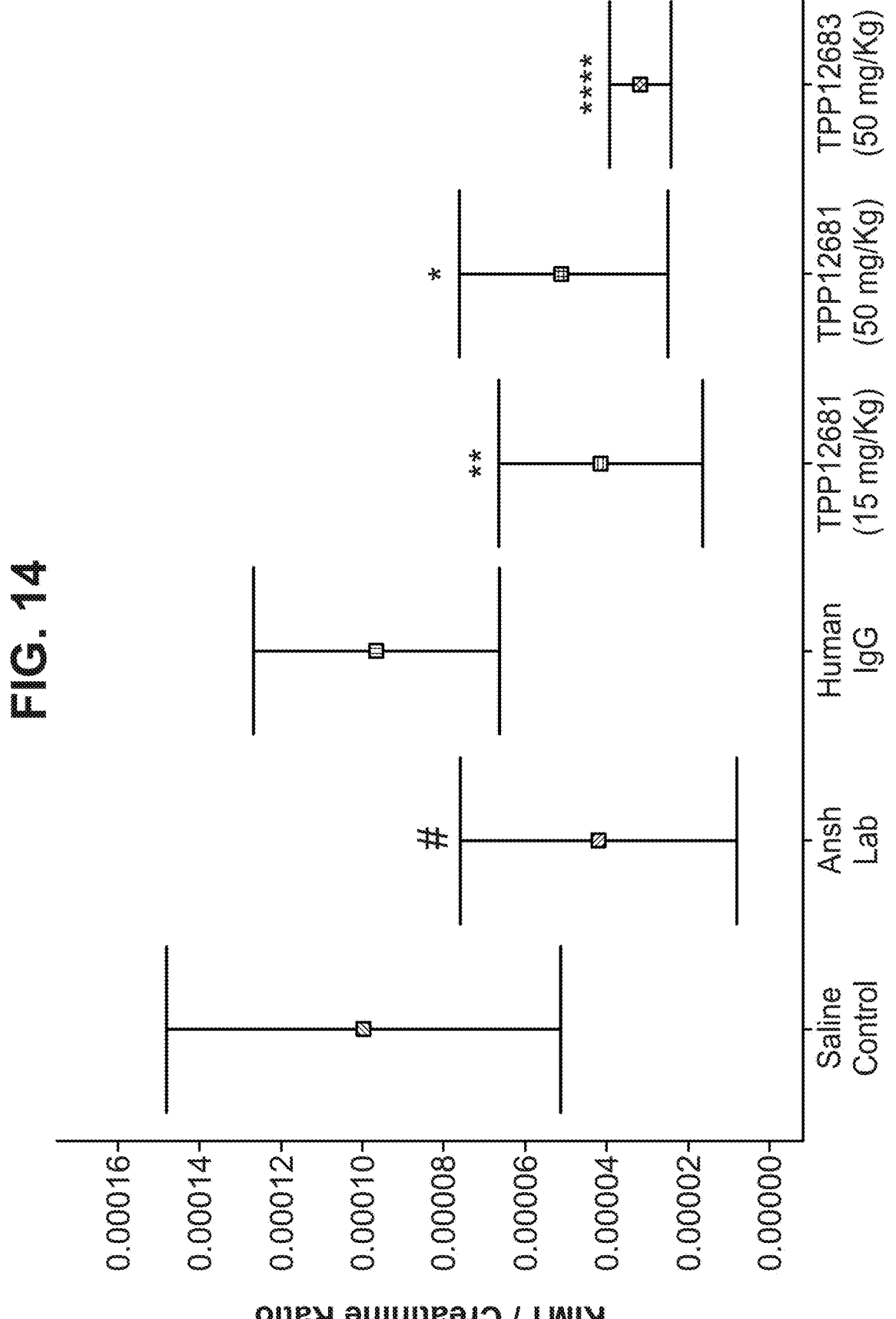

FIG. 14: Effect of anti-PAPPA mAb treatments on urinary $KIM^{-1}$: creatinine ratio. End of study $uKIM^{-1}$/Creatinine Ratio changes were plotted using Bonferroni correction applied to the ANOVA model accounting for heterogenous variances with adjusted+95% Confidence Intervals around model means (#p<0.05 vs Saline control;  p<0.01, ** p<0.0001 vs human IgG).

Figure 15:
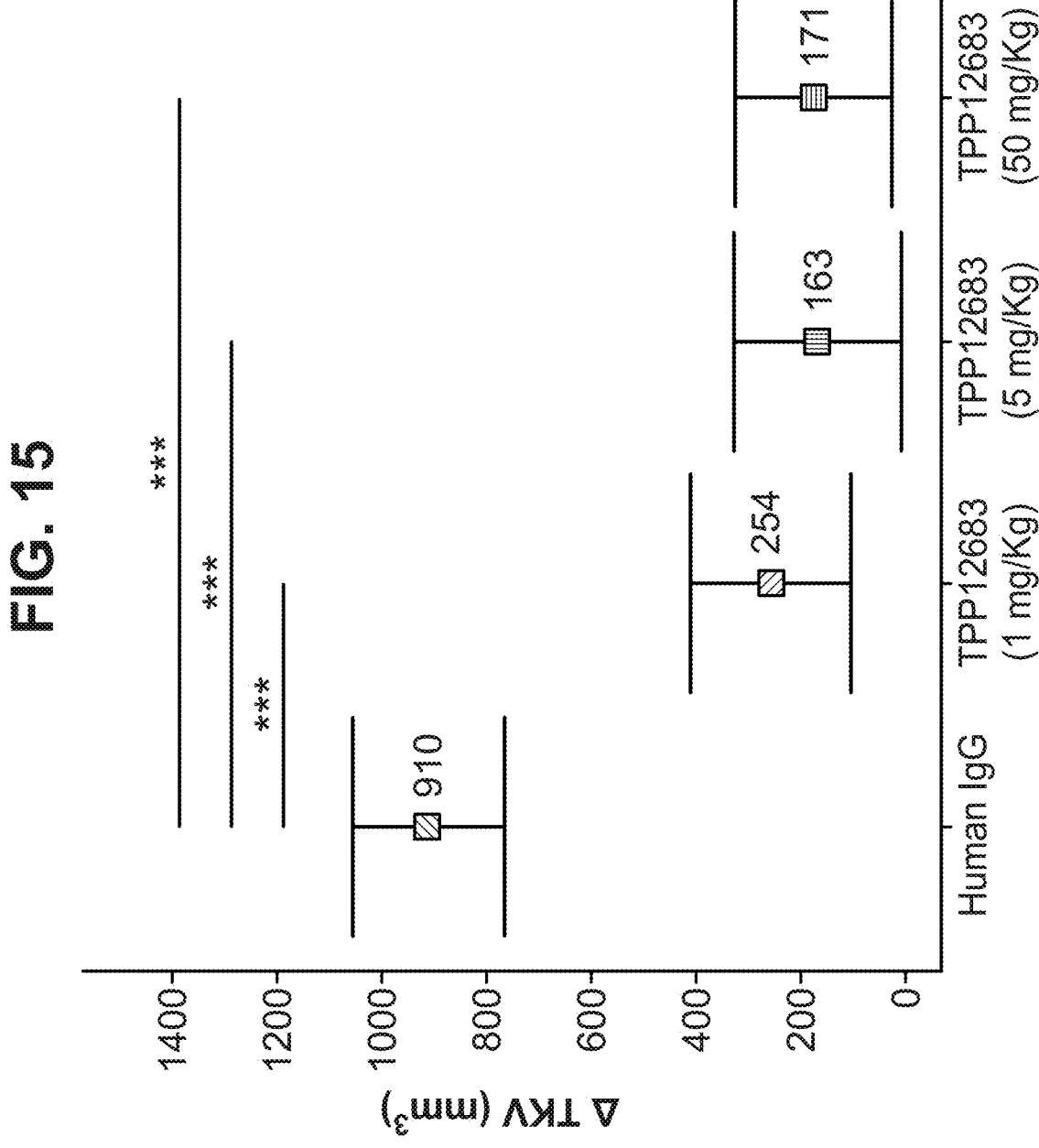

FIG. 15: Effect of anti-PAPPA mabs on ATKV. Changes in total kidney volume were plotted as ATKV in mm3 with a Bonferroni correction applied to the ANCOVA model which included baseline TKV and tibia length as covariates. Values on plot denote the estimated ANCOVA model means with adjusted +95% confidence interval (**** p<0.0001 vs human IgG).

Figures 16A, 16B:
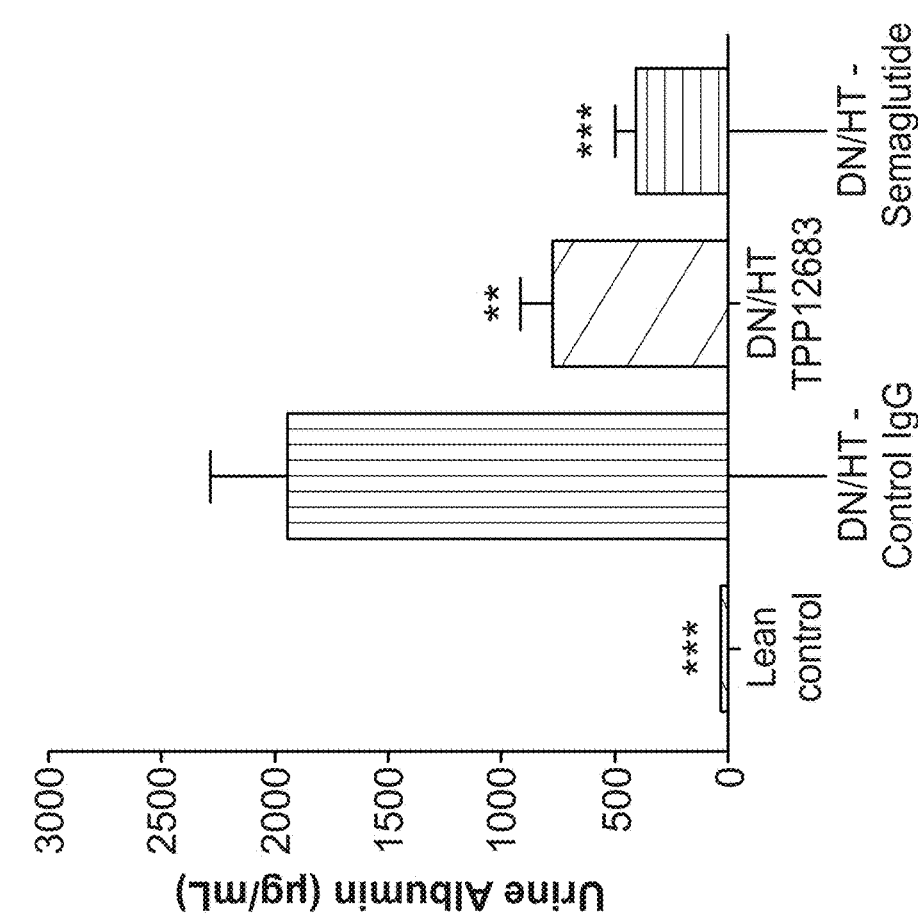

FIG. 16A-16B: Urinary creatinine (FIG. 16A) and urinary albumin levels (FIG. 16B) at termination in diabetic kidney disease (DKD) mice treated with TPP12683. Values expressed as mean of n=11-16+SEM. Dunnett's test one-factor linear model. ***: p<0.001 compared to DN/HT-control IgG.

Figures 17A, 17B:
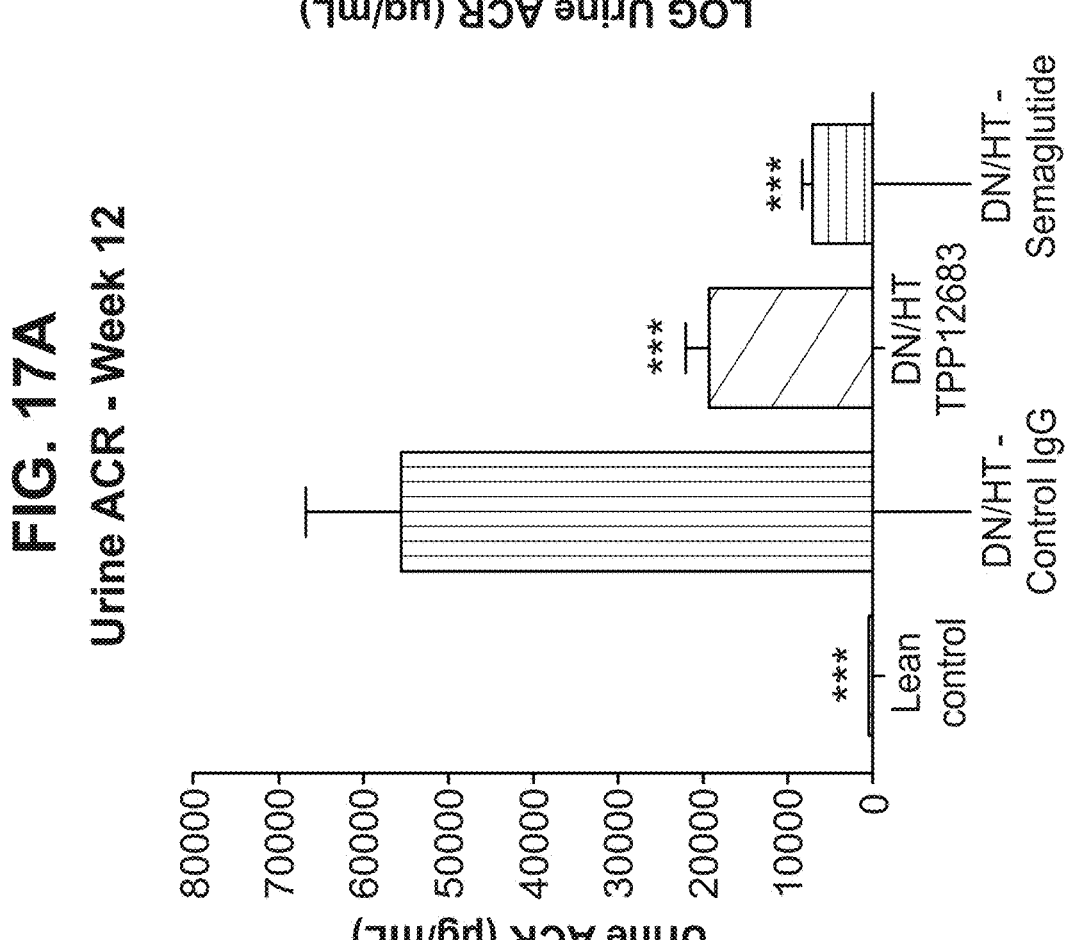

FIG. 17A-17B: Urinary albumin-to-creatinine ratio (UACR) at termination (normal [FIG. 17A] and log transformed [FIG. 17B] values). Values expressed as mean of n=11-16+SEM. Dunnett's test one-factor linear model. : p<0.01, *: p<0.001 compared to DN/HT-control IgG.

Figure 19B:
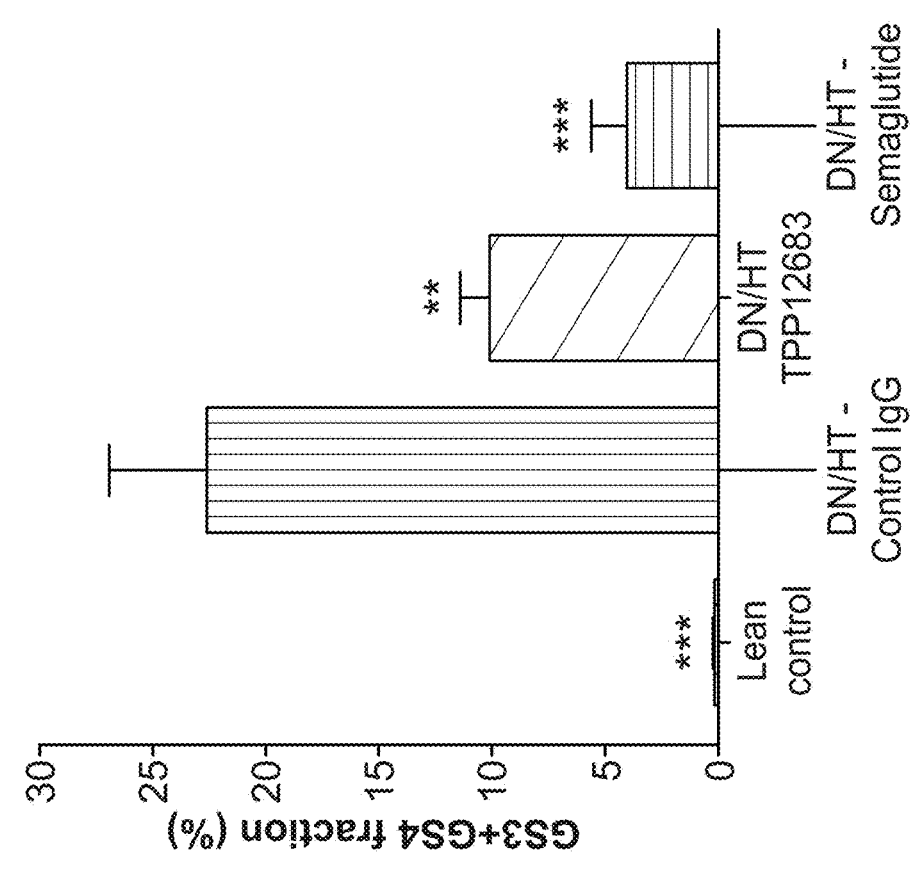
Figure 19A:
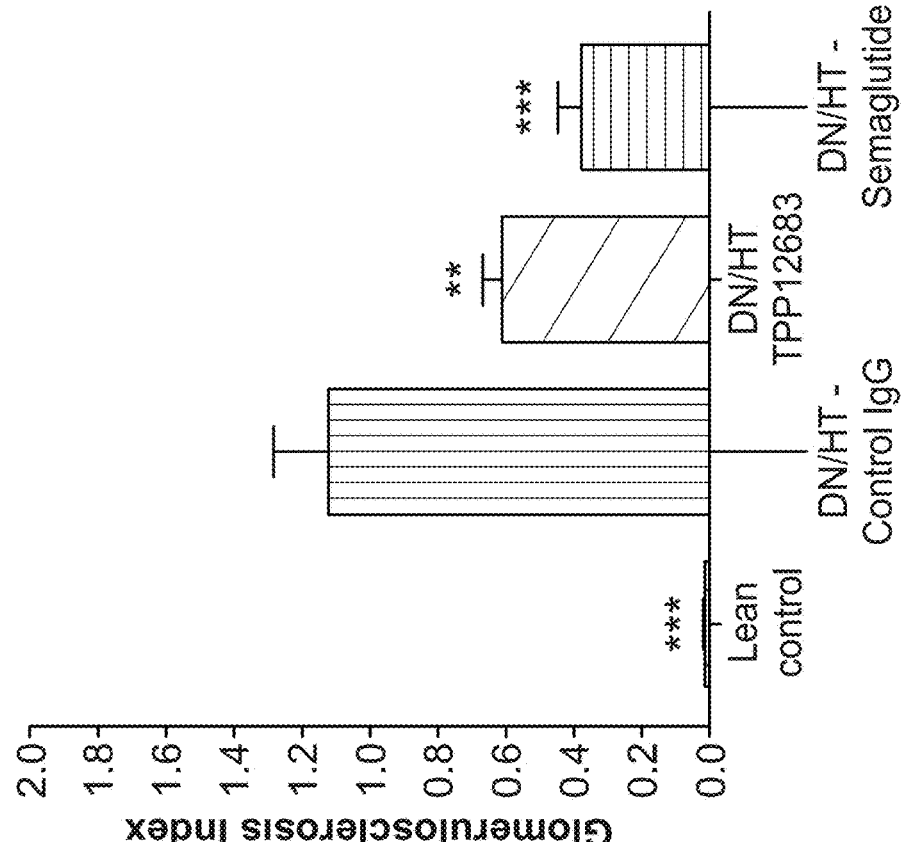

FIG. 18A-18C: Urinary $KIM^{-1}$ (FIG. 18A), $KIM^{-1}$/Creatinine ratio (FIG. 18B) and log transformed value (FIG. 18C) at termination. Values expressed as mean of n=11-16+SEM. Dunnett's test one-factor linear model. : p<0.01, *: p<0.001 compared to DN/HT-control IgG FIG. 19A-19B: Glomerulosclerosis index (FIG. 19A) after histology evaluation by blinded pathologist. GS3 and GS4 were designated as more severe glomerulosclerotic pathology and these data were graphed separately as the GS3+GS4 fraction (FIG. 19B). Values expressed as mean of n=11-16+SEM. Dunnett's test one-factor linear model. : p<0.01, *: p<0.001 compared to DN/HT-control IgG.

Figures 20A, 20B:
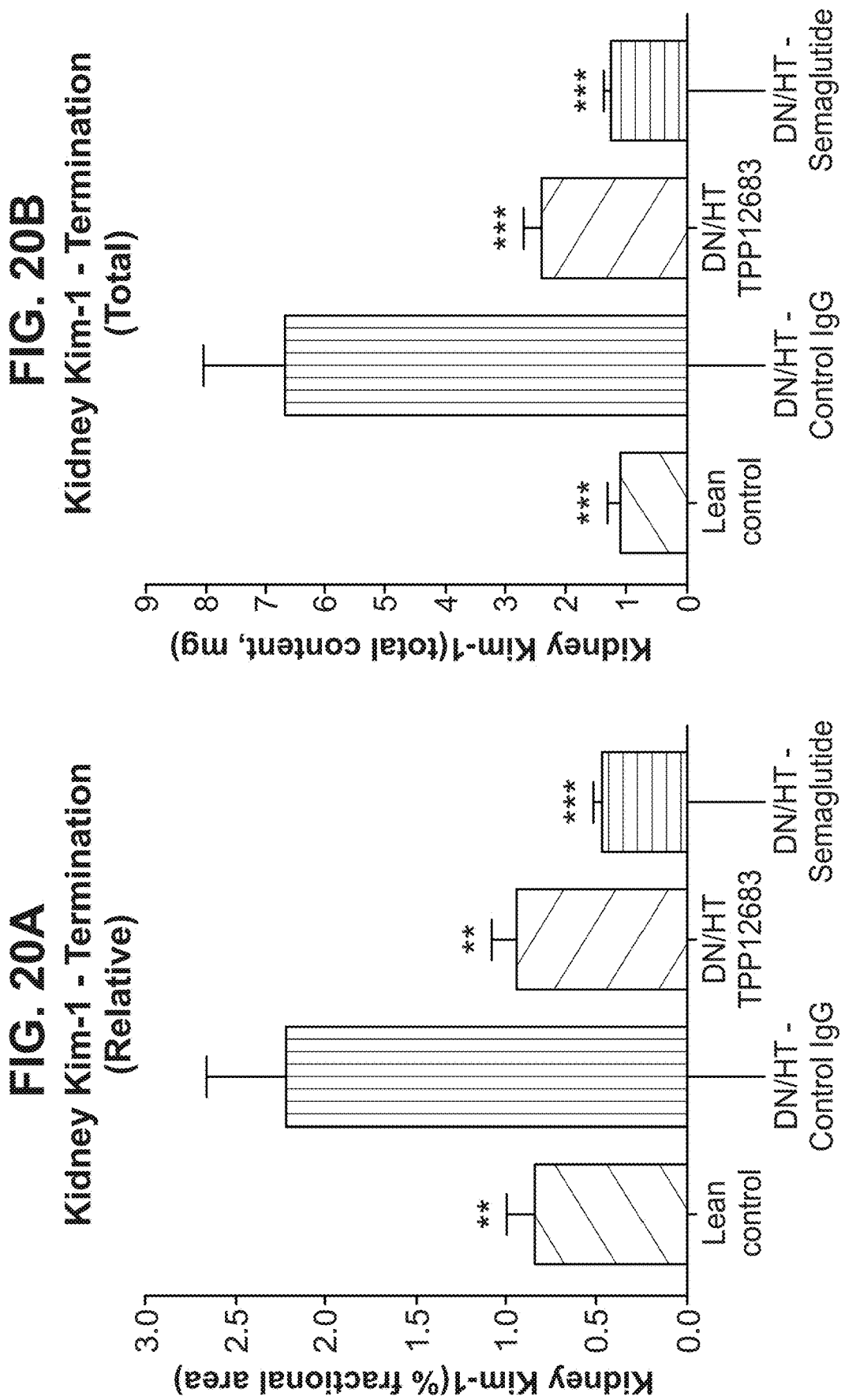

FIG. 20A-20B: Expression of KIM1 in kidney tissues by IHC (immunohistochemistry). Data was reported both as relative % (FIG. 20A), which was the % of tissue stained with $KIM^{-1}$ compared to non-stained kidney tissue in analysed sections, as well at total $KIM^{-1}$ (FIG. 20B) that was calculated by multiplying relative % $KIM^{-1}$ and total kidney weight to estimate the total amount of $KIM^{-1}$ present in the kidney. Values expressed as mean of n=11-15+SEM. Dunnett's test one-factor linear model. : p<0.01, *: p<0.001 compared to DN/HT-control IgG.

Figures 21A, 21B:
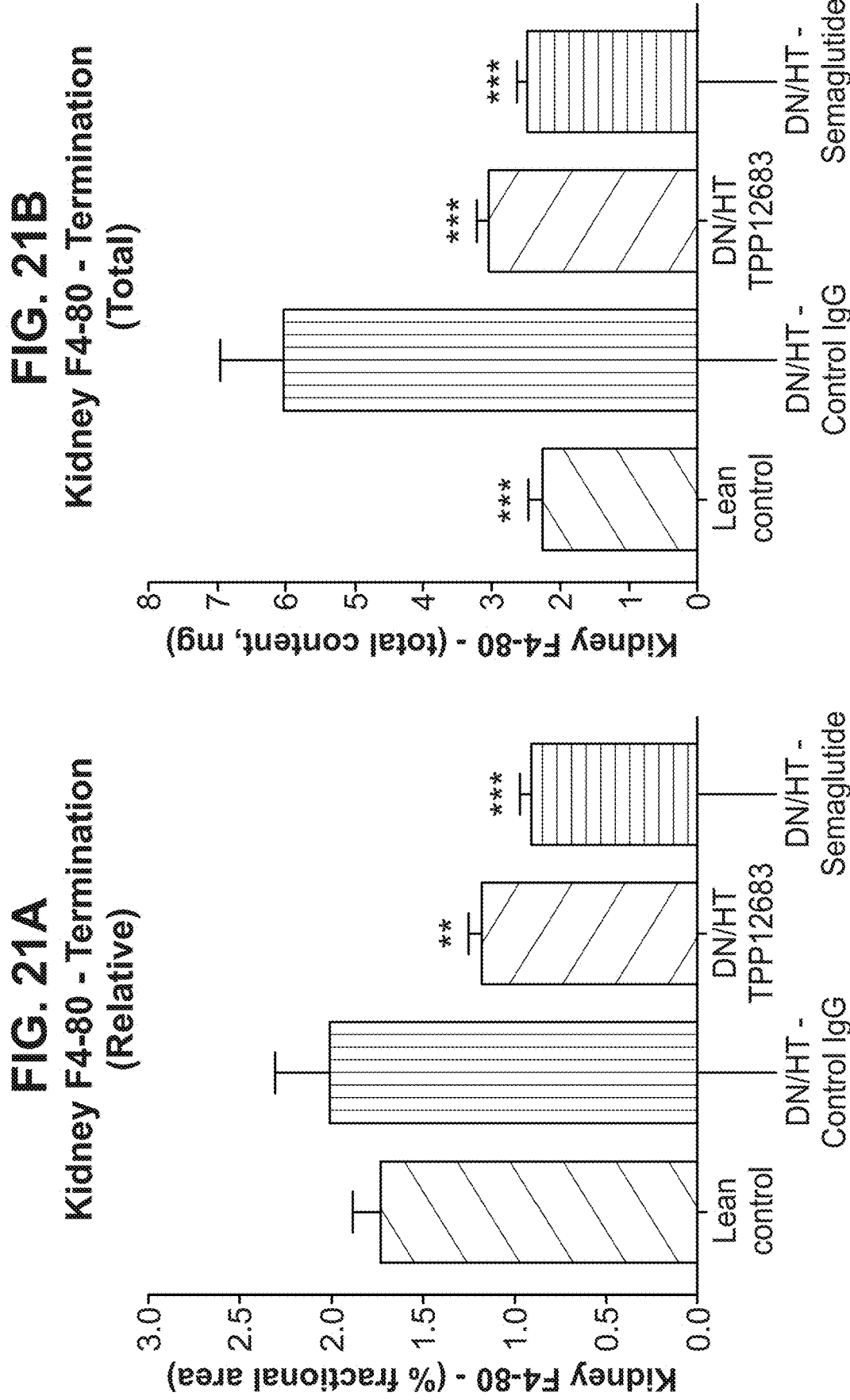

FIG. 21A-21B: Macrophage infiltration as measured by F4/80 signal in immunohistochemistry reported as both relative (FIG. 21A) and total (FIG. 21B) values. Values expressed as mean of n=11-16+SEM. Dunnett's test one-factor linear model. : p<0.01, *: p<0.001 compared to DN/HT-control IgG.

Figure 22:
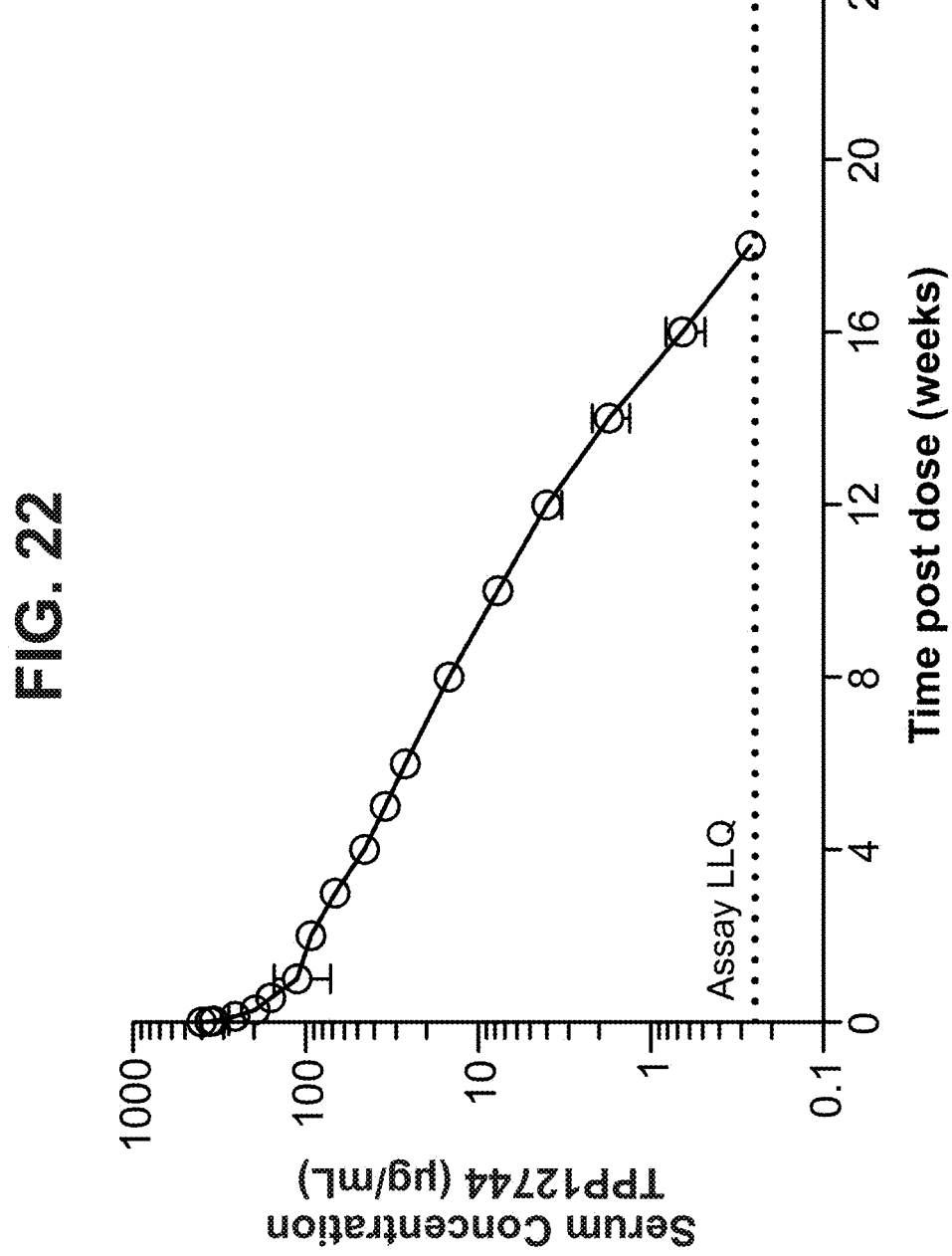

FIG. 22: Serum Concentrations of TPP12744 (ug/ml) Following Intravenous Administration at 10 mg/kg in the Cynomolgus Monkey (n=4). Data displayed as mean+/−SD.

Figure 23A:
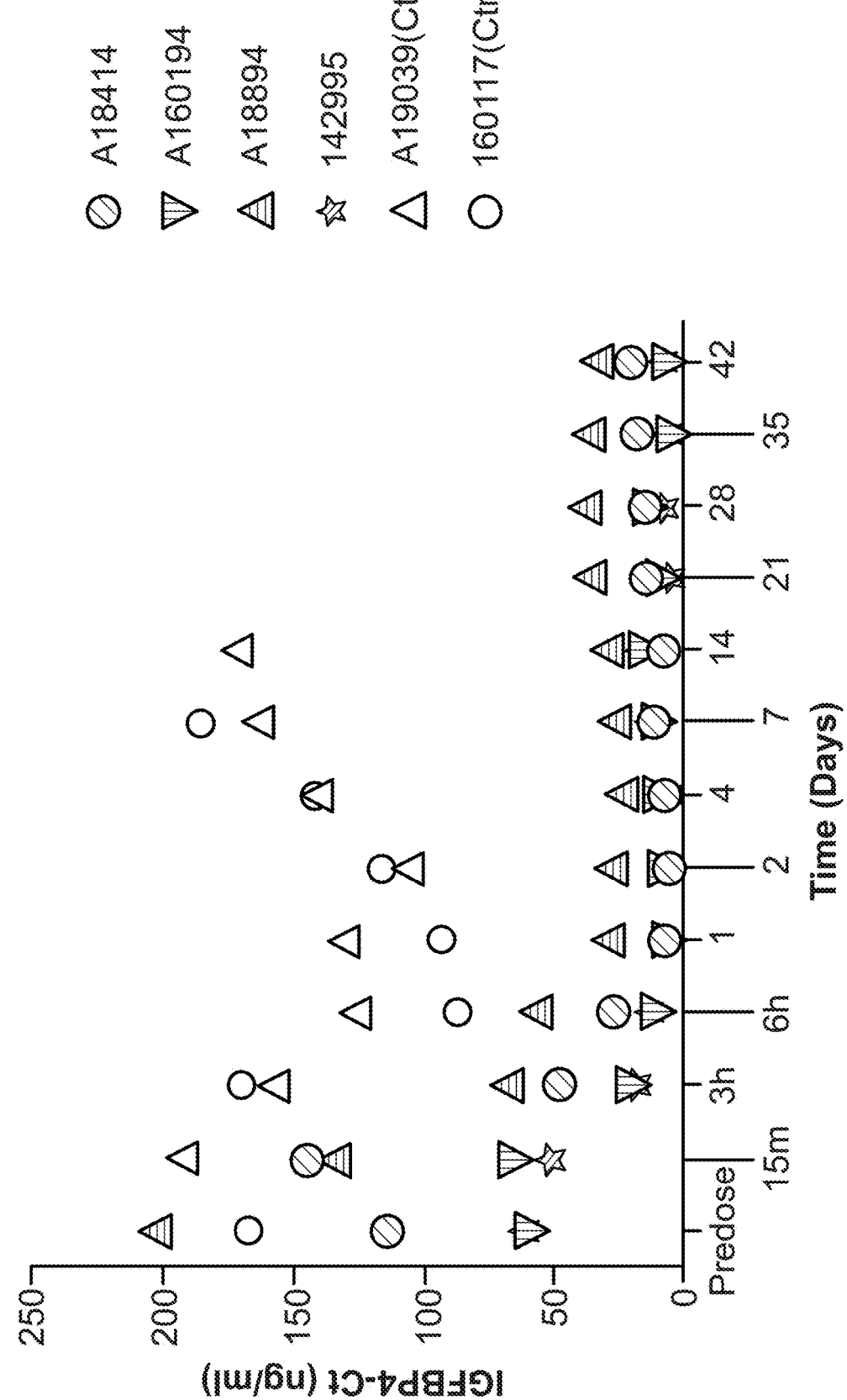
Figure 23B:
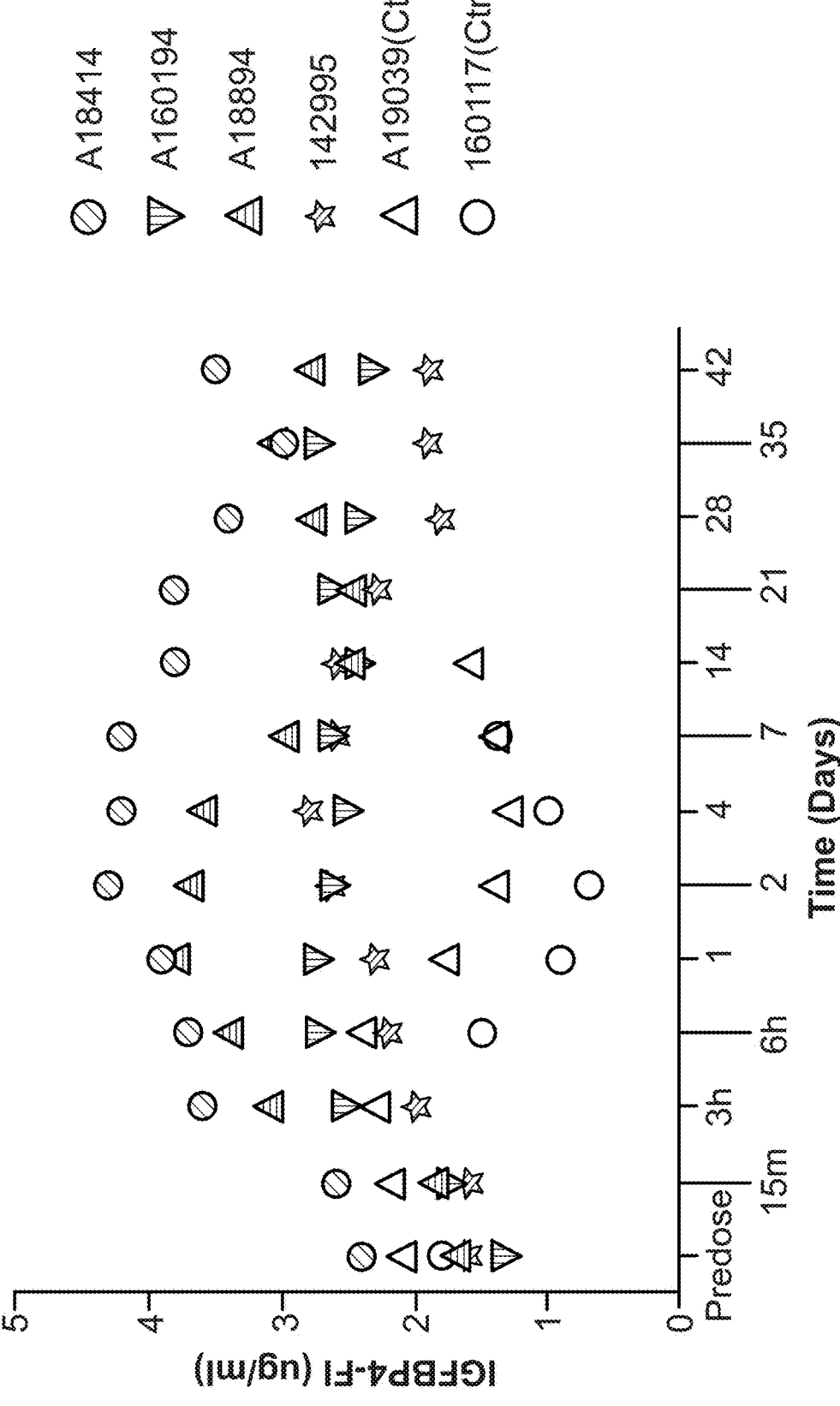
Figure 23C:
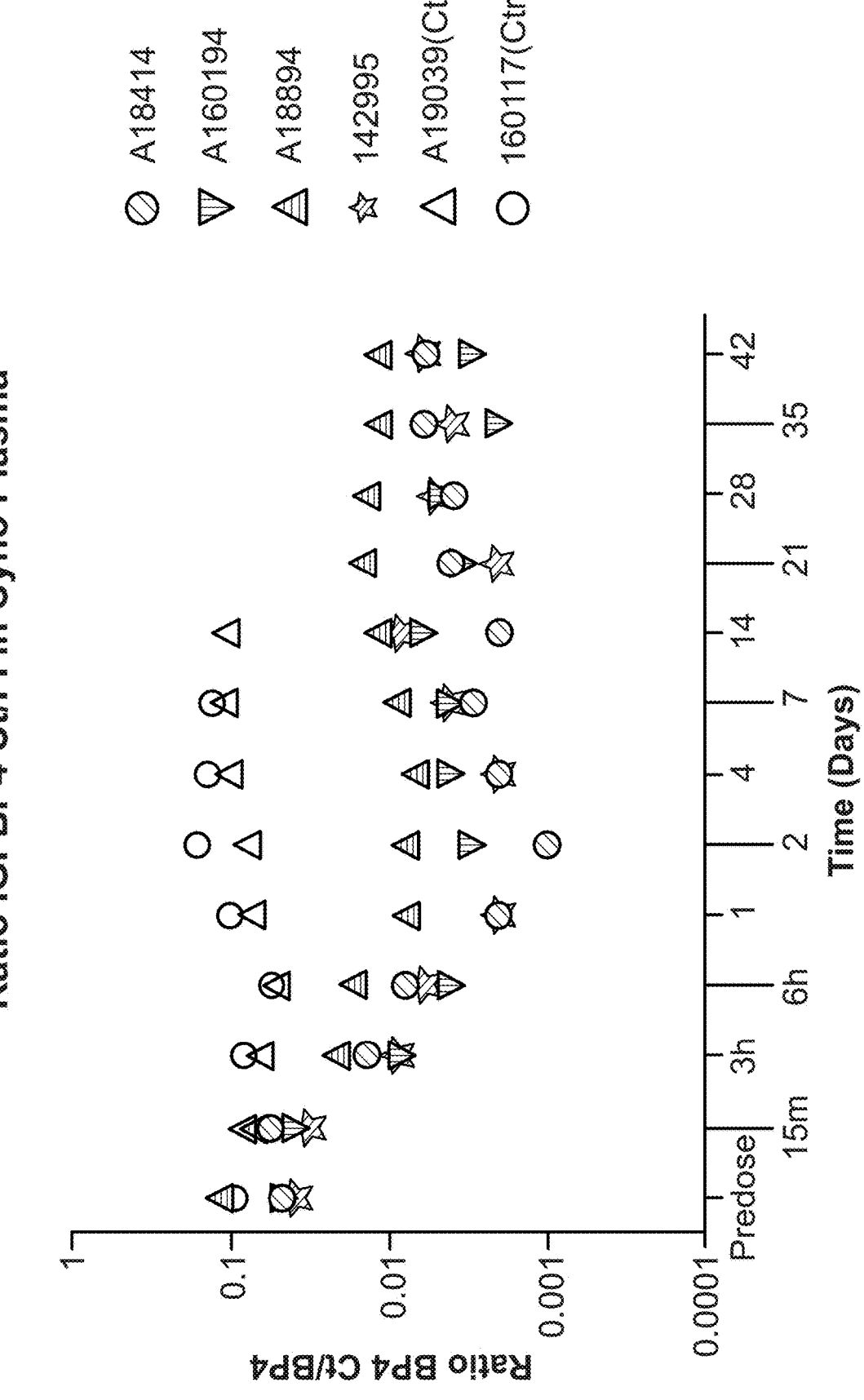

FIG. 23A-23C: Change in IGFBP4-Ct (FIG. 23A), IGFBP4-FI (FIG. 23B), and IGFBP4 Ct/FI ratio (FIG. 23C), in plasma over 6 weeks following IV administration of either vehicle (control, n=2) or TPP12744 at 10 mg/kg (n=4) to male cynomolgus monkey. Data plotted as individual animal results (with individual animals labelled as A18414, A160194, A18894, 142995, A19039 [control] and 160117 [control]).

Figure 24:
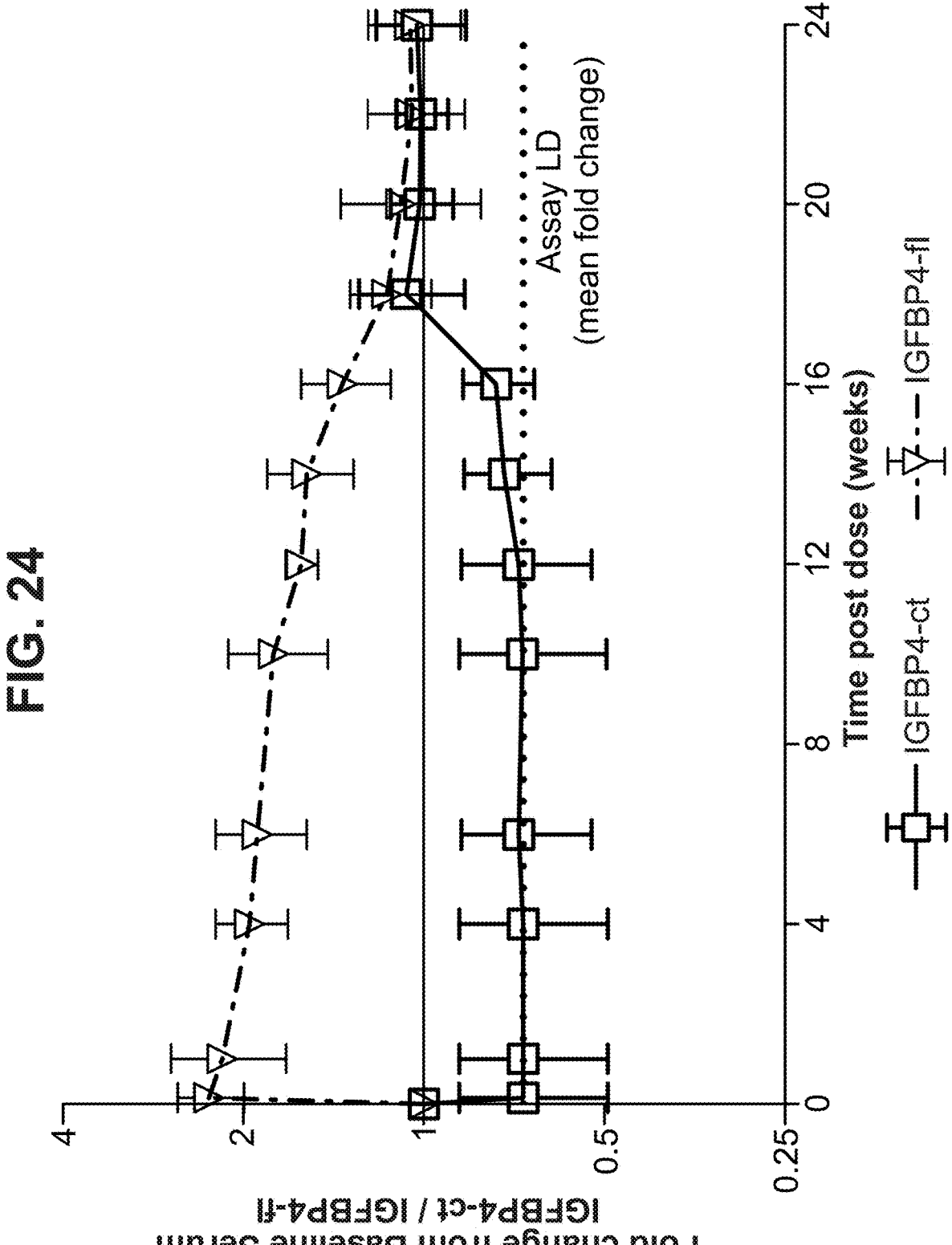

FIG. 24: Effect of TPP12744 on baseline plasma IGFBP4-FI/IGFBP4-Ct fragment in cynomolgus monkey following IV administration at 10 mg/kg (n=4). Data displayed as mean fold change from baseline+/−SD.

Figure 25:
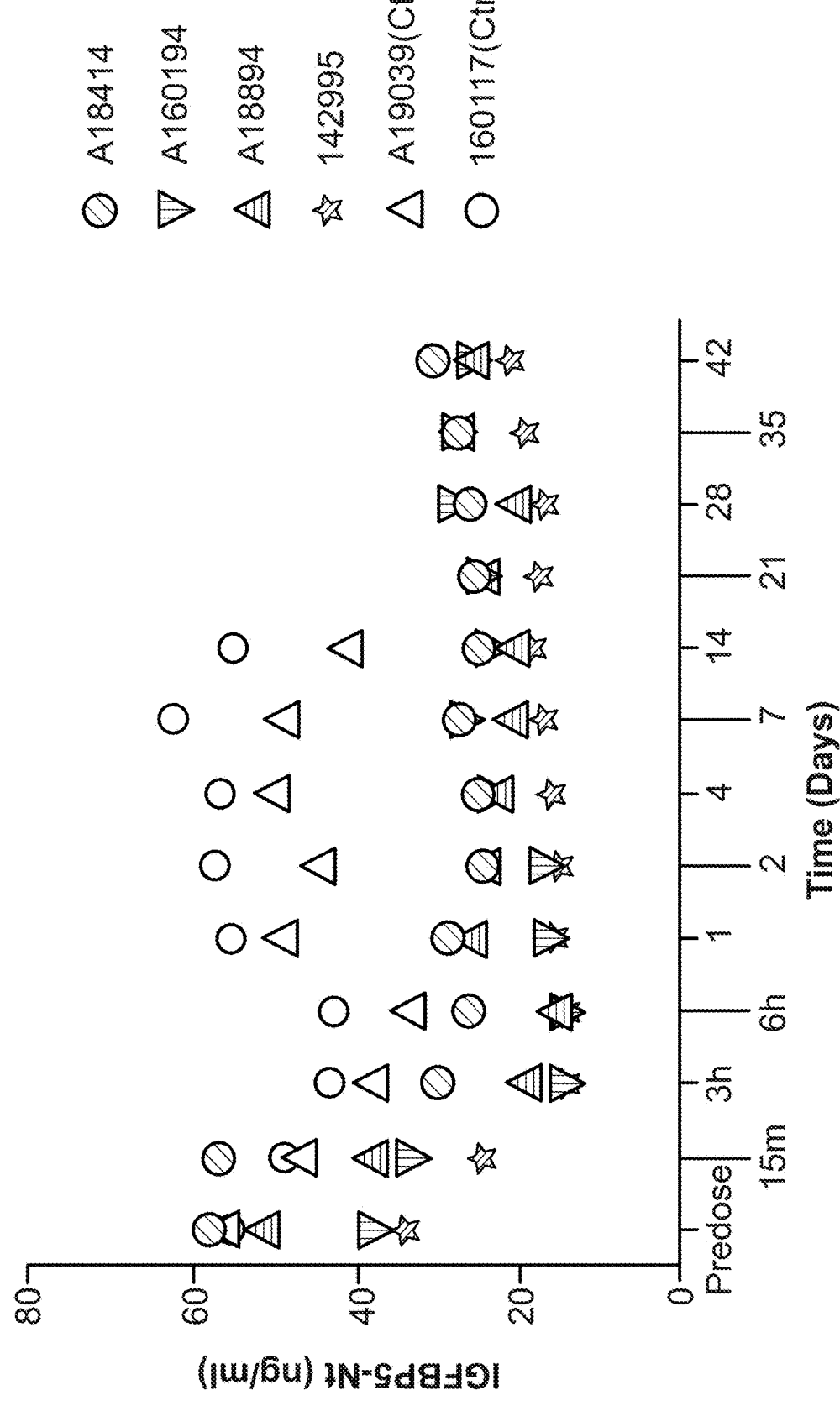

FIG. 25: Change in IGFBP5-Nt in Cyno plasma over 6 weeks following IV administration of either vehicle (control, n=2) or TPP12744 at 10 mg/kg (n=4) to male cynomolgus monkey. Data plotted as individual animal results.

Figure 26:
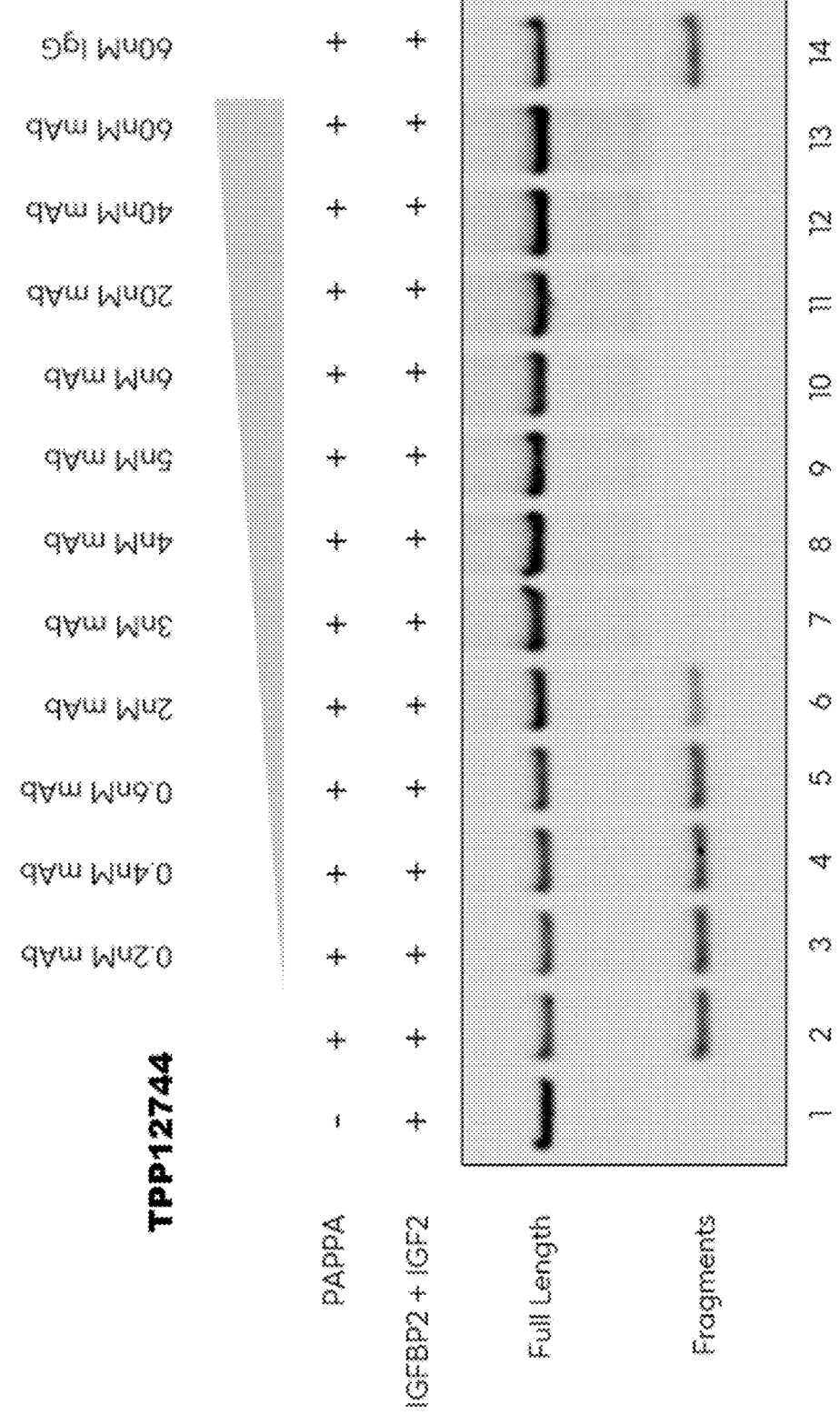

FIG. 26: Western blot analysis of IGFBP2 cleavage by PAPPA and inhibition by TPP12744. Lane 1 depicts IGFBP2 cleavage under baseline conditions with no PAPPA enzyme (0% cleavage), while lane 2 depicts IGFBP2 cleavage with addition of PAPPA enzyme (~50% cleavage). TPP12744 concentration-dependently inhibited PAPPA-mediated IGFBP2 cleavage, as depicted in lanes 3-13. Lane 14 contained IgG control.

Figure 27:
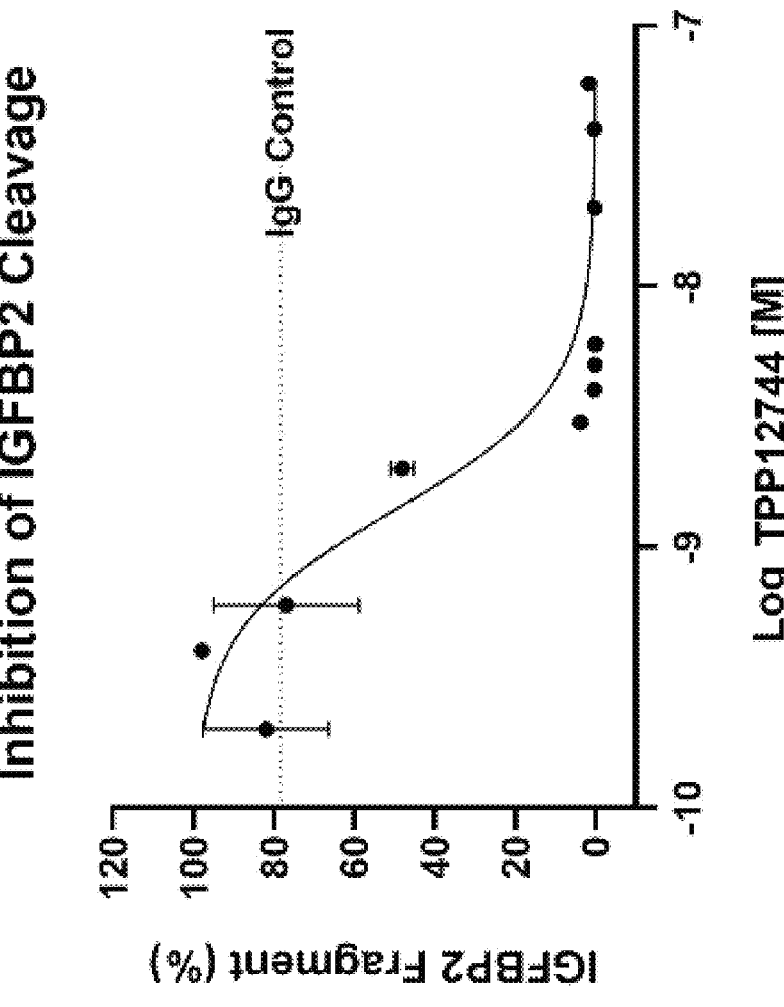

FIG. 27: Concentration response curves were derived from two independent experiments; SEM is plotted. Normalized fragment levels for 60 nM IgG controls were plotted as horizontal dotted lines and were determined to be 78.34% for IGFBP2. The average IC$_{50}$ value for TPP12744 inhibitory effect on IGFBP2 cleavage (closed circles) was 1.39 nM across the two experiments.

Figure 28:
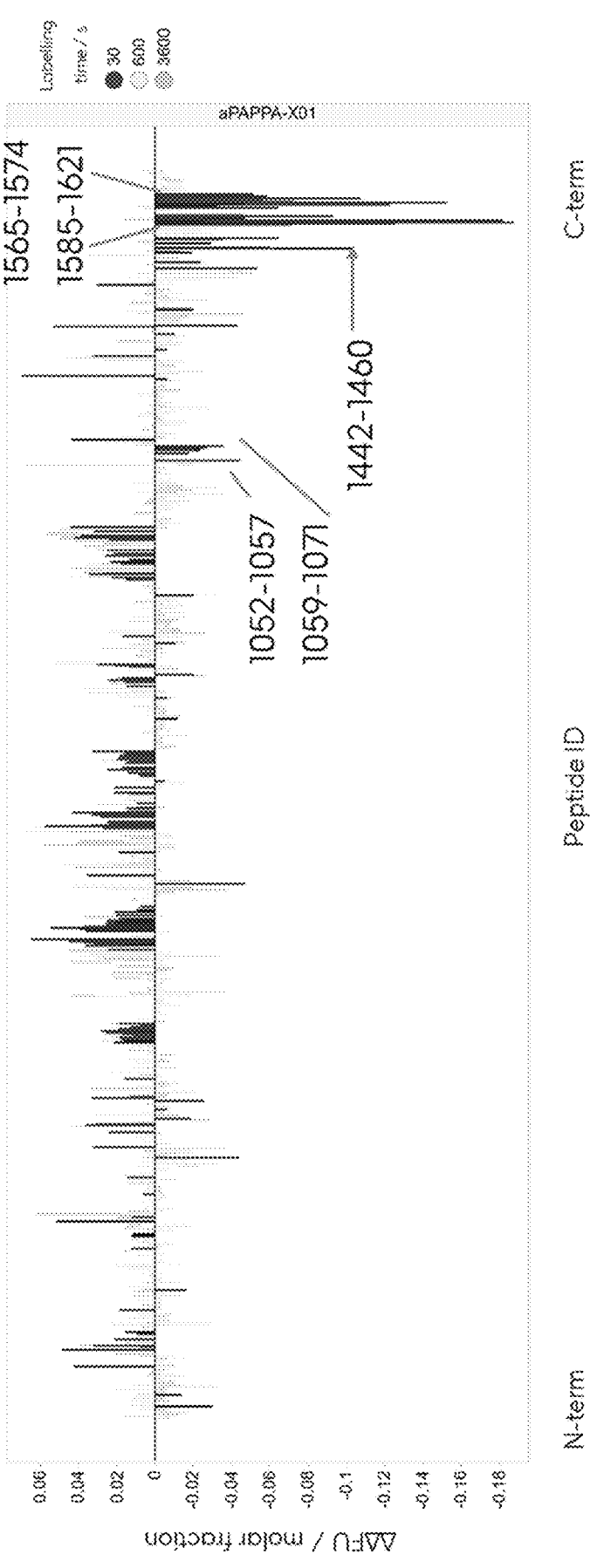

FIG. 28: Plot of differential fractional deuterium uptake values (AAFU) expressed as molar fraction of the maximum theoretical uptake for each peptide of human PAPPA in complex with Comparator anti-PAPPA mAb 1. Labelling times are printed in greyscale. Some regions are indicated for reference and refer to the amino acid residue numbers of the peptides spanning these regions. Opaque bars correspond to those that meet the statistical threshold p<0.01.

DETAILED DESCRIPTION

Unless defined otherwise, all technical and scientific terms used herein have the same meaning as commonly understood by one of ordinary skill in the art to which this disclosure belongs.

The term "antigen binding protein" as used herein refers to isolated proteins, antibodies, antigen binding fragments thereof (e.g. Fabs), and other protein constructs, such as domains, that are capable of binding to an antigen. Antigen binding proteins include alternative antibody formats including triabody, tetrabody, miniantibody, and a minibody. Also included are alternative scaffolds in which the one or more CDRs of any molecules in accordance with the disclosure can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain. An antigen binding protein also includes antigen binding fragments of such antibodies or other molecules. Further, an antigen binding protein may comprise the VH regions of the invention formatted into a full-length antibody, a (Fab')$_2$ fragment, a Fab fragment, a bi-specific or biparatopic molecule or equivalent thereof (such as scFV, bi-tri- or tetrabodies, Tandabs, etc.), when paired with an appropriate light chain. The antigen binding protein may comprise an antibody that is an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. The antigen binding protein may also be a chimeric antibody of the type described in WO86/01533, which comprises an antigen binding region and a non-immunoglobulin region. The term "PAPPA binding protein" as used herein refers to antigen binding proteins that are capable of binding to PAPPA. A PAPPA binding protein may be capable of binding to one or more of human PAPPA and a PAPPA protein of another organism (e.g., mouse, rat, cow, dog, cat, pig, monkey, etc.). A PAPPA binding protein may be capable of binding to a fragment of, a variant of, or a mutant of PAPPA. A PAPPA binding protein as used herein is different from naturally occurring binding proteins that bind PAPPA.

One or more antigen binding proteins (i.e., PAPPA binding proteins) described herein may show cross-reactivity between human PAPPA and PAPPA from another species, such as cynomolgus PAPPA, rabbit PAPPA etc. PAPPA binding proteins described herein may specifically bind human PAPPA and cynomolgus PAPPA. Optionally, the binding affinity of the antigen binding protein for cynomolgus PAPPA and the binding affinity for human PAPPA differ by no more than a factor of 2, 5, 10, 50, or 100.

In some embodiments the PAPPA binding proteins described herein are capable of specifically binding to murine PAPPA, meaning said PAPPA binding proteins can be exploited in mouse models of disease (e.g. mouse models of PKD). Results from these studies can be used to inform the development of other PAPPA binding proteins with similar properties (e.g. binding affinity, cellular potency etc) but which may not specifically bind to mouse PAPPA.

As used herein "PAPPA" means pregnancy associated plasma protein-A. Pseudonyms for PAPPA include PAPP-A or Pappalysin-1. PAPPA is a molecule that is encoded by the PAPPA gene in humans. The human PAPPA protein is 1627 amino acids in length as shown in SEQ ID NO: 1 and in UniProt Q13219. However, the first 80 amino acids of PAPPA correspond to a signal peptide that is naturally cleaved off during protein production (Judge et al *Nat Commun* 13, 5500 (2022)). The resulting peptide is 1547 amino acids in length as shown in SEQ ID NO: 2 (i.e., starting from R81 of SEQ ID NO: 1). Throughout the present disclosure reference to amino acid residues of human PAPPA are numbered in accordance with the full-length PAPPA protein of SEQ ID NO: 1, such as to be aligned with the UniProt defined sequence. However, it would be within the remit of the skilled person to identify the corresponding positions within SEQ ID NO: 2 (i.e., by subtracting 80 amino acids) or indeed to identify the corresponding positions within the PAPPA protein of other non-human species.

The 1627 amino acid full-length PAPPA protein comprises a Laminin G-like domain, a metalloprotease domain, a central M1/M2 domain, the Complement Control Protein domains (or SCR, short consensus repeats) CCP2, CCP3, CCP4 and CCP5, and the Lin12-Notch Repeats (LNR 1, 2, 3). The positioning of these domains within the full-length PAPPA protein is reported in Judge et al, with residue numbering accounting for the presence of the 80 aa signal peptide.

PAPPA is a metalloproteinase which specifically cleaves Insulin Like Growth Factor Binding Proteins (IGFBP) 2 (IGFBP-2), 4 (IGFBP-4) and 5 (IGFBP-5) resulting in release of IGF-1 (Oxvig et al. J Cell Commun Signal. 2015 June; 9 (2): 177-87). PAPPA is expressed in both secreted and cell-associated forms and unless specified otherwise, PAPPA is used generally herein to refer to PAPPA in either form.

In one aspect there is provided a pregnancy associated plasma protein-A (PAPPA) binding protein wherein said PAPPA binding protein inhibits cleavage of both insulin like growth factor binding protein-4 (IGFBP-4) and insulin like growth factor binding protein-5 (IGFBP-5). In an embodiment said PAPPA binding protein inhibits PAPPA-mediated IGFBP-4 and IGFBP-5 cleavage i.e., said PAPPA binding protein inhibits PAPPA's proteolytic cleavage of both IGFBP-4 and IGFBP-5.

As used herein "IGFBP-4" or "IGFBP4" refers to insulin like growth factor binding protein 4 and "IGFBP-5" or "IGFBP5" refers to insulin like growth factor binding protein 5. Both IGFBP-4 and IGFBP-5 are members of a family of secreted IGF binding proteins (IGFBPs) that bind to IGFs with high affinity and modulate local IGF bioactivity (Chernausek et al, Journal of Biological Chemistry, Volume 270, Issue 19, 1995, Pages 11377-11382). In an embodiment said IGFBP-4 and said IGFBP-5 are human IGFBP-4 and human IGFBP-5 respectively.

As used herein the term "IGF-1" refers to insulin-like growth factor 1. IGF-1 is a hormone that plays important and diverse roles in a variety of metabolic functions. "IGF-1" may also be referred to herein as "IGF1" or "mature IGF-1".

IGF-1 is a 70 amino acid protein with a molecular weight 7.6 kDa. The amino acid sequence of IGF-1 is shown in SEQ ID NO: 119. In humans, IGF-1 is encoded for by the IGF1 gene. The IGF1 gene is first translated into a Pre-pro-IGF-I precursor protein which is then cleaved to form IGF-1.

As described above, PAPPA is a proteinase enzyme that is responsible for cleavage of IGFBP-4 and IGFBP-5. PAPPA cleaves IGFBP-4 between Met-135 and $Lys^{-136}$ on IGFBP-4, and IGFBP-5 between Ser-143 and $Lys^{-144}$ on IGFBP-5 (Laursen et al. FEBS Letters 504 (2001) pg 36-40 & Conover et al (1995) J. Biol. Chem 270, 4395-4400). Numbering of these cleavage sites is provided in respect of the mature IGFBP-4 and mature IGFBP-5 proteins following cleavage of a 20 amino acid and a 21 amino acid signal peptide respectively. The cleavage sites are indicated in SEQ ID NO: 11 for IGFBP-4 and SEQ ID NO: 15 for IGFBP-5 but are also shown in FIG. 6.

When cleaved by PAPPA, full length IGFBP-4 (also referred to herein as "intact IGFBP-4") is cleaved into two fragments of similar size, referred to herein as N-terminal (Nt) and C-terminal (Ct) fragments. Full-length IGFBP-4 is shown in SEQ ID NO: 7.

Likewise, when cleaved by PAPPA, full length IGFBP-5 (also referred to herein as "intact IGFBP-5") is also cleaved into two fragments of similar size, referred to herein as N-terminal (Nt) and C-terminal (Ct) fragments. Full-length IGFBP-5 is shown in SEQ ID NO: 12.

In an embodiment there is provided a PAPPA binding protein wherein said binding protein inhibits cleavage of i) full length IGFBP-4 into an IGFBP-4 Ct fragment and a IGFBP-4 Nt fragment; and ii) full length IGFBP-5 into a IGFBP-5 Ct fragment and a IGFBP-5 Nt fragment. In an embodiment said PAPPA binding protein inhibits cleavage of i) full length IGFBP-4 of SEQ ID NO: 7 into a IGFBP-4 Ct fragment and a IGFBP-4 Nt fragment; and ii) full length IGFBP-5 of SEQ ID NO: 12 into a IGFBP-5 Ct fragment and a IGFBP-5 Nt fragment. In an embodiment said PAPPA binding protein inhibits cleavage of i) full length IGFBP-4 of SEQ ID NO: 7 into a IGFBP-4 Ct fragment of SEQ ID NO: 9 and a IGFBP-4 Nt fragment of SEQ ID NO: 8; and ii) full length IGFBP-5 of SEQ ID NO: 12 into a IGFBP-5 Ct fragment of SEQ ID NO: 14 and a IGFBP-5 Nt fragment of SEQ ID NO: 13.

Each of IGFBP-4 and IGFBP-5 exist in both IGF-1 bound and IGF-1-unbound states. When IGF-1 is bound to IGFBP-4 this forms IGF-1/IGFBP-4 complexes and when IGF-1 is bound to IGFBP-5 this forms IGF-1/IGFBP-5 complexes. IGF-1, in either bound form, is sequestered and is inactive towards the IGF-1 receptor (IGF1R). PAPPA cleavage of IGF-1/IGFBP-4 complex results in said complex cleaving into three principle molecules i.e., IGFBP-4 Ct fragment, IGFBP-4 Nt fragment and free IGF-1. PAPPA cleavage of IGF-1/IGFBP-5 complex results in said complex cleaving into three principle molecules i.e., IGFBP-5 Ct fragment, IGFBP-5 Nt fragment and free IGF-1.

The PAPPA binding proteins disclosed herein may inhibit the cleavage of IGFBP-4 and IGFBP-5 in either of their IGF-1 bound or IGF-1-unbound states, however in particular, the PAPPA binding proteins disclosed herein inhibit the cleavage of IGF-1/IGFBP-4 complexes and IGF-1/IGFBP5 complexes. Thus, in an embodiment there is provided a PAPPA binding protein wherein said PAPPA binding protein inhibits cleavage of IGF-1/IGFBP-4 complex(es) and IGF-1/IGFBP-5 complex(es). In an embodiment there is provided a PAPPA binding protein, wherein said PAPPA binding protein inhibits cleavage of i) IGF-1/IGFBP-4 complex(es) into a IGFBP-4 Ct fragment, a IGFBP-4 Nt fragment and free IGF-1; and ii) IGF-1/IGFBP-5 complex(es) into a IGFBP-5 Ct fragment, a IGFBP-5 Nt fragment and free IGF-1. In an embodiment said PAPPA binding protein inhibits cleavage of i) IGF-1/IGFBP-4 complex(es) into a IGFBP-4 Ct fragment of SEQ ID NO: 9, a IGFBP-4 Nt fragment of SEQ ID NO: 8 and free IGF-1; and ii) IGF-1/IGFBP-5 complex(es) into a IGFBP-5 Ct fragment of SEQ ID NO: 14, a IGFBP-5 Nt fragment of SEQ ID NO: 13 and free IGF-1. In an embodiment the PAPPA binding proteins disclosed herein inhibit IGF-1 liberation from both IGF-1/IGFBP-4 complex(es) and IGF-1/IGFBP-5 complex(es). In an embodiment said PAPPA binding proteins decrease IGF-1 bioavailability.

In an embodiment the PAPPA binding proteins disclosed herein further inhibit cleavage of insulin like growth factor binding protein-2 (IGFBP-2), optionally wherein said IGFBP-2 is human IGFBP-2. It is recognised that IGFBP-2 cleavage by PAPPA is similar to IGFBP-4. Cleavage of both IGFBP-2 and IGFBP-4 are dependent on IGF-1 and a published report indicated that IGFBP-2 and -4 are inhibited to the same degree by a particular anti-PAPPA mAb, but IGFBP5 cleavage is not inhibited, supporting the notion that these two substrates (i.e., IGFBP-2 and IGFBP-4) behave similarly (Mohrin et al. Aging Cell. 2021 March; 20 (3)). In an embodiment the PAPPA binding proteins disclosed herein further inhibit IGF-1 liberation from IGF-1/IGFBP-2 complex(es).

Another member of the pappalysin subfamily is pregnancy-associated plasma protein A2 (PAPPA2 or PAPP-A2). Human PAPPA2 shares 46% homology with human PAPPA and includes a conserved zinc binding site (Barrios et al. Cells. 2021 Dec. 18; 10 (12): 3576). PAPPA2 is encoded by PAPPA2 gene which is located on chromosome 1q25.2 and the encoded protein preferentially cleaves IGFBP-5 with lower proteolytic activity for IGFBP-3. In a particular embodiment the PAPPA binding protein disclosed herein does not bind to PAPPA2. Said PAPPA2 may be human PAPPA2 but may also be PAPPA2 from other non-human species (e.g. cynomolgus monkey, mouse, rat, rabbit etc.) The term "does not bind to PAPPA2" means that the PAPPA binding proteins disclosed herein either do not specifically bind to or associate with PAPPA2 or do so but only with low affinity i.e., with a Kd of $1\times10^{-6}$ M or more (for example, $1\times10^{-5}$ M or more, $1\times10^{-4}$ M or more, $1\times10^{-3}$ M or more, or $1\times10^{-2}$ M or more).

Affinity, also referred to as "binding affinity", is the strength of binding at a single interaction site, i.e., of one molecule, e.g., a PAPPA binding protein, to another molecule, e.g., PAPPA, at a single binding site. The binding affinity of an antigen binding protein to its target may be determined by equilibrium methods (e.g., using enzyme-linked immunosorbent assay (ELISA) or radioimmunoassay (RIA)), or kinetics (e.g., BIACORE analysis). For example, SPR methods described in Example 1 (method #4 and #6) may be used to measure binding affinity. Avidity, also referred to as functional affinity, is the cumulative strength of binding at multiple interaction sites, e.g., the sum total of the strength of binding of two molecules (or more, e.g., in the case of a bispecific or multispecific molecule) to one another at multiple sites, e.g., taking into account the valency of the interaction.

The equilibrium dissociation constant (KD) of the antigen binding protein (i.e., PAPPA binding protein)-PAPPA interaction may be 100 nM or less, 10 nM or less, 5 nM or less, 2 nM or less, or 1 nM or less. More specifically, the KD of the PAPPA binding protein to human PAPPA interaction may be 100 nM or less 10 nM or less, 5 nM or less, 2 nM or less, or 1 nM or less. In an embodiment, the PAPPA binding protein binds to human PAPPA with an affinity (KD) of less than 1 nM. More particularly, the PAPPA binding protein binds to human PAPPA with an affinity (KD) of less than 500 pM, less than 250 pM, less than 200 pM or less than 150 pM. For example, particular PAPPA binding proteins bind to human PAPPA with an affinity (KD) of between 75 pM and 150 pM, such as between 90 pM and 135 pM. In an embodiment, binding affinity is measured using surface plasmon resonance (SPR) at 25° C. or 37° C. In a particular embodiment binding affinity is measured by BIACORE SPR at 37° C. For antigen binding proteins herein (i.e., PAPPA binding proteins) a smaller KD numerical value corresponds with stronger binding to an antigen such as PAPPA.

The dissociation rate constant (KD) or "off-rate" describes the stability of the antigen binding protein (i.e., PAPPA binding protein)-antigen (i.e., PAPPA) complex, i.e., the fraction of complexes that decay per second. For example, a kd of 0.01 $s^{-1}$ equates to 1% of the complexes decaying per second.

The dissociation rate constant (KD) of the PAPPA binding protein-PAPPA interaction may be $1\times10^{-3}$ $s^{-1}$ or less, $1\times10^{-4}$ $s^{-1}$ or less, $1\times10^{-5}$ $s^{-1}$ or less, or $1\times10^{-6}$ $s^{-1}$ or less. Alternatively, the kd may be between $1\times10^{-5}$ $s'1$ and $1\times10^{-4}$ $s^{-1}$ or between $1\times10^{-4}$ $s^{-1}$ and $1\times10^{-3}$ $s^{-1}$. Alternatively, the kd may be between $1\times10^{-3}$ $s^{-1}$ and $1\times10^{-2}$ $s^{-1}$-1.

The association rate constant (ka) or "on-rate" describes the rate of antigen binding protein (i.e., PAPPA binding protein)-antigen (i.e., PAPPA) complex formation. The ka of the PAPPA binding protein-PAPPA interaction may be about $1.5\times10^{5}$ $M^{-1}$ $s^{-1}$. Alternatively, the ka may be between $1\times10^{-6}$ $M^{-1}$ $s^{-1}$ and $1\times10^{5}$ $M^{-1}$ $s^{-1}$. Alternatively, the ka may be between $1\times10^{5}$ $M^{-1}$ $s^{-1}$ and $5\times10^{5}$ $M^{-1}$ $s^{-1}$ or between $1\times10^{5}$ $M^{-1}$ $s^{-1}$ and $8\times10^{5}$ $M^{-1}$ $s^{-1}$.

The PAPPA binding proteins disclosed herein fully or partially inhibits the biological activity of PAPPA such as the proteolytic cleavage activity of PAPPA. The PAPPA binding proteins disclosed herein can be neutralizing. As used herein the term "neutralize" or "neutralizing" refers to a reduction or elimination of the biological activity of the antigen (i.e., PAPPA) in the presence of a PAPPA binding protein as described herein, in comparison to the biological activity of the antigen (i.e., PAPPA) in the absence of the PAPPA binding protein, in vitro or in vivo. Antagonism and/or neutralization may be determined or measured using one or more assays, for example, as described herein. For example, the pAKT assay described in Example 1 (see method #3 and #5) or the ELISA assay for detection of IGFBPS full-length and fragments described in Example 4 (Method #1) may be used to assess the neutralizing capability of PAPPA binding proteins disclosed herein. Direct assessment of PAPPA neutralizing activity can also be envisaged using labelled recombinant IGFBP-4 or IGFBP-5 with FRET (fluorescence resonance energy transfer) assay for higher throughput screening.

The PAPPA binding proteins described herein inhibit cleavage of both IGFBP-4 and IGFBP-5. The cellular potency of the PAPPA binding proteins for inhibiting PAPPA-mediated cleavage of these IGFBPS was assessed. As used herein "$IC_{50}$" refers to the half maximal inhibitory concentration. As will be understood to the skilled person, $IC_{50}$ may also be expressed as "$pIC_{50}$" which refers to the negative log of the $IC_{50}$ value when converted to molar. In an embodiment, the PAPPA binding proteins disclosed herein have an $IC_{50}$ for inhibiting cleavage of IGFBP-4 and an $IC_{50}$ for inhibiting cleavage of IGFBP-5 both of which being 20 nM or less, 10 nM or less, 5 nM or less or 2.5 nM or less. In an embodiment the $IC_{50}$ for inhibiting cleavage of IGFBP-4 and the $IC_{50}$ for inhibiting cleavage of IGFBP-5 are both less than 2 nM. In an embodiment the $IC_{50}$ for inhibiting cleavage of IGFBP-4 and the $IC_{50}$ for inhibiting cleavage of IGFBP-5 are both between 0.1 nM and 2 nM.

In an embodiment the $IC_{50}$ for inhibiting cleavage of IGFBP-4 and IGFBP4 is determined using a pAKT response assay. Examples of a pAKT response assay are for example shown in (but are not limited to) the methods described in Example 1 (method #3 and #5). The principle of this assay is that IGF-1 is able to induce a pAKT response which can be measured (e.g. using ELISA) and which serves as a distal marker of IGF-1-IGF1R pathway engagement. Addition of IGFBP-4 or IGFBP-5 (either human or non-human) seques-ters the IGF-1 by forming IGF-1/IGFBP-4 complexes or IGF-1/IGFBP-5 complexes in turn reducing the IGF-1 related pAKT signal. Further addition of recombinant PAPPA results in cleavage of the IGF-1/IGFBP-4 complexes or IGF-1/IGFBP-5 complexes thus restoring the IGF-1 mediated pAKT signal. Using this approach, the PAPPA binding proteins disclosed herein were then assessed for their ability to inhibit restoration of the IGF-1 mediated pAKT signal (i.e., inhibit IGF-1 dependent phosphorylation of the AKT protein). In an embodiment, the $IC_{50}$ for inhib-iting cleavage of IGFBP-4 and IGFBP-5 was determined by measuring inhibition of IGF-1 dependent phosphorylation of the AKT protein induced by PAPPA mediated IGF-1 release from IGF-1/IGFBP-4 complexes and IGF-1/IGFBP-5 com-plexes.

The assay may be conducted using any suitable cell which has a robust pAKT response (i.e., robust IGF-1 dependent phosphorylation of the AKT protein) following addition of IGF-1. In an embodiment said inhibition of IGF-1 dependent phosphorylation of the AKT protein is measured using G401 cells or A549 cells. In an embodiment, the assay is con-ducted in G401 cells. In an embodiment the assay is con-ducted in G401 cells using recombinant PAPPA to cleave the IGF-1/IGFBP complexes and restore the pAKT signal. In an embodiment the assay is conducted in A549 cells. In an embodiment the assay is conducted in A549 cells wherein said A549 cells natively secrete PAPPA (i.e., human endog-enous PAPPA).

In an embodiment, the PAPPA binding proteins disclosed herein inhibit IGF-1 dependent phosphorylation of the AKT protein induced by PAPPA mediated IGF-1 release from both IGF-1/IGFBP4 complexes and IGF-1/IGFBP5 com-plexes with an $IC_{50}$ of less than 20 nM, less than 10 nM, less than 5 nM or less than 2.5 nM. In an embodiment, the PAPPA binding proteins disclosed herein inhibit IGF-1 dependent phosphorylation of the AKT protein induced by PAPPA mediated IGF-1 release from both IGF-1/IGFBP4 complexes and IGF-1/IGFBP5 complexes with an $IC_{50}$ less than 2 nM. In an embodiment the IGF-1/IGFBP4 complexes and the IGF-1/IGFBP5 complexes are human IGF-1/IG-FBP4 complexes and human IGF-1/IGFBP5 complexes. In an embodiment the PAPPA binding proteins disclosed herein reduce IGF-1/IGF1R pathway engagement.

In another embodiment the PAPPA binding proteins described herein were assessed for their ability to inhibit cleavage of both IGFBP-4 and IGFBP-5 by measuring the levels of full-length (i.e., intact) IGFBP-4 and IGFB-5 and/or by measuring the levels of IGFBP-4 and IGFBP-5 C-or N-terminal fragments. As previously described, PAPPA cleaves IGFBP4 and IGFBP5 at one site on each respective IGFBP. Cleavage of full length IGFBP-4 (as shown in SEQ ID NO: 7) or full length IGFBP5 (as shown in SEQ ID NO: 12) results in the IGFBP-4 or IGFBP-5 cleaving into two fragments of similar sizes referred to herein as N-terminal (Nt) and C-terminal (Ct) fragments. However, in the presence of the PAPPA binding proteins disclosed herein, PAPPA mediated cleavage of full length IGFBP-4 (or IGF-1/IGFBP-4 complexes) and full length IGFBP-5 (or IGF-1/ IGFBP-5 complexes) is inhibited. Thus, the levels of full length IGFBP-4 (or IGF-1/IGFBP-4 complexes) and full-length IGFBP-5 (or IGF-1/IGFBP-5 complexes) increase and the levels of IGFBP-4 C- and N-terminal fragments and IGFBP-5 C- and N-terminal fragments decrease. The increase in full-length IGFBP-4 (or IGF-1/IGFBP-4 complexes) and full length IGFBP-5 (or IGF-1/IGFBP-5 complexes) and/or said decrease in the levels of IGFBP-4 C- and/or N-terminal fragment and IGFBP-5 C- and/or N-terminal fragments can be detected using any suitable assay for measuring protein concentration (for example but not limited to mass spectrometry, ELISA, Western blot etc.). It is not considered necessary to measure decrease in the levels of both the N- and C-terminal fragments of IGFBP-4 and IGFBP-5 as measuring either will provide a measure of inhibited PAPPA-mediated IGFBP cleavage.

In an embodiment the PAPPA binding proteins disclosed herein inhibit cleavage of IGFBP4 (or IGF-1/IGFBP4 complexes) and IGFBP5 (or IGF-1/IGFBP5 complexes) into IGFBP-4 C-terminal and/or N-terminal fragments and IGFBP-5 C-terminal and/or N-terminal fragments respectively with a $pIC_{50}$ of between 8 and 12, for example between 8.2 and 11.8, 8.4 and 11.6, 8.6 and 11.4, 8.8 and 11.2 or between 9 and 11. In an embodiment, IGFBP4 corresponds to the sequence shown in SEQ ID NO: 7 and IGFBP5 corresponds to the sequence shown in SEQ ID NO: 12. In an embodiment, the IGFBP4 C-terminal fragment and the IGFBP-4 N-terminal fragment are the sequences shown in SEQ ID NO: 9 and SEQ ID NO: 8 respectively and the IGFBP5 C-terminal fragment and the IGFBP-5 N-terminal fragment are the sequences shown in SEQ ID NO: 14 and SEQ ID NO: 13 respectively. In an embodiment the PAPPA binding proteins disclosed herein inhibit cleavage of IGFBP4 into its IGFBP-4 C-terminal fragment with a $pIC_{50}$ of between 9 and 11. In an embodiment, the $pIC_{50}$ for inhibiting cleavage of IGFBP4 into its IGFBP-4 C-terminal fragment and/or N-terminal fragment is measured using A549 and/or 9-7 cells. In an embodiment said PAPPA binding proteins increase intact IGFBP4 with a $pEC_{50}$ of between 8 and 11, for example between 8.2 and 10.8, 8.4 and 10.6, 8.6 and 10.4, 8.8 and 10.2 or between 9 and 10. In an embodiment said PAPPA binding proteins increase intact IGFBP4 with a $pEC_{50}$ of between 9 and 10. In an embodiment the $pEC_{50}$ for increasing intact IGFBP4 is measured using A549 cells and/or 9-7 cells.

It has been reported that IGF-1 plays a role in cyst proliferation in patients suffering from polycystic kidney disease (PKD) (Kashyap et al JCI Insight. 2020 Feb. 27; 5 (4)). These reports suggest that cyst cells are hypersensitive to IGF-1-induced proliferation. Since PAPPA functions by cleaving IGFBP2, 4 and 5, thereby releasing IGF-1 from IGFBP-mediated sequestration (thus increasing its local signalling and paracrine effect on cell proliferation and metabolism) it has thus been hypothesised that inhibiting PAPPA's protease cleavage activity may prevent, slow or reduce cyst growth in a subject (e.g. a human subject). In an embodiment the PAPPA binding proteins disclosed herein reduce kidney and/or liver cyst growth following administration to a subject suffering from a polycystic kidney disease (PKD), optionally wherein said PKD is autosomal dominant PKD (ADPKD). In an embodiment said subject is a human being. In an embodiment said PAPPA binding protein reduces kidney cyst growth by greater than 10%, greater than 20%, greater than 30% greater than 40%, greater than 50%, greater than 55% or greater than 60%. In an embodiment said binding protein reduces kidney cyst growth by greater than 50%, greater than 55% or greater than 60%. In an embodiment, said PAPPA binding protein reduces kidney cyst growth by between 50% and 95%, by between 50% and 90% or by 50% and 85%. In an embodiment said reduction in kidney cyst growth is measured by determining reduction in total kidney volume (tKV). In some embodiments, total kidney volume may be adjusted for height of the subject. In an embodiment, said reduction in liver cyst growth is measured by determining reduction in liver volume (LV). Said reduction in kidney cyst growth is measured by determining reduction in total kidney volume (tKV) compared to the patients tKV prior to commencing treatment with the PAPPA binding proteins disclosed herein. In an embodiment, reduction in tkV is assessed at least 1-month following the subjects first treatment with the PAPPA binding protein, but more particularly at least 3-months, at least 6-months, at least 8-months, at least 10 months, at least 12-months, at least 18-months or at least 24-months following the subjects first treatment with the PAPPA binding protein. It is within the remit of the person skilled in the art to measure tKV (and LV) in a subject for example (but not in any way limited to) using the methods described in Example 4 (method #5) or for example using the methods outlined in Sharma et al. PLOS One. 2017 May 30; 12 (5).

In an embodiment the PAPPA binding proteins disclosed herein slow kidney and/or liver cyst growth following administration to a subject suffering from a polycystic kidney disease (PKD), optionally wherein said PKD is autosomal dominant PKD (ADPKD). In an embodiment, speed of kidney cyst growth is measured by monitoring tKV over a period of time. In an embodiment, following administration of the PAPPA binding proteins disclosed herein to a subject suffering from a PKD (optionally ADPKD), the rate of kidney cyst growth is reduced by greater than 2.5%, greater than 5%, greater than 7.5%, greater than 10%, greater than 15%, greater than 20%, greater than 25%, greater than 30%, greater than 35%, greater than 40%, greater than 50%, greater than 60%, greater than 65%, greater than 70%, greater than 85%, greater than 90% or greater than 95%. Reduction in cyst growth rate can be calculated by dividing absolute change in tKV values (i.e., the change in tKV value between a first tKV reading and a second tKV reading whereby a period of time has elapsed between said first and second tKV reading) by the previously obtained tKV. It can be represented by cyst growth rate=absolute change in tKV value/previously obtained tKV value. In an embodiment the PAPPA binding proteins disclosed herein slow kidney cyst growth following administration to a subject suffering from a PKD compared to said subject's pre-treatment growth rate. In an embodiment said pre-treatment growth rate is calculated by monitoring tKV over a period of time up to their first treatment with a PAPPA binding protein as disclosed herein. In an embodiment the PAPPA binding proteins disclosed herein slow kidney cyst growth following administration to a subject suffering from a PKD compared to the kidney cyst growth observed in a subject suffering from PKD who is administered a placebo.

As is further described in the section entitled "Epitope" below, the PAPPA binding proteins of the present disclosure (i.e., wherein said binding proteins inhibit cleavage of both IGFBP-4 and IGFBP-5) may bind to an epitope within the central M region of human PAPPA, more specifically to an epitope within the M1/M2 region of human PAPPA. In an embodiment said M1/M2 region of human PAPPA corresponds to amino acid residues 673-1213 of SEQ ID NO: 1. In an embodiment, the PAPPA binding proteins bind to an epitope within the M1/M2 region of human PAPPA wherein said epitope comprises one or more amino acids within residues 1031-1079 of SEQ ID NO: 1 (the corresponding residues within SEQ ID NO: 2 being 951-999). In an embodiment said epitope is represented by the amino acid sequence of SEQ ID NO: 118. In an embodiment, said epitope comprises one or more amino acids within residues 1067-1079 of SEQ ID NO: 1 (the corresponding residues within SEQ ID NO: 2 being 987-999). In an embodiment said epitope is represented by the amino acid sequence of SEQ ID NO: 4. In an embodiment, said epitope comprises residues Pro1075, Tyr1076 and Leu1079 of SEQ ID NO: 1.

However, in an alternative embodiment the PAPPA binding proteins disclosed herein (i.e., wherein said binding protein inhibits cleavage of both IGFBP-4 and IGFBP-5) binds to an epitope within the LNR3 domain of human PAPPA. In an embodiment the LNR3 domain of human PAPPA corresponds to amino acid residues 1558-1584 of SEQ ID NO:1 (the corresponding residues within SEQ ID NO: 2 being 1478-1504). In an embodiment said epitope comprises one or more amino acid residues 1557-1595 of SEQ ID NO: 1 (the corresponding residues within SEQ ID NO: 2 being 1477-1515). In an embodiment, the epitope is represented by the amino acid sequence of SEQ ID NO: 6.

In an embodiment the PAPPA binding proteins of the present disclosure have an AC-SINS Assay Score of less than 10, less than 8 or less than 6. As used herein the term "AC-SINS" refers to affinity-capture self-interaction nanoparticle spectroscopy. The lower the AC-SINS score the lower the propensity of a given antigen binding protein for self-association. AC-SINS score can be measured for example using the methodology described in Example 11 herein. In an embodiment, the PAPPA binding proteins of the present disclosure have an AC-SINS assay score that is reduced by greater than 60% compared to the AC-SINS Assay Score of Vesencumab.

There is herein provided PAPPA binding proteins comprising complementarity determining region (CDR) amino acid sequences. These are the hypervariable regions of PAPPA binding proteins herein, such as immunoglobulin heavy and light chains. Typically, there are three heavy chain and three light chain CDRs (or CDR regions) in the variable portion of a PAPPA binding protein such as an immunoglobulin. Thus, "CDRs" as used herein can refer to three heavy chain CDRs of a PAPPA binding protein, three light chain CDRs of a PAPPA binding protein, all heavy and light chain CDRs of a PAPPA binding protein, or at least two CDRs of a PAPPA binding protein. However, the present disclosure does foresee PAPPA binding proteins having heavy and/or light chains with less than three CDR's for example when it is discovered using appropriate structural methods (e.g., Cryo Electron Microscopy) that a region identified as being a CDR region does not in fact bind to the antigen. Throughout this specification, amino acid residues in variable domain sequences and variable domain regions within full-length PAPPA binding sequences, e.g., within an antibody heavy chain sequence or antibody light chain sequence, are numbered according to the Kabat numbering convention. Similarly, the terms "CDR", "CDRL1", "CDRL2", "CDRL3", "CDRH1", "CDRH2", and "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

There are alternative numbering conventions for amino acid residues in variable domain sequences and full-length antibody sequences. Throughout this specification, amino acid residues in Fc regions, in antibody sequences or full-length PAPPA binding protein sequences, are numbered according to the EU index numbering convention.

There are also alternative numbering conventions for CDR sequences, for example, those set out in Chothia et al. (1989) Nature 342:877-883. The structure and protein folding of the PAPPA binding protein may mean that other residues are considered part of the CDR sequence and would be understood to be so by a skilled person. Other numbering conventions for CDR sequences available to a skilled person include "AbM" (University of Bath) and "contact" (University College London) methods. The CDR regions for SEQ ID NOs: 21, 33, 45, 57, 69, 81, 93 or 105 and SEQ ID NOs: 27, 39, 51, 63, 75, 87, 99 or 111 can be defined by any numbering convention, for example, the Kabat, Chothia, AbM, and contact conventions. Table 1 below represents one definition using each numbering convention for CDRs, or binding unit, provided herein. The Kabat numbering scheme is used in Table 1 to number the variable domain amino acid sequence. It should be noted that CDR definitions can vary depending on the individual publication used.

TABLE 1

| CDR Numbering | | | |
|---|---|---|---|
| | Kabat CDR | Chothia CDR | AbM CDR | Contact CDR |
|---|---|---|---|---|
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

CDRs of a PAPPA binding protein provided herein can be modified by one or by more than one amino acid substitution, deletion, or addition, wherein the variant PAPPA binding protein substantially retains the biological characteristics of the unmodified protein, such as inhibiting the cleavage of both IGFBP-4 and IGFB-5. It will be appreciated that each of CDRH1, CDRH2, CDRH3, CDRL1, CDRL2, or CDRL3 may be modified alone or in combination with any other CDR, in any permutation or combination. A CDR may be modified by the substitution, deletion, or addition of up to 3 amino acids, for example, 1 or 2 amino acids, for example, 1 amino acid. Each modification of a CDR, VH, VL, or other protein provided herein can be a conservative substitution. A modification can be a conservative substitution, for example, as shown in Table 2a or in Table 2b below.

TABLE 2a

| Examples of conservative substitutions by side chain type | |
|---|---|
| Side chain | Members |
|---|---|
| Hydrophobic | Met, Ala, Val, Leu, Ile |
| Neutral hydrophilic | Cys, Ser, Thr |
| Acidic | Asp, Glu |

TABLE 2a-continued

Examples of conservative substitutions by side chain type

| Side chain | Members |
| --- | --- |
| Basic | Asn, Gln, His, Lys, Arg |
| Residues that influence chain orientation | Gly, Pro |
| Aromatic | Trp, Tyr, Phe |

TABLE 2b

Examples of conservative substitutions by amino acid

| Amino Acid | Conservative Substitution |
| --- | --- |
| A | D, E, G, S, T |
| C | G, R, S, W, Y |
| D | A, E, G, H, N, V, Y |
| E | A, D, G, K, Q, V |
| F | I, L, Y |
| G | A, C, D, E, R |
| H | D, L, N, P, Q, R, Y |
| I | F, L, M, N, V |
| K | E, M, N, Q, R, T |
| L | F, H, I, M, P, Q, R, V, W |
| M | I, K, L, R, T, V |
| N | D, H, I, K, S, T, Y |
| P | H, L, Q, R, S |
| Q | E, H, L, L, P, R |
| R | C, G, H, K, L, M, P, Q, T, W |
| S | A, C, N, P, T, W, Y |
| T | A, K, M, N, R, S |
| V | D, E, I, L, M |
| W | C, L, R, S |
| Y | C, D, F, H, N, S |

For example, in a variant CDR, one or more flanking residues that comprise the CDR as part of alternative definition(s), e.g., Kabat or Chothia, may be substituted with a conservative amino acid residue. Such PAPPA binding proteins comprising variant CDRs as described above may be referred to herein as "functional CDR variants".

In a particular aspect there is provided a PAPPA binding protein comprising: (a) (i) any one or a combination of CDRs selected from CDRH1, CDRH2, CDRH3 from SEQ ID NOs: 21, 33, 45, 57, 69, 81, 93 and 105, and/or CDRL1, CDRL2, CDRL3 from SEQ ID NOs: 27, 39, 51, 63, 75, 87, 99 and 111; or (ii) a CDR variant of (i), wherein the variant has 1, 2, or 3 amino acid modifications; or (b) a VH region comprising a sequence at least 80% identical to the sequence of SEQ ID NOs: 21, 33, 45, 57, 69, 81, 93 or 105; and/or a VL region comprising a sequence at least 80% identical to the sequence of SEQ ID NOS: 27, 39, 51, 63, 75, 87, 99 or 111. In an embodiment the CDR of (a) (i) is: a CDRH1 selected from SEQ ID NOs: 23, 35, 47, 59, 71, 83, 95 and 107; a CDRH2 selected from SEQ ID NOs: 24, 36, 48, 60, 72, 84, 96 and 108; and/or a CDRH3 selected from SEQ ID NOs: 25, 37, 49, 61, 73, 85, 97 and 109; a CDRL1 selected from SEQ ID NOs: 29, 41, 53, 65, 77, 89, 101 and 113; a CDRL2 selected from SEQ ID NOs: 30, 42, 54, 66, 78, 90, 102 and 114; and/or CDRL3 selected from SEQ ID NOs: 31, 43, 55, 67, 79, 91, 103 and 115.

In an embodiment said PAPPA binding protein comprises: (a) (i) any one or a combination of CDRs selected from CDRH1, CDRH2 and/or CDRH3 from SEQ ID NO: 45 and/or CDRL1, CDRL2 and/or CDRL3 from SEQ ID NO: 51; or (ii) a CDR variant of (i), wherein the variant has 1, 2, or 3 amino acid modifications; or (b) a VH region comprising a sequence at least 80% identical to the sequence of SEQ ID NO: 45; and/or a VL region comprising a sequence at least 80% identical to the sequence of SEQ ID NO: 51. In an embodiment the CDR of (a) (i) is: a CDRH1 of SEQ ID NO: 47; a CDRH2 of SEQ ID NO: 48; and/or a CDRH3 of SEQ ID NO: 49; a CDRL1 of SEQ ID NO: 53; a CDRL2 of SEQ ID NO: 54; and/or a CDRL3 of SEQ ID NO: 55.

In an embodiment said PAPPA binding protein comprises: (a) (i) any one or a combination of CDRs selected from CDRH1, CDRH2 and/or CDRH3 from SEQ ID NO: 69 and/or CDRL1, CDRL2 and/or CDRL3 from SEQ ID NO: 75; or (ii) a CDR variant of (i), wherein the variant has 1, 2, or 3 amino acid modifications; or (b) a VH region comprising a sequence at least 80% identical to the sequence of SEQ ID NO: 69; and/or a VL region comprising a sequence at least 80% identical to the sequence of SEQ ID NO: 75. In an embodiment the CDR of (a) (i) is: a CDRH1 of SEQ ID NO: 71; a CDRH2 of SEQ ID NO: 72; and/or a CDRH3 of SEQ ID NO: 73; a CDRL1 of SEQ ID NO: 77; a CDRL2 of SEQ ID NO: 78; and/or a CDRL3 of SEQ ID NO: 79.

In an embodiment said PAPPA binding protein comprises: (a) (i) any one or a combination of CDRs selected from CDRH1, CDRH2 and/or CDRH3 from SEQ ID NO: 93 and/or CDRL1, CDRL2 and/or CDRL3 from SEQ ID NO: 99; or (ii) a CDR variant of (i), wherein the variant has 1, 2, or 3 amino acid modifications; or (b) a VH region comprising a sequence at least 80% identical to the sequence of SEQ ID NO: 93; and/or a VL region comprising a sequence at least 80% identical to the sequence of SEQ ID NO: 99. In an embodiment the CDR of (a) (i) is: a CDRH1 of SEQ ID NO: 95; a CDRH2 of SEQ ID NO: 96; and/or a CDRH3 of SEQ ID NO: 97; a CDRL1 of SEQ ID NO: 101; a CDRL2 of SEQ ID NO: 102; and/or a CDRL3 of SEQ ID NO: 103.

In an embodiment said PAPPA binding protein comprises: (a) (i) any one or a combination of CDRs selected from CDRH1, CDRH2 and/or CDRH3 from SEQ ID NO: 105 and/or CDRL1, CDRL2 and/or CDRL3 from SEQ ID NO: 111; or (ii) a CDR variant of (i), wherein the variant has 1, 2, or 3 amino acid modifications; or (b) a VH region comprising a sequence at least 80% identical to the sequence of SEQ ID NO: 105; and/or a VL region comprising a sequence at least 80% identical to the sequence of SEQ ID NO: 111. In an embodiment the CDR of (a) (i) is: a CDRH1 of SEQ ID NO: 107; a CDRH2 of SEQ ID NO: 108; and/or a CDRH3 of SEQ ID NO: 109; a CDRL1 of SEQ ID NO: 113; a CDRL2 of SEQ ID NO: 114; and/or a CDRL3 of SEQ ID NO: 115.

"Percent identity" or "% identity" between a query nucleic acid sequence and a subject nucleic acid sequence is the "Identities" value, expressed as a percentage, that is calculated using a suitable algorithm (e.g., BLASTN, FASTA, Needleman-Wunsch, Smith-Waterman, LALIGN, or GenePAST/KERR) or software (e.g., DNASTAR Lasergene, GenomeQuest, EMBOSS needle, or EMBOSS infoalign), over the length of the query sequence after alignment, such as a pair-wise global sequence alignment, has been performed using a suitable algorithm (e.g., Needleman-Wunsch or GenePAST/KERR) or software (e.g., DNASTAR Lasergene or GenePAST/KERR). A query nucleic acid sequence may be a nucleic acid sequence disclosed herein, in particular in one or more of the claims or clauses. "Percent identity" or "% identity" between a query amino acid sequence and a subject amino acid sequence is the "Identities" value, expressed as a percentage, that is calculated using a suitable algorithm (e.g., BLASTP, FASTA, Needleman-Wunsch, Smith-Waterman, LALIGN, or GenePAST/KERR) or software (e.g., DNASTAR Lasergene, GenomeQuest, EMBOSS needle, or EMBOSS infoalign), over the length of the query sequence after alignment, such as a pair-wise global sequence alignment, has been performed using a suitable algorithm (e.g., Needleman-Wunsch or GenePAST/KERR) or software (e.g., DNASTAR Lasergene or GenePAST/KERR). A query amino acid sequence may be described by an amino acid sequence disclosed herein, in particular in one or more of the claims or clauses.

A query sequence may be 100% identical to a subject sequence, or it may include up to an integer number of amino acid or nucleotide alterations as compared to the subject sequence, such that the % identity is less than 100%. For example, a query sequence can be at least at least 50%, at least 60%, at least 70%, at least 75%, at least 80%, at least 85%, at least 90%, at least 95%, at least 96%, at least 97%, at least 98%, or at least 99% identical to a subject sequence. In the case of nucleic acid sequences, such alterations can comprise at least one nucleotide residue deletion, substitution, or insertion, wherein said alterations may occur at the 5'- or 3'-terminal positions of the query sequence, at one or more positions between those terminal positions, interspersed either individually among the nucleotide residues in a query sequence, or in one or more contiguous groups within a query sequence. In the case of amino acid sequences, such alterations can comprise at least one amino acid residue deletion, substitution (including conservative and non-conservative substitutions), or insertion, wherein said alterations may occur at the amino- or carboxy-terminal positions of a query sequence, or at one or more positions between those terminal positions, interspersed either individually among the amino acid residues in a query sequence, or in one or more contiguous groups within a query sequence.

For antibody sequences, a % identity may be determined across the entire length of a query sequence, including the CDRs. A calculated % identity may exclude one or more or all of the CDRs. For example, all of the CDRs of an antibody may be 100% identical to a subject sequence, while a % identity in the remaining portion of the query sequence, e.g., the framework sequence, can be less than 100%, such that that the CDR sequences are fixed and intact.

In an embodiment said PAPPA binding protein comprises: a CDRH1 that is 100% identical to SEQ ID NOs: 23, 35, 47, 59, 71, 83, 95 or 107; a CDRH2 that is 100% identical to SEQ ID NOs: 24, 36, 48, 60, 72, 84, 96 or 108; and/or a CDRH3 that is 100% identical to SEQ ID NOs: 25, 37, 49, 61, 73, 85, 97 or 109; a CDRL1 that is 100% identical to SEQ ID NOs: 29, 41, 53, 65, 77, 89, 101 or 113; a CDRL2 that is 100% identical to SEQ ID NOs: 30, 42, 54, 66, 78, 90, 102 or 114; and/or a CDRL3 that is 100% identical to SEQ ID NOs: 31, 43, 55, 67, 79, 91, 103 and 115. In an embodiment said PAPPA binding protein comprises: a CDRH1 that is 100% identical to SEQ ID NOs: 23, 35, 47, 59, 71, 83, 95 or 107; a CDRH2 that is 100% identical to SEQ ID NOs: 24, 36, 48, 60, 72, 84, 96 or 108; and a CDRH3 that is 100% identical to SEQ ID NOs: 25, 37, 49, 61, 73, 85, 97 or 109; a CDRL1 that is 100% identical to SEQ ID NOs: 29, 41, 53, 65, 77, 89, 101 or 113; a CDRL2 that is 100% identical to SEQ ID NOs: 30, 42, 54, 66, 78, 90, 102 or 114; and a CDRL3 that is 100% identical to SEQ ID NOs: 31, 43, 55, 67, 79, 91, 103 and 115.

In an embodiment, five CDRs are present in the PAPPA binding protein. In an embodiment the PAPPA binding protein comprises the following five CDRs: CDRH1 of SEQ ID NO: 107; CDRH2 of SEQ ID NO: 108 and CDRH3 of SEQ ID NO: 109; and CDRL1 of SEQ ID NO: 113; and CDRL3 of SEQ ID NO: 115. Alternatively, in an embodiment six CDRs are identifiable in the PAPPA binding protein using an annotation scheme such as Chothia, Kabat etc., however only five of said six CDRs bind to human PAPPA. In an embodiment the PAPPA binding protein comprises the following six CDRs: CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114 and CDRL3 of SEQ ID NO: 115, but wherein CDRL2 does not bind to human PAPPA.

In an embodiment all six CDRs are present in the PAPPA binding protein. In an embodiment, the PAPPA binding protein comprises the following 6 CDRs: a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 55; or b) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

In an embodiment, said PAPPA binding protein comprises the following 6 CDRs: CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115. In an embodiment, said PAPPA binding protein is an anti-PAPPA antibody, said antibody comprising a variable heavy chain sequence comprising three heavy chain CDR sequences (CDRH1, CDRH2 and CDRH3) and a variable light chain sequence comprising three light chain CDR sequences (CDRL1, CDRL2 and CDRL3) wherein CDRH1 comprises the sequence as shown in SEQ ID NO: 107, CDRH2 comprises the sequence as shown in SEQ ID NO: 108, CDRH3 comprises the sequence as shown in SEQ ID NO: 109, CDRL1 comprises the sequence as shown in SEQ ID NO: 113, CDRL2 comprises the sequence as shown in SEQ ID NO: 114 and CDRL3 comprises the sequence as shown in SEQ ID NO: 115.

In an embodiment, said PAPPA binding protein comprises a) a VH region that is 90% identical to SEQ ID NO: 45 and/or a VL region that is 90% identical to SEQ ID NO: 51; or b) a VH region that is 90% identical to SEQ ID NO: 69 and/or a VL region that is 90% identical to SEQ ID NO: 75; or c) a VH region that is 90% identical to SEQ ID NO: 93 and/or a VL region that is 90% identical to SEQ ID NO: 99; or d) a VH region that is 90% identical to SEQ ID NO: 105 and/or a VL region that is 90% identical to SEQ ID NO: 111. In an embodiment said PAPPA binding protein comprises a VH region that is 90% identical to SEQ ID NO: 105 and/or a VL region that is 90% identical to SEQ ID NO: 111. In an embodiment, said PAPPA binding protein comprises a) a VH region that is 90% identical to SEQ ID NO: 45 and a VL region that is 90% identical to SEQ ID NO: 51; or b) a VH region that is 90% identical to SEQ ID NO: 69 and a VL region that is 90% identical to SEQ ID NO: 75; or c) a VH region that is 90% identical to SEQ ID NO: 93 and a VL region that is 90% identical to SEQ ID NO: 99; or d) a VH region that is 90% identical to SEQ ID NO: 105 and a VL region that is 90% identical to SEQ ID NO: 111. In an embodiment said PAPPA binding protein comprises a VH region that is 90% identical to SEQ ID NO: 105 and a VL region that is 90% identical to SEQ ID NO: 111.

In an embodiment said PAPPA binding protein comprises a) a VH region that is 100% identical to SEQ ID NO: 45 and/or a VL region that is 100% identical to SEQ ID NO: 51; or b) a VH region that is 100% identical to SEQ ID NO: 69 and/or a VL region that is 100% identical to SEQ ID NO: 75; or c) a VH region that is 100% identical to SEQ ID NO: 93 and/or a VL region that is 100% identical to SEQ ID NO: 99; or d) a VH region that is 100% identical to SEQ ID NO: 105 and/or a VL region that is 100% identical to SEQ ID NO: 111. In an embodiment said binding protein comprises a VH region that is 100% identical to SEQ ID NO: 105 and/or a VL region that is 100% identical to SEQ ID NO: 111. In an embodiment said PAPPA binding protein comprises a) a VH region that is 100% identical to SEQ ID NO: 45 and a VL region that is 100% identical to SEQ ID NO: 51; or b) a VH region that is 100% identical to SEQ ID NO: 69 and a VL region that is 100% identical to SEQ ID NO: 75; or c) a VH region that is 100% identical to SEQ ID NO: 93 and a VL region that is 100% identical to SEQ ID NO: 99; or d) a VH region that is 100% identical to SEQ ID NO: 105 and a VL region that is 100% identical to SEQ ID NO: 111. In an embodiment said binding protein comprises a VH region that is 100% identical to SEQ ID NO: 105 and a VL region that is 100% identical to SEQ ID NO: 111.

In an embodiment, said PAPPA binding protein is an anti-PAPPA antibody, said antibody comprising the variable heavy chain sequence as shown in SEQ ID NO: 105 and the variable light chain sequence as shown in SEQ ID NO: 111.

In an embodiment said PAPPA binding protein comprises a heavy chain constant region as shown in SEQ ID NO: 17 and a light chain constant region as shown in SEQ ID NO: 19. In an embodiment, the PAPPA binding proteins disclosed herein comprise an IgG1 Fc region.

In an embodiment, said PAPPA binding protein comprises a heavy chain and a light chain, wherein the amino acid sequence of the heavy chain is shown in SEQ ID NOs: 20, 32, 44, 56, 68, 80, 92 and 104; and/or the amino acid sequence of the light chain is shown in SEQ ID NOs: 26, 38, 50, 62, 74, 86, 98 and 110. In an embodiment said PAPPA binding protein comprises a heavy chain and a light chain, wherein the amino acid sequence of the heavy chain is shown in SEQ ID NO: 104 and/or the amino acid sequence of the light chain is shown in SEQ ID NO: 110. In an embodiment, said PAPPA binding protein comprises a heavy chain and a light chain, wherein the amino acid sequence of the heavy chain is shown in SEQ ID NOs: 20, 32, 44, 56, 68, 80, 92 and 104; and the amino acid sequence of the light chain is shown in SEQ ID NOs: 26, 38, 50, 62, 74, 86, 98 and 110. In an embodiment said PAPPA binding protein comprises a heavy chain and a light chain, wherein the amino acid sequence of the heavy chain is shown in SEQ ID NO: 104 and the amino acid sequence of the light chain is shown in SEQ ID NO: 110. In an embodiment, said PAPPA binding protein is an anti-PAPPA antibody, said antibody comprising the heavy chain sequence as shown in SEQ ID NO: 104 and the light chain sequence as shown in SEQ ID NO: 110.

There is further provided a PAPPA binding protein that binds to human PAPPA and competes for binding to said human PAPPA with a reference PAPPA binding protein, wherein said reference PAPPA binding protein comprises a variable heavy chain sequence of SEQ ID NO: 21, 33, 45, 57, 69, 81, 93 or 105; and a variable light chain sequence of SEQ ID NO: 27, 39, 51, 63, 75, 87, 99 or 111. Competition between a PAPPA binding protein described herein and a reference PAPPA binding protein, e.g., a reference antibody, may be determined by one or more techniques known to the skilled person such as ELISA, FMAT, Surface Plasmon Resonance (SPR) or FORTEBIO OCTET Bio-Layer Interferometry (BLI). Such techniques can be referred to as epitope binning. A competition assay may be carried out, for example, using flow cytometry-based epitope binning. Competition can occur, for example, when two proteins bind to the same or overlapping epitopes, when there is steric inhibition of binding, or in a case wherein binding of the first protein induces a conformational change in the antigen that can prevent or reduce binding of the second protein. A PAPPA binding protein may bind to human PAPPA and compete for binding to human PAPPA with a reference PAPPA binding protein. A reference PAPPA binding protein may comprise (a) a VH region sequence of SEQ ID NO: 45 and a VL region sequence of SEQ ID NO: 51; (b) a VH region sequence of SEQ ID NO: 69 and a VL region sequence of SEQ ID NO: 75; (c) a VH region sequence of SEQ ID NO: 93 and a VL region sequence of SEQ ID NO: 99; or (d) a VH region sequence of SEQ ID NO: 105 and a VL region sequence of SEQ ID NO: 111.

In an embodiment the PAPPA binding proteins disclosed herein is derived from a mammal. In an embodiment, the PAPPA binding protein disclosed herein are human PAPPA binding proteins.

In a preferred embodiment the PAPPA binding proteins disclosed herein may be an antibody or an antigen binding fragment thereof.

The term "antibody" is used herein in the broadest sense to refer to molecules with an immunoglobulin-like domain (for example, IgG, IgM, IgA, IgD, or IgE) and includes monoclonal, recombinant, polyclonal, chimeric, human, humanized, multispecific antibodies, including bispecific antibodies, and heteroconjugate antibodies; a single variable domain (e.g., a domain antibody (DAB)), antigen binding antibody fragments, Fab, F(ab')$_2$, Fv, disulfide linked Fv, single chain Fv, disulfide-linked scFv, diabodies, TANDABS, etc. and modified versions of any of the foregoing. In a particular embodiment the antibody is a monoclonal antibody.

An antibody as provided herein (also known as an immunoglobulin, or Ig) can comprise a heterotetrameric glycoprotein with an approximate molecular weight of 150,000 daltons. An antibody comprises two heavy chains (HCs) (which are typically identical) and two light chains (LCs) (which are typically identical) linked by covalent disulfide bonds. This $H_2L_2$ structure can fold to form three functional domains: two fragment antigen binding regions (Fab regions) and a crystallisable fragment region (Fc region). A Fab region comprises a variable domain, which comprises variable heavy (VH) and variable light (VL) chains, at the amino-terminus, and a constant domain, which comprises a first domain of a constant heavy chain (CH) and a constant light chain (CL) at the carboxyl-terminus. An Fc region comprises two domains formed by dimerization of paired second and third domains (CH2 and CH3) of two constant heavy chains (CH). An Fc region may elicit effector functions, for example, by binding to receptors on immune cells or by binding C1q, the first component of the classical complement pathway. Five classes of antibodies IgM, IgA, IgG, IgE, and IgD are defined by distinct heavy chain amino acid sequences: μ, α, γ, ε, and δ; each heavy chain can pair with either a K or A light chain. Typically, the majority of antibodies in the serum belong to the IgG class; there are four isotypes of human IgG (IgG1, IgG2, IgG3, and IgG4), the sequences of which differ mainly in their hinge region.

Antibodies provided herein can be fully human antibodies, and can be obtained using a variety of methods, for example, using a library of human antibodies or fragments in conjunction with an antibody display system like phage or yeast display or immunizing transgenic animals (e.g., mice) that are capable of producing repertoires of human antibodies. In some cases, transgenic animals that have been modified to express human immunoglobulin genes can be immunised with an antigen of interest and antigen specific human antibodies can be isolated using a variety of antibody discovery techniques including B-cell cloning, hybridoma, and repertoire sequencing. Human antibodies produced using these techniques can then be screened for desired properties such as activity, affinity, developability, and selectivity.

Alternative antibody formats can include alternative scaffolds in which the one or more CDRs of the antigen binding protein (e.g., PAPPA binding protein) can be arranged onto a suitable non-immunoglobulin protein scaffold or skeleton, such as an affibody, a SpA scaffold, an LDL receptor class A domain, an avimer, or an EGF domain.

An antibody provided herein can be a "humanized antibody," which refers to a type of engineered antibody having CDRs derived from a non-human donor immunoglobulin, the remaining immunoglobulin-derived parts of the molecule being derived from one or more human immunoglobulin(s). In addition, framework support residues may be altered to preserve binding affinity. A suitable human acceptor antibody may be one selected from a conventional database (e.g., the KABAT database, Los Alamos database, and Swiss Protein database), or by homology to the nucleotide and/or amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains may originate from the same acceptor antibody or different acceptor antibodies.

The term "donor antibody" refers to an antibody that contributes the amino acid sequences of one or more of its variable regions, CDRs, or other functional fragments or analogues thereof to a first immunoglobulin partner. A donor, therefore, provides the altered immunoglobulin coding region and thus provides the resulting expressed altered antibody with the antigenic specificity and neutralising activity characteristic of a donor antibody. The term "acceptor antibody" refers to an antibody that is heterologous to a donor antibody, which contributes all (or any portion) of the amino acid sequences encoding its heavy and/or light chain framework regions and/or its heavy and/or light chain constant regions to the first immunoglobulin partner. A human antibody may be an acceptor antibody.

The term "domain" refers to a folded polypeptide structure that can retain its tertiary structure independent of the rest of the polypeptide. Generally, domains are responsible for discrete functional properties of polypeptides and in many cases may be added, removed, or transferred to other polypeptides without loss of function of the remainder of the protein and/or of the domain. The term "single variable domain" refers to a folded polypeptide domain comprising sequences characteristic of antibody variable domains. It therefore includes complete antibody variable domains such as VH, VHH, and VL and/or modified antibody variable domains, for example, in which one or more loops have been replaced by sequences that are not characteristic of antibody variable domains, or antibody variable domains that have been truncated or comprise N- or C-terminal extensions, as well as folded fragments of variable domains that retain at least the binding activity and specificity of the full-length domain. A single variable domain herein is capable of binding an antigen or epitope independently of a different variable region or domain. A "domain antibody" or "DAB" can be a human "single variable domain". A single variable domain may be a human single variable domain but can also be a single variable domain from a non-human species such as rodent (for example, as in WO 00/29004), a nurse shark, or a Camelid. Notably, camelid VHHs are immunoglobulin single variable domain polypeptides that are derived from camelid species, such as camel, llama, alpaca, dromedary, and guanaco, which produce heavy chain only antibodies that are naturally devoid of light chains. Such VHH domains may be humanized according to standard techniques available in the art, and such domains can be "single variable domains".

An antigen binding fragment may be provided by means of arrangement of one or more CDRs on one or more non-antibody protein scaffolds. "Protein Scaffold" as used herein includes, but is not limited to, an immunoglobulin (Ig) scaffold, for example, an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. A protein scaffold may be an Ig scaffold, for example, an IgG or IgA scaffold. An IgG scaffold may comprise some or all the domains of an antibody (i.e., CH1, CH2, CH3, VH, VL). An antigen binding protein may comprise an IgG scaffold selected from IgG1, IgG2, IgG3, IgG4, or IgG4PE. For example, a scaffold may be IgG1. A scaffold may consist of, or comprise, an Fc region of an antibody or a fragment thereof. A protein scaffold may be a derivative of a scaffold selected from the group consisting of CTLA-4, lipocalin, Protein A derived molecules such as Z-domain of Protein A (Affibody, SpA), Adomain (Avimer/Maxibody); heat shock proteins such as GroEl and GroES; transferrin (trans-body); ankyrin repeat protein (DARPin); peptide aptamer; C-type lectin domain (Tetranectin); human g-crystallin and human ubiquitin (affilins); PDZ domains; scorpion toxin kunitz type domains of human protease inhibitors; and fibronectin/adnectin which has been subjected to protein engineering in order to obtain binding to an antigen, such as PAPPA, other than a natural ligand.

The term multi-specific antigen binding protein refers to an antigen binding protein that comprises at least two different antigen binding sites. Each of these antigen-binding sites can be capable of binding to a different epitope than another of the antigen-binding sites; the antigen binding sites can be present on the same antigen or on different antigens. A multi-specific antigen binding protein may have specificity for more than one antigen, for example, two antigens, or three antigens, or four antigens. A multi-specific antigen binding protein having specificity for two antigens can be referred to as a bispecific antigen binding protein. A bispecific antigen binding protein (i.e., a bispecific) can be classified as having a symmetric or asymmetric architecture. A bispecific antigen binding protein can be a bispecific antibody. A bispecific may have an Fc region or may be fragment-based (lacking an Fc region). A fragment-based bispecific can combine multiple antigen-binding fragments in one molecule without an Fc region or with a portion of an Fc region e.g., Fab-scFv, Fab-scFv2, orthogonal Fab-Fab, Fab-Fv, tandem scFc (e.g., BiTE and BiKE molecules), Diabody, DART, TandAb, scDiabody, tandem dAb, etc. A symmetric format can combine multiple binding specificities in a single polypeptide chain or single HL pair. Examples can include an Fc-fusion protein(s) of a fragment-based format or a format whereby one or more antibody fragments are fused to an antibody molecule or other antigen binding protein. Examples of symmetric formats may include DVD-Ig, TVD-Ig, CODV-Ig, (scFv) 4-Fc, IgG-(scFv) 2, Tetravalent DART-Fc, F(ab)₄CrossMab, IgG-HC-scFv, IgG-LC-scFv, mAb-dAb, etc. An asymmetric format can retain as closely as possible the native architecture of a natural antibody by forcing correct HL chain pairing and/or promoting H chain heterodimerization during the co-expression of three (if common heavy or light chains are used) or four polypeptide chains, e.g., Triomab, asymmetric reengineering technology immunoglobulin (ART-Ig), CrossMab, Biclonics common light chain, ZW1 common light chain, DuoBody and knobs into holes (KiH), DuetMab, KA body, Xmab, YBODY, HET-mAb, HET-Fab, DART-Fc, SEED-body, mouse/rat chimeric IgG. Bispecific formats can also include an antibody fused to a non-Ig scaffold, such as Affimabs, Fynomabs, Zybodies, Anticalin-IgG fusions, or ImmTAC.

A PAPPA binding protein provided herein can comprise a sequence that is a variant amino acid sequence. A nucleic acid sequence of a PAPPA binding protein provided herein can comprise a variant nucleic acid sequence. A variant nucleic acid sequence herein can be of a PAPPA binding protein provided herein or of a variant thereof.

A VH or VL (or heavy chain or light chain) sequence may be a variant sequence of a VH or VL (or heavy chain or light chain) sequence provided herein with up to 10 amino acid substitutions, additions or deletions. Such variant sequence may have 10, 9, 8, 7, 6, 5, 4, 3, 2 or 1 amino acid substitution(s), addition(s) or deletion(s). A heavy chain sequence may be a variant sequence of an heavy chain sequence provided herein with up to 40 amino acid substitutions, additions or deletions. A heavy chain variant sequence may have up to 35, up to 30, up to 25, up to 20, up to 15 or up to 10 amino acid substitutions, additions or deletions. A heavy chain variant sequence may have 10, 9, 8, 7, 6, 5, 4, 3, 2, or 1 amino acid substitutions, additions, or deletions. A light chain sequence may be a variant sequence of an light chain sequence provided herein with up to 20 amino acid substitutions, additions or deletions. A light chain variant sequence may have up to 15, up to 10 or up to 5 amino acid substitutions, additions or deletions. A light chain variant sequence may have 10, 9, 8, 7, 6, 5, 4, 3, 2, or 1 amino acid substitutions, additions, or deletions.

A sequence variation may exclude one or more or all of the CDRs. For example, the CDRs portion of the VH or VL (or heavy chain or light chain) sequence can be free of a sequence variation, and the variation can be present in a non-CDR portion of a VH or VL (or heavy chain or light chain) sequence, i.e., such that the CDR sequences are intact.

A variation can be a substitution, such as a conservative substitution, for example as provided in Table 2a or Table 2b above.

A PAPPA binding protein having a variant sequence can substantially retain the biological characteristics of an unmodified PAPPA binding protein, such as inhibiting cleavage of IGFBP4 and IGFBP5. A binding property (e.g., KD, Kd, or Ka) of a PAPPA binding protein having a variant sequence can be substantially identical to an unmodified PAPPA binding protein. A binding property (e.g., KD, Kd, or Ka) of a variant sequence can be at least 75%, at least 90%, at least 95%, or at least 99% identical to that of an unmodified PAPPA binding protein.

In an embodiment the PAPPA binding proteins disclosed herein (e.g. antibody or antigen binding fragment thereof) comprises a modified Fc region. Fc engineering methods can be applied to modify the functional or pharmacokinetic properties of a PAPPA binding protein comprising an Fc region, such as an antibody. Binding to Fcγ can promote ADCC activity; thus ADCC activity may be altered by making mutations in the Fc region that can increase or decrease binding to Fcγ receptors. Binding to C1q can promote CDC activity; thus, CDC activity may be altered by making mutations in the Fc region that can increase or decrease binding to C1q receptor. Modifications to the glycosylation pattern of an antigen binding protein can also be made to change the effector function. The in vivo half-life of an antigen binding protein can be altered by making mutations that affect binding of the Fc region to the FcRn (Neonatal Fc Receptor).

The term "Effector Function" as used herein refers to one or more antigen binding protein (e.g., antibody) mediated effects, including but not limited to antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

The interaction between the Fc region of an antigen binding protein comprising an Fc region, such as an antibody, and various Fc receptors (FcR), including FcγRI (CD64), FcγRII (CD32), FcγRIII (CD16), FcRn, C1q, and type II Fc receptors can mediate the effector functions of the antigen binding protein. Significant biological effects can be a consequence of effector functionality. The ability to mediate effector function can require binding of the antigen binding protein to an antigen. An antigen binding protein can mediate one of, a plurality of, or each effector function.

Effector function can be assessed in a number of ways including, for example, by evaluating ADCC effector function of an antibody coated to target cells mediated by Natural Killer (NK) cells via FcγRIII, or monocytes/macrophages via FcγRI, or by evaluating CDC effector function of an antigen binding protein coated to target cells mediated by complement cascade via C1q. For example, an antigen binding protein described herein can be assessed for ADCC effector function in a Natural Killer cell assay.

The effects of mutations, including mutations in the Fc region, on effector functions (including but not limited to FcRn binding, FcγRs and C1q binding, CDC, ADCML, ADCC, ADCP) can be assessed. A PAPPA binding protein can comprise one or more of such mutations.

Some isotypes of human constant regions of antigen binding proteins provided herein, in particular IgG4 and IgG2 isotypes, can partially or fully lack the functions of a) activation of complement by the classical pathway; and b) ADCC. Various modifications to the heavy chain constant region of antigen binding proteins may be carried out to alter effector function depending on the desired effector property. IgG1 constant regions containing specific mutations that reduce binding to Fc receptors and reduce an effector function, such as ADCC and CDC, have been described.

Provided herein are PAPPA binding proteins comprising a constant region such that said PAPPA binding protein has reduced effector function, such as reduced ADCC and/or CDC. The heavy chain constant region may comprise a naturally disabled constant region of an IgG2 or IgG4 isotype or a mutated IgG1 constant region. Non-limiting examples of suitable modifications are described in EP0307434. In an embodiment, the PAPPA binding proteins disclosed herein comprise a constant region wherein said constant region comprises substitution with alanine at positions 235 and 237 (EU index numbering), i.e., L235A and G237A (commonly referred to as "LAGA" mutations). Other examples can comprise substitution with alanine at positions 234 and 235 (EU index numbering), i.e., L234A and L235A (commonly referred to as "LALA" mutations). Additional examples can comprise substitution with alanine at positions 234, 235 and 237 (EU index numbering), i.e., L234A, L235A, and G237A (referred to as "LALAGA" mutations). Further examples, such as described in EP2691417 and U.S. Pat. No. 8,969,526, can comprise a substitution with glycine or arginine at position 329 (i.e., P329G or P329R), in combination with the LALA mutations (EU index numbering) for Fc regions including IgG1 Fc regions. Yet further examples can comprise a substitution with glycine or arginine at position 329 (i.e., P329G or P329R), in combination with a substitution with proline at position 228 and glutamic acid at position 235 (i.e., S228P and L235E) for Fc domains including IgG4 Fc regions (EU index numbering).

Other mutations that can be employed to decrease effector function can include: (with reference to IgG1 unless otherwise noted): a glycosylated N297A or N297Q or N297G; L235E; IgG4: F234A/L235A; or chimeric IgG2/IgG4. IgG2 comprising $H_{268}Q$/V309L/A330S/P331S or V234A/ G237A/P238S/$H_{268}$A/V309L/A330S/P331S substitutions can be employed to reduce Fc$\gamma$R and/or C1q binding.

Other mutations that can be employed to decrease effector function can include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 ($H_{268}Q$, V309L, A330S and P331S); IgG20 that contains V234A/G237A/ P238S/$H_{268}$A/V309L/A330S/P331S substitutions to eliminate affinity for Fc$\gamma$ receptors and C1q complement protein; IgG2m4 ($H_{268}Q$/V309L/A330S/P331S, changes to IgG4); IgG4 (S228P/L234A/L235A); huIgG1 L234A/L235A (AA); huIgG4 S228P/L234A/L235A; IgG1s (L234A/L235A/ G237A/P238S/$H_{268}$A/A330S/P331S); IgG4s1 (S228P/ F234A/L235A/G237A/P238S); and IgG4s2 (S228P/F234A/ L235A/DG236/G237A/P238S, wherein D denotes a deletion) (Tam et al., Antibodies 2017, 6 (3)).

Half-life (t1/2) refers to the time required for the serum concentration of an antigen binding protein to reach half of its original value (i.e., half of a determined serum concentration achieved post administration). The serum half-life of proteins can be measured by pharmacokinetic (or "PK") studies, for example, according to a method wherein radio-labelled protein is injected intravenously into a preclinical species (e.g., mice) and its plasma concentration is periodically measured as a function of time, for example, at about 3 minutes to about 72 hours after the injection. Other methods for PK analysis and determination of the half-life of a molecule can be envisioned by a skilled artisan.

Long half-lives of IgG antibodies can be dependent on their binding to FcRn. Therefore, substitutions that increase the binding affinity of IgG to FcRn at pH 6.0 while maintaining the pH dependence of the interaction with target, for example, by engineering the constant region, may be employed. The in vivo half-life of PAPPA binding proteins described herein may be altered, for example, by modification of a heavy chain constant domain or by modification of an FcRn binding domain therein.

In adult mammals, FcRn, also known as the neonatal Fc receptor, can play a key role in maintaining serum antibody levels by acting as a protective receptor that binds and salvages antibodies of the IgG isotype from degradation. IgG molecules are endocytosed by endothelial cells and, if they bind to FcRn, are recycled out of the cells back into circulation. In contrast, IgG molecules that enter the cells and do not bind to FcRn and are targeted to the lysosomal pathway where they are degraded. FcRn may be involved in both antibody clearance and the transcytosis across tissues. Human IgG1 residues determined to interact directly with human FcRn include Ile253, Ser254, Lys288, Thr307, Gln311, Asn434, and His435. Mutations at any of these positions may be employed in a PAPPA binding protein herein, for example, to enable increased serum half-life and/or altered effector properties of PAPPA binding proteins provided herein.

PAPPA binding proteins described herein may have amino acid modifications that increase the affinity of the constant domain or fragment thereof for FcRn. Increasing the half-life (i.e., serum half-life) of therapeutic and diagnostic IgG antibodies and other bioactive molecules can provide benefits, which can include reducing the amount and/or frequency of dosing of these molecules. A PAPPA binding protein may comprise all or a portion (an FcRn binding portion) of an IgG constant domain having one or more of the following amino acid modifications.

For example, with reference to IgG1, M252Y/S254T/ T256E (commonly referred to as "YTE mutations) and M428L/N434S (commonly referred to as "LS" mutations) can increase FcRn binding at pH 6.0. A YTE or LS modification can increase FcRn binding at a pH higher than 6.0 or at a pH lower than 6.0.

Half-life can also be increased by T250Q/M428L, V259I/ V308F/M428L, N434A, and T307A/E380A/N434A mutations (with reference to IgG1 and Kabat numbering) in a PAPPA binding protein provided herein.

Half-life and FcRn binding can also be increased by introducing H433K and N434F mutations (commonly referred to as "HN" or "NHance" mutations) (with reference to IgG1) (WO2006/130834) in a PAPPA binding protein provided herein.

A PAPPA binding protein provided herein can comprise a variant Fc region with altered FcRn binding affinity, which can comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region (EU index numbering). A modified IgG comprising an IgG constant domain of an antigen binding protein can comprise one or more amino acid modifications relative to a wild-type IgG constant domain, wherein the modified IgG can have an increased half-life compared to the half-life of an IgG having a wildtype IgG constant domain, and wherein the one or more amino acid modifications are at one or more of positions 251, 253, 255, 285-290, 308-314, 385-389, and 428-435.

Alanine scanning mutagenesis can be employed to alter residues in the Fc region of a PAPPA binding protein provided herein, for example, a human IgG1 antibody, and thus alter binding to human FcRn. Positions that can effectively abrogate binding to FcRn when changed to alanine include I253, S254, H435, and Y436. Other positions can result in a less pronounced reduction in binding when mutated, for example, as follows: E233-G236, R255, K288, L309, S415, and H433. Several amino acid positions can exhibit improvement in FcRn binding when changed to alanine; notable among these include P238, T256, E272, V305, T307, Q311, D312, K317, D376, E380, E382, S424, and N434. Other amino acid positions can exhibit a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

In some PAPPA binding proteins provided herein, combination variants can yield a pronounced effect with respect to improved FcRn binding. For example, at least at pH 6.0, the E380A/N434A variant can display over 8-fold increase in binding to FcRn, relative to wild type IgG1, compared with a 2-fold increase for E380A and a 3.5-fold increase for N434A. The addition of T307A to this combination (E380A/N434A/T307A) can result in a 12-fold increase in binding relative to wild type IgG1. Antigen binding proteins described herein may comprise the E380A/N434A or E380A/N434A/T307A mutations and have increased binding to FcRn. In some PAPPA binding proteins provided herein, an improvement in IgG1-human FcRn complex stability can occur when substituting residues located in a band across the Fc-FcRn interface (e.g., M252, S254, T256, H433, N434, and Y436) or at the periphery (e.g., V308, L309, Q311, G385, Q386, P387, and N389). M252Y/S254T/T256E ("YTE") and H433K/N434F/Y436H mutations can be combined to yield a high affinity to human FcRn. In some cases, such a combination can exhibit a 57-fold increase in affinity relative to the wild-type IgG1. The in vivo behaviour of such a mutated human IgG1 can exhibit an increase in serum half-life of up to at least 4-fold as compared to wild-type IgG1. Such an increase in serum half-life can be in the serum of a human, a cynomolgus monkey, or another subject.

Also provided are PAPPA binding proteins with optimized binding to FcRn. A PAPPA binding protein may comprise at least one amino acid modification in the Fc region of said PAPPA binding protein, for example, wherein said modification is at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446, and 447 of the Fc region. A PAPPA binding protein can have 2, 3, 4, 5, 6, or more of such amino acid modifications in the Fc region of said PAPPA binding protein. A PAPPA binding protein can have an amino acid modification in the Fc region of said PAPPA binding protein at another amino acid position, either instead of or in addition to an amino acid modification provided herein.

A PAPPA binding protein can have a modified half-life, either by introducing an FcR binding polypeptide into the PAPPA binding protein (for example, as in WO97/43316, U.S. Pat. Nos. 5,869,046, 5,747,035, WO96/32478, or WO91/14438), by fusing the PAPPA binding protein with antibodies whose FcRn-binding affinities are preserved, but affinities for other Fc receptors have been greatly reduced (for example, as in WO99/43713), or by fusing the antigen binding protein with FcRn binding domains of antibodies (for example, as in WO00/09560 or U.S. Pat. No. 4,703,039).

PAPPA binding proteins herein can comprise FcRn affinity enhanced Fc variants that can improve antibody cytotoxicity and/or half-life at pH 6.0. Such IgG variants can be produced as low fucosylated molecules. The resulting variants can result in increased serum persistence in hFcRn mice, as well as conserved enhanced ADCC. Exemplary variants can include (with reference to IgG1 and Kabat numbering): P230T/V303A/K322R/N389T/F404L/N434S; P228R/N434S; Q311R/K334R/Q342E/N434Y; C226G/Q386R/N434Y; T307P/N389T/N434Y; P230S/N434S; P230T/V305A/T307A/A378V/L398P/N434S; P23OT/P387S/N434S; P230Q/E269D/N434S; N276S/A378V/N434S; T307A/N315D/A330V/382V/N389T/N434Y; T256N/A378V/S383N/N434Y; N315D/A330V/N361D/A387V/N434Y; V259I/N315D/M428L/N434Y; P230S/N315D/M428L/N434Y; F241L/V264E/T307P/A378V/H433R; T250A/N389K/N434Y; V305A/N315D/A330V/P395A/N434Y; V264E/Q386R/P396L/N434S/K439R; or E294del/T307P/N434Y (wherein 'del' indicates a deletion).

Although substitutions in the constant region can significantly improve the functions of PAPPA binding proteins, such as therapeutic IgG antibodies, substitutions in the strictly conserved constant region can yield immunogenicity in humans, while substitution in the highly diverse variable region sequence can be less immunogenic. The CDR residues of a PAPPA binding protein provided herein can be engineered to improve binding affinity of the PAPPA binding protein to the antigen. The CDR and/or framework residues can be engineered to improve stability and decrease immunogenicity risk of a PAPPA binding protein provided herein. Improved affinity to the antigen can be achieved by affinity maturation using the phage or ribosome display of a randomized library.

Improved stability of a PAPPA binding protein provided herein can be rationally obtained from sequence- or structure-based rational design. Decreasing the immunogenicity risk (deimmunization) of a PAPPA binding protein can be accomplished, for example, by one or more humanization methodologies and/or the removal of potential T-cell epitopes, which in some cases can be predicted using in silico technologies or anticipated by in vitro assays. Additionally, the variable region of a PAPPA binding protein can be engineered to lower its isoelectric point (pI). For a PAPPA binding protein, a longer half-life can be associated with such a reduced pI compared to wild type antigen binding proteins, in some cases despite comparable FcRn binding. A similar increase in half life can be achieved with other binding proteins. Engineering or selecting antigen binding proteins with pH-dependent antigen binding can be used to modify antigen binding protein and/or antigen half-life. For example, the half-life of an IgG2 antibody can be shortened if antigen-mediated clearance mechanisms can degrade the antibody when bound to the antigen. Similarly, an antigen:antibody complex can impact the half-life of an antigen (e.g., PAPPA), for example, by extending half-life by protecting the antigen from the typical degradation processes, or by shortening the half-life via antibody-mediated degradation (e.g., target-mediated drug disposition). PAPPA binding proteins may have higher affinity for antigen at pH 7.4 as compared to endosomal pH (i.e., pH 5.5-6.0) such that the KD ratio at pH 5.5/pH 7.4 or at pH 6.0/pH 7.4 can be 2 or more. For example, to enhance the PK and pharmacodynamic ("PD") properties of the PAPPA binding protein, pH-sensitive binding to the PAPPA binding protein can be achieved by introducing one or more histidine residues into one or more of the CDRs.

A PAPPA binding protein described herein can comprise a recycling antibody engineered so that a single antibody molecule can bind to an antigen multiple times. A recycling antibody can dissociate from an antigen (e.g., PAPPA) under acidic conditions within the cell. An antibody bound to a membrane-bound antigen can dissociate from the antigen in a pH-dependent manner. The dissociated antibody can then be recycled by FcRn while the antigen is transferred to lysosome and degraded. This mechanism can enable the antibody to bind to other antigens repeatedly in plasma and reduces the antibody clearance.

A PAPPA binding protein can comprise a sweeping antibody, which can be engineered, for example, using a combination of variable region engineering to enable the antibody to bind to an antigen (i.e., PAPPA) in plasma and dissociate from the antigen in endosomes (after which the antigen undergoes lysosomal degradation), and constant region engineering to increase the cellular uptake of the antibody-antigen complex into endosomes mediated for example through FcRn, FcγRIIb or potentially other surface receptors. A sweeping antibody can therapeutically target a soluble antigen enhancing elimination of the antigen from the circulation. In some cases, one or more of a panel of Fc variants with enhanced binding to FcRn, including M252Y, V308P, or N434Y, in combination with pH-dependent binding to a target antigen (e.g., PAPPA), can enhance clearance of a target antigen in comparison with a wild-type Fc region. FcγRIIb can be used to accelerate the uptake rate of antibody-antigen complexes into cells. A PAPPA binding protein can comprise an FcγRIIb sweeping antibody, or an Fc region thereof, in which the Fc region of a pH-dependent antibody can be engineered to selectively increase human FcγRIIb binding. This inhibitory receptor can mediate the uptake of antibody-antigen complexes into liver endothelial cells (LSEC). Therefore, mediation of the uptake of an antigen binding protein (e.g., antibody): antigen complex into a cell by FcγRIIb (e.g., human FcγRIIb) can reduce antigen concentration in the circulation. A PAPPA binding protein can comprise an Fc variant (v12) comprising the following mutations: E233D/G237D/P238D/H268D/P271G/A330R, and can have selectively increased binding affinity to human FcγRIIb. In some cases, such a v12 variant can accelerate the clearance of antigen (e.g., PAPPA) over that of a pH-dependent antibody with wildtype hIgG1 while maintaining comparable PK.

Further provided herein are nucleic acid sequences that encode the PAPPA binding proteins as disclosed herein. In an embodiment said nucleic acid sequences are isolated nucleic acid sequences. In an embodiment said nucleic acid sequences encodes one of or both of the heavy chain and light chain of the PAPPA binding protein as described herein.

In an embodiment there is provided nucleic acid sequences (e.g. an isolated polynucleotide) encoding a PAPPA binding protein for example an antibody that is capable of binding to SEQ ID NO: 1 and/or SEQ ID NO: 2, wherein said PAPPA binding protein comprises two variable heavy (VH) chain sequences and two variable light (VL) chain sequences wherein each of the VH sequences comprise the VH sequence set forth in SEQ ID NO: 105 and each of the VL sequences comprise the VL sequence set forth in SEQ ID NO: 111. In an embodiment there is provided nucleic acid sequences (e.g. an isolated polynucleotide) encoding a PAPPA binding protein for example an antibody that is capable of binding to SEQ ID NO: 1 and/or SEQ ID NO: 2, wherein said PAPPA binding protein comprises a human IgG1 Fc region, two heavy chains each of which comprise the sequence set forth in SEQ ID NO: 104, and two light chains each of which comprise the sequence set forth in SEQ ID NO: 110.

In an embodiment, there is provided nucleic acid sequences encoding a PAPPA binding protein or an antigen binding fragment thereof, wherein the PAPPA binding protein or antigen-binding fragment thereof comprises a heavy chain variable region according to SEQ ID NO: 45 and/or a light chain variable region according to SEQ ID NO: 51. In an embodiment, there is provided nucleic acid sequences encoding a PAPPA binding protein or an antigen binding fragment thereof, wherein the PAPPA binding protein or antigen-binding fragment thereof comprises a heavy chain variable region according to SEQ ID NO: 69 and/or a light chain variable region according to SEQ ID NO: 75. In an embodiment, there is provided nucleic acid sequences encoding a PAPPA binding protein or an antigen binding fragment thereof, wherein the PAPPA binding protein or antigen-binding fragment thereof comprises a heavy chain variable region according to SEQ ID NO: 93 and/or a light chain variable region according to SEQ ID NO: 99.

However, in a particular embodiment, there is provided nucleic acid sequences encoding a PAPPA binding protein or an antigen binding fragment thereof, wherein the PAPPA binding protein or antigen-binding fragment thereof comprises a heavy chain variable region according to SEQ ID NO: 105 and/or a light chain variable region according to SEQ ID NO: 111. In an embodiment, there is provided an isolated nucleic acid encoding a polypeptide according to SEQ ID NO: 104. In another embodiment, there is provided an isolated nucleic acid encoding a polypeptide according to SEQ ID NO: 110. In a further embodiment, there is provided an isolated nucleic acid encoding a polypeptide according to SEQ ID NO: 104 and a polypeptide according to SEQ ID NO: 110.

In an embodiment, said nucleic acid sequence comprises SEQ ID NO: 22, 34, 46, 58, 70, 82, 94 or 106 encoding the heavy chain; and/or SEQ ID NO: 28, 40, 52, 64, 76, 88, 100 or 112 encoding the light chain. In a particular embodiment the nucleic acid sequence comprises SEQ ID NO: 106 encoding the heavy chain; and/or SEQ ID NO: 112 encoding the light chain. In an embodiment, the nucleic acid comprises SEQ ID NO: 106 encoding the heavy chain. In another embodiment, the nucleic acid comprises SEQ ID NO: 112 encoding the light chain. In a further embodiment, the nucleic acid comprises SEQ ID NO: 106 and SEQ ID NO: 112.

The nucleic acids coding for the PAPPA binding proteins may comprise at least one chemical modification. Nucleic acids (e.g., mRNAs) can be modified to enhance stability by including one or more chemical modifications. Such chemical modifications include, but are not limited to, a modified nucleotide, a modified sugar backbone, and the like.

A subject in need may be delivered one or more nucleic acids encoding a PAPPA binding protein provided herein, such as a heavy chain and a light chain of an anti-PAPPA antibody. The heavy chain and the light chain of the antibody may be delivered by the same or separate nucleic acids. The nucleic acids may be DNA or RNA. The nucleic acids encoding the PAPPA binding protein may be delivered to the subject naked (i.e., without an encapsulating particle) or packaged (i.e., encapsulated in liposomes or polymer-based vehicles). The nucleic acids encoding the PAPPA binding protein may be delivered without a delivery vehicle (i.e., "naked") or delivered with a viral or non-viral delivery vehicle (i.e., as a viral vector, adsorbed to or encapsulated in liposomes or polymer-based vehicles, and the like). The nucleic acid may include elements such as a poly-A tail, and a 5' and/or 3' untranslated region (UTR). The nucleic acids may be mRNA. The mRNA may include a cap structure. The mRNA may be self-amplifying RNA.

Further provided herein are expression vectors comprising the nucleic acid sequences described herein. As such, there is provided an expression vector comprising a nucleic acid sequence encoding the PAPPA binding proteins described herein. In an embodiment, there is provided an expression vector comprising nucleic acid sequence(s) wherein said nucleic acid sequences comprise SEQ ID NO: 22, 34, 46, 58, 70, 82, 94 or 106 encoding the heavy chain; and/or SEQ ID NO: 28, 40, 52, 64, 76, 88, 100 or 112 encoding the light chain. In an embodiment the expression vector comprises the nucleic acid sequence of the heavy chain of SEQ ID NO: 116 and the nucleic acid sequence of the light chain of SEQ ID NO: 117.

In an embodiment there is provided an expression vector, or set of expression vectors comprising nucleic acid sequences encoding a PAPPA binding protein for example an antibody that is capable of binding to SEQ ID NO: 1 and/or SEQ ID NO: 2, wherein said PAPPA binding protein comprises two variable heavy (VH) chain sequences and two variable light (VL) chain sequences wherein each of the VH sequences comprise the VH sequence set forth in SEQ ID NO: 105 and each of the VL sequences comprise the VL sequence set forth in SEQ ID NO: 111. In an embodiment there is provided an expression vector, or set of expression vectors comprising nucleic acid sequences encoding a PAPPA binding protein for example an antibody that is capable of binding to SEQ ID NO: 1 and/or SEQ ID NO: 2, wherein said PAPPA binding protein comprises a human IgG1 Fc region, two heavy chains each of which comprise the sequence set forth in SEQ ID NO: 104, and two light chains each of which comprise the sequence set forth in SEQ ID NO: 110.

In an embodiment there is provided an expression vector comprising the nucleic acid of SEQ ID NO: 106. In another embodiment, there is provided an expression vector comprising the nucleic acid of SEQ ID NO: 112. In a further embodiment, there is provided an expression vector comprising a nucleic acid comprising SEQ ID NO: 106 and SEQ ID NO: 112.

Said expression vector can be an isolated nucleic acid which can be used to introduce nucleic acid sequences of interest into a cell, such as a eukaryotic cell or prokaryotic cell, or a cell free expression system where the nucleic acid sequence of interest is expressed as a peptide chain such as a protein. The nucleic acid sequences described herein may encode any of the PAPPA binding proteins provided herein or a fragment thereof. Such expression vectors may be, for example, cosmids, plasmids, viral sequences, transposons, and linear nucleic acids comprising a nucleic acid of interest. Once the expression vector is introduced into a cell or cell free expression system (e.g., reticulocyte lysate) the protein encoded by the nucleic acid of interest is produced by the transcription/translation machinery. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, *Drosophila* expression vectors, and expression vectors that are driven by mammalian gene promoters such as human Ig gene promoters. Other examples include prokaryotic expression vectors, such as T7 promoter driven vectors, e.g., pET41, lactose promoter driven vectors, and arabinose gene promoter driven vectors. Those of ordinary skill in the art will recognise many other suitable expression vectors and expression systems.

Further provided are recombinant host cells comprising the nucleic acid sequence or the expression vector(s) described herein. The term "recombinant host cell" as used herein refers to a cell that comprises a nucleic acid sequence of interest that was isolated prior to its introduction into the cell. For example, the nucleic acid sequence of interest may be in an expression vector. Host cells described herein may be prokaryotic or eukaryotic. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells, or any derivative thereof. The eukaryotic cell may be HEK293, NS0, SP2/0, or CHO cell. *E. coli* is an exemplary prokaryotic cell. A recombinant host cell according to the disclosure may be generated by transfection, cell fusion, immortalisation, or other procedures well known in the art. A nucleic acid of interest, such as an expression vector, transfected into a cell may be extrachromosomal or stably integrated into the chromosome of the cell. Further provided are cell lines engineered to express any of the PAPPA binding proteins disclosed herein.

PAPPA binding proteins may be prepared by any of a number of conventional techniques. For example, a PAPPA binding protein as disclosed herein may be purified from one or more cells that naturally express it (e.g., an antibody can be purified from a hybridoma that produces it) or produced in a recombinant expression system. More than one PAPPA binding protein can be expressed (and therefore purified) from such a natural cell or recombinant expression system. A number of different expression systems and purification regimes can be used to generate a PAPPA binding protein. Generally, host cells can be transformed with a recombinant expression vector encoding the PAPPA binding protein. The expression vector may be maintained by the host as a separate genetic element or integrated into the host chromosome depending on the expression system. A wide range of host cells can be employed, for example, Prokaryotes (including Gram negative or Gram-positive bacteria, for example, *Escherichia coli, Bacilli* sp., *Pseudomonas* sp., *Corynebacterium* sp.), Eukaryotes including yeast (for example, *Saccharomyces cerevisiae, Pichia pastoris*), fungi (for example, *Aspergillus* sp.), or higher Eukaryotes including insect cells and cell lines of mammalian origin (for example, CHO, NSO, PER.C6, HEK293, HeLa). Further provided are methods for the production of a PAPPA binding protein, said method comprising culturing the recombinant host cells described herein under conditions suitable for expression of said nucleic acid or vector(s), whereby a PAPPA binding protein is produced. Methods of producing a PAPPA binding protein in a cell, tissue, or organism may comprise contacting said cell, tissue, or organism with a composition comprising an isolated nucleic acid that encodes the PAPPA binding protein, optionally wherein said nucleic acid comprises at least one chemical modification. Further provided are PAPPA binding protein produced by these methods.

Epitope

Further provided herein are PAPPA binding proteins, or PAPPA binding fragments thereof that bind to an epitope within the central M region of human PAPPA. The term "epitope" as used herein refers to that portion of the antigen (i.e., PAPPA) that makes contact with a particular binding domain of a PAPPA binding protein provided herein (i.e., a paratope). An epitope may be linear, conformational, or discontinuous. A conformational or discontinuous epitope comprises amino acid residues that are separated, for example, by one or more other amino acids, i.e., not in a continuous sequence in the antigen's primary sequence when assembled by tertiary folding of the polypeptide chain. Although the residues may be from different regions of the polypeptide chain, they can be in close proximity in the three-dimensional structure of the antigen (i.e., PAPPA). For example, for multimeric antigens, a conformational or discontinuous epitope may include residues from different peptide chains. Particular residues comprised within an epitope can be determined via a computer modelling program or via one or more three-dimensional structures obtained through a structural method such as X-ray crystallography. An epitope can be determined using epitope mapping, such as by one or more techniques, for example, peptide-based approaches such as pepscan, whereby a series of overlapping peptides can be screened for binding using one or more techniques such as ELISA or by in vitro display of large libraries of peptides or protein mutants, e.g., on phage. Detailed epitope information can be determined by structural techniques, for example, X-ray crystallography, solution nuclear magnetic resonance (NMR) spectroscopy, and cryogenic-electron microscopy (cryo-EM). Mutagenesis, such as alanine scanning, can be an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

In an embodiment, the PAPPA binding proteins that bind to an epitope within the central M region of human PAPPA bind to an epitope within the M1/M2 region of human PAPPA. For the purposes of the present disclosure regions of the human PAPPA protein are reported in line with Judge et al Nat Commun. 2022 Sep. 20; 13 (1).

In an embodiment said M1/M2 region of human PAPPA corresponds to amino acids 673-1213 of SEQ ID NO: 1. In an embodiment therefore, there is provided a PAPPA binding protein (e.g. an anti-PAPPA antibody or antigen binding fragment thereof) that binds to an epitope located between positions 673 and 1213 of the human PAPPA protein as shown in SEQ ID NO: 1. The location of the M1/M2 region of human PAPPA in secreted PAPPA (i.e., following signal peptide cleavage) is between positions 593 and 1133 of the human PAPPA protein as shown in SEQ ID NO: 2. In an embodiment, said M1/M2 region of human PAPPA is shown in SEQ ID NO: 3.

In an embodiment, the PAPPA binding proteins bind to an epitope within the M1/M2 region of human PAPPA wherein said epitope comprises one or more amino acids within residues 1031-1079 of SEQ ID NO: 1 (the corresponding residues within SEQ ID NO: 2 being 951-999). In an embodiment said epitope is represented by the amino acid sequence of SEQ ID NO: 118.

In an embodiment, said epitope comprises one or more amino acids within residues 1067-1079 of SEQ ID NO: 1 (the corresponding residues within SEQ ID NO: 2 being 987-999). In an embodiment said epitope is represented by the amino acid sequence of SEQ ID NO: 4. In an embodiment, the PAPPA binding protein protects residues 1067-1079 of SEQ ID NO: 1 from deuterium exchange in HDX-MS analysis.

In an embodiment said epitope comprises one or more of amino acid residues His1031, Asp1033, Ile1056, Asp1057, Leu1058, Ser1059, Pro1075, Tyr1076 and Leu1079 of SEQ ID NO: 1.

In an embodiment, said epitope comprises one or more of amino acid residues Pro1075, Tyr1076 and Leu1079 of SEQ ID NO: 1. In an embodiment said epitope comprises Pro1075, Tyr1076 and Leu1079 of SEQ ID NO: 1.

In nature, PAPPA is secreted as a dimer and is dimerized by a single disulfide bond (Overgaard et al, J Biol Chem. 2003 Jan. 24; 278 (4): 2106-17). In an embodiment, two of said PAPPA binding proteins bind to human PAPPA when said human PAPPA is dimerized.

The PAPPA binding protein that binds to an epitope within the central M region of human PAPPA as described in this section may be any of the PAPPA binding proteins described throughout this specification. However, in particular there is provided a PAPPA binding protein that binds to an epitope within the M1/M2 region of human PAPPA wherein said binding protein inhibits cleavage of both IGFBP-4 and IGFBP-5 and wherein the M1/M2 region of human PAPPA corresponds to amino acids 673-1213 of SEQ ID NO: 1. In an embodiment, there is provided a PAPPA binding protein that binds to an epitope within the M1/M2 region of human PAPPA wherein said binding protein inhibits cleavage of both IGFBP-4 and IGFBP-5 and wherein said epitope comprises one or more amino acids within residues 1067-1079 of SEQ ID NO: 1. In an embodiment, there is provided A PAPPA binding protein that binds to an epitope comprising one or more amino acids within residues 1031-1079 of SEQ ID NO: 1, wherein said PAPPA binding protein inhibits cleavage of both IGFBP-4 and IGFBP-5 and comprises the following 6 CDRs a) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or b) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115. In an embodiment, there is provided A PAPPA binding protein that binds to an epitope comprising one or more amino acids within residues 1067-1079 of SEQ ID NO: 1, wherein said PAPPA binding protein inhibits cleavage of both IGFBP-4 and IGFBP-5 and comprises a) a VH region that is 100% identical to SEQ ID NO: 69 and a VL region that is 100% identical to SEQ ID NO: 75; or b) a VH region that is 100% identical to SEQ ID NO: 105 and a VL region that is 100% identical to SEQ ID NO: 111.

Pharmaceutical Compositions and Methods of Use

The PAPPA binding proteins as described herein may be incorporated into pharmaceutical compositions for use in medicine. Provided herein therefore are pharmaceutical compositions, wherein said pharmaceutical compositions comprise the PAPPA binding proteins disclosed herein in combination with a pharmaceutically acceptable carrier and/or excipient. Pharmaceutical compositions herein can be for use in the treatment of diseases, including human diseases, described herein.

In a particular embodiment there is provided a pharmaceutical composition wherein said pharmaceutical composition comprises a PAPPA binding protein in combination with a pharmaceutically acceptable carrier and/or excipient wherein said PAPPA binding protein comprises the following 6 CDRs: CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115. Further provided is a pharmaceutical composition wherein said pharmaceutical composition comprises a PAPPA binding protein in combination with a pharmaceutically acceptable carrier and/or excipient wherein said PAPPA binding protein comprises a VH region that is 100% identical to SEQ ID NO: 105 and/or a VL region that is 100% identical to SEQ ID NO: 111. Further provided is a pharmaceutical composition wherein said pharmaceutical composition comprises a PAPPA binding protein in combination with a pharmaceutically acceptable carrier and/or excipient wherein said PAPPA binding protein comprises a heavy chain and a light chain, wherein the amino acid sequence of the heavy chain is shown in SEQ ID NO: 104 and the amino acid sequence of the light chain is shown in SEQ ID NO: 110.

The PAPPA binding proteins disclosed herein or pharmaceutical compositions comprising said binding proteins may be administered by injection or continuous infusion via a route, that can include for example, intravenous, intraperitoneal, intradermal, subcutaneous, intramuscular, intraocular, intraportal, or another route. A pharmaceutical composition may be suitable for intravenous administration. A pharmaceutical composition may be suitable for subcutaneous administration. Pharmaceutical compositions may be suitable for topical administration (which can include, but is not limited to, epicutaneous, intranasal, or ocular administration), inhalational administration, or enteral administration.

A pharmaceutical composition may be included in a kit containing the PAPPA binding protein together with other medicaments, and/or with instructions for use. For convenience, the kit may comprise the reagents in predetermined amounts with instructions for use. The kit may also include one or more devices, such as a syringe, a needle, a length of tubing, or another device, that can be used for administration of the pharmaceutical composition.

The terms "individual", "subject" and "patient" are used herein interchangeably. In one embodiment the subject is a human.

The PAPPA binding protein described herein may also be used in methods of treatment. It will be appreciated by those skilled in the art that references herein to treatment refer to the treatment of established conditions. However, PAPPA binding proteins disclosed herein may, depending on the condition, also be useful in the prevention of certain diseases. The PAPPA binding protein described herein is used in an effective amount for therapeutic, prophylactic, or preventative treatment. A therapeutically effective amount of the PAPPA binding protein described herein is an amount effective to ameliorate or reduce one or more symptoms of, or to prevent or cure, the disease.

Provided herein are methods of treating a disease in a subject in need thereof comprising administering to said subject a therapeutically effective amount of the PAPPA binding proteins or the pharmaceutical compositions disclosed herein. In particular there is provided a method for the treatment of a polycystic kidney disease (PKD) in a subject in need thereof comprising administering to said subject a therapeutically effective amount of the PAPPA binding proteins or pharmaceutical compositions disclosed herein. The PAPPA binding protein administered to said subject in need thereof may be any PAPPA binding protein as disclosed herein. However in a particular embodiment there is provided a method for the treatment of a polycystic kidney disease (PKD) in a subject in need thereof comprising administering to said subject a therapeutically effective amount of either a) a PAPPA binding protein (or PAPPA binding fragment thereof) wherein said PAPPA binding protein inhibits cleavage of IGFBP-2, IGFBP-4 and IGFBP-5 or b) a pharmaceutical composition comprising the PAPPA binding protein in a) in combination with a pharmaceutically acceptable carrier and/or excipient. In an embodiment there is provided a method for the treatment of a polycystic kidney disease (PKD) in a subject in need thereof comprising administering to said subject a therapeutically effective amount of either a) a PAPPA binding protein (or PAPPA binding fragment thereof) wherein said PAPPA binding protein binds to one or more amino acids within the M1/M2 region of human PAPPA or b) a pharmaceutical composition comprising the PAPPA binding protein in a) in combination with a pharmaceutically acceptable carrier and/or excipient. In an embodiment there is provided a method for the treatment of a polycystic kidney disease (PKD) in a subject in need thereof comprising administering to said subject a therapeutically effective amount of either a) a PAPPA binding protein (or PAPPA binding fragment thereof) comprising a VH region and a VL region wherein the VH region comprises CDRH1 of SEQ ID NO: 107; CDRH2 of SEQ ID NO: 108 and CDRH3 of SEQ ID NO: 109; and the VL region comprises CDRL1 of SEQ ID NO: 113; CDRL2 of SEQ ID NO: 114; and CDRL3 of SEQ ID NO: 115, or b) a pharmaceutical composition comprising the PAPPA binding protein in a) in combination with a pharmaceutically acceptable carrier and/or excipient. In an embodiment there is provided a method for the treatment of a polycystic kidney disease (PKD) in a subject in need thereof comprising administering to said subject a therapeutically effective amount of either a) a PAPPA binding protein (or PAPPA binding fragment thereof) comprising a VH region that is 100% identical to SEQ ID NO: 105 and/or a VL region that is 100% identical to SEQ ID NO: 111; or b) a pharmaceutical composition comprising the PAPPA binding protein in a) in combination with a pharmaceutically acceptable carrier and/or excipient. In an embodiment said PKD is autosomal dominant PKD (ADPKD) or autosomal recessive PKD (ARPKD) but is preferably ADPKD.

Liver cysts are the most common extrarenal manifestations of PKD (e.g., ADPKD). In an embodiment, the methods of treatment disclosed herein further treats polycystic liver disease.

Further provided are methods for the treatment of chronic kidney disease (CKD) in a subject in need thereof comprising administering to said subject a therapeutically effective amount of the PAPPA binding proteins or pharmaceutical compositions as disclosed herein. In an embodiment said CKD is a CKD whereby PAPPA expression and/or activity is shown to be elevated in comparison to a healthy control (e.g., as demonstrated by increased IGFBP-4 Ct, IGFBP-4 Nt, IGFBP-5 Ct and/or IGFBP-5 Nt fragment levels).

Further provided are methods for the treatment of diabetic kidney disease (DKD) in a subject in need thereof comprising administering to said subject a therapeutically effective amount of the PAPPA binding proteins or pharmaceutical compositions as disclosed herein. In a particular embodiment there is provided a method for the treatment of DKD in a subject in need thereof comprising administering to said subject a therapeutically effective amount of either a) a PAPPA binding protein (or PAPPA binding fragment thereof) wherein said PAPPA binding protein inhibits cleavage of both IGFBP-4 and IGFBP-5 or b) a pharmaceutical composition comprising the PAPPA binding protein in a) in combination with a pharmaceutically acceptable carrier and/ or excipient. In an embodiment there is provided a method for the treatment of DKD in a subject in need thereof comprising administering to said subject a therapeutically effective amount of either a) a PAPPA binding protein (or PAPPA binding fragment thereof) wherein said PAPPA binding protein binds to one or more amino acids within the M1/M2 region of human PAPPA or b) a pharmaceutical composition comprising the PAPPA binding protein in a) in combination with a pharmaceutically acceptable carrier and/ or excipient. In an embodiment there is provided a method for the treatment of DKD in a subject in need thereof comprising administering to said subject a therapeutically effective amount of either a) a PAPPA binding protein (or PAPPA binding fragment thereof) comprising a VH region and a VL region wherein the VH region comprises CDRH1 of SEQ ID NO: 107; CDRH2 of SEQ ID NO: 108 and CDRH3 of SEQ ID NO: 109; and the VL region comprises CDRL1 of SEQ ID NO: 113; CDRL2 of SEQ ID NO: 114; and CDRL3 of SEQ ID NO: 115, or b) a pharmaceutical composition comprising the PAPPA binding protein in a) in combination with a pharmaceutically acceptable carrier and/ or excipient. In an embodiment there is provided a method for the treatment of DKD in a subject in need thereof comprising administering to said subject a therapeutically effective amount of either a) a PAPPA binding protein (or PAPPA binding fragment thereof) comprising a VH region that is 100% identical to SEQ ID NO: 105 and/or a VL region that is 100% identical to SEQ ID NO: 111; or b) a pharmaceutical composition comprising the PAPPA binding protein in a) in combination with a pharmaceutically acceptable carrier and/or excipient.

Further provided are methods of slowing kidney and/or liver cyst growth in a subject in need thereof comprising administering to said subject a therapeutically effective amount of the PAPPA binding proteins or the pharmaceutical compositions disclosed herein. Further provided are methods of reducing tKV in a subject in need thereof comprising administering to said subject a therapeutically effective amount of the PAPPA binding proteins or the pharmaceutical compositions disclosed herein. Further provided are methods of reducing IGF-1 stimulated kidney and/or liver cyst growth in a subject in need thereof comprising administering to said subject a therapeutically effective amount of the PAPPA binding proteins or the pharmaceutical compositions disclosed herein.

Further provided are methods of increasing the time until a subject suffering from a PKD, in particular ADPKD, is diagnosed with end-stage kidney disease, requires a kidney transplant and/or requires dialysis, said method comprising administering to said subject a therapeutically effective amount of the PAPPA binding proteins or the pharmaceutical compositions disclosed herein. Further provided are methods of slowing eGFR decline said method comprising administering to said subject a therapeutically effective amount of the PAPPA binding proteins or the pharmaceutical compositions disclosed herein.

Further provided are methods for the treatment of thyroid eye disease (TED) in a subject in need thereof comprising administering to said subject a therapeutically effective amount of the PAPPA binding protein or pharmaceutical composition as disclosed herein.

Further provided herein are methods for the treatment of atherosclerosis in a subject in need thereof comprising administering to said subject a therapeutically effective amount of a PAPPA binding protein or pharmaceutical composition as disclosed herein. In an embodiment, said method of treating atherosclerosis is a method of preventing or slowing the formation of atherosclerotic lesions. In an embodiment, said method of treating atherosclerosis is a method of decelerating atherosclerosis development. In an embodiment, there is provided a method for the treatment of cardiovascular disease, (for example coronary artery disease (CAD), stroke and/or peripheral arterial disease) in a subject in need thereof comprising administering to said subject a therapeutically effective amount of a PAPPA binding protein or pharmaceutical composition as disclosed herein.

Further provided are PAPPA binding proteins or pharmaceutical compositions disclosed herein for use in the treatment of a disease in a subject. In particular there is provided PAPPA binding proteins or pharmaceutical compositions disclosed herein for use in the treatment of a PKD in a subject. The PAPPA binding proteins for use in the treatment of a PKD in a subject may be any PAPPA binding protein as disclosed herein. However, in a particular embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of a PKD wherein said PAPPA binding protein inhibits cleavage of IGFBP-2, IGFBP-4 and IGFBP-5. In an embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of a PKD wherein said PAPPA binding protein binds to one or more amino acids within the M1/M2 region of human PAPPA. In an embodiment there is provided a PAPPA binding protein (or PAPPA binding fragment thereof) or a pharmaceutical composition comprising said PAPPA binding protein in combination with a pharmaceutically acceptable carrier and/ or excipient for use in the treatment of a PKD wherein said PAPPA binding protein comprises a VH region and a VL region wherein the CH region comprises CDRH1 of SEQ ID NO: 107; CDRH2 of SEQ ID NO: 108 and CDRH3 of SEQ ID NO: 109; and the VL region comprises CDRL1 of SEQ ID NO: 113; CDRL2 of SEQ ID NO: 114; and CDRL3 of SEQ ID NO: 115. In an embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of a PKD wherein said PAPPA binding protein comprises a VH region that is 100% identical to SEQ ID NO: 105 and/or a VL region that is 100% identical to SEQ ID NO: 111. In an embodiment said PKD is autosomal dominant PKD (ADPKD) or autosomal recessive PKD (ARPKD) but is preferably ADPKD. In an embodiment said use further treats polycystic liver disease.

Further provided are PAPPA binding proteins or pharmaceutical compositions of the present disclosure for use in the treatment of chronic kidney disease (CKD) in a subject. In an embodiment said CKD is a CKD whereby PAPPA expression and/or activity is shown to be elevated, for example in comparison to a healthy control (e.g., as demonstrated by increased IGFBP-4 Ct, IGFBP-4 Nt, IGFBP-5 Ct and/or IGFBP-5 Nt fragment levels).

Further provided are PAPPA binding proteins or pharmaceutical compositions disclosed herein for use in the treatment of diabetic kidney disease in a subject. The PAPPA binding proteins for use in the treatment of DKD in a subject may be any PAPPA binding protein as disclosed herein. However, in a particular embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of DKD wherein said PAPPA binding protein inhibits cleavage of both IGFBP-4 and IGFBP-5. In an embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of DKD wherein said PAPPA binding protein binds to one or more amino acids within the M1/M2 region of human PAPPA. In an embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of DKD wherein said PAPPA binding protein comprises a VH region and a VL region wherein the CH region comprises CDRH1 of SEQ ID NO: 107; CDRH2 of SEQ ID NO: 108 and CDRH3 of SEQ ID NO: 109; and the VL region comprises CDRL1 of SEQ ID NO: 113; CDRL2 of SEQ ID NO: 114; and CDRL3 of SEQ ID NO: 115. In an embodiment there is provided a PAPPA binding protein (or PAPPA binding fragment thereof) or a pharmaceutical composition comprising said PAPPA binding protein in combination with a pharmaceutically acceptable carrier and/or excipient for use in the treatment of DKD wherein said PAPPA binding protein comprises a VH region that is 100% identical to SEQ ID NO: 105 and/or a VL region that is 100% identical to SEQ ID NO: 111.

Further provided are the PAPPA binding proteins or pharmaceutical compositions disclosed herein for use in the treatment of thyroid eye disease (TED) in a subject.

There is further provided the PAPPA binding proteins or pharmaceutical compositions disclosed herein for use in reducing tKV in a subject, for use in in slowing kidney and/or liver cyst growth in a subject and/or for use in reducing IGF-1 stimulated kidney and/or liver cyst growth in a subject.

Further provided are the PAPPA binding proteins or pharmaceutical compositions disclosed herein for use in a method of increasing the time until a subject suffering from a PKD, in particular ADPKD, is diagnosed with end-stage kidney disease, requires a kidney transplant and/or requires dialysis. Further provided are the PAPPA binding proteins or pharmaceutical compositions disclosed herein for use in a method of slowing eGFR decline.

Further provided are the PAPPA binding proteins or pharmaceutical compositions disclosed herein for use in the treatment of atherosclerosis in a subject. In an embodiment, said PAPPA binding proteins or pharmaceutical compositions for use in treating atherosclerosis in a subject are for use in preventing or slowing the formation of atherosclerotic lesions. In an embodiment, said PAPPA binding proteins or pharmaceutical compositions for use in treating atherosclerosis in a subject are for use in decelerating atherosclerosis development. In an embodiment, there is provided the PAPPA binding proteins or pharmaceutical compositions disclosed herein for use in the treatment of cardiovascular disease in a subject, for example coronary artery disease (CAD), stroke and/or peripheral arterial disease.

Further provided is the use of the PAPPA binding proteins or the pharmaceutical compositions as disclosed herein in the manufacture of a medicament for use in the treatment of a disease. In an embodiment said disease is a renal disease, optionally a PKD. In a particular embodiment there is provided the use of the PAPPA binding proteins, or the pharmaceutical compositions as disclosed herein in the manufacture of a medicament for use in the treatment of ADPKD.

Biomarkers

As used herein the term "biomarker" is defined as "a characteristic that is objectively measured and evaluated as an indicator of normal biologic or pathogenic processes or pharmacological response to a therapeutic intervention" (Biomarkers Definitions Working Group, 2001, Clin. Pharmacol. Ther. 69:89-95). There are a number of different types of biomarkers described herein. Firstly, predictive biomarkers are provided which, for example, assess the probability that a particular subject will benefit from treatment with a PAPPA binding protein or predict a patients susceptibility to develop a PKD. Secondly pharmacodynamic biomarkers are provided which provide an indication of the effect(s) the PAPPA binding protein (or a pharmaceutical composition comprising said binding protein) on its molecular target (i.e., PAPPA) while the subject is receiving treatment or following treatment.

Predictive Biomarkers:

Further provided herein is a method of determining whether a subject (optionally wherein the subject is suspected of suffering with a PKD) is a candidate for treatment with a PAPPA binding protein, said method comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level the subject is identified as a candidate for treatment with a PAPPA binding protein.

Further provided herein is a method of identifying a susceptibility to develop PKD in a subject, comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level it is indicative of a susceptibility to develop PKD.

Further provided is a method of treating a PKD in a subject said method comprising a) selecting a subject that is identified as having high levels of an IGFBP-C-terminal (Ct) fragment and/or an IGFBP-N-terminal (Nt) fragment relative to a reference level having previously subjected a biological sample obtained from said subject to at least one assay to measure the level of an IGFBP-Ct fragment and/or an IGFBP-Nt fragment and b) administering a PAPPA binding protein to said subject.

Said methods are preferably ex vivo methods. Regarding said methods, in an embodiment the subject is a human. In an embodiment, said PKD is ADPKD.

Further provided is a pharmaceutical composition comprising a PAPPA binding protein (for example any of the PAPPA binding proteins disclosed herein) for use in the treatment of a polycystic kidney disease (most particularly ADPKD) in a patient, wherein the patient is identified as having high levels of an IGFBP-C-terminal (Ct) fragment and/or an IGFBP-N-terminal (Nt) fragment relative to a reference level having previously subjected a biological sample obtained from said subject to at least one assay to measure the level of an IGFBP-Ct fragment and/or an IGFBP-Nt fragment.

To the extent the methods and pharmaceutical compositions described above refer to PAPPA binding proteins, these may be any of the PAPPA binding proteins disclosed herein. However, in a particular embodiment the PAPPA binding protein is a PAPPA binding protein that inhibits cleavage of both IGFBP-4 and IGFBP-5. In a further particular embodiment the PAPPA binding protein is a PAPPA binding protein that binds to an epitope within the M1/M2 region of human PAPPA. In a further particular embodiment, the PAPPA binding protein comprises a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 55; or b) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115. In a further embodiment the PAPPA binding protein is a PAPPA binding protein that comprises a) a VH region that is 100% identical to SEQ ID NO: 45 and/or a VL region that is 100% identical to SEQ ID NO: 51; or b) a VH region that is 100% identical to SEQ ID NO: 69 and/or a VL region that is 100% identical to SEQ ID NO: 75; or c) a VH region that is 100% identical to SEQ ID NO: 93 and/or a VL region that is 100% identical to SEQ ID NO: 99; or d) a VH region that is 100% identical to SEQ ID NO: 105 and/or a VL region that is 100% identical to SEQ ID NO: 111.

It has previously been reported that human kidney tissues obtained from patients with ADPKD demonstrate increased PAPPA protein expression (Kashyap et al, 2020). Thus, in an embodiment, the level of said IGFBP-Ct fragments and/or IGFBP-Nt fragments are high (relative to a reference level) as a result of increased PAPPA expression and/or activity.

In an embodiment, the IGFBP-Ct fragment is IGFBP4-Ct fragment or IGFBP5-Ct fragment. In an embodiment said IGFBP4-Ct fragment is a polypeptide that comprises or consists of SEQ ID NO: 9. In an embodiment the IGFBP5-Ct fragment is a polypeptide that comprises or consists of SEQ ID NO: 14. Preferably the IGFBP-Ct fragment is IGFBP-4 Ct fragment i.e a polypeptide that comprises or consists of SEQ ID NO: 9. The rationale for this preference is that PAPPA is not the only protease enzyme which cleaves IGFBP-5 (PAPPA2 also cleaves IGFBP-5).

In an embodiment the IGFBP-Nt fragment is IGFBP4-Nt fragment or IGFBP5-Nt fragment. In an embodiment the IGFBP4-Nt fragment is a polypeptide that comprises or consists of SEQ ID NO: 8. In an embodiment, the IGFBP5-Nt fragment is a polypeptide that comprises or consists of SEQ ID NO: 13. Preferably the IGFBP-Nt fragment is IGFBP4-Nt fragment i.e., a polypeptide that comprises or consists of SEQ ID NO: 8.

As used herein "reference level" may also be referred to as predetermined threshold. The reference level is a predetermined value or range, which is employed as a benchmark against which to assess the measured result. The reference level is determined according to the level of the biomarker (in this case the levels of the IGFBP C-terminal and/or IGFBP N-terminal fragments) in a control group. "Control group" as used herein refers to a group of control subjects. A control subject may be a healthy or normal subject or a subject having no clinical signs or symptoms of renal disease such as no clinical signs or symptoms of polycystic kidney disease (e.g., ADPKD). The reference level may be a cutoff value from a control group. The reference level may be an average from a control group. The amount or concentration of the biomarker (in this case the IGFBP C-terminal and/or IGFBP N-terminal fragments) may be "high" or "elevated" or "increased" in a test sample obtained from a subject when said amount or concentration is greater than a reference level. The amount or concentration of the biomarker (in this case the IGFBP C-terminal and/or IGFBP N-terminal fragments) may be "low" or "decreased" or "reduced" in a test sample obtained from a subject when said amount or concentration is less than a reference level. Reference levels may be determined statistically using methods known to the person skilled in the art for example by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another.

In an embodiment, the reference level is pre-determined according to the level of said IGFBP-Ct fragment and/or IGFBP-Nt fragment in healthy individuals. In an embodiment, the reference level is pre-determined according to the level of said IGFBP-Ct fragment and/or IGFBP-Nt fragment in a subject(s) not suffering or not suspected of suffering from any renal disease, optionally wherein said renal disease is a PKD.

In an embodiment, the level of IGFBP-Ct fragment and/or IGFBP-Nt fragment is high relative to a reference level when the level of IGFBP-Ct fragment is increased by at least 5%, at least 10%, at least 25%, at least 50%, at least 100%, at least 200%, at least 300%, at least 500% or at least 600% relative to said reference level.

In an embodiment the reference level is around 150 ng/ml, around 200 ng/ml or around 250 ng/ml. In an embodiment the reference level is between 100-250 ng/ml, 110-240 ng/ml, 120-230 ng/ml, 130-220 ng/ml, 140-210 ng/ml or 150-200 ng/ml.

In an embodiment, the level of IGFBP-Ct fragment and/or IGFBP-Nt fragment is high relative to a reference level when the level of IGFBP-Ct fragment and/or IGFBP-Nt fragment is greater than 150 ng/ml, greater than 200 ng/ml or greater than 250 ng/ml.

In a particular embodiment there is provided a method of determining whether a subject suspected of suffering with a PKD is a candidate for treatment with a PAPPA binding protein, said method comprising the step of subjecting a biological sample obtained from the subject to at least one assay to measure the level of the IGFBP-4 Ct fragment wherein when the level of said IGFBP4-Ct fragment is greater than 150 ng/ml, greater than 200 ng/ml or greater than 250 ng/ml the subject is identified as a candidate for treatment with a PAPPA binding protein. In an embodiment there is provided a method of identifying a susceptibility to develop PKD in a subject, comprising the step of subjecting a biological sample obtained from the subject to at least one assay to measure the level of an IGFBP4 C-terminal (Ct) fragment wherein when the level of said IGFBP4-Ct fragment is greater than 150 ng/ml, greater than 200 ng/ml or greater than 250 ng/ml it is indicative of a susceptibility to develop PKD. In an embodiment, there is provided a method of treating a PKD in a subject said method comprising a) selecting a subject that is identified as having greater than 150 ng/ml, greater than 200 ng/ml or greater than 250 ng/ml IGFBP4-C-terminal (Ct) fragment having previously subjected a biological sample obtained from said subject to at least one assay to measure the level of said IGFBP4 Ct fragment and b) administering a PAPPA binding protein to said subject.

Said at least one assay to measure the level of an IGFBP-Ct fragment and/or IGFBP-full length polypeptide can be any suitable assay to measure protein abundance, for example but not limited to fluorescence-activated cell sorting (FACS), enzyme-linked immunosorbent assay (ELISA), any kind of mulit-plex immunoassay (e.g. Meso Scale discovery), radioimmuno assays, radioassays, western blot, immunoprecipitation, immunofluorescence, mass spectrometry, liquid chromatography including high-performance liquid chromatography, combinations thereof or other techniques known in the art. In an embodiment, the at least one assay to measure the level of an IGFBP-Ct fragment and/or IGFBP-Nt fragment is an ELISA assay. In an embodiment, said ELISA assay comprises i) permitting said IGFBP-Ct fragment and/or IGFBP-Nt fragment present within the biological sample obtained from the subject to interact with at least one antibody that specifically binds to said IGFBP-Ct fragment and/or IGFBP-Nt fragment and ii) measuring the interaction between said IGFBP-Ct fragment and/or IGFBP-Nt fragment and antibody from step i). In an embodiment said measurement in step ii) quantitatively indicates the concentration of IGFBP-Ct fragment and/or IGFBP-Nt fragment within the biological sample obtained from the subject. In an embodiment said measurement in step ii) uses a secondary antibody labelled with an enzyme, optionally wherein said enzyme is a peroxidase (e.g. horseradish peroxidase), or a phosphatase (e.g. alkaline phosphatase).

As used herein, the term "biological sample" refers to a quantity of a substance (a sample) that is isolated from a living being. In an embodiment, the biological sample is sputum, kidney cyst fluid, urine, whole blood, plasma or serum sample. In an embodiment the biological sample is plasma. In an embodiment the biological sample is serum. In an embodiment the biological sample is urine. The biological sample can be in any form that allows measurement of said IGFBP-Ct fragment and/or IGFBP-Nt fragment. The biological sample can be fresh, preserved through suitable cryogenic techniques, or preserved through non-cryogenic techniques.

Pharmacodynamic Biomarkers:

Further provided herein is a method of monitoring the effectiveness of a PAPPA binding protein in treating PKD in a subject said method comprising a) subjecting a first biological sample obtained from the subject to at least one assay to measure the level of an IGFBP-C-terminal (Ct) fragment, an IGFBP-N-terminal (Nt) fragment and/or an IGFBP-full length polypeptide, b) subjecting a second biological sample obtained from the subject to at least one assay to measure the level of an IGFBP-C-terminal (Ct) fragment, an IGFBP-N-terminal (Nt) fragment and/or an IGFBP-full length polypeptide wherein said second biological sample is obtained from the subject following treatment with the PAPPA binding protein; and c) comparing the level of said IGFBP-C-terminal (Ct) fragment, IGFBP-N-terminal (Nt) fragment and/or IGFBP-full length polypeptide obtained in steps a) and b), wherein decreased levels of said IGFBP-Ct fragment and/or IGFBP-Nt fragment in the second biological sample relative to the levels of said IGFBP-Ct fragment and/or IGFBP-Nt fragment in the first biological sample and/or increased levels of said IGFBP-full length polypeptide in the second biological sample relative to the levels of said IGFBP-full length polypeptide in the first biological sample is indicative of therapeutic efficacy in the treatment of the subjects PKD. In a preferable embodiment, the subject is a human being. In a preferable embodiment, said PKD is ADPKD.

Said method is preferably performed ex vivo. Regarding said methods, in an embodiment the subject is a human. In an embodiment, said PKD is ADPKD.

In an embodiment the first biological sample is obtained from the subject either prior to their first administration with the PAPPA binding protein or prior to their second or subsequent administrations. In this regard the method can used to monitor the effectiveness of the PAPPA binding protein in treating PKD following their first administration with the PAPPA binding protein or can also be used to monitor the ongoing effectiveness of the PAPPA binding protein over a period of time, and after receiving numerous doses of said binding protein. However, it will be appreciated by the skilled person that the second or subsequent administrations of the PAPPA binding proteins disclosed herein may serve to maintain suppression (i.e. maintain the decreased levels) of said IGFBP-Ct fragment and/or IGFBP-Nt fragment and/or may serve to maintain the elevated levels of the IGFBP-full length polypeptide. As such, the magnitude of the decrease or increase respectively (i.e. percentage change relative to the levels of the biomarker in the first biological sample) may be smaller when monitoring ongoing effectiveness compared to the magnitude of the decrease or increase when monitoring the effectiveness of the PAPPA binding protein following a subjects first administration.

In an embodiment said method monitors the effectiveness of a PAPPA binding protein wherein said PAPPA binding protein includes any of the PAPPA binding proteins disclosed herein. However, in a particular embodiment the PAPPA binding protein is a PAPPA binding protein that inhibits cleavage of both IGFBP-4 and IGFBP-5. In a further particular embodiment, the PAPPA binding protein is a PAPPA binding protein that binds to an epitope within the M1/M2 region of human PAPPA. In a further particular embodiment, the PAPPA binding protein comprises a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 55; or b) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115. In a further embodiment the PAPPA binding protein is a PAPPA binding protein that comprises a) a VH region that is 100% identical to SEQ ID NO: 45 and/or a VL region that is 100% identical to SEQ ID NO: 51; or b) a VH region that is 100% identical to SEQ ID NO: 69 and/or a VL region that is 100% identical to SEQ ID NO: 75; or c) a VH region that is 100% identical to SEQ ID NO: 93 and/or a VL region that is 100% identical to SEQ ID NO: 99; or d) a VH region that is 100% identical to SEQ ID NO: 105 and/or a VL region that is 100% identical to SEQ ID NO: 111. In a further embodiment, the method of monitoring effectiveness is a method of monitoring the effectiveness of a PAPPA binding protein that comprises a) a heavy chain as shown in SEQ ID NO: 120 and a light chain as shown in SEQ ID NO: 121; b) a heavy chain as shown in SEQ ID NO: 122 and a light chain as shown in SEQ ID NO: 123 or c) a heavy chain as shown in SEQ ID NO: 124 and a light chain as shown in SEQ ID NO: 125.

In an embodiment said IGFBP-Ct fragment is an IGFBP-4-Ct fragment or an IGFBP-5-Ct fragment. In an embodiment said IGFBP-4-Ct fragment is a polypeptide that comprises or consists of SEQ ID NO: 9. In an embodiment said IGFBP-5-Ct fragment is a polypeptide that comprises or consists of SEQ ID NO: 14. Preferably however, the IGFBP-Ct fragment is IGFBP-4 Ct fragment (i.e., of SEQ ID NO: 9)

In an embodiment, said IGFBP-Nt fragment is an IGFBP-4-Nt fragment or IGFBP-5-Nt fragment. In an embodiment said IGFBP-4-Nt fragment is a polypeptide that comprises or consists of SEQ ID NO: 8. In an embodiment said IGFBP-5-Nt fragment is a polypeptide that comprises or consists of SEQ ID NO: 13. Preferably however the IGFBP-Nt fragment is IGFBP-4 Nt fragment (i.e., of SEQ ID NO: 8).

In an embodiment wherein said IGFBP-full length polypeptide is IGFBP-4 or IGFBP-5 full-length polypeptide. In an embodiment said IGFBP-4-full length polypeptide comprises or consists of SEQ ID NO: 7. In an embodiment said IGFBP-5-full length polypeptide comprises or consists of SEQ ID NO: 12. Preferably however the IGFBP-full length polypeptide is IGFBP-4 full length (i.e., of SEQ ID NO: 7)

Thus in an embodiment there is provided a method of monitoring the effectiveness of a PAPPA binding protein in treating PKD in a subject said method comprising a) subjecting a first biological sample obtained from the subject to at least one assay to measure the level of an IGFBP4-C-terminal (Ct) fragment, an IGFBP-4 N-terminal (Nt) fragment and/or an IGFBP4-full length polypeptide, b) subjecting a second biological sample obtained from the subject to at least one assay to measure the level of an IGFBP4-Ct fragment, an IGFBP4-Nt fragment and/or an IGFBP4-full length polypeptide wherein said second biological sample is obtained from the subject following treatment with the PAPPA binding protein; and c) comparing the level of said IGFBP4-Ct fragment, IGFBP4-Nt fragment and/or an IGFBP4-full length polypeptide obtained in steps a) and b), wherein decreased levels of said IGFBP4-Ct fragment and/or IGFBP4-Nt fragment in the second biological sample relative to the levels of said IGFBP4-Ct fragment and/or IGFBP4-Nt fragment in the first biological sample and/or increased levels of said IGFBP4-full length polypeptide in the second biological sample relative to the levels of said IGFBP4-full length polypeptide in the first biological sample is indicative of therapeutic efficacy in the treatment of the subjects PKD. In an embodiment there is provided a method of monitoring the effectiveness of a PAPPA binding protein in treating PKD in a subject said method comprising a) subjecting a first biological sample obtained from the subject to at least one assay to measure the level of IGFBP4-C-terminal (Ct) fragment and/or IGFBP4-full length polypeptide, b) subjecting a second biological sample obtained from the subject to at least one assay to measure the level of an IGFBP4-Ct fragment and/or an IGFBP4-full length polypeptide wherein said second biological sample is obtained from the subject following treatment with the PAPPA binding protein; and c) comparing the level of said IGFBP4-Ct fragment and/or an IGFBP4-full length polypeptide obtained in steps a) and b), wherein decreased levels of said IGFBP4-Ct fragment in the second biological sample relative to the levels of said IGFBP4-Ct fragment in the first biological sample and/or increased levels of said IGFBP4-full length polypeptide in the second biological sample relative to the levels of said IGFBP4-full length polypeptide in the first biological sample is indicative of therapeutic efficacy in the treatment of the subjects PKD.

In an embodiment decreased levels of said IGFBP-Ct or IGFBP-Nt fragment in the second biological sample relative to the levels of said IGFBP-Ct or IGFBP-Nt fragment in the first biological sample correlates with improved estimated glomerular filtration rate (eGFR). In particular decreased levels of said IGFBP4-Ct fragment in the second biological sample relative to the levels of said IGFBP4-Ct fragment in the first biological sample correlates with improved estimated glomerular filtration rate (eGFR).

In an embodiment the levels of said IGFBP-Ct and/or IGFBP-Nt fragment in the second biological sample are considered decreased relative to the levels of said IGFBP-Ct or IGFBP-Nt fragment in the first biological sample when said level is reduced by greater than 5%, reduced by greater than 10%, reduced by greater than 25%, reduced by greater than 50%, reduced by greater than 75% or reduced by greater than 90% relative to the levels in the first biological sample. In an embodiment the levels of said IGFBP4-Ct fragment in the second biological sample are considered decreased relative to the levels of said IGFBP4-Ct fragment in the first biological sample when said level is reduced by greater than 5%, reduced by greater than 10%, reduced by greater than 25%, reduced by greater than 50%, reduced by greater than 75% or reduced by greater than 90% relative to the levels in the first biological sample. In a particular embodiment the levels of said IGFBP4-Ct fragment in the second biological sample are considered decreased relative to the levels of said IGFBP4-Ct fragment in the first biological sample when said level is reduced by greater than 85% or greater than 90%.

In an embodiment, the levels of said IGFBP-full length polypeptide in the second biological sample are considered increased relative to the levels of said IGFBP-full length polypeptide in the first biological sample when said level is increased by at least 5%, at least 10%, at least 25%, at least 50%, at least 100%, at least 200%, at least 300% or at least 500% relative to the levels in the first biological sample. In an embodiment, the levels of said IGFBP4-full length polypeptide in the second biological sample are considered increased relative to the levels of said IGFBP4-full length polypeptide in the first biological sample when said level is increased by at least 5%, at least 10%, at least 25%, at least 50%, at least 100%, at least 200%, at least 300% or at least 500% relative to the levels in the first biological sample. It will be appreciated by those of skill in the art that during step b) a sufficient period of time needs to have elapsed between treating the subject with the PAPPA binding protein and obtaining the second biological sample. In an embodiment, said second biological sample is obtained from the subject at least 12 hours following treatment with said PAPPA binding protein, for example said second biological sample is obtained from the subject approximately 24 hours, approximately 36 hours, approximately 48 hours or approximately 72 hours following treatment with said PAPPA binding protein. In an embodiment, said second biological sample is obtained from the subject within 1 week, within 2 weeks or within 1 month following treatment with said PAPPA binding protein.

In a similar manner to that described above (in the section entitled Predictive Biomarkers) said at least one assay to measure the level of an IGFBP-C-terminal (Ct) or N-terminal (Nt) fragment and/or an IGFBP-full length polypeptide can be any suitable assay to measure protein abundance but in a particular embodiment said at least one assay is an ELISA. In an embodiment, the biological sample is sputum, kidney cyst fluid, urine, whole blood, plasma or serum sample. In an embodiment the biological sample is plasma. In an embodiment the biological sample is serum. In an embodiment the biological sample is urine.

Embodiments are further described in the subsequent numbered clauses

1. A pregnancy associated plasma protein-A (PAPPA) binding protein wherein said PAPPA binding protein inhibits cleavage of both insulin like growth factor binding protein-4 (IGFBP-4) and insulin like growth factor binding protein-5 (IGFBP-5).

2. The PAPPA binding protein of clause 1 wherein said IGFBP-4 and said IGFBP-5 are human IGFBP-4 and human IGFBP-5 respectively.

3. The PAPPA binding protein of clause 1 or clause 2 wherein said PAPPA binding protein inhibits PAPPA-mediated IGFBP-4 and IGFBP-5 cleavage.

4. The PAPPA binding protein of clauses 1-3 wherein said PAPPA binding protein inhibits IGF-1 liberation from both IGF-1/IGFBP-4 complex(es) and IGF-1/IGFBP-5 complex(es).

5. The PAPPA binding protein of clauses 1~4 wherein said PAPPA binding protein decreases IGF-1 bioavailability.

6. The PAPPA binding protein of any preceding clause wherein said PAPPA binding protein further inhibits cleavage of insulin like growth factor binding protein-2 (IGFBP-2), optionally wherein said IGFBP-2 is human IGFBP-2 and optionally wherein said PAPPA binding protein inhibits IGF-1 liberation from IGF-1/IGFBP-2 complex(es).

7. The PAPPA binding protein of any preceding clause wherein said PAPPA binding protein does not bind to PAPPA2.

8. The PAPPA binding protein of clauses 1-7 wherein said PAPPA binding protein binds to human PAPPA with an affinity (KD) of less than 1 nM.

9. The PAPPA binding protein according to clause 8 wherein said PAPPA binding protein binds to human PAPPA with an affinity (KD) of less than 500 pM, less than 250 pM, less than 200 pM or less than 150 pM.

10. The PAPPA binding protein of clause 8 or clause 9 wherein said affinity (KD) is measured using surface plasmon resonance (SPR) at 25° C. or 37° C.

11. The PAPPA binding protein according to any preceding clause wherein the $IC_{50}$ for inhibiting cleavage of IGFBP-4 and the $IC_{50}$ for inhibiting cleavage of IGFBP-5 are both 20 nM or less, 10 nM or less, 5 nM or less or 2.5 nM or less.

12. The PAPPA binding protein of clause 11 wherein the $IC_{50}$ for inhibiting cleavage of IGFBP-4 and and the $IC_{50}$ for inhibiting cleavage of IGFBP-5 was determined by measuring inhibition of IGF-1 dependent phosphorylation of the AKT protein induced by PAPPA mediated IGF-1 release from IGF-1/IGFBP-4 complexes and IGF-1/IGFBP-5 complexes.

13. The binding protein of clause 12 wherein said inhibition of IGF-1 dependent phosphorylation of the AKT protein is measured using G401 cells or A549 cells.

14. The PAPPA binding protein of any preceding clause wherein said binding protein reduces IGF-1/IGF1R pathway engagement.

15. The PAPPA binding protein of any preceding clause wherein said PAPPA binding protein inhibits cleavage of IGFBP4 into its IGFBP-4 C-terminal fragment with a $pIC_{50}$ of between 9 and 11.

16. The PAPPA binding protein of clause 15 wherein the $pIC_{50}$ for inhibiting cleavage of IGFBP4 into its IGFBP-4 C-terminal fragment is measured using A549 and/or 9-7 cells.

17. The PAPPA binding protein of any preceding clause wherein said binding protein increases intact IGFBP4 with a $pEC_{50}$ of between 9 and 10.

18. The PAPPA binding protein of clause 17 wherein the $pEC_{50}$ for increasing intact IGFBP4 is measured using A549 cells and/or 9-7 cells.

19. The PAPPA binding protein of any preceding clause wherein said binding protein reduces kidney and/or liver cyst growth following administration to a subject suffering from a polycystic kidney disease (PKD), optionally wherein said PKD is autosomal dominant PKD (ADPKD).

20. The PAPPA binding protein of clause 19 wherein said binding protein reduces kidney cyst growth by greater than 50%, greater than 55% or greater than 60%.

21. The PAPPA binding protein of clause 19 or clause 20 wherein said reduction in kidney cyst growth is measured by determining reduction in total kidney volume (tKV).

22. The PAPPA binding protein of any preceding clause comprising: (a) (i) any one or a combination of CDRs selected from CDRH1, CDRH2, CDRH3 from SEQ ID NOs: 21, 33, 45, 57, 69, 81, 93 and 105, and/or CDRL1, CDRL2, CDRL3 from SEQ ID NOs: 27, 39, 51, 63, 75, 87, 99 and 111; or (ii) a CDR variant of (i), wherein the variant has 1, 2, or 3 amino acid modifications; or (b) a VH region comprising a sequence at least 80% identical to the sequence of SEQ ID NOs: 21, 33, 45, 57, 69, 81, 93 or 105; and/or a VL region comprising a sequence at least 80% identical to the sequence of SEQ ID NOS: 27, 39, 51, 63, 75, 87, 99 or 111.

23. The PAPPA binding protein of clause 22 wherein the CDR of (a) (i) is: a CDRH1 selected from SEQ ID NOs: 23, 35, 47, 59, 71, 83, 95 and 107; a CDRH2 selected from SEQ ID NOs: 24, 36, 48, 60, 72, 84, 96 and 108; and/or a CDRH3 selected from SEQ ID NOs: 25, 37, 49, 61, 73, 85, 97 and 109; a CDRL1 selected from SEQ ID NOs: 29, 41, 53, 65, 77, 89, 101 and 113; a CDRL2 selected from SEQ ID NOs: 30, 42, 54, 66, 78, 90, 102 and 114; and/or a CDRL3 selected from SEQ ID NOs: 31, 43, 55, 67, 79, 91, 103 and 115.

24. The PAPPA binding protein of any preceding clause wherein said binding protein comprises: a CDRH1 that is 100% identical to SEQ ID NOs: 23, 35, 47, 59, 71, 83, 95 or 107; a CDRH2 that is 100% identical to SEQ ID NOs: 24, 36, 48, 60, 72, 84, 96 or 108; and/or a CDRH3 that is 100% identical to SEQ ID NOs: 25, 37, 49, 61, 73, 85, 97 or 109; a CDRL1 that is 100% identical to SEQ ID NOs: 29, 41, 53, 65, 77, 89, 101 or 113; a CDRL2 that is 100% identical to SEQ ID NOs: 30, 42, 54, 66, 78, 90, 102 or 114; and/or a CDRL3 that is 100% identical to SEQ ID NOs: 31, 43, 55, 67, 79, 91, 103 and 115.

25. The PAPPA binding protein of clauses 22-24 wherein all six CDRs are present in the binding protein.

26. The PAPPA binding protein according to any preceding clause comprising the following 6 CDRs: a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 5; or b) CDRH1 of SEQ ID NO: 71; CDRH2 of SEQ ID NO: 72 and CDRH3 of SEQ ID NO: 73; and CDRL1 of SEQ ID NO: 77;

CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

27. The PAPPA binding protein according to clause 26 comprising the following 6 CDRs: CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

28. The PAPPA binding protein according to any preceding clause wherein said binding protein comprises a) a VH region that is 90% identical to SEQ ID NO: 45 and/or a VL region that is 90% identical to SEQ ID NO: 51; or b) a VH region that is 90% identical to SEQ ID NO: 69 and/or a VL region that is 90% identical to SEQ ID NO: 75; or c) a VH region that is 90% identical to SEQ ID NO: 93 and/or a VL region that is 90% identical to SEQ ID NO: 99; or d) a VH region that is 90% identical to SEQ ID NO: 105 and/or a VL region that is 90% identical to SEQ ID NO: 111.

29. The PAPPA binding protein according to clause 28 wherein said binding protein comprises a VH region that is 90% identical to SEQ ID NO: 105 and/or a VL region that is 90% identical to SEQ ID NO: 111.

30. The PAPPA binding protein according to any preceding clause wherein said binding protein comprises a) a VH region that is 100% identical to SEQ ID NO: 45 and/or a VL region that is 100% identical to SEQ ID NO: 51; or b) a VH region that is 100% identical to SEQ ID NO: 69 and/or a VL region that is 100% identical to SEQ ID NO: 75; or c) a VH region that is 100% identical to SEQ ID NO: 93 and/or a VL region that is 100% identical to SEQ ID NO: 99; or d) a VH region that is 100% identical to SEQ ID NO: 105 and/or a VL region that is 100% identical to SEQ ID NO: 111.

31. The PAPPA binding protein according to clause 30 wherein said binding protein comprises a VH region that is 100% identical to SEQ ID NO: 105 and/or a VL region that is 100% identical to SEQ ID NO: 111.

32. The PAPPA binding protein of clauses 1-31 wherein said PAPPA binding protein binds to an epitope within the M1/M2 region of human PAPPA.

33. The PAPPA binding protein of clause 32 wherein said M1/M2 region of human PAPPA corresponds to amino acid residues 673-1213 of SEQ ID NO: 1.

34. The PAPPA binding protein of clause 32 or clause 33 wherein said epitope comprises one or more amino acids within residues 1031-1079 of SEQ ID NO: 1.

35. The PAPPA binding protein of clauses 32-34 wherein said epitope comprises one or more amino acids within residues 1067-1079 of SEQ ID NO: 1.

36. The PAPPA binding protein of clauses 32-35 wherein said epitope comprises residues Pro1075, Tyr1076 and Leu1079 of SEQ ID NO: 1.

37. The PAPPA binding protein of clauses 1-31 wherein said PAPPA binding protein binds to an epitope within the LNR3 domain of human PAPPA.

38. The PAPPA binding protein of clause 37 wherein said LNR3 domain of human PAPPA corresponds to amino acid residues 1558-1584 of SEQ ID NO:1.

39. The PAPPA binding protein of clause 37 or clause 38 wherein said epitope comprises one or more amino acid residues 1557-1595 of SEQ ID NO: 1.

40. The PAPPA binding protein of any preceding clause wherein said binding protein has an AC-SINS Assay Score of less than 10, less than 8 or less than 6.

41. A PAPPA binding protein that binds to an epitope within the central M region of human PAPPA.

42. The PAPPA binding protein of clause 41 wherein said binding protein binds to an epitope within the M1/M2 region of human PAPPA.

43. The PAPPA binding protein of clause 42 wherein said M1/M2 region of human PAPPA corresponds to amino acids 673-1213 of SEQ ID NO: 1.

44. The PAPPA binding protein of clauses 41-43 wherein said epitope comprises one or more amino acids within residues 1031-1079 of SEQ ID NO: 1.

45. The PAPPA binding protein of clauses 41-44 wherein said epitope comprises one or more amino acids within residues 1067-1079 of SEQ ID NO: 1.

46. The PAPPA binding protein of clauses 41-45 wherein said epitope comprises one or more of amino acid residues His1031, Asp1033, Ile1056, Asp1057, Leu1058, Ser1059, Pro1075, Tyr1076 and Leu1079 of SEQ ID NO: 1.

47. The PAPPA binding protein of clauses 41-46 wherein said epitope comprises one or more of amino acid residues Pro1075, Tyr1076 and Leu1079 of SEQ ID NO: 1.

48. The PAPPA binding protein of clauses 41-47 wherein two of said PAPPA binding proteins bind to human PAPPA when said human PAPPA is dimerized.

49. The PAPPA binding protein of clauses 41-48 wherein said PAPPA binding protein is the PAPPA binding protein according to any of clauses 1-40 or clauses 51-83.

50. The PAPPA binding protein of clauses 41-49 wherein said binding protein has an AC-SINS Assay Score of less than 10, less than 8 or less than 6.

51. A PAPPA binding protein comprising: (a) (i) any one or a combination of CDRs selected from CDRH1, CDRH2, CDRH3 from SEQ ID NOs: 21, 33, 45, 57, 69, 81, 93 and 105, and/or CDRL1, CDRL2, CDRL3 from SEQ ID NOs: 27, 39, 51, 63, 75, 87, 99 and 111; or (ii) a CDR variant of (i), wherein the variant has 1, 2, or 3 amino acid modifications; or (b) a VH region comprising a sequence at least 80% identical to the sequence of SEQ ID NOs: 21, 33, 45, 57, 69, 81, 93 or 105; and/or a VL region comprising a sequence at least 80% identical to the sequence of SEQ ID NOs: 27, 39, 51, 63, 75, 87, 99 or 111.

52. The PAPPA binding protein of clause 51 wherein the CDR of (a) (i) is: a CDRH1 selected from SEQ ID NOs: 23, 35, 47, 59, 71, 83, 95 and 107; a CDRH2 selected from SEQ ID NOs: 24, 36, 48, 60, 72, 84, 96 and 108; and/or a CDRH3 selected from SEQ ID NOs: 25, 37, 49, 61, 73, 85, 97 and 109; a CDRL1 selected from SEQ ID NOs: 29, 41, 53, 65, 77, 89, 101 and 113; a CDRL2 selected from SEQ ID NOs: 30, 42, 54, 66, 78, 90, 102 and 114; and/or CDRL3 selected from SEQ ID NOs: 31, 43, 55, 67, 79, 91, 103 and 115.

53. The PAPPA binding protein of any clause 51 or clause 52 wherein said binding protein comprises: a CDRH1 that is 100% identical to SEQ ID NOs: 23, 35, 47, 59, 71, 83, 95 or 107; a CDRH2 that is 100% identical to SEQ ID NOs: 24, 36, 48, 60, 72, 84, 96 or 108; and/or a CDRH3 that is 100% identical to SEQ ID NOs: 25, 37, 49, 61, 73, 85, 97 or 109; a CDRL1 that is 100% identical to SEQ ID NOs: 29, 41, 53, 65, 77, 89, 101 or 113; a CDRL2 that is 100% identical to SEQ ID NOs: 30, 42, 54, 66, 78, 90, 102 or 114; and/or a CDRL3 that is 100% identical to SEQ ID NOs: 31, 43, 55, 67, 79, 91, 103 and 115.

54. The PAPPA binding protein according to clauses 51-53 wherein five CDRs are present in the binding protein.

55. The PAPPA binding protein according to clause 54 comprising the following five CDRs: CDRH1 of SEQ ID NO: 107; CDRH2 of SEQ ID NO: 108 and CDRH3 of SEQ ID NO: 109; and CDRL1 of SEQ ID NO: 113; and CDRL3 of SEQ ID NO: 115.

56. The PAPPA binding protein of clause 51-53 wherein all six CDRs are present in the binding protein.

57. A PAPPA binding protein comprising the following 6 CDRs: a) CDRH1 of SEQ ID NO: 47; CDRH2 of SEQ ID NO: 48 and CDRH3 of SEQ ID NO: 49; and CDRL1 of SEQ ID NO: 53; CDRL2 of SEQ ID NO: 54; and CDRL3 of SEQ ID NO: 55; or b) CDRH1 of SEQ ID NO: 71; CDRH2 of SEQ ID NO: 72 and CDRH3 of SEQ ID NO: 73; and CDRL1 of SEQ ID NO: 77; CDRL2 of SEQ ID NO: 78; and CDRL3 of SEQ ID NO: 79; or c) CDRH1 of SEQ ID NO: 95; CDRH2 of SEQ ID NO: 96 and CDRH3 of SEQ ID NO: 97; and CDRL1 of SEQ ID NO: 101; CDRL2 of SEQ ID NO: 102; and CDRL3 of SEQ ID NO: 103 or d) CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

58. The PAPPA binding protein according to clause 57 comprising the following 6 CDRs: CDRH1 of SEQ ID NO: 107; CDRH2 of SEQ ID NO: 108 and CDRH3 of SEQ ID NO: 109; and CDRL1 of SEQ ID NO: 113; CDRL2 of SEQ ID NO: 114; and CDRL3 of SEQ ID NO: 115.

59. The PAPPA binding protein according to clause 57 or clause 58 wherein said binding protein comprises a) a VH region that is 90% identical or 95% identical to SEQ ID NO: 45 and/or a VL region that is 90% identical or 95% identical to SEQ ID NO: 51; or b) a VH region that is 90% identical or 95% identical to SEQ ID NO: 69 and/or a VL region that is 90% identical or 95% identical to SEQ ID NO: 75; or c) a VH region that is 90% identical or 95% identical to SEQ ID NO: 93 and/or a VL region that is 90% identical or 95% identical to SEQ ID NO: 99; or d) a VH region that is 90% identical or 95% identical to SEQ ID NO: 105 and/or a VL region that is 90% identical or 95% identical to SEQ ID NO: 111.

60. The PAPPA binding protein according to clause 59 wherein said binding protein comprises a VH region that is 90% identical to SEQ ID NO: 105 and/or a VL region that is 90% identical or 95% identical to SEQ ID NO: 111.

61. The PAPPA binding protein according to clauses 57-60 wherein said binding protein comprises a) a VH region that is 100% identical to SEQ ID NO: 45 and/or a VL region that is 100% identical to SEQ ID NO: 51; or b) a VH region that is 100% identical to SEQ ID NO: 69 and/or a VL region that is 100% identical to SEQ ID NO: 75; or c) a VH region that is 100% identical to SEQ ID NO: 93 and/or a VL region that is 100% identical to SEQ ID NO: 99; or d) a VH region that is 100% identical to SEQ ID NO: 105 and/or a VL region that is 100% identical to SEQ ID NO: 111.

62. The PAPPA binding protein according to clause 61 wherein said binding protein comprises a VH region that is 100% identical to SEQ ID NO: 105 and/or a VL region that is 100% identical to SEQ ID NO: 111.

63. The PAPPA binding protein according to clauses 57-62 wherein said binding protein comprises a heavy chain constant region as shown in SEQ ID NO: 17 and a light chain constant region as shown in SEQ ID NO: 19.

64. The PAPPA binding protein of clauses 57-63 wherein said binding protein comprises a heavy chain and a light chain, wherein the amino acid sequence of the heavy chain is shown in SEQ ID NOs: 20, 32, 44, 56, 68, 80, 92 and 104; and the amino acid sequence of the light chain is shown in SEQ ID NOs: 26, 38, 50, 62, 74, 86, 98 and 110.

65. The PAPPA binding protein of clause 64 wherein said binding protein comprises a heavy chain and a light chain, wherein the amino acid sequence of the heavy chain is shown in SEQ ID NO: 104 and the amino acid sequence of the light chain is shown in SEQ ID NO: 110.

66. A PAPPA binding protein that binds to human PAPPA and competes for binding to said human PAPPA with a reference PAPPA binding protein, wherein said reference PAPPA binding protein comprises a variable heavy chain sequence of SEQ ID NO: 21, 33, 45, 57, 69, 81, 93 or 105; and a variable light chain sequence of SEQ ID NO: 27, 39, 51, 63, 75, 87, 99 or 111.

67. The PAPPA binding protein of clauses 51-66 wherein said binding protein inhibits cleavage of both IGFBP-4 and IGFBP-5, optionally wherein said binding protein inhibits PAPPA-mediated cleavage of both IGFBP-4 and IGFBP-5 and optionally wherein said IGFBP-4 and said IGFBP-5 are human IGFBP-4 and human IGFBP-5 respectively.

68. The PAPPA binding protein of clauses 51-67 wherein said binding protein inhibits IGF-1 liberation from both IGF-1/IGFBP-4 complex(es) and IGF-1/IGFBP-5 complex(es).

69. The PAPPA binding protein of clauses 51-68 wherein said binding protein decreases IGF-1 bioavailability.

70. The PAPPA binding protein of clauses 51-69 wherein said binding protein further inhibits cleavage of IGFBP-2, optionally wherein said IGFBP-2 is human IGFBP-2 and optionally wherein said PAPPA binding protein inhibits IGF-1 liberation from IGF-1/IGFBP-2 complex(es).

71. The PAPPA binding protein of clauses 51-70 wherein said binding protein binds to human PAPPA with an affinity (KD) of less than 1 nM, optionally with an affinity (KD) of less than 500 pM, less than 250 pM, less than 200 pM or less than 150 pM, optionally wherein affinity (KD) is measured using surface plasmon resonance (SPR) at 25° C. or 37° C.

72. The PAPPA binding protein of clauses 51-71 wherein said binding protein has an AC-SINS Assay Score of less than 10, less than 8 or less than 6.

73. The PAPPA binding protein according to clauses 51-72 wherein the $IC_{50}$ for inhibiting cleavage of IGFBP-4 and the $IC_{50}$ for inhibiting cleavage of IGFBP-5 are both 20 nM or less, 10 nM or less, 5 nM or less or 2 nM or less, optionally wherein the $IC_{50}$ for inhibiting cleavage of IGFBP-4 and IGFBP-5 was determined by measuring inhibition of IGF-1 dependent phosphorylation of the AKT protein induced by PAPPA mediated IGF-1 release from IGF-1/IGFBP-4 complexes and IGF-1/IGFBP-5 complexes.

74. The PAPPA binding protein of clauses 51-73 wherein said binding protein reduces kidney and/or liver cyst growth following administration to a subject suffering from a polycystic kidney disease (PKD), optionally wherein said PKD is autosomal dominant PKD (ADPKD).

75. The PAPPA binding protein of clause 74 wherein said binding protein reduces kidney cyst growth by greater than 50%, greater than 55% or greater than 60%.

76. The PAPPA binding protein of clause 74 or clause 75 wherein said reduction in kidney cyst growth is measured by determining reduction in total kidney volume (tKV).

77. The PAPPA binding protein of any preceding clause wherein said binding protein is derived from a mammal.

78. The PAPPA binding protein of any preceding clause wherein said PAPPA binding protein is a human or humanized PAPPA binding protein.

79. The PAPPA binding protein of clause 78 wherein said PAPPA binding protein is a human PAPPA binding protein.

80. The PAPPA binding protein of any preceding clause wherein said PAPPA binding protein is an antibody or an antigen binding fragment thereof.

81. The PAPPA binding protein of clause 80 wherein said antibody or antigen binding fragment thereof comprises a modified Fc region.

82. The PAPPA binding protein of clause 80 or clause 81 wherein said antibody or antigen binding fragment thereof has reduced effector function, such as reduced ADCC and/or CDC.

83. The PAPPA binding protein of clause 81 or clause 82 wherein said modified Fc region comprises the amino acid substitutions L235A and G237A (EU index numbering).

84. A nucleic acid sequence that encodes the PAPPA binding protein as defined in any of the preceding clauses.

85. The nucleic acid sequence of clause 84 wherein said nucleic acid sequence encodes one of or both of the heavy chain and light chain of the PAPPA binding protein as defined in any of clauses 1-83.

86. The nucleic acid sequence of clause 84 or clause 85 wherein said nucleic acid sequence comprises SEQ ID NO: 22, 34, 46, 58, 70, 82, 94 or 106 encoding the heavy chain; and/or SEQ ID NO: 28, 40, 52, 64, 76, 88, 100 or 112 encoding the light chain.

87. The nucleic acid sequence of clause 86 wherein said nucleic acid sequence comprises SEQ ID NO: 106 encoding the heavy chain; and/or SEQ ID NO: 112 encoding the light chain.

88. An expression vector comprising the nucleic acid sequence of clauses 84-87.

89. The expression vector of clause 88 comprising the nucleic acid sequence of the heavy chain of SEQ ID NO: 116 and the nucleic acid sequence of the light chain of SEQ ID NO: 117.

90. A recombinant host cell comprising the nucleic acid sequence of clauses 84-87 or the expression vector(s) of clauses 88 or 89.

91. A method for the production of a PAPPA binding protein, said method comprising culturing the host cell of clause 90 under conditions suitable for expression of said nucleic acid or vector(s), whereby a PAPPA binding protein is produced.

92. A PAPPA binding protein produced by the method of clause 91.

93. A cell line engineered to express the PAPPA binding protein of any of clauses 1-83.

94. A pharmaceutical composition comprising the PAPPA binding protein of clauses 1-83 and a pharmaceutically acceptable excipient.

95. A method for the treatment of a disease in a subject in need thereof comprising administering to said subject a therapeutically effective amount of the PAPPA binding protein as defined in any of clauses 1-83 or the pharmaceutical composition of clause 94.

96. A method for the treatment of a polycystic kidney disease (PKD) in a subject in need thereof comprising administering to said subject a therapeutically effective amount of the PAPPA binding protein as defined in any of clauses 1-83 or the pharmaceutical composition of clause 94.

97. The method of clause 96 wherein the PKD is autosomal dominant PKD (ADPKD) or autosomal recessive PKD (ARPKD).

98. The method of clause 96 or clause 97 wherein the PKD is ADPKD.

99. The method of clauses 96-98 wherein said method further treats polycystic liver disease.

100. A method for the treatment of diabetic kidney disease in a subject in need thereof comprising administering to said subject a therapeutically effective amount of the PAPPA binding protein as defined in any of clauses 1-83 or the pharmaceutical composition of clause 94.

101. A method for the treatment of polycystic liver disease in a subject in need thereof comprising administering to said subject a therapeutically effective amount of the PAPPA binding protein as defined in any of clauses 1-83 or the pharmaceutical composition of clause 94.

102. A method of slowing kidney and/or liver cyst growth in a subject in need thereof comprising administering to said subject a therapeutically effective amount of the PAPPA binding protein as defined in any of clauses 1-83 or the pharmaceutical composition of clause 94.

103. A method of reducing tKV in a subject in need thereof comprising administering to said subject a therapeutically effective amount of the PAPPA binding protein as defined in any of clauses 1-83 or the pharmaceutical composition of clause 94.

104. A method of reducing IGF1 stimulated kidney and/or liver cyst growth in a subject in need thereof comprising administering to said subject a therapeutically effective amount of the PAPPA binding protein as defined in any of clauses 1-83 or the pharmaceutical composition of clause 94.

105. A method for the treatment of atherosclerosis in a subject in need thereof comprising administering to said subject a therapeutically effective amount of the PAPPA binding protein as defined in any of clauses 1-83 or the pharmaceutical composition of clause 94.

106. The method of any of clauses 95-105 wherein the subject is a human subject.

107. A PAPPA binding protein as defined in clauses 1-83 or a pharmaceutical composition as defined in clause 94 for use in the treatment of a disease in a subject.

108. A PAPPA binding protein as defined in clauses 1-83 or a pharmaceutical composition as defined in clause 94 for use in the treatment of a PKD in a subject.

109. The PAPPA binding protein for use according to clause 108 wherein said PKD is ADPKD or ARPKD.

110. The PAPPA binding protein for use according to clause 108 or clause 109 wherein said PKD is ADPKD.

111. The PAPPA binding protein for use according to clauses 108-110 wherein said use further treats polycystic liver disease.

112. A PAPPA binding protein as defined in clauses 1-83 or a pharmaceutical composition as defined in clause 94 for use in the treatment of diabetic kidney disease in a subject.

113. A PAPPA binding protein as defined in clauses 1-83 or a pharmaceutical composition as defined in clause 94 for use in the treatment of polycystic liver disease in a subject.

114. A PAPPA binding protein as defined in clauses 1-83 or a pharmaceutical composition as defined in clause 94 for use in reducing tKV in a subject.

115. A PAPPA binding protein as defined in clauses 1-83 or a pharmaceutical composition as defined in clause 94 for use in reducing IGF-1 stimulated kidney and/or liver cyst growth in a subject.

116. A PAPPA binding protein as defined in clauses 1-83 or a pharmaceutical composition as defined in clause 94 for use in the treatment of atherosclerosis in a subject.

117. A PAPPA binding protein as defined in clauses 1-83 or a pharmaceutical composition as defined in clause 94 for use in slowing kidney and/or liver cyst growth in a subject.

118. The PAPPA binding protein for use according to clauses 107-117 wherein said subject is a human subject.

119. Use of a PAPPA binding protein according to any of clauses 1-83 or the pharmaceutical composition of clause 94 in the manufacture of a medicament for use in the treatment of a disease.

120. The use of clause 119 wherein said disease is a renal disease, optionally a polycystic kidney disease, optionally ADPKD.

121. A method of determining whether a subject suspected of suffering with a PKD is a candidate for treatment with a PAPPA binding protein, said method comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level the subject is identified as a candidate for treatment with a PAPPA binding protein.

122. A method of identifying a susceptibility to develop PKD in a subject, comprising the step of subjecting a biological sample obtained from the subject to at least one assay to measure the level of an IGFBP-C-terminal (Ct) fragment and/or an IGFBP-N-terminal (Nt) fragment wherein when the level of said IGFBP-Ct fragment and/or IGFBP-Nt fragment is high relative to a reference level it is indicative of a susceptibility to develop PKD.

123. A method of treating a PKD in a subject said method comprising a) selecting a subject that is identified as having high levels of an IGFBP-C-terminal (Ct) fragment and/or an IGFBP-N-terminal (Nt) fragment relative to a reference level having previously subjected a biological sample obtained from said subject to at least one assay to measure the level of an IGFBP-Ct fragment and/or an IGFBP-Nt fragment and b) administering a PAPPA binding protein to said subject.

124. The method of clauses 121-123 wherein the reference level is pre-determined according to the level of said IGFBP-Ct fragment and/or IGFBP-Nt fragment in healthy individuals.

125. The method of clause 121-124 wherein the reference level is pre-determined according to the level of said IGFBP-Ct fragment and/or IGFBP-Nt fragment in a subject(s) not suffering or not suspected of suffering from any renal disease, optionally wherein said renal disease is a PKD, optionally ADPKD.

126. The method of clauses 121-125 wherein the level of IGFBP-Ct fragment and/or IGFBP-Nt fragment is high relative to a reference level when the level of IGFBP-Ct fragment and/or IGFBP-Nt fragment is increased by at least 5%, at least 10%, at least 25%, at least 50%, at least 100%, at least 200%, at least 300%, at least 500% or at least 600% relative to said reference level.

127. The method of clauses 121-125 wherein the level of IGFBP-Ct fragment and/or IGFBP-Nt fragment is high relative to a reference level when the level of IGFBP-Ct fragment and/or IGFBP-Nt fragment is greater than 150 ng/ml, greater than 200 ng/ml or greater than 250 ng/ml.

128. The method of clauses 121-127 wherein the IGFBP-Ct fragment is IGFBP4-Ct fragment or IGFBP5-Ct fragment.

129. The method of clause 128 wherein the IGFBP4-Ct fragment is a polypeptide that comprises or consists of SEQ ID NO: 9 and wherein the IGFBP5-Ct fragment is a polypeptide that comprises or consists of SEQ ID NO: 14.

130. The method of clauses 121-127 wherein the IGFBP-Nt fragment is IGFBP4-Nt fragment or IGFBP5-Nt fragment.

131. The method of clause 130 wherein the IGFBP4-Nt fragment is a polypeptide that comprises or consists of SEQ ID NO: 8 and wherein the IGFBP5-Nt fragment is a polypeptide that comprises or consists of SEQ ID NO: 13.

132. A method of monitoring the effectiveness of a PAPPA binding protein in treating PKD in a subject said method comprising a) subjecting a first biological sample obtained from the subject to at least one assay to measure the level of an IGFBP-C-terminal (Ct) fragment, an IGFBP-N-terminal (Nt) fragment and/or an IGFBP-full length polypeptide, b) subjecting a second biological sample obtained from the subject to at least one assay to measure the level of an IGFBP-C-terminal (Ct) fragment, an IGFBP-N-terminal (Nt) fragment and/or an IGFBP-full length polypeptide wherein said second biological sample is obtained from the subject following treatment with the PAPPA binding protein; and c) comparing the level of said IGFBP-C-terminal (Ct) fragment, IGFBP-N-terminal (Nt) fragment and/or IGFBP-full length polypeptide obtained in steps a) and b), wherein decreased levels of said IGFBP-Ct fragment and/or IGFBP-Nt fragment in the second biological sample relative to the levels of said IGFBP-Ct fragment and/or IGFBP-Nt fragment in the first biological sample and/or increased levels of said IGFBP-full length polypeptide in the second biological sample relative to the levels of said IGFBP-full length polypeptide in the first biological sample is indicative of therapeutic efficacy in the treatment of the subjects PKD.

133. The method of clause 132 wherein decreased levels of said IGFBP-Ct or IGFBP-Nt fragment in the second biological sample relative to the levels of said IGFBP-Ct or IGFBP-Nt fragment in the first biological sample correlates with improved estimated glomerular filtration rate (eGFR).

134. The method of clause 132 wherein the first biological sample is obtained from the subject either prior to their first administration with the PAPPA binding protein or prior to their second or subsequent administrations.

135. The method of clauses 132-134 wherein the levels of said IGFBP-Ct and/or IGFBP-Nt fragment in the second biological sample are considered decreased relative to the levels of said IGFBP-Ct and/or IGFBP-Nt fragment in the first biological sample when said level is reduced by greater than 5%, reduced by greater than 10%, reduced by greater than 25%, reduced by greater than 50%, reduced by greater than 75% or reduced by greater than 90% relative to the levels in the first biological sample.

136. The method of clauses 127-130 wherein the levels of said IGFBP-full length polypeptide in the second biological sample are considered increased relative to the levels of said IGFBP-full length polypeptide in the first biological sample when said level is increased by at least 5%, at least 10%, at least 25%, at least 50%, at least 100%, at least 200%, at least 300% or at least 500% relative to the levels in the first biological sample.

137. The method of any of clauses 132-136 wherein said IGFBP-Ct fragment is an IGFBP-4-Ct fragment or an IGFBP-5-Ct fragment.

138. The method of clause 137 wherein said IGFBP-4-Ct fragment is a polypeptide that comprises or consists of SEQ ID NO: 9.

139. The method of clause 137 wherein said IGFBP-5-Ct fragment is a polypeptide that comprises or consists of SEQ ID NO: 14.

140. The method of any of clauses 132-136 wherein said IGFBP-Nt fragment is an IGFBP-4-Nt fragment or IGFBP-5-Nt fragment.

141. The method of clause 140 wherein said IGFBP-4-Nt fragment is a polypeptide that comprises or consists of SEQ ID NO: 8.

142. The method of clause 140 wherein said IGFBP-5-Nt fragment is a polypeptide that comprises or consists of SEQ ID NO: 13.

143. The method of any of clauses 132-136 wherein said IGFBP-full length polypeptide is IGFBP-4 or IGFBP-5 full-length polypeptide.

144. The method of clause 143 wherein said IGFBP-4-full length polypeptide comprises or consists of SEQ ID NO: 7.

145. The method of clause 143 wherein said IGFBP-5-full length polypeptide comprises or consists of SEQ ID NO: 12.

146. The method of clauses 132-145 wherein during step b) said second biological sample is obtained from the subject at least 12 hours following treatment with said PAPPA binding protein.

147. The method of clause 132-145 wherein during step b) said second biological sample is obtained from the subject within 1 month following treatment with said PAPPA binding protein.

148. The method of clauses 121-147 wherein said subject is a human.

149. The method of any of clauses 121-148 wherein said PKD is ADPKD.

150. The method of clauses 121-149 wherein said method is an ex vivo method.

151. The method of any of clauses 121-150 wherein the at least one assay to measure the level of an IGFBP-Ct fragment and/or IGFBP-full length polypeptide is an ELISA assay.

152. The method of clause 151 wherein said ELISA assay comprises i) permitting said IGFBP-Ct fragment and/or IGFBP-full length polypeptide present within the biological sample obtained from the subject to interact with at least one antibody that specifically binds to said IGFBP-Ct fragment and/or IGFBP-full length polypeptide and ii) measuring the interaction between said IGFBP-Ct fragment and/or IGFBP-full length polypeptide and antibody from step i).

153. The method of clause 152 wherein said measurement in step ii) quantitatively indicates the concentration of IGFBP-Ct fragment and/or IGFBP-full length polypeptide within the biological sample obtained from the subject.

154. The method of clauses 152 or 153 wherein said measurement in step ii) uses a secondary antibody labelled with an enzyme, optionally wherein said enzyme is a peroxidase (e.g. horseradish peroxidase), or a phosphatase (e.g. alkaline phosphatase).

155. The method of clauses 121-154 wherein the biological sample is sputum, kidney cyst fluid, urine, whole blood, plasma or serum sample.

156. The method according to clause 121 or any of clause 123-155 wherein said PAPPA binding protein is the PAPPA binding protein of any of clauses 1-83 or is a PAPPA binding comprising a) the heavy chain as shown in SEQ ID NO: 120 and the light chain as shown in SEQ ID NO: 121; b) the heavy chain as shown in SEQ ID NO: 122 and the light chain as shown in SEQ ID NO: 123 or c) the heavy chain as shown in SEQ ID NO: 124 and the light chain as shown in SEQ ID NO: 125.

The invention is further illustrated by the following non-limiting examples.

EXAMPLES

Example 1: Material and Methods

Method #1 OCTET Binding Assay

Affinity determination of antibodies was determined using an OCTET red BLI platform. Briefly, Protein G biosensors were loaded with the antibodies at a concentration of 20 ug/ml (1 nm threshold), washed in running buffer and a baseline signal obtained. Sensors were then added to wells containing antigen at 100 nM for 240 seconds to measure association kinetics, followed by a 300 second dissociation phase with sensors in running buffer. Sensor regeneration was performed by placing sensors in a glycine pH1.5 solution followed by neutralisation in running buffer.

Method #2 PAPP-A FRET-IGFBP Cleavage Assay

Assays were set up to determine PAPP-A activity via cleavage of tagged IGFBP4&5 using FRET (Förster resonance energy transfer) detection to monitor enzyme activity. Briefly, IGFBP4 & 5 were designed with N- and C-terminal tags (FLAG & Myc) and upon addition of anti-FLAG Terbium donor and anti-Myc-d2 acceptor a FRET signal was generated and read on a plate reader. Cleavage of the IGFBP resulted in spatial separation of the tags and prevented the FRET signal from developing, allowing a measurement of PAPPA activity.

Test inhibitors at 10× final concentration in enzyme buffer were added to the relevant wells in a polypropylene dilution plate containing 60 μL of enzyme buffer in all other wells. Serial dilutions of both Isotype control mAb and anti-PAPPA mAbs 1:3 (30 μL+60 μL buffer) were then generated over 11 points in enzyme buffer. IGFBP 4 or 5 protein and PAPPA were diluted to 5× final concentration in enzyme buffer and the HTRF detection mix was prepared as follows; anti-FLAG Terbium donor and anti-Myc-d2 acceptor were diluted together to 2× final concentration in enzyme buffer containing 20 mM EDTA. 2 μL of the prepared test inhibitor mAbs were added to the corresponding wells of the 384-well white assay plate followed by 4 μL PAPPA to all wells of the 384-well white assay plate excluding columns for negative controls and incubated for 30 minutes at room temperature with gentle shaking. 4 μL IGFBP4/5 was then added to all wells, followed by another incubation step for 30 minutes at room temperature with gentle shaking. Finally 10 μL of HTRF mix containing 20 mM EDTA was added to all wells of the assay plate. The plate was then covered with a plate sealer and incubated for 1 hour in the dark at room temperature with gentle agitation. Assay plates were then read on the Pherastar FS plate reader using 665/620 emission settings.

Method #3 G-401 pAKT HTRF Assay

The G-401 cellular pAKT assay was used to determine the ability of anti-PAPPA mAbs to inhibit PAPPA and therefore cleavage of IGFBPs thus preventing release of IGF-1. This was measured via a reduction in pAKT signal in G-401 cells, induced by IGF-1 binding to its receptor. Briefly, G-401 cells were routinely cultured using RPMI1640 plus Heat Inactivated FBS, Glutamax and sodium pyruvate and incubated at 37° C. with 5% $CO_2$. Cells were split at $1.0 \times 10^{-6}$ cells/mL in T175 flask for 3 days culture or $0.8 \times 10^{-6}$ cells/mL in T175 flask for 4 days culture. On assay day #1 cells were seeded into a 96-well flat-bottomed plate at $2.5 \times 10^4$ cells per well in 100 μl of culture media and incubated over night at 37° C. with 5% $CO_2$. On assay day #2 cells were serum starved by carefully removing the culture media and replacing with 100 μl culture media minus FBS (RPMI, Glutamax and Sodium Pyruvate) after a single wash step with 150 μl PBS per well and returned to the incubator for a further 24 hours. On assay day #3 controls and test articles were prepared and added to the relevant wells on the plate. Assay controls were performed as follows;

Positive control for pAKT signalling by IGF-1, 1.97 nM final concentration of IGF-1 for G-401 cellular assays, no inhibitors or PAPPA.

Negative control for pAKT signalling by IGF-1 and IGFBP binding to IGF-1

IGFBP-4 containing assay; IGFBP-4 plus IGF-1 (pre-incubated for 1 hour at RT at a 1:5 molar ratio)-IGF-1 1.97 nM, IGFBP-4, 9.85 nM.

IGFBP-5 containing assay; IGFBP-5 plus IGF-1 (pre-incubated for 1 hour at RT at a 1:5 molar ratio)-IGF-1 1.97 nM, IGFBP-5, 9.85 nM.

Positive control for PAPPA activity for G-401 cellular assays with exogenous PAPPA and IGFBP-4, either 2 nM Human PAPPA, 2 nM Cyno PAPPA, 2 nM Mouse PAPPA, 10 nM Rat PAPPA or 2 nM Rabbit PAPPA, plus IGFBP-4-IGF-1 complex described above.

Positive control for PAPPA activity for G-401 cellular assays with exogenous PAPPA and IGFBP-5, 0.6 nM Human PAPPA plus IGFBP-5-IGF-1 complex described above.

The remaining test wells received the relevant species' PAPPA for the experiment, IGFBP-4 or -5-IGF-1 complex and control inhibitors STC1 (IGFBP-5 assays)/Ansh labs (AB-301-AP031) positive control mAb (IGFBP-4), Isotype controls or the test anti-PAPPA mAbs as a 9-point dose response curve. Cells were incubated with test articles for 1 hour at 37° C., 5% $CO_2$ prior to cell lysis, transfer to a 384-well plate (Greiner) and pAKT measurement by HTRF (Perkin Elmer, Phoshpo-AKT (THR308) Kit, Cat #64AKT-PEH) using a BMG Pherastar FS plate reader.

Method #4 Assessment of SPR Kinetics of Human, PAPP-A Binding to Antibodies at 25° C.

Binding of anti-PAPPA mAbs to recombinant human, cynomolgus monkey and rabbit PAPPA was assessed using non-regenerative capture kinetics on the Carterra LSA (Carterra) high throughput SPR instrument. The antibodies (2-8 ug/ml), were captured onto an anti-human Fc antibody (Southern Biotech) immobilized on a HC30M biosensor surface (Carterra). Analytes were injected over the captured antibodies as a concentration series including eight 2× serial dilutions with the highest concentration of 64 nM. Analytes were injected from the lowest to the highest concentration. Association phase was 300 seconds, followed by a dissociation phase of 1200 seconds. A buffer only (0 nM analyte) injection was used to double reference the binding curves. Regeneration of the chip surface was carried out using 10 mM Glycine pH1.5. The assay was run at 25° C. in HBS-EP+ buffer. Anti-PAPPA mAbs were analysed as three independently prepared replicates.

Method #5 A549 pAKT HTRF Assay

The A549 cellular pAKT assay was used to determine the ability of anti-PAPPA mAbs to inhibit PAPPA as described above in the G-401 assay. A549 cells natively secrete human PAPPA and this cell line was used to determine the ability of anti-PAPPA mAbs to inhibit a non-recombinant (i.e native) form of PAPPA.

Briefly, A549 cells were routinely cultured using Ham's F-12K nutrient media plus Heat Inactivated FBS, and incubated at 37° C. with 5% $CO_2$. Cells were split at $1.0 \times 10^{-6}$ cells/mL in T175 flask for 3 days culture or $0.8 \times 10^{-6}$ cells/mL in T175 flask for 4 days culture. On assay day #1 cells were seeded into a 96-well flat-bottomed plate at $2.5 \times 10^4$ cells per well in 100 μl of culture media and incubated over night at 37° C. with 5% $CO_2$. On assay day #2 cells were serum starved by carefully removing the culture media and replacing with 100 μl culture media minus FBS after a single was step with 150 μl PBS per well and returned to the incubator for a further 24 hours. On assay day #3 controls and test articles were prepared and added to the relevant wells on the plate. Controls were as follows;

Positive control for pAKT signalling by IGF-1, 6.58 nM IGF-1.

Positive control for PAPPA activity via IGF-1 signalling; IGFBP-4 containing assay; IGFBP-4 plus IGF-1 (pre-incubated for 1 hour at RT at a 1:5 molar ratio)-IGF-1 6.58 nM, IGFBP-4, 32.9 nM.

The remaining test wells received IGFBP4-IGF-1 complex and control inhibitors STC1, Ansh labs positive control mAb, Isotype controls or test anti-PAPPA mAbs as a 9-point dose response curve. Cells were incubated with test articles for 1 hour at 37° C., 5% $CO_2$ prior to cell lysis transfer to a 384-well plate (Greiner) and pAKT measurement by HTRF (Perkin Elmer, Phoshpo-AKT (THR308) Kit, Cat #64AKT-PEH) using a BMG Pherastar FS plate reader.

Method #6 BIACORE Analysis

Binding of TPP12744 to recombinant human, cynomolgus monkey and rabbit PAPPA was assessed using capture kinetics method on BIACORE 8K+ (Cytiva) SPR instrument. The antibodies, including controls, were captured on PrismA biosensor surface (Cytiva) at injection rate of 10 µl/min. Analytes were injected at injection rate of 30 µl/min over the captured antibodies as a concentration series including eight 2× serial dilutions with the highest concentration of 32 nM. Association phase was 160 seconds, followed by a dissociation phase of 600 seconds. Buffer only (0 nM analyte) injection was used to double reference the binding curves. Regeneration of the chip surface between cycles was carried out using 10 mM Glycine pH 1.5. The assay was run at 37° C. in HBS-EP+ buffer with 0.1% BSA to minimize the nonspecific binding of the analytes to the chip surface. TPP12744 was analyzed as three independently prepared replicates.

Example 2: Generation of PAPPA Binding Proteins

Generation and Identification of Functionally Active PAPPA Inhibitory mAbs

Naive selections were performed using a yeast-based platform. Four sequential rounds of selections were carried out, toggling between in-house generated recombinant biotinylated Human PAPPA (8.4 biotin/molecule, TPP-5400), recombinant biotinylated Cynomolgus PAPPA (9.6 biotin/molecule, TPP-5401) and recombinant biotinylated Mouse PAPPA (5.8 biotin/molecule, TPP-5402) starting with Magnetic cell sorting (MACS) and Fluorescence Activated Cell Selection (FACS) based selection techniques.

Heavy chains from the final selection rounds' outputs were PCR amplified and used in the constructions of optimisation libraries with naive light chains. Further iterative rounds of selections were carried out on the resulting libraries as previously described. A total of 443 antibodies were expressed and characterised.

Main outputs, post light-chain batch shuffle, were screened in various assays. Primary screening was performed using FRET-based PAPPA-IGFBP-4 & 5 cleavage assays (method #2) and BLI-based affinity measurement (method #1) with 87 antibodies identified as functional from the total panel. Of these 87 antibodies, 10 were discarded upon assessment for biophysical characteristics using SEC, NanoDSF and HIC and the remaining 77 were screened using a cellular functional assay with an IGF-1 downstream pAKT readout (method #3) and an SPR-based epitope binning analysis using the Carterra LSA. Results from these assays allowed a triage to a panel of 16 antibodies.

The 16 antibodies left after the processes described above were clustered by VH gene sequence resulting in 3 clusters and 6 uniques. The 3 clusters were analysed across the range of data available and 1 antibody from each cluster taken forward. Of the 6 uniques two were selected thus resulting in a panel of five taken forward for further optimisation.

The 5 antibodies taken forward for optimisation all demonstrated activity against PAPPA cleavage of both IGFBP-4 and IGFBP-5. The heavy chain and light chains CDRs were diversified independently through the introduction of random mutations at a low frequency.

The amino acid sequence of 22 anti-PAPPA antibodies of interest were analysed for sequence liabilities, including predicted post translational modifications (PTMs) and immunogenic peptides. Engineered variants were designed to mitigate these predicted risks using single point mutations, plus all combinations of these. All clones were in silico cloned onto a human IgG1/kappa Fc-disabled (L235A and G237A) backbone. This resulted in the generation of 148 engineered variants, making 170 antibodies in total. This panel was later triaged to 90 molecules to progress for CHO cell expression and final lead panel screening.

The final screening process was conducted using the following criteria. Firstly, antibodies were checked for affinity to human PAPPA (method #4). Only antibodies with low nanomolar affinity for human PAPPA were retained. For one antibody (TPP12744) binding to PAPPA was assessed at 37° C. using the methodology described in Example 1, method #6. Data is shown in Table 3 below.

TABLE 3

Summary of affinity data generated for TPP12744 binding to PAPPA. TPP12744 did not show significant binding to murine & rat PAPPA (data not shown).

| | Analyte | expt# | Ka (1/Ms) | Kd 1/s | KD (M) @37° C. |
|---|---|---|---|---|---|
| TPP12744 | human PAPPA | Mean (n = 3) | 2.51E+06 | 3.19E−04 | 1.27E−10 |
| TPP12744 | human PAPPA (Common variant) | Mean (n = 3) | 1.87E+06 | 3.93E−04 | 2.10E−10 |
| TPP12744 | Cyno PAPPA | Mean (n = 3) | 2.68E+06 | 4.33E−04 | 1.61E−10 |
| TPP12744 | Rabbit PAPPA | Mean (n = 3) | 3.28E+06 | 5.59E−04 | 1.70E−10 |

Antibodies were then assessed for potency in terms of inhibition of human PAPPA-mediated cleavage of human IGFBP-4 (table 4a) and IGFBP-5 (table 4b below) using method #3 described in Example 1 above.

Table 4: Table showing mean $pIC_{50}$ values for antibodies in a cell-based assay measuring cleavage of IGFBP-4 (Table 4a) and IGFBP-5 (Table 4b) by human PAPPA. Antibodies marked in the tables below as ND were "not determined" due to assay failure.

TABLE 4a

| Antibody ID | PAPP-A cleavage of IGFBP-4 Mean $pIC_{50}$ |
|---|---|
| TPP-12681 | 10.14 |
| TPP-12682 | 8.41 |
| TPP-12683 | 8.80 |
| TPP-12686 | 10.02 |
| TPP-12688 | 10.24 |
| TPP-12689 | 10.49 |
| TPP-12690 | 10.36 |
| TPP-12692 | 8.31 |
| TPP-12693 | 9.77 |
| TPP-12694 | 9.11 |
| TPP-12695 | 8.62 |
| TPP-12696 | 10.01 |
| TPP-12698 | 7.23 |
| TPP-12699 | 7.72 |
| TPP-12700 | 9.99 |

TABLE 4a-continued

| Antibody ID | PAPP-A cleavage of IGFBP-4 Mean $pIC_{50}$ |
|---|---|
| TPP-12701 | 9.27 |
| TPP-12702 | 8.62 |
| TPP-12703 | 7.75 |
| TPP-12704 | 7.13 |
| TPP-12705 | 9.87 |
| TPP-12706 | 7.91 |
| TPP-12707 | 7.81 |
| TPP-12708 | 10.19 |
| TPP-12741 | 9.98 |
| TPP-12742 | 9.24 |
| TPP-12743 | 10.03 |
| TPP-12744 | 10.01 |
| TPP-12768 | 9.15 |
| TPP-12769 | 9.69 |
| TPP-12770 | 7.78 |
| TPP-12771 | 8.96 |
| TPP-12772 | 7.95 |
| TPP-12773 | 10.61 |
| TPP-12774 | 7.53 |
| TPP-12775 | 10.24 |
| TPP-12776 | 7.92 |
| TPP-12777 | 9.57 |
| TPP-12778 | 8.26 |
| TPP-12779 | 8.90 |
| TPP-12780 | 7.41 |
| TPP-12781 | 10.16 |
| TPP-12782 | ND |
| TPP-12783 | 10.20 |
| TPP-12784 | 8.75 |
| TPP-12785 | 7.92 |
| TPP-12786 | 7.10 |
| TPP-12787 | 10.04 |
| TPP-12788 | ND |
| TPP-12789 | 9.80 |
| TPP-12790 | 7.33 |
| TPP-12791 | ND |
| TPP-12792 | 9.53 |
| TPP-12801 | 8.96 |
| TPP-12802 | 7.06 |
| TPP-12803 | 8.51 |
| TPP-12805 | 7.66 |
| TPP-12806 | 7.48 |
| TPP-12807 | 9.06 |
| TPP-12808 | ND |
| TPP-12809 | ND |
| TPP-12810 | 8.93 |
| TPP-12811 | 8.61 |
| TPP-12812 | 8.97 |
| TPP-12813 | 9.33 |
| TPP-12814 | 9.91 |
| TPP-12815 | 10.16 |
| TPP-12816 | 7.87 |
| TPP-12817 | 9.64 |
| TPP-12818 | 8.75 |
| TPP-12819 | 9.58 |
| TPP-12820 | 10.25 |
| TPP-12821 | 10.47 |
| TPP-12822 | 8.18 |
| TPP-12823 | 9.64 |
| TPP-12824 | ND |
| TPP-12825 | 9.15 |
| TPP-12826 | 8.34 |
| TPP-12827 | 10.26 |
| TPP-12828 | 8.16 |
| TPP-12829 | ND |
| TPP-12830 | ND |
| TPP-12831 | ND |
| TPP-12832 | 8.96 |
| TPP-12833 | 9.88 |

TABLE 4b

| Antibody ID | PAPP-A cleavage of IGFBP-5 Mean $pIC_{50}$ |
|---|---|
| TPP-12681 | ND |
| TPP-12682 | 8.24 |
| TPP-12683 | 8.69 |
| TPP-12686 | 10.02 |
| TPP-12688 | 9.26 |
| TPP-12689 | 8.51 |
| TPP-12690 | 8.79 |
| TPP-12692 | 7.42 |
| TPP-12693 | 8.20 |
| TPP-12694 | 7.85 |
| TPP-12695 | 7.93 |
| TPP-12696 | 9.83 |
| TPP-12698 | 8.72 |
| TPP-12699 | 7.60 |
| TPP-12700 | 7.99 |
| TPP-12701 | 8.18 |
| TPP-12702 | 8.18 |
| TPP-12703 | 8.08 |
| TPP-12704 | 7.48 |
| TPP-12705 | 10.05 |
| TPP-12706 | 8.29 |
| TPP-12707 | 8.29 |
| TPP-12708 | 11.10 |
| TPP-12741 | 11.38 |
| TPP-12742 | 9.66 |
| TPP-12743 | 10.37 |
| TPP-12744 | 10.70 |
| TPP-12768 | 8.77 |
| TPP-12769 | 9.71 |
| TPP-12770 | 7.70 |
| TPP-12771 | 9.18 |
| TPP-12772 | 7.92 |
| TPP-12773 | ND |
| TPP-12774 | 7.52 |
| TPP-12775 | 10.62 |
| TPP-12776 | ND |
| TPP-12777 | 9.78 |
| TPP-12778 | 8.93 |
| TPP-12779 | 9.18 |
| TPP-12780 | 7.69 |
| TPP-12781 | 10.97 |
| TPP-12782 | 7.62 |
| TPP-12783 | 10.84 |
| TPP-12784 | 8.31 |
| TPP-12785 | 7.92 |
| TPP-12786 | 7.38 |
| TPP-12787 | 11.31 |
| TPP-12788 | 7.25 |
| TPP-12789 | 10.69 |
| TPP-12790 | 7.13 |
| TPP-12791 | ND |
| TPP-12792 | 9.78 |
| TPP-12801 | 9.10 |
| TPP-12802 | 7.90 |
| TPP-12803 | 8.54 |
| TPP-12805 | 7.26 |
| TPP-12806 | ND |
| TPP-12807 | 9.04 |
| TPP-12808 | ND |
| TPP-12809 | 8.07 |
| TPP-12810 | 10.41 |
| TPP-12811 | 8.57 |
| TPP-12812 | 9.51 |
| TPP-12813 | 8.32 |
| TPP-12814 | 8.22 |
| TPP-12815 | 7.99 |
| TPP-12816 | 9.00 |
| TPP-12817 | 7.78 |
| TPP-12818 | 8.94 |
| TPP-12819 | 8.73 |
| TPP-12820 | 9.25 |
| TPP-12821 | 9.10 |
| TPP-12822 | 7.39 |
| TPP-12823 | 10.08 |
| TPP-12824 | 7.28 |
| TPP-12825 | 9.42 |

TABLE 4b-continued

| Antibody ID | PAPP-A cleavage of IGFBP-5 Mean $pIC_{50}$ |
|---|---|
| TPP-12826 | 10.01 |
| TPP-12827 | 10.47 |
| TPP-12828 | 7.80 |
| TPP-12829 | 7.81 |
| TPP-12830 | 8.29 |
| TPP-12831 | 7.30 |
| TPP-12832 | ND |
| TPP-12833 | 9.17 |

Antibodies were also assessed for developability using various assays and those that did not meet pre-specified criteria were discarded. Assays included serum stability assessment which identified several that lost binding upon incubation with human serum, propensity for non-specific binding as determined by binding to Heparin and a measurement of bioavailability upon sub-cutaneous delivery as determined by CIEX. Serum stability analysis, followed by heparin binding and bioavailability analysis reduced antibody numbers further to 13 in total (data not shown). Subsequent sequence analysis allowed a further reduction to 8 antibodies based on lineage.

Following completion of this screening process the eight lead molecules were sequenced and all sequence details are provided in the sequence listing provided herein. SEQ ID numbering is also summarised in Table 12 at the end of the Examples section.

The potency and selectivity of the 8 anti-PAPPA mAbs selected as well as the tool compound Ansh labs PAPPA mab (clone 1/41A, Cat #AB-301-AP031) is shown below.

The Ansh labs anti-PAPPA mAb (as described in Mikkelson et al 2014, Oncotarget, Vol. 5, No. 4 μg 1014-1025) is active against PAPPA-mediated IGFBP4 cleavage with a Kd of ~100 pM (Mikkelsen et al 2014), but it is not active against PAPPA-mediated IGFBP5 cleavage. This was confirmed herein by Western Blot (see FIG. 1A and FIG. 1B). Data obtained using the IGFBP4 and IGFBP5 protein-based FRET assay (method #2 in Example 1) further demonstrated that the Ansh labs mAb inhibited PAPPA-mediated IGFBP4 cleavage with a $pIC_{50}$ of ~10.2 but was inactive against IGFBP5 (data not shown).

In contrast, the 8 anti-PAPPA mAbs generated herein and selected as described above actively blocked both PAPPA-mediated IGFBP4 and IGFBP5 cleavage (see table 5 below). Original N=2 high-throughput screening data (table 4 above) was supplemented with multiple separate repeats to clearly determine the potency of the 8 antibodies against PAPPA. Experiments were performed to determine $pIC_{50}$ values of antibodies inhibiting recombinant Human, Cyno and Murine PAPPA cleavage of IGFBP-4 (Example 1 method #3), recombinant human PAPPA cleavage of IGFBP-5 (Example 1 method #3) and against natively secreted human PAPPA cleavage of IGFBP-4 in A549 cells (Example 1 method #5).

TABLE 5

Cellular potency and selectivity profile for selected anti-PAPPA mAbs

| antibody ID | rec. Human PAPP-A IGFBP4 $pIC_{50}$ | N= | rec. Human PAPP-A IGFBP5 $pIC_{50}$ | N= | rec. Cyno PAPP-A IGFBP4 $pIC_{50}$ | N= | rec. Mouse PAPP-A IGFBP4 $pIC_{50}$ | N= | A549 cells endogenous human PAPP-A $pIC_{50}$ | N= |
|---|---|---|---|---|---|---|---|---|---|---|
| TPP-12681 | 9.57 | 12 | 9.68 | 9 | 9.46 | 8 | 9.51 | 8 | 9.70 | 6 |
| TPP-12683 | 8.84 | 10 | 8.81 | 7 | 8.48 | 2 | 8.88 | 10 | 8.44 | 2 |
| TPP-12708 | 9.59 | 8 | 9.92 | 6 | 9.70 | 2 | Non-active | | 9.86 | 3 |
| TPP-12743 | 9.36 | 8 | 9.66 | 6 | 10.01 | 2 | Non-active | | 9.76 | 3 |
| TPP-12744 | 9.46 | 13 | 9.81 | 11 | 9.56 | 8 | Non-active | | 9.49 | 7 |
| TPP-12792 | 9.18 | 8 | 9.35 | 5 | 9.23 | 2 | Non-active | | 8.92 | 3 |
| TPP-12801 | 9.22 | 8 | 9.05 | 6 | 9.76 | 2 | Non-active | | 9.33 | 3 |
| TPP-12821 | 9.45 | 8 | 9.04 | 5 | 9.85 | 2 | 9.28 | 8 | 9.50 | 2 |

Based on potency, sequence and lineage the remaining 8 antibodies were further triaged to a final panel of four (TPP12744, TPP12681, TPP12801, TPP12683) to be tested in vivo. As shown in table 6 below, the final four selected antibodies included one antibody from each of four sequence clusters present within the above-mentioned panel of 8 (arbitrarily named clusters 1, 2, 3 and 4).

TABLE 6

Sequences of final 8 antibodies showing sequence clusters 1-4. Antibodies shown in bold represent the four selected for further research.

| # | ID | LCDR1 | HCDR1 | LCDR2 | HCDR2 | LCDR3 | HCDR3 |
|---|---|---|---|---|---|---|---|
| 1 | TPP-12681 | RASQSVGSYLA SEQ ID NO: 53 | SYWTG SEQ ID NO: 47 | RGSTRAT SEQ ID NO: 54 | IIYPGGSVARYSPSFQG SEQ ID NO: 48 | QQPYVWPIT SEQ ID NO: 55 | GPLRSDYPDV SEQ ID NO: 49 |

TABLE 6-continued

Sequences of final 8 antibodies showing sequence clusters 1-4. Antibodies
shown in bold represent the four selected for further research.

| # | ID | LCDR1 | HCDR1 | LCDR2 | HCDR2 | LCDR3 | HCDR3 |
|---|----|-------|-------|-------|-------|-------|-------|
| | TPP-12821 | RASQSVGSNLA SEQ ID NO: 65 | SDWIG SEQ ID NO: 59 | RASTRAT SEQ ID NO: 66 | IIYPGGSDTRYSPSFRG SEQ ID NO: 60 | QQPYVWPIT SEQ ID NO: 67 | GPLRSDYVDV SEQ ID NO: 61 |
| 2 | TPP-12683 | RASQDISYWLA SEQ ID NO: 101 | SSSYNWG SEQ ID NO: 95 | AASSLQS SEQ ID NO: 102 | SISSSGSTYFNPSLKS SEQ ID NO: 96 | QQAYLLHT SEQ ID NO: 103 | SGYRPSFYAMDA SEQ ID NO: 97 |
| 3 | TPP-12708 | RASQGISRWLA SEQ ID NO: 41 | SYAMH SEQ ID NO: 35 | STSSLQL SEQ ID NO: 42 | WINAGTGATKYARKFQG SEQ ID NO: 36 | QQENDYPFT SEQ ID NO: 43 | GPSMETPTTYGMEV SEQ ID NO: 37 |
| | TPP-12743 | RASQGISRWLA SEQ ID NO: 29 | SYAMH SEQ ID NO: 23 | AASSLQS SEQ ID NO: 30 | WMNAGTGATKSSQKFQG SEQ ID NO: 24 | QQENAYPFT SEQ ID NO: 31 | GPSLETPTTFGMDV SEQ ID NO: 25 |
| | TPP-12744 | RASQGISRWLA SEQ ID NO: 113 | SYAMH SEQ ID NO: 107 | AASSLQS SEQ ID NO: 114 | WMNAGTGATKSSQKFQG SEQ ID NO: 108 | QQENAYPFT SEQ ID NO: 115 | GPSMETPTTFGMDV SEQ ID NO: 109 |
| 4 | TPP-12792 | RASQGISRWLA SEQ ID NO: 89 | SSDYYWG SEQ ID NO: 83 | AASSVQS SEQ ID NO: 90 | SIFYSGSTYYNPSLKS SEQ ID NO: 84 | QQGNVPPLT SEQ ID NO: 91 | ATTSSSADY SEQ ID NO: 85 |
| | TPP-12801 | RASQGVSRWLA SEQ ID NO: 77 | SSDYYWG SEQ ID NO: 71 | AASSLQS SEQ ID NO: 78 | SIFYSGSTYYNPSLKS SEQ ID NO: 72 | QQGNVPPLT SEQ ID NO: 79 | ATTSSSADY SEQ ID NO: 73 |

Example 3: HDX-MS and Cryo-EM Studies

Epitope Mapping of Human PAPPA in Complex with Anti-PAPPA Antibodies by HDX-MS

The aim of this study was to characterise the molecular details of the interaction between human PAPPA and monoclonal antibodies TPP12744, TPP12681, TPP12801, TPP12683 using H/D Exchange Mass Spectrometry (HDX-MS). A HDX-MS epitope mapping experiment was performed by obtaining differential exchange profiles for each PAPPA-mAb complex relative to that of apo PAPPA indicating regions of structural change or protection upon mAb binding.

HDX-MS Method:

Epitope mapping. PAPPA was incubated with a 1.5-fold excess of each mAb. After incubation in a 50 mM MOPS, 150 mM NaCl D2O buffer, pD 7.2, resulting in a 12-fold dilution, for periods of 30, 600 and 3600 s samples were quenched by an equivalent volume of a 6M Urea+1M TCEP (pH 3.1) solution for 10 minutes at 0° C. 20 pmol of quenched sample was then loaded on to an online pepsin digest column followed by a trapping to a C18 column and following reverse phase gradient at 0.5° C. Samples were then analysed online using a Waters Synapt G2si mass spectrometer in V and sensitivity mode. 4 Repeats were performed per time point per complex. Peptide identification was performed in a similar manner with a mass loading of 40 pmol using Waters PLGS 3.0.3 software. All data including pairwise Welch's t-tests were processed in HDExaminer 3.2.0.

Paratope mapping. TPP12744 was incubated with a 2-fold excess of hPAPPA. After incubation in a 50 mM MOPS, 150 mM NaCl D2O buffer, pD 7.2, resulting in a 12-fold dilution, for periods of 15, 150, 1500 and 15000 s samples were quenched by an equivalent volume of a 6M GdCl+500 mM TCEP (pH 2.5) solution for 10 minutes at 0° C. 20 pmol of quenched sample was then loaded on to an online Nepenthesin 2 digest column followed by a trapping to a C18 column and following reverse phase gradient at 0.5° C. Samples were then analysed online using a Waters Select Series Cyclic IMS mass spectrometer. Four repeats were performed per time point per complex. Peptide identification was performed in a similar manner with a mass loading of 40 pmol using Waters PLGS 3.0.3 software. All data were processed in HDExaminer 3.4.0 and statistical analysis was performed in HDXStats, a Bayes functional modelling approach, through a local R Studio package.

Results: When differential exchange was plotted against the residue number, TPP12744 and TPP12801 showed a maximum response between res. 1067 to 1079 of human PAPPA corresponding to the M1/M2 domain (FIG. 2). Whilst TPP12681 and TPP12683 showed a maximum response between res. 1557 to 1595 of human PAPPA in the LNR3 region which was previously demonstrated to interact with natural substrates STC1 and 2 (Kobberø 2022). Whilst the greatest differential magnitude of the complexes were centered as described above, a number of other regions displayed statistically significant peptides (p<0.01) when comparing single time-points using a pairwise Welch's t-test.

A similar paratope mapping experiment was also conducted for TPP12744. All CDR regions of TPP12744 were found to possess at least 1 peptide with significant (p<0.01) differential protection from deuteration upon complex with human PAPPA. However, CDRL3 unlike other regions only has a single significant peptide with a reduced magnitude of protection. Only a small number of significantly protected peptides contain no residues that lie within the CDRs. This indicates the interaction with PAPPA is largely localised to the CDRs. Significance for paratope mapping was determined using HDXStats analysis software (Crook, O. M., Chung, Cw. & Deane, C. M. Empirical Bayes functional models for hydrogen deuterium exchange mass spectrometry. *Commun Biol* 5, 588 (2022)).

For TPP12744 and TPP12801, the most significant PAPPA HDX protected regions: res. 1067 to 1079, was localised to the M1/M2 domain of PAPPA. This is spatially close to the entrance of the catalytic binding site on another domain; a helix of IGFBP5 substrate bound in the catalytic site was resolved in the cryo-EM structure. (Judge et al., 2022; PDB code 7UFG). The implications of the sterics of the mAb and substrate relative to the epitope are discussed in the following cryo-EM study.

Structural Determination of PAPPA in Complex with Anti-PAPPA Fab Derived from mAb TPP12744 by Cryo-EM The aim of this study was to characterise the molecular details of the interaction between human PAPPA and the monoclonal antibody TPP12744 using cryo-electron microscopy Samples of recombinantly purified Wild type (WT) full length PAPPA complexed with Fab and Fab2 fragments of TPP12744 at a molar ratio of 1:3 were generated for this purpose. The samples were plunge-frozen in liquid ethane using a Thermo Fisher Vitrobot Mark IV and Cryo-EM movies were collected on a 300 keV Thermo Scientific Krios G2 electron microscope equipped with a Falcon 4i direct electron detector.

The cryo-EM movies collected on WT PAPPA in complex with Fab or Fab2 were subjected to image processing using RELION 4.0 and Cryosparc v4.2.1 to generate 3D cryo-electron potential maps. The maps were determined to overall resolution of approximately 3A. All maps are consistent with a PAPPA dimeric structure, sometimes referred to as a "butterfly" architecture in the literature (Judge et al 2022). The maps were used for atomic model building and refinement. Manual building was carried out using Coot (v0.9.8.91, CCP4). Rigid body fitting was conducted using Chimera v1.11 or within Phenix v1.20.1-4487. Phenix was also used for real-space refinement.

The Laminin-G like domain (LG), metalloprotease domain (MP), and central M1/M2 domain pack tightly to form a core that resembles the wing of the butterfly (although their respective orientations can vary). No direct interactions are observed between the contiguous LG and MP domains as these are arranged on opposite sides of the central M1/M2 domain, with the LG domain serving as a scaffold for inter-dimer interactions.

To overcome orientational flexibility of the two PAPPA subunits relative to one another, a mask was imposed on a single protomer PAPPA-Fab2 and focused refined to generate higher resolution final maps. This allowed the sidechain interactions at the PAPPA-Fab interface to be better resolved. The PAPPA epitope lies within the M1/M2 domain. It is centered on the helix encompassing residues Pro1069 to Thr1082, with particularly high buried surface areas (BSA) for Pro1075, Tyr1076 and Leu1079. His1031 and Asp1033. The region Ile1056-Ser1059 can also be found in contact with the Fab. Levels of BSA were determined using the PISA (Protein Interfaces, Surfaces and Assemblies) analysis tool where interface residues are defined as those with >0 buried surface area (BSA) by Qt-PISA v2.1.0.

A similar analysis of the corresponding paratope identifies that residues in CDRL1, CDRL3, CDRH1, CDRH2 and CDRH3 all lie within the antibody binding interface (FIG. 3). CDRL2 does not appear to directly contact despite HDX-MS showing differential protection on binding PAPPA. Interestingly some light chain residues outside the CDRs are also close to the binding interface, namely Ile2 at the N-terminus, Ser67 and Gly68. However, their contribution to the binding energy is predicted by PISA to be small.

Mass photometry has shown evidence that more than one TPP12744 mAb/Fab molecule can bind the PAPPA dimer at the same time. A structure obtained by model building into a non-focused classified map without any symmetry imposed generated from the PAPPA-Fab sample shows evidence of simultaneous binding of two Fab molecules to the PAPPA dimer (FIG. 4)

A literature structure of PAPPA complexed to IGFBP5 (RCSB: 7UFG) could only resolve the anchoring peptide from IGFBP5 within the catalytic site of the MP domain. A superposition of this peptide onto the structure derived from the PAPPA-Fab2 complex is shown in FIG. 5. This implies binding of the full IGFBP5 protein would be blocked by TPP12744. This antibody binds close enough to the entrance of the catalytic site to suggest the mechanism of inhibition for protein substrates beyond IGFBP5, such as IGFBP2 and IGFBP4 may also be due to steric hinderance.

Example 4—Materials and Methods for Examples 5-9

Method #1). Customized ELISA assay for detection of IGFBP4 full length and IGFBP4-Ct fragment.

A neo-epitope rabbit polyclonal antibody (pAb) that specifically recognized human IGFBP4 C-terminal (IGFBP4-Ct) was generated and used to configure a robust ELISA that detected the C-terminal fragments (see FIG. 6.A). The pAb (KEG731) was generated using a peptide C-terminal to the cleavage site, and selected against a bridging peptide as shown in SEQ ID NO: 11 (Laursen et al FEBS Letters 504 (2001) pg 36-40). The resulting pAb was highly specific against the IGFBP4-Ct. Subsequently a commercial mAb from Hytest (HyTest Ltd. Finland, Ab #IBP163) was characterised that also specifically recognizes IGFBP4-Ct, and this mAb was validated using purified IGFBP4 fragment.

An antibody pair that specifically recognized the full length IGFBP4 in an ELISA assay was also configured and validated using commercially available reagents. This assay enabled the detection of intact human IGFBP4, but not its cleaved products. The capture and detection antibody combinations for both IGFBP4 full length and Ct fragment ELISA assay are summarized in Table 7. The established ELISA assays also recognized NHP (non-human primate) IGFBP4 full length and IGFBP4-Ct fragment due to high degree of amino acid sequence identity between human and NHP IGFBP4 proteins.

TABLE 7

| Summary of Antibody combinations for IGFBP4-FL and Ct fragment using ELISAs: | | | |
|---|---|---|---|
| ELISA Analyte | Capture Ab | Detection Ab | Secondary labelled Ab |
| IGFBP4-Fl | IBP182 (HyTest) | BAF804 (R&D systems) | Streptavidin-HRP |
| IGFBP4-Ct (rabbit pAb KEG731 as detection Ab) | IBP182 (HyTest) | KEG731 (custom-made Ab) | Anti-rabbit-HRP |
| IGFBP4-Ct (biotin-labelled IBP163 as detection Ab) | IBP182 (HyTest) | IBP163-biotin (Modified from HyTest) | Streptavidin-HRP |

ELISA Procedure:

A. ELISA plates were coated with a capture antibody and incubated with shaking (~750 rpm) for one hour at room temperature. After incubation, plates were washed 4 times with 1×Phosphate Buffered Saline containingTween-20 (PBST) as Wash Buffer.

B. Protein standards, cell supernatants or patient samples were diluted in 1×Phosphate Buffered Saline (PBS) or Reagent Diluent 3 and added to plates at 50 µl/well. The detection antibodies were added at 50 µl/well. Plates were incubated for 1 hour with shaking and washed 4 times after incubation.

C. 200× diluted Streptavidin-HRP or 10,000× diluted anti-rabbit-HRP was added to plates at 50 µl/well and incubated with shaking for 30 min. Plates were washed 4 times.

D. Substrate solution TMB was added at 100 µl/well and covered with foil, colour development was terminated after 3-10 min and 50 µl Stop solution added per well.

E. Plates were immediately read for optical density using a PHERAstar FSX ELISA reader with wavelength set at 450/540 nm. After background (OD540 nm) and blank reading were subtracted, a standard curve was generated using Nonlinear regression (curve fit), with $Y=Bottom+(Top-Bottom)/(1+(IC_{50}/X)\hat{}HillSlope)$ in GraphPad Prism 8.4. Sample concentration was inter-polated using standard curve and dilution factor cor-rected. The calculated final concentration was copied to GraphPad Prism 8.4, and dose-response curve was generated using Nonlinear regression (curve fit), $Y=Bottom+(Top-Bottom)/(1+10\hat{}((LogEC50-X)))$. Purified IGFBP4-fl and IGFBP4-ct fragment were used as standard for quantification.

The customized ELISA assays were utilized for analyzing both cell supernatants and human plasma samples.
Method #2). Customized ELISA assay for detection of IGFBP5 full length and IGFBP5-Nt fragment.

Using similar strategies, a neo-epitope rabbit polyclonal antibody (pAb) that specifically recognize human IGFBP5 N-terminal (IGFBP5-Nt) was generated and used to config-ure an ELISA that detected the N-terminal fragment (see FIG. 6B). A rabbit antibody that specifically recognize the uncleaved IGFBP5 (IGFBP5-FI) was also generated using the bridging peptide. The capture and detection antibody combinations for IGFBP5 full length and Nt fragment ELISA assay are summarized in Table 8. The established ELISA assays also recognized NHP IGFBP5 full length and IGFBP5-Nt fragment due to high degree of amino acid identify between human and HNP IGFBP5 proteins.

TABLE 8

| Antibody combination for IGFBP5-Fl and IGFBP5-Nt fragment ELISA | | | |
| --- | --- | --- | --- |
| ELISA Analyte | Capture Ab | Detection Ab | Secondary labelled Ab |
| IGFBP5-Fl | AF875 (R&D systems) | KEG820 (custom-made Ab) | Anti-rabbit-HRP |
| IGFBP5-Nt | AF875 (R&D systems) | KEG816 (custom-made Ab) | Anti-rabbit-HRP |

The ELISA assay procedure was identical to that described for IGFBP4 protein and fragments shown above.
Method #3). Cellular assay to detect PAPPA-mediated IGFBP4 cleavage in native human A549 and 9-7 cells.

To evaluate the impact of anti-PAPPA mAbs on IGFBP4 full length and fragments on endogenous PAPPA from human cells, two human epithelial cell lines were selected to establish a cellular assay. IGFBP4-FI and Ct fragment ELISA assay described in earlier section were used to assess the PAPPA protease activity and the impact of anti-PAPPA mAbs. Human lung adenocarcinoma A549 cells were iden-tified as having higher PAPPA expression (Mikkelson et al 2014, Oncotarget, Vol. 5, No. 4 µg 1014-1025). 9-7 cells were ADPKD patient cyst derived epithelial cells and were selected due its relevance to cyst cell proliferation. The level of IGFBP4 full length and Ct fragment were analyzed in cell supernatant after various treatments. Cell treatments were carried out as follows:

A. A549 or 9-7 cells were detached with 0.25% Trypsin, collected and resuspended in culture medium. Cells were seeded in 96-well plates at a density of 10,000/ well for A549 cells and 5000/well for 9-7 cells.

B. After 5 hours of seeding, 9-7 cells were treated with 10 µM Forskolin or DMSO for overnight to induce PAPPA expression.

C. On day 2, both A549 or 9-7 cells were treated with either control mAb hIgG1 or anti-PAPPA mAb at a concentration ranging from 30 nM to 0.002 nM with 3-fold dilution in A549 or 9-7 culture medium in triplicates.

D. After 48 hours of treatment, cell supernatants were collected and stored at −80° C. for ELISA assays. Cell supernatant from these treatments were analyzed via ELISA assay as described for IGFBP4-fl, IGFBP4-Ct fragment. Free IGF-1 levels were assessed using a commercial ELISA kit (Ansh Labs, Webster, TX).

Method #4). Detection of IGFBP4 full length and Ct frag-ment in ADPKD and DKD patient plasma.

Customized IGFBP4 Fl and Ct fragment ELISA were also used to assess these analytes in normal human plasma and plasma from ADPKD patients. Plasma samples from normal human volunteer and ADPKD patients were obtained from external collaborators in accordance with GSK human sample management policies. These samples contained age, kidney functions parameters including estimated glomerular filtration rate (eGFR), blood urea nitrogen (BUN) and total kidney volume (tKV). This information was later used to assist correlation analysis. Samples were diluted in either 1×PBS or reagent diluents at different concentrations prior to performing ELISA.

ELISA assays were performed as described in above sections. Data analysis was carried out as described below:

A. ELISA data was captured with a PheraStar ELISA plate reader at OD 450/540 nm. After background (OD540 nm) and blank reading were subtracted. A standard curve was generated using Nonlinear regres-sion (curve fit), with $Y=Bottom+(Top-Bottom)/(1+(IC_{50}/X)\hat{}HillSlope)$ in GraphPad Prism 8.4. Sample concentration was interpolated using standard curve and dilution factor corrected.

B. When there was no standard protein available, graphs were generated directly using background and blank subtracted OD450 nm C. The OD450 nm data or calculated final concentration was copied to GraphPad Prism 8.4, and dose-response curve was generated using Nonlinear regression (curve fit), $Y=Bottom+(Top-Bottom)/(1+10\hat{}((LogEC50-X)))$.

D. Statistics were conducted using GraphPad Prism 8.4. Correlation between IGFBP4-Ct fragments and eGFR was generated with R2 and p-value. Patient samples were not blinded in these experiments.

This procedure was also used to evaluate human plasma samples from DKD (diabetic kidney disease patients) with samples procured from a commercial source.

Method #5). Evaluation of Anti-PAPPA mAbs in JCK Mice.

Juvenile cystic kidney (JCK) mice carry a Nek8 mutation that causes spontaneous development and worsening of kidney cysts (Atala, 1993). The JCK phenotype resembles aspects of PKD and has been widely used to evaluate various therapeutic agents for PKD (Natoli, 2010). This PKD mouse model was utilized to evaluate multiple anti-PAPPA mAbs in vivo for their effect on cyst growth and renal injury markers.

4- to 5-week-old male JCK homozygous mice were obtained from Jackson Labs. Mice were randomized into treatment groups (N=10 per group) with body weight as the covariate. Treatment groups included Ansh labs mAb (50 mg/kg, Catalog #AB-301-AP031), Saline control, multiple anti-PAPPA mAbs (at indicated dosages) and human control IgG (30 mg/kg). All antibodies were administered via IP injection once weekly for 6 weeks.

The primary end point for JCK mouse study was change of total kidney volume (tKV) after 6 weeks of treatments. Baseline MRI images for tKV were obtained, and compared to tKV value at the end of 6-week study. Delta tKV (ΔtKV) was calculated as tKV (6 wks)-tkV (baseline). End of study parameters included body weight, kidney weight, urinary renal injury markers (KIM1, UACR). Additional end of study parameters included PAPPA plasma levels, mAb concentrations, and histology.

Method #6). Evaluation of Anti-PAPPA mAb in Diabetic Kidney Disease (DKD) Mouse Model This study was aimed at evaluating the impact of an anti-PAPPA neutralizing mAb in a well-established DKD mouse model (Østergaard, 2021). In this model, diabetic kidney disease phenotypes including proteinuria and glomerulosclerosis are recapitulated in hypertensive db/db mouse after surgical uni-nephrectomy and renin-expressing AAV (adenovirus associated virus) administration.

The study outline was similar in design to a previously published DKD study (Dalboge, 2022). At study week-5, female db/db mice received a single IV dose of Renin expressing Adeno-associated viruses (AAV; 3*10^{10} gene copies, n=48), and underwent unilateral nephrectomy at study week-4, resulting in diabetic nephropathy hypertensive mice. Db/+ mice (n=11) served as lean control mice (group 1: Lean control, no dosing), and did not receive Renin AAV dosing or nephrectomy. Prior to treatment, diabetic hypertensive uninephrectomized mice (DN/HT) were randomized at week-1 into 3 treatment groups (n=16) based on body weight and fed blood glucose; group 2: DN/HT-Control IgG (25 mg/kg IP, QW), group 3: DN/HT-anti-PAPPA mAb at 25 mg/kg IP, QW) and group 4: DN/HT-Semaglutide (3.0 nmol/kg (day 1-4) SC, 10 nmol/kg (day 5-termination) SC, QD). Animal treatment groups were summarized in table 9 below.

Fed blood glucose was assessed at week-1 and every 3rd week after study start. Blood pressure (BP) was measured in week 5. Urine creatinine, albumin and KIM-1 were evaluated at week 12. Blood HbA1c levels and plasma urea were evaluated at termination. Kidney was sampled for weight, for PAPPA, and total IGF-1 analysis, and further processed for histological evaluation of glomerulosclerosis, and markers of inflammation (F4/80) and kidney injury molecule (KIM^{-1}). Terminal samples were also analyzed for creatinine, circulating PAPPA, and circulating total IGF-1; kidney homogenate was further analyzed for PAPPA and total IGF-1; and the urine was analyzed for KIM^{-1} and NGAL.

Method #7). Pharmacokinetic (PK) and Pharmacodynamic (PD) Analysis of Anti-PAPPA mAb in NHP (Non-Human Primate) Studies This study was conducted to investigate the intravenous pharmacokinetic (PK) and pharmacodynamic (PD) parameters of an anti-PAPPA mAb in the male cynomolgus monkey. A total of six animals divided into two groups were used on study. Group 1, n=4, received the anti-PAPPA mAb at 10 mg/kg (IV administration) and were sampled up to Day 168, Group 2, n=2, received vehicle only and were sampled up to Day 14. Throughout the study, samples were collected to measure drug levels for PK, total circulating PAPPA for target engagement (TE), IGFBP4 full length and IGFBP4-Ct fragment for pharmacodynamic (PD) effects, fasting glucose and insulin levels, along with hematology parameters that were determined as safety biomarkers.

Cynomolgus monkey serum samples were analyzed for anti-PAPPA mAb levels using a qualified analytical method based on sample dilution, followed by immunoassay analysis. The lower limit of quantification (LLQ) for the mAb was 0.25 ug/mL using a 10 μL aliquot of 21-fold diluted Cynomolgus monkey serum with a higher limit of quantification (HLQ) of 200 μg/mL. The anti-PAPPA mAb being tested was captured with a Biotinylated Mouse anti-human IgG CH2 domain antibody and detected with a Mouse Anti-Human IgG K Light Chain-AF647 antibody. The computer systems that were used on this study to acquire and quantify data included Gyrolab Workstation Version 8.1.5 and Watson LIMS version 7.6.1 SP1.

IGFBP4 Fl, IGFBP4-Ct fragment, IGFBP5 FL, and IGFBP5-Nt fragment levels were analyzed using customized ELISA described above. Fasting glucose, insulin and hematological parameters were measured as routine laboratory procedures in DMPK studies.

Example 5: Plasma Levels of IGFBP4-Ct Fragment as a Novel Biomarker for ADPKD Disease Progression Using a customized IGFBP4-Ct ELISA assay, we measured IGFBP4 fragment levels in ADPKD patient samples,

TABLE 9

| | | | | | | Dosing |
|---|---|---|---|---|---|---|
| # | Group | N | Animal model | Dose | Route | Frequency |
| 1 | Lean Control | 11 | Db/+ | NA | NA | NA |
| 2 | DN/HT - Control IgG | 15 | DN* + HT** | 25 mg/kg | IP | QW |
| 3 | DN/HT - anti-PAPPA | 16 | DN + HT | 25 mg/kg | IP | QW |
| 4 | DN/HT Semaglutide | 15 | DN + HT | 10 nmol/kg*** | SC | QD |

*DN: Uninephrectomized db/db,
**HT: Hypertensive, single-injection (IV) of renin-encoding AAV (3e10 GC),
***Semaglutide dose titration: 3.0 nmol/kg (day 1-4), 10 nmol/kg (day 5-termination)

and compared them to normal healthy controls (see Example 4, Method #1 and Method #4).

RESULTS: The IGFBP4-Ct levels were significantly elevated in ADPKD plasma samples as compared to normal healthy individuals (FIG. 7, panel A), while IGFBP4-Fl levels were not significantly changed (FIG. 7, Panel B). Most importantly, the elevated IGFBP4-Ct level was inversely correlated with eGFR, a marker for kidney function in these patients (FIG. 7, panel C), while a more modest association was observed for tKV (FIG. 7, panel D). These data suggest increased IGFBP4 Ct fragment levels in plasma, as a reflection of increased PAPPA activity, is correlated with decrease renal function in ADPKD patients. To our knowledge, this study was the first to measure IGFBP4 fragment in ADPKD patients and demonstrate the increased PAPPA-mediated IGFBP4 cleavage in ADPKD patient plasma.

Additional data was generated using plasma from 12 DKD patients and an increase in IGFBP4-Ct fragment levels were observed in DKD samples as compared to normal human control (FIG. 8). Due to lack of clinical renal function data for DKD patient procured from commercial sources, correlation between IGFBP4-Ct level and renal function (eGFR) could not be assessed.

Example 6: Effect of Anti-PAPPA mAb In Vitro in Native Human Cells

Anti-PAPPA mAb Treatment Modulates IGFBP4 Cleavage in A549 Human Lung Epithelial Cells.

In order to evaluate the anti-PAPPA activity in native human cells, we established a highly selective, customized ELISA to detect IGFBP4-fl (full length or intact) and IGFBP4-Ct (c-terminal fragment) in cell supernatant and evaluate the effect of anti-PAPPA mAb after initial recombinant cell (G401 cell) assay (Method #1 in Example 4). A549 cells were selected due to its high endogenous PAPPA levels (Mikkelsen, 2014).

In this example, A549 cells were treated with anti-PAPPA mAb TPP12744, and an isotype hIgG1 control, in a 10-point dose curve in triplicate, starting from 30 nM with 3× serial dilution for a total of 10 dilution points. After 48h treatment, cell supernatants were collected and IGFBP4-fl, IGFBP4-Ct and free-IGF-1 ELISAs were carried out.

Results: TPP12744 dose-dependently increased IGFBP4-fl and decreased IGFBP4-Ct levels with $EC_{50}/IC_{50}$ both at around 0.8 nM ($pEC_{50}/pIC_{50}$=9.09/9.07), while control hIgG1 had no effect. A decrease in free-IGF-1 level was also observed in TPP12744 treated cell supernatants with a $IC_{50}$ of 0.03 nM ($pIC_{50}$=10.53). (FIG. 9).

FIG. 10 Illustrates several anti-PAPPA mAb (TPP12681, TPP12744, TPP12801, TPP12683) differentially induced IGFBP4-FL protein levels with varying $EC_{50}$ values in this assay, while negative control mAbs (denoted Neg Control A & B, anti-RSV mAbs) had no effect.

These data suggest that the PAPPA neutralizing mAbs inhibit endogenous PAPPA protease activity, leading to increased IGFBP4-FL and decreased IGFBP4-Ct in a dose-dependent manner in A549 human lung epithelial cells. To the best of our knowledge this is the first demonstration in native human epithelial cells that endogenous PAPPA neutralization by an antibody results in an increase of IGFBP4 full length and a corresponding decrease of IGFBP4-Ct fragment in cell supernatant. This assay therefore can be utilized to measure cellular potency of any antibody against endogenous PAPPA protease activity.

Anti-PAPPA mAb Treatment Modulates IGFBP4 Cleavage in ADPKD Patient-Derived Cyst 9-7 Cells.

9-7 cells are human epithelial cells derived from a human ADPKD patient cyst and was widely used in vitro to evaluate cell signaling pathways and effect of potential therapeutic agents (Loghman-Adham, 2003). It has been shown Forskolin induces PAPPA expression in similarly derived ADPKD cell line 9-12 (Kashyap et al). To directly assess the effect of anti-PAPPA mAb in human cyst derived cells, TPP12744 was used to treat 9-7 cells similar to A549 cells, after initial forskolin treatment and IGFBP4-FL and IGFBP4-Ct fragment were evaluated by customized ELISA.

Similar to results observed for A549 cells, TPP12744 treatment led to a dose-dependent increase of IGFBP4-fl levels ($EC_{50}$=0.4 nM) and decrease of IGFBP4-Ct levels ($IC_{50}$=0.02 nM) in cell supernatants (FIG. 11). It was noted that the baseline levels of intact IGFBP4 or IGFBP4-Ct fragment were lower in 9-7 cells as compared to A549 cells and this contributed to increased variability. Free-IGF-1 was not detectable in this cell line.

Taken together, results obtained from both human lung epithelial A549 cells and ADPKD patient derived 9-7 suggest PAPPA inhibition using anti-PAPPA mAb lead to reduced IGFBP4 cleavage as demonstrated by increased intact IGFBP4 and decreased IGFBP4-Ct fragment in treated cell supernatants.

Example 7: Effect of Multiple Anti-PAPPA mAbs on Cyst Growth and Renal Function In Vivo in a PKD Model (JCK Mouse)

In this example, effects of a tool anti-PAPPA mab (Ansh Labs AB-301-AP031) and various anti-PAPPA mabs (TPP12681, TPP12683) were investigated in a relevant PKD mouse model [juvenile cystic kidney (JCK) mouse]. JCK mice carry a Nek8 mutation that causes spontaneous development and worsening of kidney cysts (Atala, 1993). The JCK phenotype resembles many aspects of human PKD and has been widely used to evaluate various therapeutic agents for PKD (Natoli, 2010).

Mice were treated via weekly IP dosing and the changes in total kidney volume (ATKV) were used as a primary marker for kidney cyst expansion and were assessed by MRI (magnetic resonance imaging) comparisons made before and after 6 weeks of mAb treatments. Additional endpoints included urinary kidney injury marker-1 ($KIM^{-1}$), neutrophil gelatinase-associated lipocalin (NGAL), PAPPA levels in plasma and kidney tissue homogenate, and cystic index based on histology.

In a first study comparing TPP12681 15 mg/kg or 50 mg/kg, TPP12683 50 mg/kg, or Ansh Labs mAb 50 mg/kg (a tool mouse anti-PAPPA mAb), all treatment groups demonstrated a significant reduction in TKV growth (shown as decreased ATKV) as compared to a control human IgG treated mice or saline control (FIG. 12). Similarly, reductions in kidney weight growth were also observed for the treatment groups with minimal changes in body weight (FIG. 13). Renal injury markers such as urinary KIM-1: creatinine ratio were significantly reduced in the TPP12681 15 mg/kg and 50 mg/kg, TPP12683 50 mg/kg, and Ansh Labs 50 mg/kg treated groups as compared to human IgG control (FIG. 14).

While both Ansh labs mAb and TPP12681 and TPP12683 reduced tKV growth as demonstrated by a decrease in AtKV compared to respective vehicles, TPP12681 and TPP12683 produced a more profound reduction in tKV as compared to Ansh labs mAb (FIG. 12). Similar findings were also observed in kidney weight reduction (FIG. 13). These data demonstrate enhanced efficacy in slowing kidney cyst growth with IGFBP4/5 dual active PAPPA mAb (e.g. as TPP12681 or TPP12683 or other non-mouse active pan IGFBP4/5 active mAbs) as compared to Ansh labs mAb that inhibits only IGFBP4 cleavage.

In a second JCK mice study all three groups (1, 5, 50 mg/kg) treated with TPP12683 demonstrated a significant reduction in TKV growth (shown as decreased ATKV) as compared to IgG treated mice (FIG. 15). Similar beneficial effects on kidney injury markers were also observed in this second study (e.g. KIM1: creatinine ratio) (data not shown).

In summary, the results from these JCK studies support the hypothesis that PAPPA neutralizing mAb treatments slow kidney cyst growth and reduce kidney damage in JCK mouse model of ADPKD. This data also show that anti-PAPPA neutralizing mAbs that block both IGFBP4 and IGFBP5 cleavage are more efficacious for cyst growth reduction as compared to mAb that blocks only IGFBP4 (Ansh labs mAb).

Example 8: Effect of Anti-PAPPA mAbs on Kidney Pathology in a Mouse Diabetic Kidney Disease (DKD) Model A study was designed to evaluate the impact of an anti-PAPPA neutralizing mAb (TPP12683) in a well-established DKD mouse model (Østergaard, 2021). In this model, diabetic kidney disease phenotypes including proteinuria and glomerulosclerosis are induced in hypertensive db/db mouse after surgical uni-nephrectomy and renin-expressing AAV (adenovirus associated virus) administration.

In this study, db/db mice was uni-nephrectomized and injected with adenovirus expressing renin (AAV-renin) to induce kidney dysfunction resemble human DKD phenotype. TPP12683 was administered by intraperitoneal injection (IP) once weekly for 12 weeks. A similar IgG1 mab against an unrelated viral (RSV) protein was used as negative control, along with Semaglutide as positive control. At the end of 12 week treatment period, mice were terminated and analyzed for kidney pathology parameters including albuminuria, glomerular sclerosis score, tubular injury marker (KIM1 IHC) and inflammation (macrophage infiltration, F4/80 IHC).

Anti-PAPPA mab TPP12683 did not affect hyperglycemia (plasma glucose) or blood pressure in these mice while positive control semaglutide reduced both plasma glucose/HbA1c and blood pressure (data not shown). However, TPP12683 significantly reduced albuminuria as compared to control IgG (FIG. 16). The reduction is less robust as compared to semaglutide, but this occurred without significant effect on glucose level and blood pressure, suggesting a distinct mechanism as compared to semaglutide. Furthermore, when normalized urinary creatinine, UACR (urinary albumin creatine ratio) also demonstrated significant reduction after TPP12683 treatment (FIG. 17). Urinary kidney tubules injury marker $KIM^{-1}$ was also significantly reduced with TPP12683 treatment to the similar degree as semaglutide (FIG. 18).

Glomerulosclerosis assessment was performed on PAS-stained sections using AI-assisted image analysis. Each glomerulus was given a glomerulosclerosis-score on a 5-point scale according to the amount of capillary tuft involvement: Score 0 (normal), score 1 (up to 25% involvement), score 2 (up to 50% involvement), score 3 (up to 75% involvement), and score 4 (global, more than 75% involvement). A glomerulosclerosis index (GSI) was calculated per animal as the average score for all glomeruli in one transverse section at the level of pelvis. GS3 and GS4 were designated as more severe glomerulosclerotic pathology and these data were graphed separately as the GS3+GS4 fraction. As shown in FIG. 19, TPP12683 significantly reduced glomerulosclerosis index and GS3+GS4 fractions as compared to control IgG.

Immunohistological (IHC) assessment of kidney sections also demonstrated that tissue $KIM^{-1}$ expression (marker of kidney tubular injury) was dramatically reduced as compared to control IgG, consistent with urinary KIM1 measurements (FIG. 20). Furthermore, F4/80, an established macrophage marker, was used in immunohistochemistry to assess macrophage infiltration in kidney. As shown in FIG. 21, F4/80 signal was significantly reduced after TPP12683 treatment, as compared to control IgG treatment.

In summary, these data strongly suggest that treatment of hypertensive uni-nephrectomized mice with anti-PAPPA neutralizing mAb TPP12683 resulted in significant beneficial effects on the biochemical and histological markers of nephropathy, including ACR, glomerulosclerosis, inflammation, and tubular injury, without adverse side effects. These data suggest PAPPA inhibition may have broader benefits in DKD and other CKD disease population where IGF-1 driven cell proliferation may play a role in disease progression. Biomarker such as IGFBP4 Ct fragment could enable identification of suitable patients for PAPPA inhibition therapies.

Example 9: Cyno PK/PD Studies and Biomarkers Analysis for PAPPA Inhibition

An in vivo study was conducted to investigate the intravenous pharmacokinetic (PK) and pharmacodynamic (PD) parameters of TPP12744 in the male cynomolgus monkey. Blood samples were collected up to 168 days post dose to quantify TPP12744, IGFBP4-full-length (fl), IGFBP4-Ct fragment, IGFBP5-fl and IGFBP5-Nt fragment to investigate the PKPD relationship of these potential biomarkers.

Results: TPP12744 demonstrated an apparent elimination half-life of approximately 15 days (FIG. 22). TPP12744 inhibited cynomolgus monkey PAPPA activity within three to six hours post-dose, as evidenced by decreased IGFBP4-Ct fragment and a concomitant increase in IGFBP4-fl in treated animals, an indication of reduced IGFBP4 cleavage and inhibition of PAPPA activity (FIG. 23). This observed reduction of PAPPA activity did not return to baseline until 18 weeks post-treatment following washout of TPP12744 (FIG. 24). In parallel untreated control animals these changes to IGFBP4-fl and IGFBP4-Ct fragment were not observed. This is the first in vivo demonstration of anti-PAPPA mAb treatment impacting plasma IGFBP4-fl and IGFBP4-Ct fragment levels, supporting the use of IGFBP4-fl and IGFBP4-Ct fragment as potential PD markers for anti-PAPPA mAb treatment.

In this study, IGFBP5-Nt fragment levels were also measured and it was shown the TPP12744 treatment resulted in a modest (~2-3 fold) reduction of IGFBP4-Nt fragment levels within three to six hours after administration (FIG. 25). This reduction is less robust as compared to the decrease of IGFBP4-Ct fragment. This could be related to the fact that IGFBP5 is also cleaved by PAPPA2, which is not inhibited by TPP12744. IGFBP5-fl protein could not be reliably measured in this study (data not shown).

In summary, TPP12744 displayed suitable PK for human administration based on this cynomolgus monkey PKPD study. Furthermore, IGFBP4-fl and IGFBP4-Ct fragment measurements enabled the assessment of PAPPA neutralization activity in vivo, supporting these as potential biomarkers of PAPPA activity.

Example 10: Determination of PAPPA-Mediated Cleavage of Human IGFBP-2

The aim of this experiment was to confirm that the anti-PAPPA mAbs disclosed herein further prevent PAPPA-mediated proteolytic cleavage of human IGFBP-2.

Methods: PAPPA-mediated cleavage of human IGFBP2 was assessed within a cell-free system utilizing purified proteins. Detection of cleavage events was performed via Western Blot analysis as follows:

IGFBP-2 and IGF2 (R&D Systems #292-G2), all at concentrations of 100 nM, were pre-incubated for 1 hour at 37° C. PAPPA at 200 nM, and varying concentrations of TPP12744 were also pre-incubated for 30 minutes at 37° C. The concentrations of TPP12744 tested were 0.2, 0.4, 0.6, 2, 3, 4, 5, 6, 20, 40, and 60 nM. An IgG control antibody (anti-RSV) was used at a single concentration of 60 nM in each experiment. Following the pre-incubation steps, IGFBP-4/IGF2 complexes were added to PAPPA/mAb complexes and incubated for 3 hours at 37° C.

Reaction tubes were removed from the incubator. Loading buffer in a volume of 10 μL (9 parts NuPAGE LDS sample buffer and 1 part bond breaker TCEP solution) was added to each reaction tube. Reaction tubes were heated to 95° C. for 10 minutes and then transferred to ice to cool. Reactions (30 μL) or SeeBlue Plus 2 Prestained Standard (10 μL) was added per well of a NuPAGE 4-12% Bis-Tris Midi Gel. The gel was run for 1 hour and 15 minutes at 120 volts in 1× NuPAGE MES Running Buffer using a Sure Lock Tandem Midi Gel Tank (Thermo Fisher) and a Power Pac 300 (Bio-Rad) power supply. The gel was transferred to a nitrocellulose membrane for 7 minutes at 23 volts using an iBlot 2 Gel Transfer Device (Thermo Fisher). The membrane was blocked for 2 hours at room temperature, shaking at 60 rpm, in SuperBlock T20 Blocking Buffer.

Primary antibodies (R&D Systems #AF674) were diluted 1:1,000 in SuperBlock T20 Blocking Buffer and added to the membrane. The membrane was incubated in primary antibody for 16 hours at 4° C., rocking. The membrane was washed 3 times with 1×TBST for 5 minutes each, shaking at 60 rpm. The secondary antibody (Licor #926-322140 was diluted 1:10,000 in SuperBlock T20 Blocking Buffer and added to the membrane. The membrane was incubated in secondary antibody for 2 hours at room temperature, shaking at 60 rpm. The membrane was washed 3 times with 1×TBST for 5 minutes each, shaking at 60 rpm. The membrane was imaged using the Licor Odyssey CLx Imaging System.

PAPPA activity was determined by measuring the cleavage products of IGFBP-2 in the absence and presence of TPP12744 by western blot. IGFBP fragment intensities were quantified using Image Studio Lite Version 5.2.5. The single fragment observed for IGFBP2 was quantified by using a single box encompassing the entire fragment(s) and providing one quantification value per lane. Percent inhibition of PAPPA cleave was calculated by dividing the quantified IGFBP-2 fragment intensity per antibody concentration (FIG. 26 lanes 3-13) by the quantified IGFBP-2 fragment intensity for the no antibody control (FIG. 26 lane 2) and multiplying by 100. Percent PAPPA activity values were transferred to Graph Pad Prism 8.4.3. TPP12744 concentrations were transformed into log 10. An XY graph was generated with log TPP12744 (M) on the x-axis and fragment levels on the y-axis and nonlinear regression analysis was performed.

Results: As shown in FIG. 26, no cleavage of IGFBP2 was observed in the absence of recombinant PAPPA protein. However, after the addition of PAPPA, approximately 50% of the total IGFBP2 was cleaved. Only one of the two potential IGFBP2 proteolytic fragments was detected with a molecular weight of ~15 kDa. However, this singlet observation was consistent with the published literature where the detection of the smaller fragment was significantly less prominent and possibly not as well detected by the IGFBP2 antibody (Monget, 2003) The addition of TPP12744 to the IGFBP2/PAPPA reactions decreased PAPPA-mediated IGFBP2 cleavage in a concentration dependent manner, while the IgG control had no effect on IGFBP2 cleavage at 60 nM. The average $IC_{50}$ value for TPP12744 inhibitory effect on IGFBP2 cleavage was 1.39 nM across the two experiments (FIG. 27).

Example 11: Comparative Experiments

Experiments were conducted to compare TPP12744 against three anti-PAPPA mAbs (herein referred to as "comparator anti-PAPPA mAb 1, 2 and 3" respectively) having the following heavy chain (HC) and light chain (LC) sequences:

Comparator anti-PAPPA mAb 1-SEQ ID Nos: 120 (HC) and 121 (LC)

Comparator anti-PAPPA mAb 2-SEQ ID Nos: 122 (HC) and 123 (LC)

Comparator anti-PAPPA mAb 3-SEQ ID Nos 124 (HC) and 125 (LC)

Production of Comparator Anti-PAPPA mAb 1, 2 and 3

For production of comparator anti-PAPPA mAbs both transient HEK expressions and stable CHO GS cell lines were utilised. Comparator anti-PAPPA mAb 1, 2 & 3 were produced using a HEK transient system. Comparator anti-PAPPA mAb 1 was also generated via a stable CHO-GS cell line. Sequences corresponding to Comparator anti-PAPPA mAb 1, 2 and 3 were codon optimized and transcribed sequences checked against reported amino acid sequences. Expression vectors suitable for HEK transient or CHO GS-stable cell lines were generated containing the derived codon-optimised sequences. mAbs were affinity purified using standard procedures and stored in comparable buffers to that used for the batch of TPP12744 being utilized for the assays described below (such as to facilitate a like-for-like assessment).

Aims:

1. To assess the non-specific binding propensity of TPP12744 compared to Comparator anti-PAPPA mAb 1 using a Heparin Binding ELISA assay; and 2. To assess the propensity of TPP12744 for aggregation (self-association) compared to Comparator anti-PAPPA mAb 1, 2 and 3 using Affinity-Capture Self-Interaction Nanoparticle Spectroscopy (AC-SINS).

The second aim listed above was established following an observation of precipitation of the comparator anti-PAPPA mAbs when the mAbs were formulated following generation.

Methods:

Heparin Binding ELISA

Non-specific binding properties of antibodies when dosed in vivo are thought to be one cause of higher-than-expected clearance, as a consequence of atypical association of the antibody to other in vivo proteins and/or cell membranes.

This association can increase both systemic and pre-systemic clearance and thus reduce the exposure of therapeutic antibodies. This can lead to very significant reductions in AUC compared to typical mAb kinetic. The heparin binding ELISA was thus used to characterise the non-specific binding potential of the anti-PAPPA antibodies. This assay was considered physiologically relevant because heparin is negatively charged and abundant in extracellular matrix and cell membranes. The following method was employed:

Heparin binding ELISA plates were generated using a 20 ug/ml solution of Heparin applied to Poly-L-lysine coated plates and left to incubate overnight. On day 2 plates were blocked using a 1% w/v BSA solution and a 150 ug/ml test antibody solution applied and incubated for 1 hour at RT. HRP conjugated anti-human IgG coupled with an absorbance measurement at 450 nm were then used to determine levels of bound mAb following three wash steps.

Affinity-Capture Self-Interaction Nanoparticle Spectroscopy (AC-SINS)

AC-SINS is a technique developed to measure the propensity of antibodies to self-associate in solution. The method takes advantage of the optical properties of colloidal gold particles, where the maximum wavelength of light absorbed (plasmon wavelength) is proportional to the distance between particles. When strongly self-associating mAbs are adsorbed to the gold nanoparticles, the plasmon wavelength shifts towards the red region of the visible light spectrum, resulting in the characteristic "red shift" measured in this assay (A) max. This assay has utility in detecting manufacturability liabilities such as poor solubility, viscosity and aggregation risks in mAbs.

In order to assess mAb self-association AC-SINS was performed. Briefly, a mixture of gold nanoparticles coated with either Anti Fc IgG or a non-capture IgG was made. Post overnight incubation a $10\,\mu M$ PEG solution was added to the Ab-nanoparticle mixtures, mixed and incubated for 1-2 hrs at room temperature. Mixtures were equally split, placed into separate siliconized tubes and centrifuged, with supernatants removed to leave $100\,\mu l$ in each tube. Pellets were resuspended before being pooled into 2 tubes.

Antibody samples were added to separate wells of a 96w polypropylene plate, including buffer only negative controls. Captured nanoparticles were subsequently added to all the wells for Fc capture followed by incubation for 90 mins. Each sample was then split to generate duplicates and read using an absorbance scan from 450n-650 nm in 1 nm increments.

Results:

Heparin Binding ELISA

Table 10 below shows the binding response of Comparator anti-PAPPA mAb 1 to heparin-coated plates, in comparison to TPP12744.

Anti-IL12/23 comparator A was considered the assay negative control and was expected to show little or no heparin binding at the concentrations used. Anti-IL12/23 comparator B was considered the assay positive control and was expected to show strong dose-dependent binding (Dyson et al Mabs. 2020; 12 (1)). All controls performed as expected and the assay was considered valid. Green, Amber and Red outcomes were assigned based on the following cut-offs [green <0.33, amber 0.33-0.66 and red >0.66].

TABLE 10

Heparin Binding Data: Comparator anti-PAPPA mAb 1 versus TPP12744

| Description | Heparin Normalized | Outcome |
|---|---|---|
| Comparator anti-PAPPA mAb 1 Expressed in: CHO | 0.349 | Amber |
| TPP12744 Expressed in: CHO | 0.11 | Green |
| Anti-IL12/23 comparator A (briakinumab) | 0.983 | Red |
| Anti-IL12/23 comparator B (ustekinumab) | 0.09 | Green |

AC-SINS

Table 11 below shows the normalised AC-SINS score calculated from the plasmon wavelength and $\Delta\lambda_{max}$ (also known as redshift (nm)), of TPP12744 and Comparator anti-PAPPA mAbs 1, 2 and 3. Vesencumab was used as positive control since it is reported to show $\Delta\lambda_{max}$ values greater than 10 nm, suggesting strong self-association (Liu et al; 2014, Mabs; 6 (2): 483-92). Internal vesencumab controls were used to normalize redshift data.

As can be seen from the table below, the self-association potential of Comparator anti-PAPPA mAb 1 and 2 were significantly higher than TPP12744. Out of the Comparator anti-PAPPA mAbs, Comparator anti-PAPPA mAb 3 showed the lowest normalized AC-SINS score but was still significantly above the level observed for TPP12744.

TABLE 11

Normalised AC-SINS Data

| Description | AC-SINS Score [Normalised to internal Vesencumab control] |
|---|---|
| Comparator anti-PAPPA mAb 1 Expressed in: HEK293 | 0.667 |
| Comparator anti-PAPPA mAb 1 Expressed in: CHO | 0.667 |
| Comparator anti-PAPPA mAb 2 Expressed in: HEK293 | 0.818 |
| Comparator anti-PAPPA mAb 3 Expressed in: HEK293 | 0.485 |
| TPP12744 Expressed in: HEK293 | 0.353 |

In conclusion, the data outlined in this Example demonstrated that TPP12744 has significantly lower propensity to self-associate compared to Comparator anti-PAPPA mAbs 1, 2 and 3. TPP12744 also demonstrated less non-specific binding as measured by binding to heparin. Together these data suggest that TPP12744 has improved biophysical properties compared to the comparator anti-PAPPA mAbs in the assays and conditions tested.

Example 12: Epitope Mapping of Comparator anti-PAPPA mAb 1

The interactions between human PAPPA and Comparator anti-PAPPA mAb 1 was studied by hydrogen-deuterium exchange mass spectrometry (HDX-MS). HDX-MS experiments were conducted essentially as described in Example 3. 633 peptides covering 83.7% of the sequence were included in the evaluation.

Results:

The regions with the greatest significant protection for the Comparator anti-PAPPA mAb 1 complex consisted of peptides spanning residues 1565-1574 and 1585-1621 of human PAPPA (FIG. 28, residue numbering in accordance with full-length human PAPPA as shown in SEQ ID NO: 1). These regions lie close to the C-terminus in the terminal SCR domains. An additional peptide covering residues 1442-1460 was also of high magnitude protection and significant but there were no overlapping peptides to increase confidence in this region.

```
1565-1574:
                            (SEQ ID NO: 126)
NYCDAINNRA 1585-1621:
                            (SEQ ID NO: 127)
TSTVKTKKVTPFPMSCDLQGDCACRDPQAQEHSRKDL
```

Whilst the greatest differential magnitude of the complexes were centred as described above, a number of other regions displayed significant peptides (p<0.01) when comparing single time-points using a pairwise Welch's t-test (as shown by the opaque bars in FIG. 28). Whilst being statistically significant the magnitude of these other differentials was low.

Conclusion:

Comparator anti-PAPPA mAb 1 displayed a different protection profile to that of TPP12744 with different domains showing regions of greatest protection. More specifically Comparator anti-PAPPA mAb 1 binding resulted in the greatest magnitude of protection in the LNR3 domain at the C-terminus spanning residues 1565-1574 and 1585-1621. This exchange pattern was observed (see Example 3) for other mAbs disclosed herein, namely TPP12681 and TPP12683 (where the magnitude of protection was relatively low but localised to the C-terminus and specifically the LNR3 domain). TPP12744 on the other hand was shown to have a maximum protection response between residues 1067 to 1079 of human PAPPA corresponding to the M1/M2 domain.

Antibody Sequences Summary Table

TABLE 12

| | | | | | Summary of SEQ ID numbering for 8 selected antibodies: | | | | | | |
|---|---|---|---|---|---|---|---|---|---|---|---|
| | | | | | SEQ ID NOs | | | | | | |
| TPP# | HC | VH (VH DNA) | CDRH1 | CDRH2 | CHRH3 | LC | VL (VL DNA) | CDRL1 | CDRL2 | CDRL3 | |
| 12743 | 20 | 21 (22) | 23 | 24 | 25 | 26 | 27 (28) | 29 | 30 | 31 | |
| 12708 | 32 | 33 (34) | 35 | 36 | 37 | 38 | 39 (40) | 41 | 42 | 43 | |
| 12681 | 44 | 45 (46) | 47 | 48 | 49 | 50 | 51 (52) | 53 | 54 | 55 | |
| 12821 | 56 | 57 (58) | 59 | 60 | 61 | 62 | 63 (64) | 65 | 66 | 67 | |
| 12801 | 68 | 69 (70) | 71 | 72 | 73 | 74 | 75 (76) | 77 | 78 | 79 | |
| 12792 | 80 | 81 (82) | 83 | 84 | 85 | 86 | 87 (88) | 89 | 90 | 91 | |
| 12683 | 92 | 93 (94) | 95 | 96 | 97 | 98 | 99 (100) | 101 | 102 | 103 | |
| 12744 | 104 | 105 (106) | 107 | 108 | 109 | 110 | 111 (112) | 113 | 114 | 115 | |

The invention claimed is:

1. A PAPPA binding protein comprising a variable heavy chain (VH) region comprising three heavy chain CDR sequences, CDRH1, CDRH2, and CDRH3, and a variable light chain (VL) region comprising three light chain CDR sequences, CDRL1, CDRL2, and CDRL3, wherein CDRH1 comprises SEQ ID NO: 107; CDRH2 comprises SEQ ID NO: 108; CDRH3 comprises SEQ ID NO: 109; CDRL1 comprises SEQ ID NO: 113; CDRL2 comprises SEQ ID NO: 114; and CDRL3 comprises SEQ ID NO: 115.

2. The PAPPA binding protein of claim 1, wherein said binding protein comprises a VH region that is 100% identical to SEQ ID NO: 105.

3. The PAPPA binding protein of claim 1, wherein said binding protein comprises a VL region that is 100% identical to SEQ ID NO: 111.

4. The PAPPA binding protein of claim 1, wherein said binding protein comprises a VH region that is 100% identical to SEQ ID NO: 105 and a VL region that is 100% identical to SEQ ID NO: 111.

5. The PAPPA binding protein of claim 1, wherein said binding protein comprises a heavy chain constant region as shown in SEQ ID NO: 17 and a light chain constant region as shown in SEQ ID NO: 19.

6. The PAPPA binding protein of claim 4, wherein said binding protein comprises a heavy chain and a light chain, wherein the amino acid sequence of the heavy chain is shown in SEQ ID NO: 104 and the amino acid sequence of the light chain is shown in SEQ ID NO: 110.

7. The PAPPA binding protein of claim 1, wherein said binding protein inhibits cleavage of IGFBP-2, IGFBP-4 and IGFBP-5.

8. The PAPPA binding protein of claim 1, wherein said binding protein binds to human PAPPA with an affinity (KD) of less than 1 nM, wherein affinity (KD) is measured using surface plasmon resonance (SPR) at 25° C. or 37° C.

9. The PAPPA binding protein of claim 1, wherein said PAPPA binding protein is a human or humanized PAPPA binding protein.

10. The PAPPA binding protein of claim 1, wherein said PAPPA binding protein is an antibody or an antigen binding fragment thereof.

11. A nucleic acid sequence that encodes a PAPPA binding protein comprising a variable heavy chain (VH) region comprising three heavy chain CDR sequences, CDRH1, CDRH2, and CDRH3, and a variable light chain (VL) region comprising three light chain CDR sequences, CDRL1, CDRL2, and CDRL3, wherein CDRH1 comprises SEQ ID NO: 107; CDRH2 comprises SEQ ID NO: 108; CDRH3 comprises SEQ ID NO: 109; CDRL1 comprises SEQ ID NO: 113; CDRL2 comprises SEQ ID NO: 114; and CDRL3 comprises SEQ ID NO: 115.

12. An expression vector comprising the nucleic acid sequence of claim 11.

13. A recombinant host cell comprising the expression vector of claim 12.

14. A pharmaceutical composition comprising the PAPPA binding protein of claim 1 and a pharmaceutically acceptable excipient.

15. A method for the treatment of a polycystic kidney disease (PKD) in a subject in need thereof comprising administering to said subject a therapeutically effective amount of a PAPPA binding protein comprising a variable heavy chain (VH) region comprising three heavy chain CDR sequences, CDRH1, CDRH2, and CDRH3, and a variable light chain (VL) region comprising three light chain CDR sequences, CDRL1, CDRL2, and CDRL3, wherein CDRH1 comprises SEQ ID NO: 107; CDRH2 comprises SEQ ID NO: 108; CDRH3 comprises SEQ ID NO: 109; CDRL1 comprises SEQ ID NO: 113; CDRL2 comprises SEQ ID NO: 114; and CDRL3 comprises SEQ ID NO: 115.

16. The method of claim 15 wherein the PKD is autosomal dominant PKD (ADPKD).

17. The method of claim 15, wherein the VH region comprises an amino acid sequence according to SEQ ID NO: 105 and the VL region comprises an amino acid sequence according to SEQ ID NO: 111.

18. The method of claim 15, wherein the PAPPA binding protein comprises a heavy chain (HC) and a light chain (LC), wherein the amino acid sequence of the HC is shown in SEQ ID NO: 104 and the amino acid sequence of the LC is shown in SEQ ID NO: 110.

19. The nucleic acid of claim 11, wherein the VH region comprises an amino acid sequence according to SEQ ID NO: 105 and the VL region comprises an amino acid sequence according to SEQ ID NO: 111.

20. The nucleic acid of claim 11, wherein the PAPPA binding protein comprises a heavy chain (HC) and a light chain (LC), wherein the amino acid sequence of the HC is shown in SEQ ID NO: 104 and the amino acid sequence of the LC is shown in SEQ ID NO: 110.

21. The PAPPA binding protein of claim 1, wherein the binding protein binds to an epitope within the M1/M2 region of human PAPPA.

22. The PAPPA binding protein of claim 21, wherein said M1/M2 region of human PAPPA corresponds to amino acids 673-1213 of SEQ ID NO: 1.

*     *     *     *     *